United States Patent
Azzedine et al.

(10) Patent No.: US 10,519,503 B2
(45) Date of Patent: Dec. 31, 2019

(54) DIAGNOSIS OF HEREDITARY SPASTIC PARAPLEGIAS (HSP) BY DETECTION OF A MUTATION IN THE KIAA1840 GENE OR PROTEIN

(71) Applicant: INSTITUT NATIONAL DE LA SANTE ET DE LA RECHERCHE MEDICALE (INSERM), Paris (FR)

(72) Inventors: Hamid Azzedine, Bagneux (FR); Alexis Brice, Paris (FR); Giovanni Stevanin, Sevran (FR); Filippo Santorelli, Naple (IT); Paola Denora, Rome (IT)

(73) Assignee: INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 15/386,571

(22) Filed: Dec. 21, 2016

(65) Prior Publication Data

US 2017/0175196 A1 Jun. 22, 2017

Related U.S. Application Data

(60) Division of application No. 14/206,840, filed on Mar. 12, 2014, now Pat. No. 9,546,402, which is a division of application No. 13/567,790, filed on Aug. 6, 2012, now Pat. No. 8,728,727, which is a continuation of application No. 12/440,644, filed as application No. PCT/IB2007/003535 on Sep. 11, 2007, now abandoned.

(30) Foreign Application Priority Data

Sep. 11, 2016 (EP) ..................................... 06291433

(51) Int. Cl.
| | | |
|---|---|---|
| C07H 21/04 | (2006.01) | |
| C12Q 1/68 | (2018.01) | |
| C12Q 1/6883 | (2018.01) | |

(52) U.S. Cl.
CPC ..... C12Q 1/6883 (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 9,546,402 B2 * | 1/2017 | Azzedine | |
| 2004/0146890 A1 * | 7/2004 | Matsuzaki | C12Q 1/6883 435/6.11 |
| 2007/0184444 A1 * | 8/2007 | Abbas | C07K 14/47 435/6.14 |
| 2011/0177960 A1 * | 7/2011 | Murphy | C12Q 1/689 506/9 |
| 2015/0038352 A1 * | 2/2015 | Cao | C12Q 1/6837 506/9 |

OTHER PUBLICATIONS

Rothstein et al. (1994) PNAS USA 91: 4155-4159 (Year: 1994).*
NEB catalog (1998/1999), pp. 121, 284. (Year: 1998).*

* cited by examiner

*Primary Examiner* — Jeanine A Goldberg
(74) *Attorney, Agent, or Firm* — B. Aaron Schulman, Esq.; Stites & Harbison, PLLC

(57) ABSTRACT

An ex vivo method of diagnosing or predicting an hereditary spastic paraplegias (HSP) in a subject is provided which comprises detecting a mutation in the KIAA1840 gene or protein (spatacsin), wherein that mutation is indicative of an hereditary spastic paraplegias (HSP).

5 Claims, 17 Drawing Sheets

Figure 2:
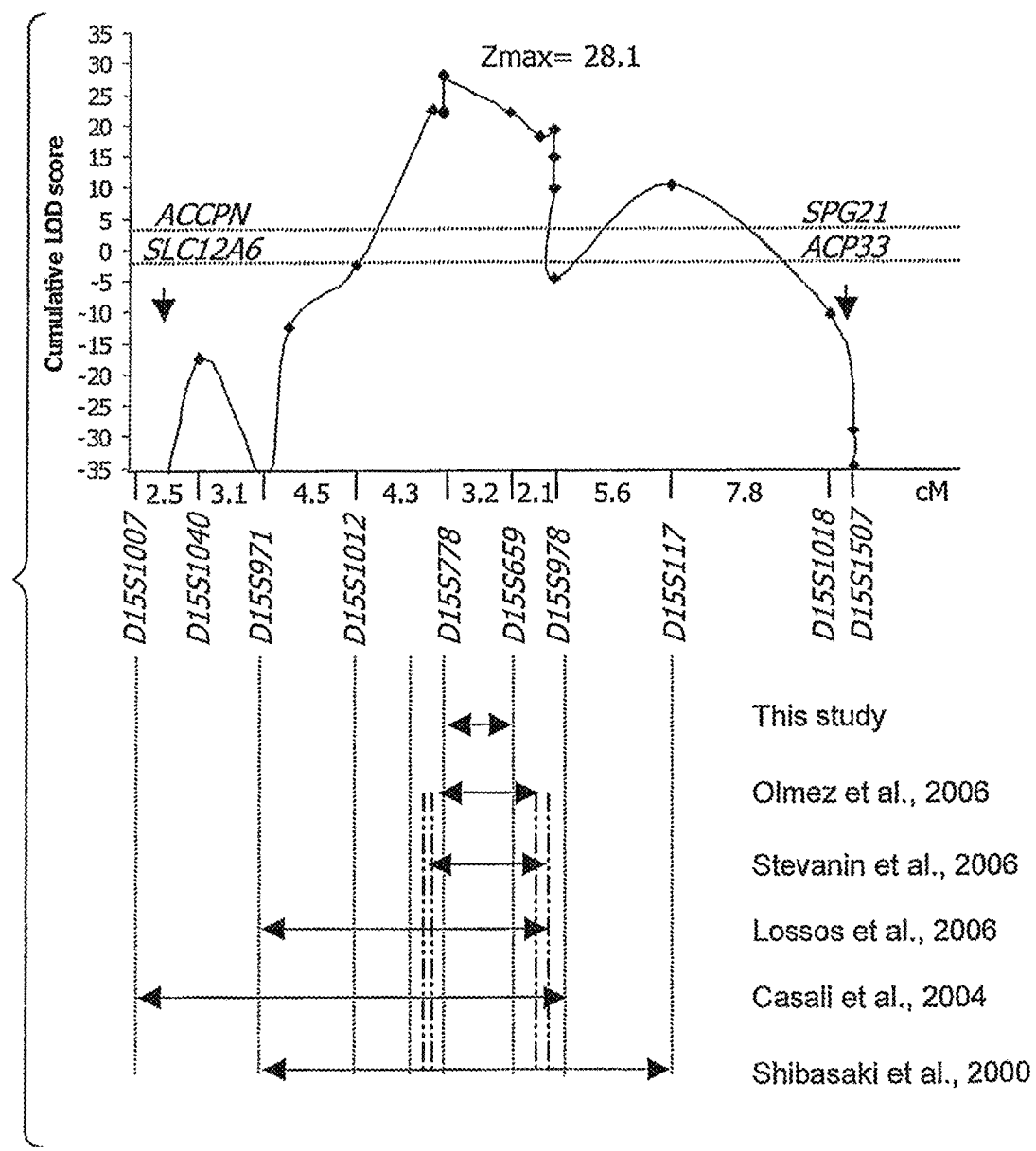

Specification includes a Sequence Listing.

FIG.1

FSP831 (Portugal)
*Exon 3: c.529_533 delATATT, p.I177_F178>S177delfsX178*
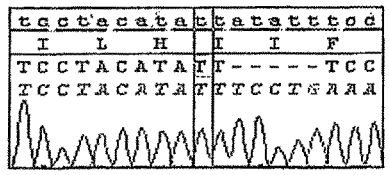
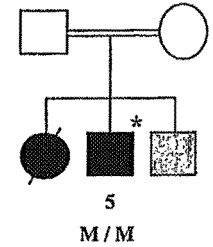
FSP792 (Morocco)
*Exon 32: c.6100 C>T, p.R2034X*
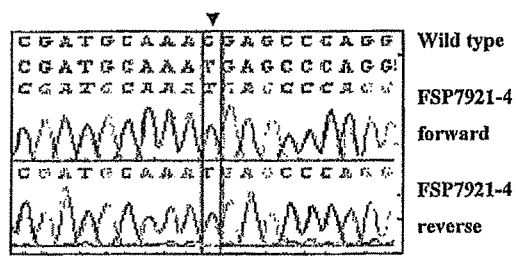
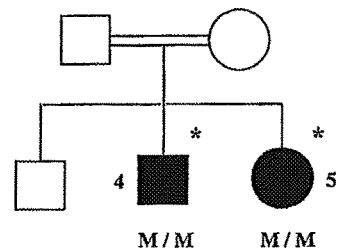
FSP845 (Morocco)
*Exon 32: c.6100 C>T, p.R2034X*
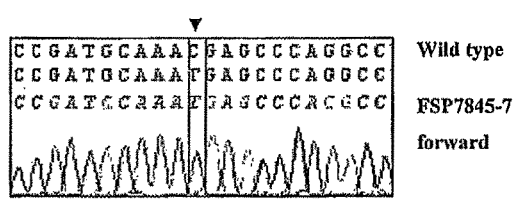
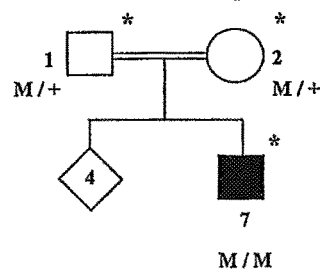
TUN9 (Tunisia)
*Exon 32: c.6100 c>t p.R2034X*
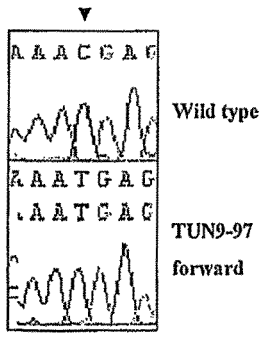
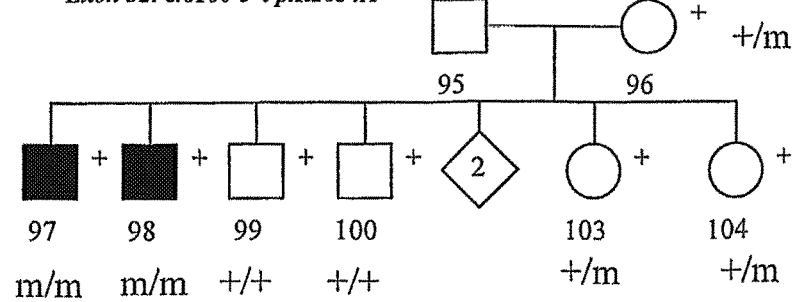
FIG.10

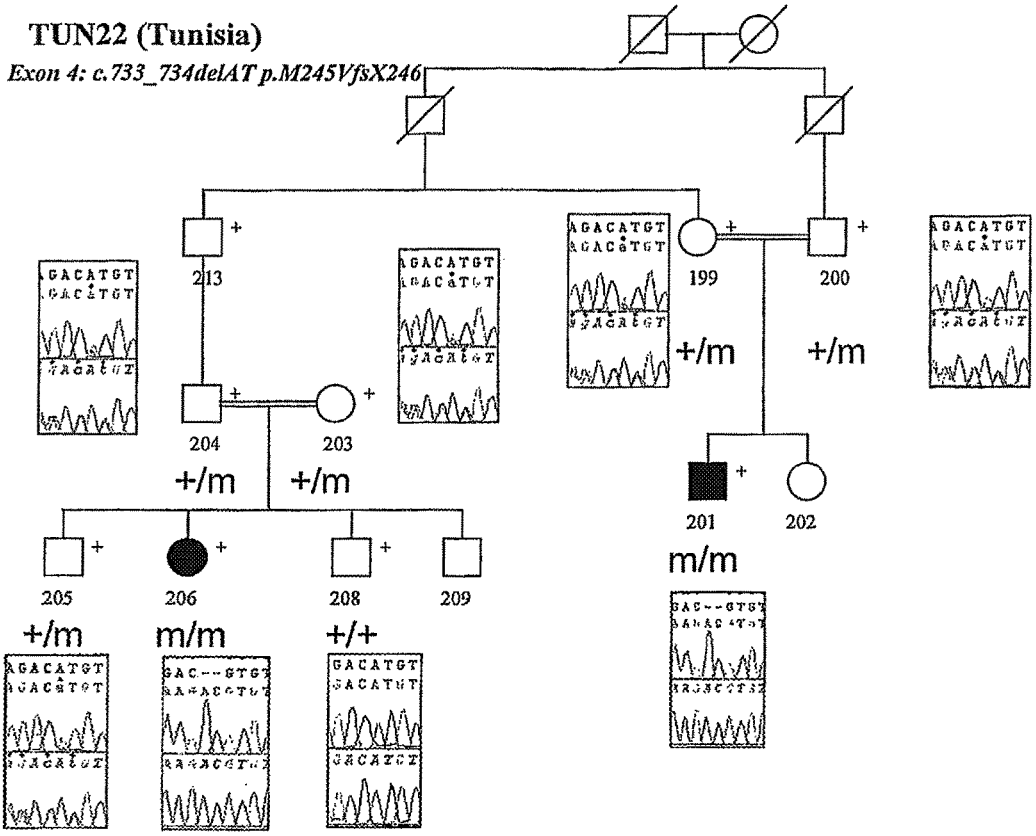
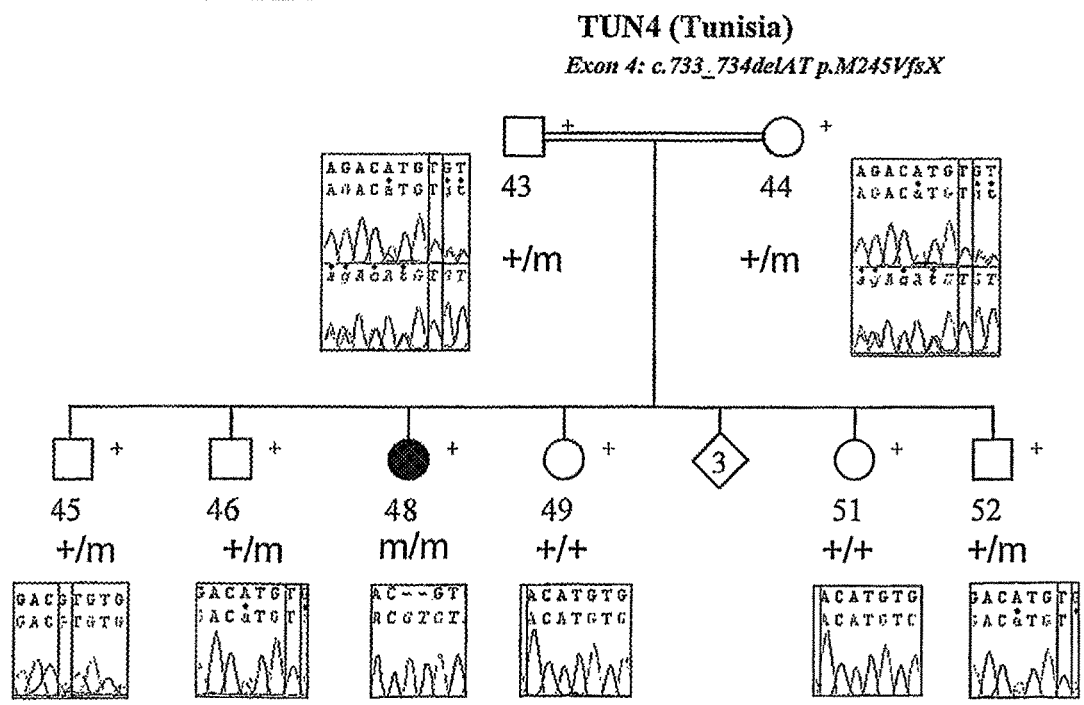
FIG.12

FSP920 (Japan)
*Exon36: c.6737_6740delTTGA; p.I2246_E2247>S2246fsX2260*
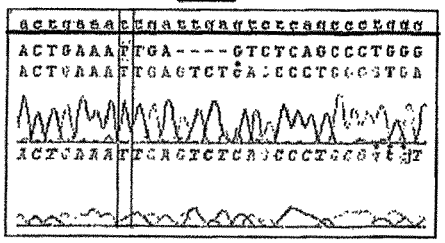
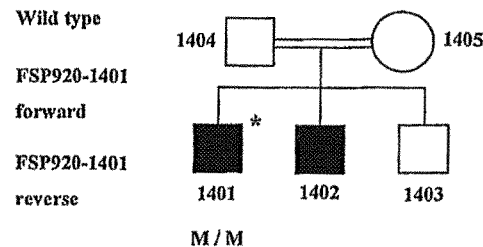
ITA1 (Trukey)
*Exon32: c.6091C>T; p.R2031X*
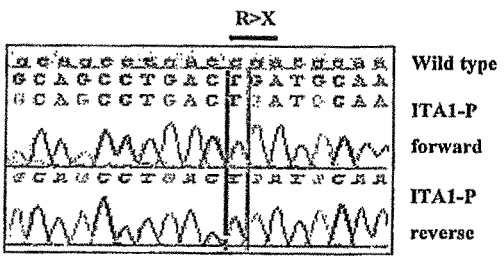
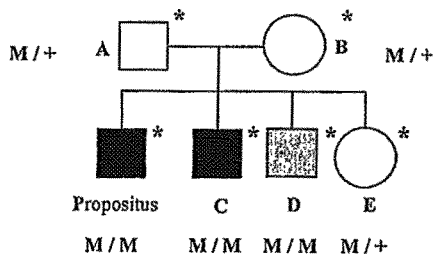
FSP838 (Saudi-Arabia)
*Exon 30: c.5769 delT, p.S1923RfsX1950*
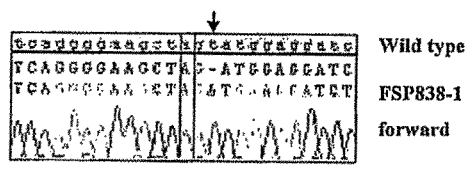
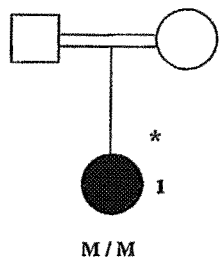
SPD199 (Turkey)
*Exon 4: c.704_705delAT, p.H235RfsX246*
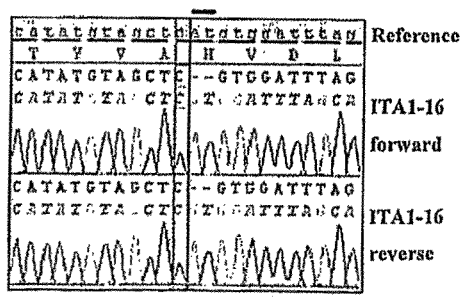
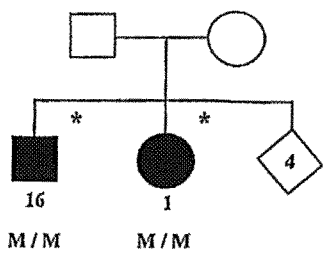
FIG.14

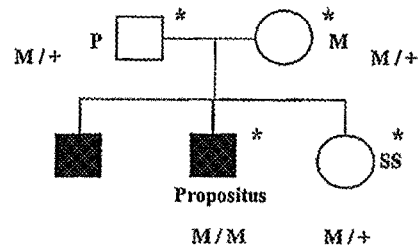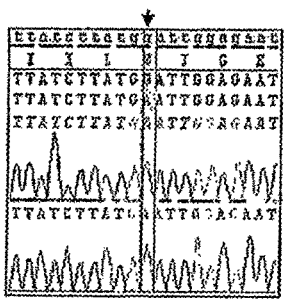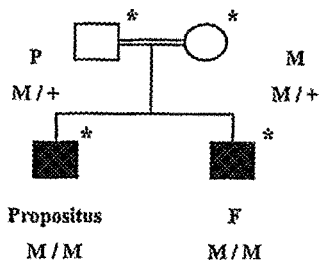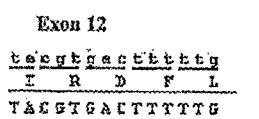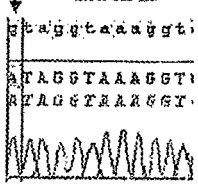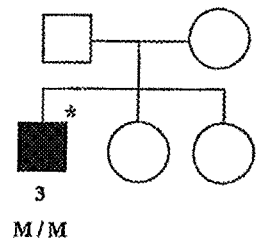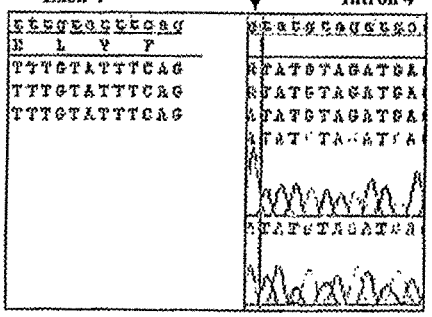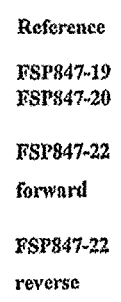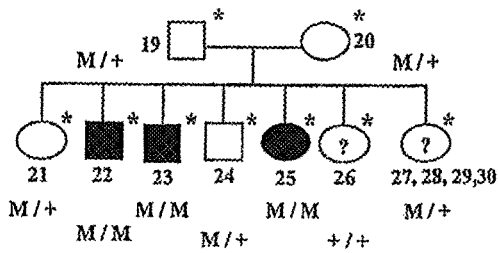
FIG.15

ITA17 (Brazil)
*Exon 3: c.529_533 delATATT, p.I177_F178>S177fsX178*
*Exon 22: c.3741_3742insA, p.P1248fsX1264*
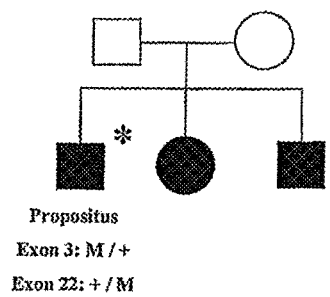
Propositus
Exon 3: M / +
Exon 22: + / M
FSP830 (Portugal)
*Exon 6: c.1282 A>T, p.K428X*
*Intron 34: c.6477+4 A>G, r.?*
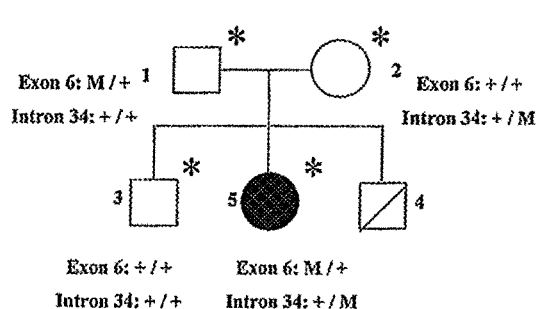
FSP522 (France)
*Exon 7: c.1471_1472delCT, p.L491DfsX556*
*Exon 30: c.5532_5533delCA, p.S1844SfsX1857*
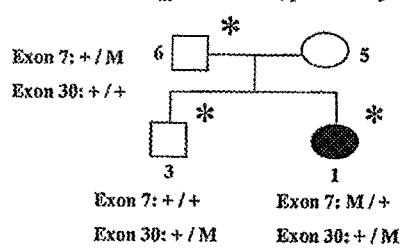
SAL646 (France)
*Exon 8: c.1668delT, p.F556LfsX577*
*Exon 36: c.6739_6742delGAGT, p.E2247_S2248>L2247fsX2260*
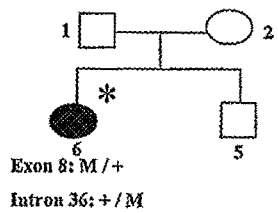
ITA16SB (Italy)
*Exon 8: c.1679C>G, p.S560X*
*Exon 31: c.5870C>G, p.S1957X*
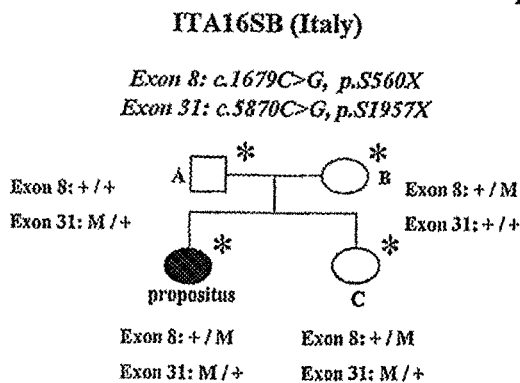
DKD (Italy)
*Exon 8: c.1692delA, p.V564VfsX577*
*Exon 31: c.5982_5983insCTCT, p.L1995LfsX2000*
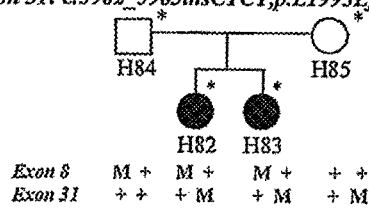
FIG. 16

FSP683 (France)
*Exon 10: c.1951C>T, R651X*
*Exon 31: c.5989_5992delCTGT,p.L1997_Y1998>M1997fsX2056*

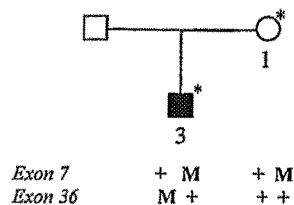

| | | |
|---|---|---|
| Exon 7 | + M | + M |
| Exon 36 | M + | + + |

ITA28VAC (Italy)
*Exon 10: c.1951C>T; p.R651X*
*Exon 13: c.2444G>T, p.R815M and/or r.?*

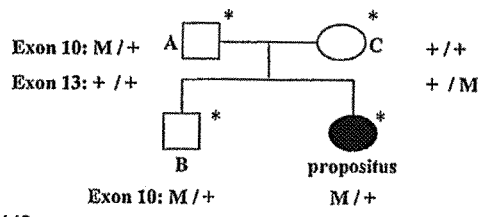

Exon 10: M / +    A          C    + / +
Exon 13: + / +                     + / M B       propositus
Exon 10: M / +              M / +
Exon 13: + / +              + / M

ITA16 (Brazil)
*Intron 13: c.2444+1G>C, r.?*
*Exon 25: c.4307_4308 delAA, p.Q1436RfsX1442*

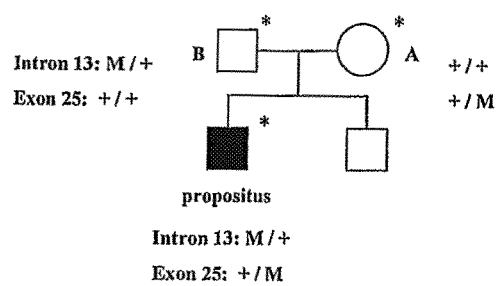

Intron 13: M / +   B       A   + / +
Exon 25: + / +                 + / M propositus
Intron 13: M / +
Exon 25: + / M

ITA 14 (Italy)
*Exon 15: c.2833 A>G, p.R945X*
*Exon 38: c.6857 C>T, p.R2286X*

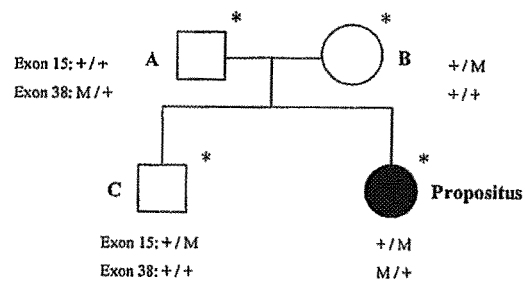

Exon 15: + / +    A          B    + / M
Exon 38: M / +                    + / +

C          Propositus
Exon 15: + / M              + / M
Exon 38: + / +              M / +

ITA8 (Germany)
*Exon 17: c.3075_3076insA, p.E1026RfsX2029*
*Exon 30: c.5471 C>T, p.R1824X*

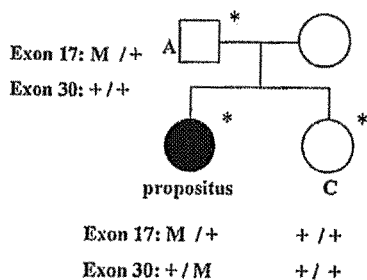

Exon 17: M / +   A
Exon 30: + / + propositus    C
Exon 17: M / +         + / +
Exon 30: + / M         + / +

FSP398 (Israel)
*Exon 25: c.4307_4308delAA, p.Q1436RfsX1442*
*Exon 31: c.5986_5987insT, p.C1996LfsX1999*

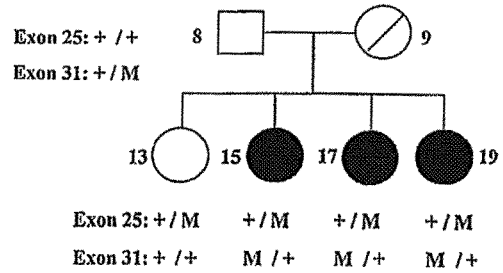

Exon 25: + / +    8              9
Exon 31: + / M 13    15    17    19
Exon 25: + / M   + / M   + / M   + / M
Exon 31: + / +   M / +   M / +   M / +

FIG. 17

SEQUENCE LISTING

```
<160> NUMBER OF SEQ ID NOS: 188

<210> SEQ ID NO 1
<211> LENGTH: 7751
<212> TYPE: DNA
<213> ORGANISM: homo sapiens

<400> SEQUENCE: 1
atggctgcag aggaaggggt cgcgagtgct gcttccgccg gcggtagctg gggcaccgcg      60
gccatggggc gggttctacc gatgctgttg gtgccagtcc ccgccgaggc gatggggcag     120
ctcggctccc gggcgcagct gcgcacacag ccggaggctc tggggagcct gacggctgcg     180
ggcagcctcc aagtgctttc tttgacgcct ggcagccggg gcggggtcg ctgctgcctg      240
```

```
gagggcccct tctggcactt tctatgggag gattctcgta acagcagcac accaactgaa      300
aagcccaaac tgctcgctct tggtgaaaat tatgaactgc ttatctatga atttaatttg      360
aaagatggaa gatgtgatgc aaccattttg tatagctgta gtagggaggc attgcaaaag      420
ctcattgacg atcaagatat cagtatttcc ttattgtctt tgagaatcct gtcatttcac      480
aataacacat cattactgtt catcaacaaa tgtgtcatcc tacatattat atttcctgaa      540
agagatgctg caattagagt actcaactgt ttcacacttc ccttgcctgc acaggcagtg      600
gacatgatta ttgacacgca gctctgcaga ggaattcttt ttgttttgag tagtttaggc      660
tggatctaca ttttgatgt tgtggatggt acatatgtag ctcatgtgga tttagcactt      720
cacaaagaag acatgtgtaa tgagcagcaa caggagccag ccaagatttc ttcatttact      780
tcactgaaag tttctcaaga cctcgatgtt gcagtgattg tcagctcctc caactccgca      840
gttgctctta acttaaattt gtatttcagg caacacccag gacacctact gtgtgaaaga      900
atactagaag atcttcctat tcaaggacct aagggcgtag atgaagatga tcctgttaac      960
tctgcctaca acatgaaact ggccaagttt tccttccaaa ttgataggtc ttggaaagcc     1020
cagctatcat cattgaatga aacaataaag aactccaaac tggaggtttc ctgttgtgct     1080
ccatggttcc aggatatttt gcatttggag tcacctgaat ctggtaacca cagtacaagt     1140
gtgcagagct gggccttcat tccacaggac ataatgcatg gcaatataa tgttctacag     1200 aaagatcatg ccaagaccag tgatccagga agatcatgga aaataatgca catcagtgaa     1260
caagaggaac ccatagagct taaatgtgtg tctgtgacag gattcactgc actgtttact     1320
tgggaagtgg aaaggatggg ctataccatt accctctggg atttggagac ccagggcatg     1380
cagtgttttt cccttggcac aaagtgtatt cctgtagaca gtagtggaga ccagcagctg     1440
tgctttgttt tgacagagaa tggactctct ctgattttgt ttggtttgac tcaagaagag     1500
tttttaaaca gactcatgat ccatggaagt gccagcactg tggacactct tgtcatctc      1560 aatggctggg gaaggtgctc aattcccata catgcactag aggccgggat agaaaatcgt     1620
cagctggaca cagtaaattt cttttttgaag agcaaggaaa atcttttaa tccatcctca     1680 aaatcttctg tatctgatca gtttgatcac ttgtcatccc atttatattt aagaaatgtg     1740
gaagagctga taccagcatt ggatttactt tgctcggcaa ttagagaaag ttattctgaa     1800
ccccaaagca aacactttc agaacaattg cttaatctta cactgtcttt ccttaacaac     1860
caaataaagg agcttttcat tcacactgaa gaactagatg aacatctgca aaaaggagtg     1920
aacattttga ctagctacat taatgaactt cgaaccttca tgataaagtt tccttggaag     1980
ctaacagatg ctatagatga atatgatgta catgaaaatg tccccaaagt aaaggagagc     2040
aatatatgga agaaactcag ctttgaggaa gttattgcca cgccatttt aaacaacaaa     2100 ataccagagg cacagacttt cttcaggatt gatagtcatt ctgctcaaaa acttgaggag     2160
cttattggca taggcctaaa tttggtcttt gacaattta aaaagaacaa tataaaggaa     2220
gcctctgaac ttttgaagaa tatggggttt gatgtaaaag gccaattgct caagatctgc     2280
ttctatacaa ctaataaaaa tatacgtgac tttttggttg aaattttaaa agaaaaaaat     2340 tattttctg aaaaagagaa aagaactata gacttcgtgc atcaagttga gaagctttat     2400
ttgggacatt tccaagaaaa tatgcaaatc cagtcatttc ccaggtactg gataaaggaa     2460
caagattttt tcaagcacaa gtctgttttg gactcattcc tgaaatatga ttgtaaagat     2520
gaatttaaca aacaggacca tagaattgtg ttaaattggg ctctgtggtg ggatcaacta     2580
```

```
acacaagaat ccatccttct ccccaggata agtccagaag aatacaaatc atattcccct    2640
gaagccctct ggagatacct cacagctcgc catgattggt taaacattat cttatggatt    2700
ggagaatttc aaacccagca tagttatgct tcacttcagc agaacaaatg gcccttctg     2760 actgttgatg ttattaacca gaatacttcc tgtaacaact acatgaggaa tgaaattta     2820 gataagctgg ccaggaatgg ggttttttg gcatctgaac tggaagactt tgaatgcttc     2880
ctcctaagac tgagccgtat tggaggtgta atacaggata ccctccctgt tcaaaactac    2940
aagaccaaag aaggttggga tttccattct caattcattc tctattgttt ggagcacagt    3000
ctgcagcatc ttctttatgt ctaccttgac tgttacaaac ttagtcctga aaattgtccc    3060
tttttggaaa aaaagagtt acatgaagca caccccttggt ttgaattttt agttcagtgt    3120
cgacaagttg ccagtaactt aacagatccc aaactgatct tccaggctag ccttgcaaat    3180
gctcagattt tgattcccac caatcaggcc agtgtaagca gtatgctatt ggaaggacat    3240
accctcctgg cccttgctac tacaatgtat tctcctgggg gtgtcagtca ggttgttcag    3300
aatgaagaaa atgaaaactg tttgaagaaa gtggatcccc agctattgaa gatggcatta    3360
actccttacc ccaagctaaa aactgctctc ttcccacagt gcactcctcc tagtgtcctg    3420
ccatctgata ttacaatcta ccaccttatt cagtcattat cacccttgga tcctagcaga    3480
ttgtttggct ggcagtctgc taacacacta gctataggag atgcatggag tcatctccca    3540
catttctcta gccctgacct ggttaataaa tatgctatag tggaacgtct gaattttgct    3600
tattatttac ataatgggcg ccatcattt gcatttggta cttttctggt ccaggaatta    3660
atcaagagca agactcccaa gcagctgatc cagcaagtag gcaatgaagc ctatgttata    3720
gggctctcct ccttccacat accttcaata ggagctgcat gtgtttgttt cttagaattg    3780
cttggccttg acagcctcaa gctcagagtt gatatgaaag tggccaatat aattttgagc    3840
tacaagtgca gaaatgaaga tgctcagtac agctttatca gagagtctgt agccgaaaaa    3900
ctatctaaac tagctgatgg tgaaaagaca accacagaag aattgcttgt tctcttagaa    3960
gaaggtacat ggaacagcat tcagcaacag gaaataaaga ggttatccag tgaatctagc    4020
agccaatggg cattagtggt gcagttctgc aggctacaca atatgaaact aagcatatct    4080
taccttagag aatgtgccaa agcaaatgat tggctgcagt tcattattca cagccaactc    4140
cacaactacc acccagcaga ggtgaaatcc cttatccagt acttcagccc agtcattcaa    4200
gaccacttaa ggctggcttt tgagaacttg ccctcagtgc ccacctccaa aatggacagc    4260
gatcaagtct gcaataagtg cccccaggaa cttcaaggaa gcaaacaaga gatgaccgat    4320
ttatttgaaa ttctgctcca atgctcagag gagccagact cctggcactg gcttctggtt    4380
gaagcagtga acaacaggc cctatcctc agtgttctgg cctcatgtct ccagggtgcc      4440
agtgccattt cttgtctctg tgtttggatc atcacttctg tggaggacaa tgttgcaact    4500
gaagcaatgg gacacattca ggactcaaca gaggaccata cctggaaacct tgaggatctt    4560 tcagtcatct ggagaacatt attaacaaga caaaagagca aaactctcat cagaggtttc    4620 cagctttttct ttaaggattc cccgttacta ctggtgatgg agatgtatga actgtgtatg    4680
ttcttcagga attataaaga agctgaagct aaacttctgg agtttcagaa gagccttgaa    4740
acgcttaaca cagcagccac aaaggtccac cctgtcatcc ctgccatgtg gctggaggat    4800
caggtgtgtt tccttttgaa gcttatgcta cagcagtgta agaccccagta tgagctgggg    4860 aagcttttac agctctttgt tgaaagagag catctcttct ctgatggtcc agatgtgaaa    4920
aagctttgca tccttttgcca gattttgaag gatacatcca tagccattaa tcatacaatt    4980
```

```
attaccagct acagcattga gaatcttcag catgaatgta gatctatttt ggaaagactg    5040
cagacagatg gacaattcgc tttggccagg agggtagcag aattagctga gttacctgtg    5100
gacaacttgg ttattaaaga gataacacag gaaatgcaga ccctaaaaca cattgaacag    5160
tggtcactaa aacaagcaag aattgacttc tggaaaaaat gccatgagaa ttttaagaaa    5220
aattcaattt caagcaaagc agcttcttcc ttttttctcaa cccaggccca tgtggcatgt    5280
gagcacccaa ctggatggag cagcatggag gagcgccatc tgctgctcac cttggcaggg    5340
cactggcttg cccaggagga cgtggtgccc ttggataagc tggaggagct ggagaagcag    5400
atctggctgt gccgcatcac ccagcacact cttggaagaa atcaggagga aacagagccc    5460 agatttctc gacagatctc aactagtggt gaactttcct ttgatagttt agccagtgag    5520
ttttccttct ccaagttggc tgctctgaac acatcaaaat acttagaact taacagcctt    5580
ccatccaaag agacatgcga gaatagattg gattggaaag agcaggagtc actaaacttt    5640
ttgattgggc gcctactgga tgatggctgt gtgcatgaag caagtagagt atgccggtat    5700
tttcattttt ataatccaga tgtcgccttg gtattgcact gcagagcact ggcctcaggg    5760
gaagctagta tggaggatct gcacccagag atccatgctc tcctacaaag tgctgagctg    5820
cttgaggaag aagcacccga cattcccta aggagagtcc acagcacttc aagtctggat    5880
agtcagaagt ttgtgacagt gccctccagt aatgaagtgg taactaacct ggaagtgctg    5940
acaagcaaat gcctccatgg gaagaactac tgtcgacagg tcctctgtct gtatgatctt    6000
gccaaggagt tgggctgttc ctacacagat gttgctgctc aggatggtga agccatgctc    6060
cggaaaatct tggcctctca gcagcctgac cgatgcaaac gagcccaggc cttcatcagc    6120
acacagggcc ttaagccaga tactgtggct gaactcgtgg cagaagagg gacacgggag    6180 ctgcttactt catcacaggg aacaggacat aagcagatgt tcaacccaac agaggaaagc    6240
cagacatttc ttcagctgac cactctgtgt caagaccgca cattggtagg catgaagttg    6300
ttggataaga tttcctccgt tccccatggg gaactgtctt gcaccacaga gctcctgatc    6360
ctggcccatc attgcttcac cctgacgtgc cacatggagg gcatcatccg agtcctacag    6420
gccgcccaca tgctcacaga taaccacctg gcccccagtg aggagtatgg gctggtggta    6480
cggctcctca ctggcattgg aaggtacaac gagatgacat acatatttga tttgctgcat    6540
aaaaagcact actttgaagt gctaatgagg aagaagttgg atccgagtgg taccctgaaa    6600
acagccctgc tggactacat caaacgctgc cgtcctggag acagtgaaaa gcacaatatg    6660
attgccctgt gcttcagcat gtgccgggag attggcgaga accacgaggc agctgcccgc    6720
atccaactga aattgattga gtctcagccc tgggaggaca gcctcaagga tgggcaccag    6780
ctgaaacaac tgctgctgaa ggccctgact ctgatgttgg atgcagcaga gagttatgcc    6840
aaggactcct gtgtgcgaca ggcccagcac tgtcagcggc tcaccaagtt gataactctg    6900
cagattcact ttctgaacac tggccagaac acaatgctca tcaacttggg ccgccacaag    6960
ctgatggact gtattctggc cctacctcgg ttctaccagg cttctattgt ggctgaggcc    7020
tacgattttg ttccagattg ggctgaaatt ttataccagc aagtgattct taaaggagac    7080
tttaattact tggaagaatt taagcagcaa aggttattaa agtccagtat atttgaagag    7140
atttccaaaa aatataaaca acatcagcct actgacatgg tcatggaaaa cctgaagaaa    7200
ttactcacat attgtgaaga tgtttacctg tattacaagt tggcatacga acacaagttt    7260
tatgaaattg taaatgtgct tctgaaggac cctcagacag gttgctgtct aaaggacatg    7320
```

```
ctagcaggtt agatgatttc ataggtgtct gttttcttgt actgttagca gattctgaca    7380
gatgtgatga gaagaagaat gcattggaga tctttgctaa agttgaacaa tcccggtact    7440
gtaccatatc agtcctttgt gggtagtagg tagcaagtaa gaaacttttc aggaggaaat    7500
tcctatttaa aatagattga ttttagatga ttgttcatcc acaccatttt atatagatac    7560
tagtattaag atcaaaagct tcctcttcct caggacagct tctactttag atgatccaat    7620
aatgattaaa gaatacctgt acctgcagat tccagtttca agaaattta attattattt    7680 acacagttaa ggaacaggtg atacatttc atttgttaga aactgatctt tctgtaataa    7740
aatagatttt c                                                         7751
```

<210> SEQ ID NO 2
<211> LENGTH: 2443
<212> TYPE: PRT
<213> ORGANISM: homo sapiens

<400> SEQUENCE: 2

```
Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
```

-continued

```
            290                 295                 300
Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Phe Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720
```

-continued

```
Leu Ile Gly Ile Gly Leu Asn Leu Val Phe Asp Asn Leu Lys Lys Asn
            725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                    805                 810                 815

Trp Ile Lys Glu Gln Asp Phe Phe Lys His Lys Ser Val Leu Asp Ser
                    820                 825                 830

Phe Leu Lys Tyr Asp Cys Lys Asp Glu Phe Asn Lys Gln Asp His Arg
                    835                 840                 845

Ile Val Leu Asn Trp Ala Leu Trp Trp Asp Gln Leu Thr Gln Glu Ser
                    850                 855                 860

Ile Leu Leu Pro Arg Ile Ser Pro Glu Tyr Lys Ser Tyr Ser Pro
865                 870                 875                 880

Glu Ala Leu Trp Arg Tyr Leu Thr Ala Arg His Asp Trp Leu Asn Ile
                    885                 890                 895

Ile Leu Trp Ile Gly Glu Phe Gln Thr Gln His Ser Tyr Ala Ser Leu
                    900                 905                 910

Gln Gln Asn Lys Trp Pro Leu Thr Val Asp Val Ile Asn Gln Asn
                    915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                    965                 970                 975

Val Gln Asn Tyr Lys Thr Lys Gly Gly Trp Phe His Ser Gln Phe
                    980                 985                 990

Ile Leu Tyr Cys Leu Glu His Ser  Leu Gln His Leu Leu  Tyr Val Tyr
            995                 1000                1005

Leu Asp  Cys Tyr Lys Leu Ser  Pro Glu Asn Cys Pro  Phe Leu Glu
   1010                1015                1020

Lys Lys  Glu Leu His Glu Ala  His Pro Trp Phe Glu  Phe Leu Val
   1025                1030                1035

Gln Cys  Arg Gln Val Ala Ser  Asn Leu Thr Asp Pro  Lys Leu Ile
   1040                1045                1050

Phe Gln  Ala Ser Leu Ala Asn  Ala Gln Ile Leu Ile  Pro Thr Asn
   1055                1060                1065

Gln Ala  Ser Val Ser Ser Met  Leu Leu Glu Gly His  Thr Leu Leu
   1070                1075                1080

Ala Leu  Ala Thr Thr Met Tyr  Ser Pro Gly Gly Val  Ser Gln Val
   1085                1090                1095

Val Gln  Asn Glu Glu Asn Glu  Asn Cys Leu Lys Lys  Val Asp Pro
   1100                1105                1110

Gln Leu  Leu Lys Met Ala Leu  Thr Pro Tyr Pro Lys  Leu Lys Thr
   1115                1120                1125
```

```
Ala Leu Phe Pro Gln Cys Thr Pro Pro Ser Val Leu Pro Ser Asp
1130                1135                1140

Ile Thr Ile Tyr His Leu Ile Gln Ser Leu Ser Pro Phe Asp Pro
1145                1150                1155

Ser Arg Leu Phe Gly Trp Gln Ser Ala Asn Thr Leu Ala Ile Gly
1160                1165                1170

Asp Ala Trp Ser His Leu Pro His Phe Ser Ser Pro Asp Leu Val
1175                1180                1185

Asn Lys Tyr Ala Ile Val Glu Arg Leu Asn Phe Ala Tyr Tyr Leu
1190                1195                1200

His Asn Gly Arg Pro Ser Phe Ala Phe Gly Thr Phe Leu Val Gln
1205                1210                1215

Glu Leu Ile Lys Ser Lys Thr Pro Lys Gln Leu Ile Gln Gln Val
1220                1225                1230

Gly Asn Glu Ala Tyr Val Ile Gly Leu Ser Ser Phe His Ile Pro
1235                1240                1245

Ser Ile Gly Ala Ala Cys Val Cys Phe Leu Glu Leu Leu Gly Leu
1250                1255                1260

Asp Ser Leu Lys Leu Arg Val Asp Met Lys Val Ala Asn Ile Ile
1265                1270                1275

Leu Ser Tyr Lys Cys Arg Asn Glu Asp Ala Gln Tyr Ser Phe Ile
1280                1285                1290

Arg Glu Ser Val Ala Glu Lys Leu Ser Lys Leu Ala Asp Gly Glu
1295                1300                1305

Lys Thr Thr Thr Glu Glu Leu Leu Val Leu Leu Glu Glu Gly Thr
1310                1315                1320

Trp Asn Ser Ile Gln Gln Gln Glu Ile Lys Arg Leu Ser Ser Glu
1325                1330                1335

Ser Ser Ser Gln Trp Ala Leu Val Val Gln Phe Cys Arg Leu His
1340                1345                1350

Asn Met Lys Leu Ser Ile Ser Tyr Leu Arg Glu Cys Ala Lys Ala
1355                1360                1365

Asn Asp Trp Leu Gln Phe Ile Ile His Ser Gln Leu His Asn Tyr
1370                1375                1380

His Pro Ala Glu Val Lys Ser Leu Ile Gln Tyr Phe Ser Pro Val
1385                1390                1395

Ile Gln Asp His Leu Arg Leu Ala Phe Glu Asn Leu Pro Ser Val
1400                1405                1410

Pro Thr Ser Lys Met Asp Ser Asp Gln Val Cys Asn Lys Cys Pro
1415                1420                1425

Gln Glu Leu Gln Gly Ser Lys Gln Glu Met Thr Asp Leu Phe Glu
1430                1435                1440

Ile Leu Leu Gln Cys Ser Glu Glu Pro Asp Ser Trp His Trp Leu
1445                1450                1455

Leu Val Glu Ala Val Lys Gln Gln Ala Pro Ile Leu Ser Val Leu
1460                1465                1470

Ala Ser Cys Leu Gln Gly Ala Ser Ala Ile Ser Cys Leu Cys Val
1475                1480                1485

Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515

Asp Leu Ser Val Ile Trp Arg Thr Leu Leu Thr Arg Gln Lys Ser
```

```
            1520                1525                1530

Lys Thr Leu Ile Arg Gly Phe Gln Leu Phe Phe Lys Asp Ser Pro
        1535                1540                1545

Leu Leu Leu Val Met Glu Met Tyr Glu Leu Cys Met Phe Phe Arg
        1550                1555                1560

Asn Tyr Lys Glu Ala Glu Ala Lys Leu Leu Glu Phe Gln Lys Ser
        1565                1570                1575

Leu Glu Thr Leu Asn Thr Ala Ala Thr Lys Val His Pro Val Ile
        1580                1585                1590

Pro Ala Met Trp Leu Glu Asp Gln Val Cys Phe Leu Leu Lys Leu
        1595                1600                1605

Met Leu Gln Gln Cys Lys Thr Gln Tyr Glu Leu Gly Lys Leu Leu
        1610                1615                1620

Gln Leu Phe Val Glu Arg Glu His Leu Phe Ser Asp Gly Pro Asp
        1625                1630                1635

Val Lys Lys Leu Cys Ile Leu Cys Gln Ile Leu Lys Asp Thr Ser
        1640                1645                1650

Ile Ala Ile Asn His Thr Ile Ile Thr Ser Tyr Ser Ile Glu Asn
        1655                1660                1665

Leu Gln His Glu Cys Arg Ser Ile Leu Glu Arg Leu Gln Thr Asp
        1670                1675                1680

Gly Gln Phe Ala Leu Ala Arg Arg Val Ala Glu Leu Ala Glu Leu
        1685                1690                1695

Pro Val Asp Asn Leu Val Ile Lys Glu Ile Thr Gln Glu Met Gln
        1700                1705                1710

Thr Leu Lys His Ile Glu Gln Trp Ser Leu Lys Gln Ala Arg Ile
        1715                1720                1725

Asp Phe Trp Lys Lys Cys His Glu Asn Phe Lys Lys Asn Ser Ile
        1730                1735                1740

Ser Ser Lys Ala Ala Ser Ser Phe Phe Ser Thr Gln Ala His Val
        1745                1750                1755

Ala Cys Glu His Pro Thr Gly Trp Ser Ser Met Glu Glu Arg His
        1760                1765                1770

Leu Leu Leu Thr Leu Ala Gly His Trp Leu Ala Gln Glu Asp Val
        1775                1780                1785

Val Pro Leu Asp Lys Leu Glu Glu Leu Glu Lys Gln Ile Trp Leu
        1790                1795                1800

Cys Arg Ile Thr Gln His Thr Leu Gly Arg Asn Gln Glu Glu Thr
        1805                1810                1815

Glu Pro Arg Phe Ser Arg Gln Ile Ser Thr Ser Gly Glu Leu Ser
        1820                1825                1830

Phe Asp Ser Leu Ala Ser Glu Phe Ser Phe Ser Lys Leu Ala Ala
        1835                1840                1845

Leu Asn Thr Ser Lys Tyr Leu Glu Leu Asn Ser Leu Pro Ser Lys
        1850                1855                1860

Glu Thr Cys Glu Asn Arg Leu Asp Trp Lys Glu Gln Glu Ser Leu
        1865                1870                1875

Asn Phe Leu Ile Gly Arg Leu Leu Asp Asp Gly Cys Val His Glu
        1880                1885                1890

Ala Ser Arg Val Cys Arg Tyr Phe His Phe Tyr Asn Pro Asp Val
        1895                1900                1905

Ala Leu Val Leu His Cys Arg Ala Leu Ala Ser Gly Glu Ala Ser
        1910                1915                1920
```

```
Met Glu Asp Leu His Pro Glu Ile His Ala Leu Leu Gln Ser Ala
    1925            1930            1935

Glu Leu Leu Glu Glu Glu Ala Pro Asp Ile Pro Leu Arg Arg Val
    1940            1945            1950

His Ser Thr Ser Ser Leu Asp Ser Gln Lys Phe Val Thr Val Pro
    1955            1960            1965

Ser Ser Asn Glu Val Val Thr Asn Leu Glu Val Leu Thr Ser Lys
    1970            1975            1980

Cys Leu His Gly Lys Asn Tyr Cys Arg Gln Val Leu Cys Leu Tyr
    1985            1990            1995

Asp Leu Ala Lys Glu Leu Gly Cys Ser Tyr Thr Asp Val Ala Ala
    2000            2005            2010

Gln Asp Gly Glu Ala Met Leu Arg Lys Ile Leu Ala Ser Gln Gln
    2015            2020            2025

Pro Asp Arg Cys Lys Arg Ala Gln Ala Phe Ile Ser Thr Gln Gly
    2030            2035            2040

Leu Lys Pro Asp Thr Val Ala Glu Leu Val Ala Glu Glu Val Thr
    2045            2050            2055

Arg Glu Leu Leu Thr Ser Ser Gln Gly Thr Gly His Lys Gln Met
    2060            2065            2070

Phe Asn Pro Thr Glu Glu Ser Gln Thr Phe Leu Gln Leu Thr Thr
    2075            2080            2085

Leu Cys Gln Asp Arg Thr Leu Val Gly Met Lys Leu Leu Asp Lys
    2090            2095            2100

Ile Ser Ser Val Pro His Gly Glu Leu Ser Cys Thr Thr Glu Leu
    2105            2110            2115

Leu Ile Leu Ala His His Cys Phe Thr Leu Thr Cys His Met Glu
    2120            2125            2130

Gly Ile Ile Arg Val Leu Gln Ala Ala His Met Leu Thr Asp Asn
    2135            2140            2145

His Leu Ala Pro Ser Glu Glu Tyr Gly Leu Val Val Arg Leu Leu
    2150            2155            2160

Thr Gly Ile Gly Arg Tyr Asn Glu Met Thr Tyr Ile Phe Asp Leu
    2165            2170            2175

Leu His Lys Lys His Tyr Phe Glu Val Leu Met Arg Lys Lys Leu
    2180            2185            2190

Asp Pro Ser Gly Thr Leu Lys Thr Ala Leu Leu Asp Tyr Ile Lys
    2195            2200            2205

Arg Cys Arg Pro Gly Asp Ser Glu Lys His Asn Met Ile Ala Leu
    2210            2215            2220

Cys Phe Ser Met Cys Arg Glu Ile Gly Glu Asn His Glu Ala Ala
    2225            2230            2235

Ala Arg Ile Gln Leu Lys Leu Ile Glu Ser Gln Pro Trp Glu Asp
    2240            2245            2250

Ser Leu Lys Asp Gly His Gln Leu Lys Gln Leu Leu Lys Ala
    2255            2260            2265

Leu Thr Leu Met Leu Asp Ala Ala Glu Ser Tyr Ala Lys Asp Ser
    2270            2275            2280

Cys Val Arg Gln Ala Gln His Cys Gln Arg Leu Thr Lys Leu Ile
    2285            2290            2295

Thr Leu Gln Ile His Phe Leu Asn Thr Gly Gln Asn Thr Met Leu
    2300            2305            2310
```

```
Ile Asn Leu Gly Arg His Lys Leu Met Asp Cys Ile Leu Ala Leu
2315                2320                2325

Pro Arg Phe Tyr Gln Ala Ser Ile Val Ala Glu Ala Tyr Asp Phe
    2330                2335                2340

Val Pro Asp Trp Ala Glu Ile Leu Tyr Gln Gln Val Ile Leu Lys
2345                2350                2355

Gly Asp Phe Asn Tyr Leu Glu Glu Phe Lys Gln Gln Arg Leu Leu
    2360                2365                2370

Lys Ser Ser Ile Phe Glu Glu Ile Ser Lys Lys Tyr Lys Gln His
2375                2380                2385

Gln Pro Thr Asp Met Val Met Glu Asn Leu Lys Lys Leu Leu Thr
    2390                2395                2400

Tyr Cys Glu Asp Val Tyr Leu Tyr Tyr Lys Leu Ala Tyr Glu His
2405                2410                2415

Lys Phe Tyr Glu Ile Val Asn Val Leu Leu Lys Asp Pro Gln Thr
    2420                2425                2430

Gly Cys Cys Leu Lys Asp Met Leu Ala Gly
2435                2440

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
ccacaggaaa cgaatggaat                                               20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
ggttctgtga ggaaaccacg                                               20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
cagggacatt gtaggccatc                                               20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ccagttgtaa aattgtgacc                                               20

<210> SEQ ID NO 7
<211> LENGTH: 20
<212> TYPE: DNA
```

```
<213> ORGANISM: Artificial
<220> FEATURE:
<223> OTHER INFORMATION: primer

<400> SEQUENCE: 7
tcccagctcc caaaactaaa                                              20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
tcaatcaaca cttctaccac                                              20

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
caggttcttt cttgtggcat ca                                           22

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
cgaggatatt tttaacctct tatca                                        25

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
gttaggcata cttacaaaac tggc                                         24

<210> SEQ ID NO 12
<211> LENGTH: 25
<212> TYPE: DNA
<213> ORGANISM: Artificial
<220> FEATURE:
<223> OTHER INFORMATION: primer

<400> SEQUENCE: 12
cgaggatatt tttaacctct tatca                                        25

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
gaacatcttt gccctggttt                                              20
```

```
<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
ctgtgacagg tgttaagtta                                              20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
caggcactga ggcagaagta                                              20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
atctaataca agacagtctc                                              20

<210> SEQ ID NO 17
<211> LENGTH: 26
<212> TYPE: DNA
<213> ORGANISM: Artificial
<220> FEATURE:
<223> OTHER INFORMATION: primer

<400> SEQUENCE: 17
aaaaatcaat tcctaaatca taatcc                                       26

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
tagtactgaa gtattgagta                                              20

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
tcttttaaag ccaaaaggg taaa                                          24

<210> SEQ ID NO 20
<211> LENGTH: 20
<212> TYPE: DNA
<213> ORGANISM: Artificial
<220> FEATURE:
```

<223> OTHER INFORMATION: primer

<400> SEQUENCE: 20
ttaagtaatg ttcttgggca                                          20

<210> SEQ ID NO 21
<211> LENGTH: 21
<212> TYPE: DNA
<213> ORGANISM: Artificial
<220> FEATURE:
<223> OTHER INFORMATION: primer

<400> SEQUENCE: 21
cccaggacta atcatgaagg a                                        21

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
atccccaaac cgataaaacc                                          20

<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
cggtgtgtct tccactagct c                                        21

<210> SEQ ID NO 24
<211> LENGTH: 23
<212> TYPE: DNA
<213> ORGANISM: Artificial
<220> FEATURE:
<223> OTHER INFORMATION: primer

<400> SEQUENCE: 24
gttacataaa tgtataatcc ctg                                      23

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
acccagccat tctcagtgtt                                          20

<210> SEQ ID NO 26
<211> LENGTH: 23
<212> TYPE: DNA
<213> ORGANISM: Artificial
<220> FEATURE:
<223> OTHER INFORMATION: primer

<400> SEQUENCE: 26
cattttaaga ctttatggat tac                                      23

```
<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
cacagcgaga tcctgtctca                                              20

<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
cctcactgta agatgatgcc c                                            21

<210> SEQ ID NO 29
<211> LENGTH: 25
<212> TYPE: DNA
<213> ORGANISM: Artificial
<220> FEATURE:
<223> OTHER INFORMATION: primer

<400> SEQUENCE: 29
cctttaaata ctacagtggt gcaga                                        25

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
tgtgggcatg atttggtcta                                              20

<210> SEQ ID NO 31
<211> LENGTH: 22
<212> TYPE: DNA
<213> ORGANISM: Artificial
<220> FEATURE:
<223> OTHER INFORMATION: primer

<400> SEQUENCE: 31
ccaactgttg agatggagaa aa                                           22

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
acctgctcaa ggacaaatgc                                              20

<210> SEQ ID NO 33
<211> LENGTH: 20
<212> TYPE: DNA
<213> ORGANISM: Artificial
<220> FEATURE:
<223> OTHER INFORMATION: primer
```

```
<400> SEQUENCE: 33
tttgaagtat cccagggtgg                                                   20

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
ccaccattcc ccaaagataa                                                   20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
ttacctggat ttggctttgg                                                   20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
cctggcttct aaaagtggcc                                                   20

<210> SEQ ID NO 37
<211> LENGTH: 22
<212> TYPE: DNA
<213> ORGANISM: Artificial
<220> FEATURE:
<223> OTHER INFORMATION: primer

<400> SEQUENCE: 37
tgcaatccag aaacttgaga ga                                                22

<210> SEQ ID NO 38
<211> LENGTH: 21
<212> TYPE: DNA
<213> ORGANISM: Artificial
<220> FEATURE:
<223> OTHER INFORMATION: primer

<400> SEQUENCE: 38
aagcacaaca tccaaatcct t                                                 21

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
atgttggcag gaactccatc                                                   20

<210> SEQ ID NO 40
<211> LENGTH: 20
```

```
<212> TYPE: DNA
<213> ORGANISM: Artificial
<220> FEATURE:
<223> OTHER INFORMATION: primer

<400> SEQUENCE: 40
ctcctttgga gcaacctctg                                               20

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
ttccaacagg aaagcacaca                                               20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
caacaggaaa gcacacatgc                                               20

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
cagctacttg ggaggctgag                                               20

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
gtgtggctgt gacctcactc                                               20

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
gcattagaag gggcactgaa                                               20

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
```
aacatggctg ggatgtttct                                          20

<210> SEQ ID NO 47
<211> LENGTH: 20
<212> TYPE: DNA
<213> ORGANISM: Artificial
<220> FEATURE:
<223> OTHER INFORMATION: primer

<400> SEQUENCE: 47
ctcacaacgg tattcacccc                                          20

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
ttcctggttg gcctatgatg                                          20

<210> SEQ ID NO 49
<211> LENGTH: 23
<212> TYPE: DNA
<213> ORGANISM: Artificial
<220> FEATURE:
<223> OTHER INFORMATION: primer

<400> SEQUENCE: 49
aagggtttaa gataatttgg gga                                      23

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
aatgccaaac acacacctga                                          20

<210> SEQ ID NO 51
<211> LENGTH: 22
<212> TYPE: DNA
<213> ORGANISM: Artificial
<220> FEATURE:
<223> OTHER INFORMATION: primer

<400> SEQUENCE: 51
ggattcttga tactgctttg cc                                       22

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
ctcaaagcag aggcaaggag                                          20

<210> SEQ ID NO 53
<211> LENGTH: 20
<212> TYPE: DNA
<213> ORGANISM: Artificial

```
<220> FEATURE:
<223> OTHER INFORMATION: primer

<400> SEQUENCE: 53
ctgagcccca cattttgtt                                          20

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
caagtgctca atagccccat                                         20

<210> SEQ ID NO 55
<211> LENGTH: 25
<212> TYPE: DNA
<213> ORGANISM: Artificial
<220> FEATURE:
<223> OTHER INFORMATION: primer

<400> SEQUENCE: 55
gctaactgcc cttaatagag taaaa                                   25

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
aaagggtaca gcgtcagcat                                         20

<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
cttgccccag attgcataat                                         20

<210> SEQ ID NO 58
<211> LENGTH: 23
<212> TYPE: DNA
<213> ORGANISM: Artificial
<220> FEATURE:
<223> OTHER INFORMATION: primer

<400> SEQUENCE: 58
tccaaaaagt acgtaaaatc cca                                     23

<210> SEQ ID NO 59
<211> LENGTH: 22
<212> TYPE: DNA
<213> ORGANISM: Artificial
<220> FEATURE:
<223> OTHER INFORMATION: primer

<400> SEQUENCE: 59
cagcaaaagg gtaatagcag tg                                      22
```

```
<210> SEQ ID NO 60
<211> LENGTH: 20
<212> TYPE: DNA
<213> ORGANISM: Artificial
<220> FEATURE:
<223> OTHER INFORMATION: primer

<400> SEQUENCE: 60
cccaaatgta gtaaatggcg                                              20

<210> SEQ ID NO 61
<211> LENGTH: 23
<212> TYPE: DNA
<213> ORGANISM: Artificial
<220> FEATURE:
<223> OTHER INFORMATION: primer

<400> SEQUENCE: 61
tttgaaagag cagaaagcta tgg                                          23

<210> SEQ ID NO 62
<211> LENGTH: 21
<212> TYPE: DNA
<213> ORGANISM: Artificial
<220> FEATURE:
<223> OTHER INFORMATION: primer

<400> SEQUENCE: 62
tgaaggggtt gtcacacttt t                                            21

<210> SEQ ID NO 63
<211> LENGTH: 22
<212> TYPE: DNA
<213> ORGANISM: Artificial
<220> FEATURE:
<223> OTHER INFORMATION: primer

<400> SEQUENCE: 63
ttgtggcaaa agaaaatttg tg                                           22

<210> SEQ ID NO 64
<211> LENGTH: 20
<212> TYPE: DNA
<213> ORGANISM: Artificial
<220> FEATURE:
<223> OTHER INFORMATION: primer

<400> SEQUENCE: 64
gagaatgcag gctcagttcc                                              20

<210> SEQ ID NO 65
<211> LENGTH: 20
<212> TYPE: DNA
<213> ORGANISM: Artificial
<220> FEATURE:
<223> OTHER INFORMATION: primer

<400> SEQUENCE: 65
atgtggaact gagcctgcat                                              20

<210> SEQ ID NO 66
<211> LENGTH: 23
<212> TYPE: DNA
<213> ORGANISM: Artificial
<220> FEATURE:
<223> OTHER INFORMATION: primer
```

```
<400> SEQUENCE: 66
cgacttgcat tttaaagaac ctg                                          23

<210> SEQ ID NO 67
<211> LENGTH: 25
<212> TYPE: DNA
<213> ORGANISM: Artificial
<220> FEATURE:
<223> OTHER INFORMATION: primer

<400> SEQUENCE: 67
ttgtttccag atcatgaaga atatg                                        25

<210> SEQ ID NO 68
<211> LENGTH: 20
<212> TYPE: DNA
<213> ORGANISM: Artificial
<220> FEATURE:
<223> OTHER INFORMATION: primer

<400> SEQUENCE: 68
tcagatagct gaccacagcc                                              20

<210> SEQ ID NO 69
<211> LENGTH: 24
<212> TYPE: DNA
<213> ORGANISM: Artificial
<220> FEATURE:
<223> OTHER INFORMATION: primer

<400> SEQUENCE: 69
tccctcttaa ggagaaaaac actg                                         24

<210> SEQ ID NO 70
<211> LENGTH: 20
<212> TYPE: DNA
<213> ORGANISM: Artificial
<220> FEATURE:
<223> OTHER INFORMATION: primer

<400> SEQUENCE: 70
accgggccga gatataaaat                                              20

<210> SEQ ID NO 71
<211> LENGTH: 25
<212> TYPE: DNA
<213> ORGANISM: Artificial
<220> FEATURE:
<223> OTHER INFORMATION: primer

<400> SEQUENCE: 71
gctagtttgt cttagaacca gaaca                                        25

<210> SEQ ID NO 72
<211> LENGTH: 23
<212> TYPE: DNA
<213> ORGANISM: Artificial
<220> FEATURE:
<223> OTHER INFORMATION: primer

<400> SEQUENCE: 72
ttttgggttg tctcactatc aca                                          23

<210> SEQ ID NO 73
```

```
<211> LENGTH: 24
<212> TYPE: DNA
<213> ORGANISM: Artificial
<220> FEATURE:
<223> OTHER INFORMATION: primer

<400> SEQUENCE: 73
aaggaacata gccagttctg tttt                                          24

<210> SEQ ID NO 74
<211> LENGTH: 21
<212> TYPE: DNA
<213> ORGANISM: Artificial
<220> FEATURE:
<223> OTHER INFORMATION: primer

<400> SEQUENCE: 74
tgcgaactat ttttcctttg g                                             21

<210> SEQ ID NO 75
<211> LENGTH: 23
<212> TYPE: DNA
<213> ORGANISM: Artificial
<220> FEATURE:
<223> OTHER INFORMATION: primer

<400> SEQUENCE: 75
tgcaacttct caggtacaca tct                                           23

<210> SEQ ID NO 76
<211> LENGTH: 20
<212> TYPE: DNA
<213> ORGANISM: Artificial
<220> FEATURE:
<223> OTHER INFORMATION: primer

<400> SEQUENCE: 76
aggctagagt gcagtggcat                                               20

<210> SEQ ID NO 77
<211> LENGTH: 20
<212> TYPE: DNA
<213> ORGANISM: Artificial
<220> FEATURE:
<223> OTHER INFORMATION: primer

<400> SEQUENCE: 77
agtcagctta agggaagcgg                                               20

<210> SEQ ID NO 78
<211> LENGTH: 22
<212> TYPE: DNA
<213> ORGANISM: Artificial
<220> FEATURE:
<223> OTHER INFORMATION: primer

<400> SEQUENCE: 78
gaagataacc attttctccc ca                                            22

<210> SEQ ID NO 79
<211> LENGTH: 20
<212> TYPE: DNA
<213> ORGANISM: Artificial
<220> FEATURE:
<223> OTHER INFORMATION: primer

<400> SEQUENCE: 79
```
ttgtgagtgt ttggggagaa                                              20

<210> SEQ ID NO 80
<211> LENGTH: 21
<212> TYPE: DNA
<213> ORGANISM: Artificial
<220> FEATURE:
<223> OTHER INFORMATION: primer

<400> SEQUENCE: 80
ggggatttag tgaaaacacc a                                            21

<210> SEQ ID NO 81
<211> LENGTH: 24
<212> TYPE: DNA
<213> ORGANISM: Artificial
<220> FEATURE:
<223> OTHER INFORMATION: primer

<400> SEQUENCE: 81
tttgttggag aatacactgt gctt                                         24

<210> SEQ ID NO 82
<211> LENGTH: 25
<212> TYPE: DNA
<213> ORGANISM: Artificial
<220> FEATURE:
<223> OTHER INFORMATION: primer

<400> SEQUENCE: 82
catgtctaca caacagaaag aatgc                                        25

<210> SEQ ID NO 83
<211> LENGTH: 21
<212> TYPE: DNA
<213> ORGANISM: Artificial
<220> FEATURE:
<223> OTHER INFORMATION: primer

<400> SEQUENCE: 83
aaaaggcacc atacagcttt g                                            21

<210> SEQ ID NO 84
<211> LENGTH: 20
<212> TYPE: DNA
<213> ORGANISM: Artificial
<220> FEATURE:
<223> OTHER INFORMATION: primer

<400> SEQUENCE: 84
ggaaacacat gctggaacct                                              20

<210> SEQ ID NO 85
<211> LENGTH: 22
<212> TYPE: DNA
<213> ORGANISM: Artificial
<220> FEATURE:
<223> OTHER INFORMATION: primer

<400> SEQUENCE: 85
cttctgtctg cttcttggtc tt                                           22

<210> SEQ ID NO 86
<211> LENGTH: 22
<212> TYPE: DNA

<213> ORGANISM: Artificial
<220> FEATURE:
<223> OTHER INFORMATION: primer

<400> SEQUENCE: 86
tatcatcatt atctgttgtt gg                                      22

<210> SEQ ID NO 87
<211> LENGTH: 20
<212> TYPE: DNA
<213> ORGANISM: Artificial
<220> FEATURE:
<223> OTHER INFORMATION: primer

<400> SEQUENCE: 87
ttaggtgatc ccactggctc                                         20

<210> SEQ ID NO 88
<211> LENGTH: 20
<212> TYPE: DNA
<213> ORGANISM: Artificial
<220> FEATURE:
<223> OTHER INFORMATION: primer

<400> SEQUENCE: 88
cccaggagtt caaggctgta                                         20

<210> SEQ ID NO 89
<211> LENGTH: 20
<212> TYPE: DNA
<213> ORGANISM: Artificial
<220> FEATURE:
<223> OTHER INFORMATION: primer

<400> SEQUENCE: 89
ctgaggaggg cttgttttg                                          20

<210> SEQ ID NO 90
<211> LENGTH: 25
<212> TYPE: DNA
<213> ORGANISM: Artificial
<220> FEATURE:
<223> OTHER INFORMATION: primer

<400> SEQUENCE: 90
tctgtaactt gtttactccc agttg                                   25

<210> SEQ ID NO 91
<211> LENGTH: 20
<212> TYPE: DNA
<213> ORGANISM: Artificial
<220> FEATURE:
<223> OTHER INFORMATION: primer

<400> SEQUENCE: 91
gatcacacca ctgcattcca                                         20

<210> SEQ ID NO 92
<211> LENGTH: 20
<212> TYPE: DNA
<213> ORGANISM: Artificial
<220> FEATURE:
<223> OTHER INFORMATION: primer

<400> SEQUENCE: 92
ggcacctgta gtcccagcta                                         20

<210> SEQ ID NO 93
<211> LENGTH: 20
<212> TYPE: DNA
<213> ORGANISM: Artificial
<220> FEATURE:
<223> OTHER INFORMATION: primer

<400> SEQUENCE: 93
tgaggtggga ggatctcttg					20

<210> SEQ ID NO 94
<211> LENGTH: 20
<212> TYPE: DNA
<213> ORGANISM: Artificial
<220> FEATURE:
<223> OTHER INFORMATION: primer

<400> SEQUENCE: 94
gatgtgttca gagcagccaa					20

<210> SEQ ID NO 95
<211> LENGTH: 20
<212> TYPE: DNA
<213> ORGANISM: Artificial
<220> FEATURE:
<223> OTHER INFORMATION: primer

<400> SEQUENCE: 95
taagctggag gagctggaga					20

<210> SEQ ID NO 96
<211> LENGTH: 20
<212> TYPE: DNA
<213> ORGANISM: Artificial
<220> FEATURE:
<223> OTHER INFORMATION: primer

<400> SEQUENCE: 96
ttgttgtccc cttaacttgg					20

<210> SEQ ID NO 97
<211> LENGTH: 20
<212> TYPE: DNA
<213> ORGANISM: Artificial
<220> FEATURE:
<223> OTHER INFORMATION: primer

<400> SEQUENCE: 97
caataggcca agggtttcaa					20

<210> SEQ ID NO 98
<211> LENGTH: 20
<212> TYPE: DNA
<213> ORGANISM: Artificial
<220> FEATURE:
<223> OTHER INFORMATION: primer

<400> SEQUENCE: 98
tataactcct gctggagggc					20

<210> SEQ ID NO 99
<211> LENGTH: 20
<212> TYPE: DNA
<213> ORGANISM: Artificial
<220> FEATURE:

<223> OTHER INFORMATION: primer

<400> SEQUENCE: 99
ggtagcctgg aaattagccc                                           20

<210> SEQ ID NO 100
<211> LENGTH: 20
<212> TYPE: DNA
<213> ORGANISM: Artificial
<220> FEATURE:
<223> OTHER INFORMATION: primer

<400> SEQUENCE: 100
tgaaccagaa tctgaagcca                                           20

<210> SEQ ID NO 101
<211> LENGTH: 20
<212> TYPE: DNA
<213> ORGANISM: Artificial
<220> FEATURE:
<223> OTHER INFORMATION: primer

<400> SEQUENCE: 101
ttttgtcctt gggctctttc                                           20

<210> SEQ ID NO 102
<211> LENGTH: 20
<212> TYPE: DNA
<213> ORGANISM: Artificial
<220> FEATURE:
<223> OTHER INFORMATION: primer

<400> SEQUENCE: 102
cctggttctg tcactagccc                                           20

<210> SEQ ID NO 103
<211> LENGTH: 20
<212> TYPE: DNA
<213> ORGANISM: Artificial
<220> FEATURE:
<223> OTHER INFORMATION: primer

<400> SEQUENCE: 103
aattagccag ggtggtgaca                                           20

<210> SEQ ID NO 104
<211> LENGTH: 20
<212> TYPE: DNA
<213> ORGANISM: Artificial
<220> FEATURE:
<223> OTHER INFORMATION: primer

<400> SEQUENCE: 104
cccacaaagg actgatatgg                                           20

<210> SEQ ID NO 105
<211> LENGTH: 20
<212> TYPE: DNA
<213> ORGANISM: Artificial
<220> FEATURE:
<223> OTHER INFORMATION: primer

<400> SEQUENCE: 105
aaggaccctc agacaggttg                                           20

```
<210> SEQ ID NO 106
<211> LENGTH: 20
<212> TYPE: DNA
<213> ORGANISM: Artificial
<220> FEATURE:
<223> OTHER INFORMATION: primer

<400> SEQUENCE: 106
tcctttaagg cagacaaggg                                               20

<210> SEQ ID NO 107
<211> LENGTH: 24
<212> TYPE: DNA
<213> ORGANISM: Artificial
<220> FEATURE:
<223> OTHER INFORMATION: primer

<400> SEQUENCE: 107
accaggtcaa ctaaactgtt ctct                                          24

<210> SEQ ID NO 108
<211> LENGTH: 23
<212> TYPE: DNA
<213> ORGANISM: Artificial
<220> FEATURE:
<223> OTHER INFORMATION: primer

<400> SEQUENCE: 108
tatgctgaaa gaccacctgt aga                                           23

<210> SEQ ID NO 109
<211> LENGTH: 20
<212> TYPE: DNA
<213> ORGANISM: Artificial
<220> FEATURE:
<223> OTHER INFORMATION: primer

<400> SEQUENCE: 109
caggagcagt agtaacacaa                                               20

<210> SEQ ID NO 110
<211> LENGTH: 20
<212> TYPE: DNA
<213> ORGANISM: Artificial
<220> FEATURE:
<223> OTHER INFORMATION: primer

<400> SEQUENCE: 110
aaagggtaca gcgtcagcat                                               20

<210> SEQ ID NO 111
<211> LENGTH: 21
<212> TYPE: DNA
<213> ORGANISM: Artificial
<220> FEATURE:
<223> OTHER INFORMATION: primer

<400> SEQUENCE: 111
gcaggtaata agcctgcaga a                                             21

<210> SEQ ID NO 112
<211> LENGTH: 20
<212> TYPE: DNA
<213> ORGANISM: Artificial
<220> FEATURE:
<223> OTHER INFORMATION: primer
```

```
<400> SEQUENCE: 112 ccccttcct agctgctatt                                           20

<210> SEQ ID NO 113
<211> LENGTH: 25
<212> TYPE: DNA
<213> ORGANISM: Artificial
<220> FEATURE:
<223> OTHER INFORMATION: primer

<400> SEQUENCE: 113
tgttcaaaat agttccatta caaaa                                    25

<210> SEQ ID NO 114
<211> LENGTH: 22
<212> TYPE: DNA
<213> ORGANISM: Artificial
<220> FEATURE:
<223> OTHER INFORMATION: primer

<400> SEQUENCE: 114
tttcttccaa ggttttcttc ca                                       22

<210> SEQ ID NO 115
<211> LENGTH: 21
<212> TYPE: DNA
<213> ORGANISM: Artificial
<220> FEATURE:
<223> OTHER INFORMATION: primer

<400> SEQUENCE: 115
tttgcaaaag tgcttgattt t                                        21

<210> SEQ ID NO 116
<211> LENGTH: 20
<212> TYPE: DNA
<213> ORGANISM: Artificial
<220> FEATURE:
<223> OTHER INFORMATION: primer

<400> SEQUENCE: 116
tgcaggctca gttccacata                                          20

<210> SEQ ID NO 117
<211> LENGTH: 20
<212> TYPE: DNA
<213> ORGANISM: Artificial
<220> FEATURE:
<223> OTHER INFORMATION: primer

<400> SEQUENCE: 117
ggaatgatgc cttttctcc                                           20

<210> SEQ ID NO 118
<211> LENGTH: 20
<212> TYPE: DNA
<213> ORGANISM: Artificial
<220> FEATURE:
<223> OTHER INFORMATION: primer

<400> SEQUENCE: 118
tctcacactt gccttctgga                                          20

<210> SEQ ID NO 119
<211> LENGTH: 20
```

```
<212> TYPE: DNA
<213> ORGANISM: Artificial
<220> FEATURE:
<223> OTHER INFORMATION: primer

<400> SEQUENCE: 119
aatcatcgcc tgagcaaaat                                                  20

<210> SEQ ID NO 120
<211> LENGTH: 20
<212> TYPE: DNA
<213> ORGANISM: Artificial
<220> FEATURE:
<223> OTHER INFORMATION: primer

<400> SEQUENCE: 120
ccagtgactg atccaaagca                                                  20

<210> SEQ ID NO 121
<211> LENGTH: 21
<212> TYPE: DNA
<213> ORGANISM: Artificial
<220> FEATURE:
<223> OTHER INFORMATION: primer

<400> SEQUENCE: 121
ccctcttaag gagaaaaaca c                                                21

<210> SEQ ID NO 122
<211> LENGTH: 20
<212> TYPE: DNA
<213> ORGANISM: Artificial
<220> FEATURE:
<223> OTHER INFORMATION: primer

<400> SEQUENCE: 122
cagccttatc ctctgctctt                                                  20

<210> SEQ ID NO 123
<211> LENGTH: 20
<212> TYPE: DNA
<213> ORGANISM: Artificial
<220> FEATURE:
<223> OTHER INFORMATION: primer

<400> SEQUENCE: 123
tggaaaaggg gagcagacta                                                  20

<210> SEQ ID NO 124
<211> LENGTH: 21
<212> TYPE: DNA
<213> ORGANISM: Artificial
<220> FEATURE:
<223> OTHER INFORMATION: primer

<400> SEQUENCE: 124
tgcgaactat ttttcctttg g                                                21

<210> SEQ ID NO 125
<211> LENGTH: 20
<212> TYPE: DNA
<213> ORGANISM: Artificial
<220> FEATURE:
<223> OTHER INFORMATION: primer

<400> SEQUENCE: 125
```
gaggaggcca caaatcacat                                                  20

<210> SEQ ID NO 126
<211> LENGTH: 20
<212> TYPE: DNA
<213> ORGANISM: Artificial
<220> FEATURE:
<223> OTHER INFORMATION: primer

<400> SEQUENCE: 126
gccttagacc tcgtcacacc                                                  20

<210> SEQ ID NO 127
<211> LENGTH: 23
<212> TYPE: DNA
<213> ORGANISM: Artificial
<220> FEATURE:
<223> OTHER INFORMATION: primer

<400> SEQUENCE: 127
tgctcaggtt ttgacttttt ctc                                              23

<210> SEQ ID NO 128
<211> LENGTH: 20
<212> TYPE: DNA
<213> ORGANISM: Artificial
<220> FEATURE:
<223> OTHER INFORMATION: primer

<400> SEQUENCE: 128
tttcactgat ggcaagatgc                                                  20

<210> SEQ ID NO 129
<211> LENGTH: 20
<212> TYPE: DNA
<213> ORGANISM: Artificial
<220> FEATURE:
<223> OTHER INFORMATION: primer

<400> SEQUENCE: 129
accaccccca cctctaattc                                                  20

<210> SEQ ID NO 130
<211> LENGTH: 20
<212> TYPE: DNA
<213> ORGANISM: Artificial
<220> FEATURE:
<223> OTHER INFORMATION: primer

<400> SEQUENCE: 130
ctacacaaca gaaagaatgc                                                  20

<210> SEQ ID NO 131
<211> LENGTH: 21
<212> TYPE: DNA
<213> ORGANISM: Artificial
<220> FEATURE:
<223> OTHER INFORMATION: primer

<400> SEQUENCE: 131
ccagctgaaa ctgaaagttg g                                                21

<210> SEQ ID NO 132
<211> LENGTH: 20
<212> TYPE: DNA
<213> ORGANISM: Artificial

```
<220> FEATURE:
<223> OTHER INFORMATION: primer

<400> SEQUENCE: 132
ctgggtactt acttcaggct                                            20

<210> SEQ ID NO 133
<211> LENGTH: 20
<212> TYPE: DNA
<213> ORGANISM: Artificial
<220> FEATURE:
<223> OTHER INFORMATION: primer

<400> SEQUENCE: 133
cactgtgccc tgccttatta                                            20

<210> SEQ ID NO 134
<211> LENGTH: 20
<212> TYPE: DNA
<213> ORGANISM: Artificial
<220> FEATURE:
<223> OTHER INFORMATION: primer

<400> SEQUENCE: 134
tgtgcctgag taaccgagtg                                            20

<210> SEQ ID NO 135
<211> LENGTH: 20
<212> TYPE: DNA
<213> ORGANISM: Artificial
<220> FEATURE:
<223> OTHER INFORMATION: primer

<400> SEQUENCE: 135
tcccagattt ggaggttttg                                            20

<210> SEQ ID NO 136
<211> LENGTH: 24
<212> TYPE: DNA
<213> ORGANISM: Artificial
<220> FEATURE:
<223> OTHER INFORMATION: primer

<400> SEQUENCE: 136
tgcattttaa tttcctaact accc                                       24

<210> SEQ ID NO 137
<211> LENGTH: 20
<212> TYPE: DNA
<213> ORGANISM: Artificial
<220> FEATURE:
<223> OTHER INFORMATION: primer

<400> SEQUENCE: 137
gctgtagtgg cattttattg                                            20

<210> SEQ ID NO 138
<211> LENGTH: 20
<212> TYPE: DNA
<213> ORGANISM: Artificial
<220> FEATURE:
<223> OTHER INFORMATION: primer

<400> SEQUENCE: 138
cctgggtgac agagcaagac                                            20
```

<210> SEQ ID NO 139
<211> LENGTH: 20
<212> TYPE: DNA
<213> ORGANISM: Artificial
<220> FEATURE:
<223> OTHER INFORMATION: primer

<400> SEQUENCE: 139
agctgcagag ctccataagc                                               20

<210> SEQ ID NO 140
<211> LENGTH: 20
<212> TYPE: DNA
<213> ORGANISM: Artificial
<220> FEATURE:
<223> OTHER INFORMATION: primer

<400> SEQUENCE: 140
taggcatcca gagcaggaac                                               20

<210> SEQ ID NO 141
<211> LENGTH: 20
<212> TYPE: DNA
<213> ORGANISM: Artificial
<220> FEATURE:
<223> OTHER INFORMATION: primer

<400> SEQUENCE: 141
ggcatctgaa agcaaccact                                               20

<210> SEQ ID NO 142
<211> LENGTH: 20
<212> TYPE: DNA
<213> ORGANISM: Artificial
<220> FEATURE:
<223> OTHER INFORMATION: primer

<400> SEQUENCE: 142
ccctccattt tcccaagagt                                               20

<210> SEQ ID NO 143
<211> LENGTH: 20
<212> TYPE: DNA
<213> ORGANISM: Artificial
<220> FEATURE:
<223> OTHER INFORMATION: primer

<400> SEQUENCE: 143
ggggtgaata ccgttgtgag                                               20

<210> SEQ ID NO 144
<211> LENGTH: 20
<212> TYPE: DNA
<213> ORGANISM: Artificial
<220> FEATURE:
<223> OTHER INFORMATION: primer

<400> SEQUENCE: 144
acctctgggt tccatgagtg                                               20

<210> SEQ ID NO 145
<211> LENGTH: 20
<212> TYPE: DNA
<213> ORGANISM: Artificial
<220> FEATURE:
<223> OTHER INFORMATION: primer -continued

<210> SEQ ID NO 145

<400> SEQUENCE: 145
agactgctcc tctgcactcc                                                    20

<210> SEQ ID NO 146
<211> LENGTH: 21
<212> TYPE: DNA
<213> ORGANISM: Artificial
<220> FEATURE:
<223> OTHER INFORMATION: primer

<400> SEQUENCE: 146
ccgggattgt tcaactttag c                                                  21

<210> SEQ ID NO 147
<211> LENGTH: 20
<212> TYPE: DNA
<213> ORGANISM: Artificial
<220> FEATURE:
<223> OTHER INFORMATION: primer

<400> SEQUENCE: 147
cagtatctta acctgtacat                                                    20

<210> SEQ ID NO 148
<211> LENGTH: 21
<212> TYPE: DNA
<213> ORGANISM: Artificial
<220> FEATURE:
<223> OTHER INFORMATION: primer

<400> SEQUENCE: 148
ccgggattgt tcaactttag c                                                  21

<210> SEQ ID NO 149
<211> LENGTH: 40
<212> TYPE: PRT
<213> ORGANISM: Homo sapiens
<220> FEATURE:
<221> NAME/KEY: misc_feature
<222> LOCATION: (40)..(40)
<223> OTHER INFORMATION: Xaa can be any naturally occurring amino acid

<400> SEQUENCE: 149

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Xaa
        35                  40

<210> SEQ ID NO 150
<211> LENGTH: 178
<212> TYPE: PRT
<213> ORGANISM: Homo sapiens
<220> FEATURE:
<221> NAME/KEY: misc_feature
<222> LOCATION: (178)..(178)
<223> OTHER INFORMATION: Xaa can be any naturally occurring amino acid

<400> SEQUENCE: 150

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

-continued

Val Pro Ala Glu Ala Met Gly Gln Leu Gly Ser Arg Ala Gln Leu Arg
         35                  40                  45

Thr Gln Pro Glu Ala Leu Gly Ser Leu Thr Ala Ala Gly Ser Leu Gln
 50                  55                  60

Val Leu Ser Leu Thr Pro Gly Ser Arg Gly Gly Arg Cys Cys Leu
 65                  70                  75                  80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ser Xaa

<210> SEQ ID NO 151
<211> LENGTH: 246
<212> TYPE: PRT
<213> ORGANISM: Homo sapiens
<220> FEATURE:
<221> NAME/KEY: misc_feature
<222> LOCATION: (246)..(246)
<223> OTHER INFORMATION: Xaa can be any naturally occurring amino acid

<400> SEQUENCE: 151

Met Ala Ala Glu Glu Gly Val Ala Ser Ala Ala Ser Ala Gly Gly Ser
 1               5                  10                  15

Trp Gly Thr Ala Ala Met Gly Arg Val Leu Pro Met Leu Leu Val Pro
             20                  25                  30

Val Pro Ala Glu Ala Met Gly Gln Leu Gly Ser Arg Ala Gln Leu Arg
         35                  40                  45

Thr Gln Pro Glu Ala Leu Gly Ser Leu Thr Ala Ala Gly Ser Leu Gln
 50                  55                  60

Val Leu Ser Leu Thr Pro Gly Ser Arg Gly Gly Arg Cys Cys Leu
 65                  70                  75                  80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu

```
                195                 200                 205
Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Val Xaa
                245

<210> SEQ ID NO 152
<211> LENGTH: 415
<212> TYPE: PRT
<213> ORGANISM: Homo sapiens
<220> FEATURE:
<221> NAME/KEY: misc_feature
<222> LOCATION: (415)..(415)
<223> OTHER INFORMATION: Xaa can be any naturally occurring amino acid

<400> SEQUENCE: 152

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300
```

-continued

```
Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Ile Met Pro Arg Pro Val Ile Gln Glu Asp His Gly Lys Xaa
            405                 410                 415
```

<210> SEQ ID NO 153
<211> LENGTH: 412
<212> TYPE: PRT
<213> ORGANISM: Homo sapiens
<220> FEATURE:
<221> NAME/KEY: misc_feature
<222> LOCATION: (412)..(412)
<223> OTHER INFORMATION: Xaa can be any naturally occurring amino acid

<400> SEQUENCE: 153

```
Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240
```

His Lys Glu Asp Met Cys Asn Glu Gln Gln Gln Pro Ala Lys Ile
            245                 250                 255

Ser Ser Phe Thr Ser Leu Lys Val Ser Gln Asp Leu Asp Val Ala Val
                260                 265                 270

Ile Val Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Xaa
            405                 410

<210> SEQ ID NO 154
<211> LENGTH: 556
<212> TYPE: PRT
<213> ORGANISM: Homo sapiens
<220> FEATURE:
<221> NAME/KEY: misc_feature
<222> LOCATION: (556)..(556)
<223> OTHER INFORMATION: Xaa can be any naturally occurring amino acid

<400> SEQUENCE: 154

Met Ala Ala Glu Glu Gly Val Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr

```
            180                 185                 190
Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
        210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Ser Ser Gln Trp Leu Gly Lys Val Leu Asn Ser
        515                 520                 525

His Thr Cys Thr Arg Gly Arg Asp Arg Lys Ser Ser Ala Gly His Ser
    530                 535                 540

Lys Phe Leu Phe Glu Glu Gln Gly Lys Ser Phe Xaa
545                 550                 555

<210> SEQ ID NO 155
<211> LENGTH: 651
<212> TYPE: PRT
<213> ORGANISM: Homo sapiens
<220> FEATURE:
<221> NAME/KEY: misc_feature
<222> LOCATION: (651)..(651)
```

<223> OTHER INFORMATION: Xaa can be any naturally occurring amino acid

<400> SEQUENCE: 155

```
Met Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65              70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400
```

```
Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Xaa
            645                 650

<210> SEQ ID NO 156
<211> LENGTH: 733
<212> TYPE: PRT
<213> ORGANISM: Homo sapiens
<220> FEATURE:
<221> NAME/KEY: misc_feature
<222> LOCATION: (733)..(733)
<223> OTHER INFORMATION: Xaa can be any naturally occurring amino acid

<400> SEQUENCE: 156

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
            50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
            85                  90                  95

Thr Pro Thr Glu Lys Pro Lys Leu Leu Ala Leu Gly Glu Asn Tyr Glu
```

```
              100                 105                 110
Leu Leu Ile Tyr Glu Phe Asn Leu Lys Asp Gly Arg Cys Asp Ala Thr
            115                 120                 125
Ile Leu Tyr Ser Cys Ser Arg Glu Ala Leu Gln Lys Leu Ile Asp Asp
            130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
            180                 185                 190
Leu Pro Leu Pro Ala Gln Ala Val Asp Met Ile Ile Asp Thr Gln Leu
            195                 200                 205
Cys Arg Gly Ile Leu Phe Val Leu Ser Ser Leu Gly Trp Ile Tyr Ile
            210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Glu Pro Ala Lys Ile
                245                 250                 255
Ser Ser Phe Thr Ser Leu Lys Val Ser Gln Asp Leu Asp Val Ala Val
                260                 265                 270
Ile Val Ser Ser Ser Asn Ser Ala Val Ala Leu Asn Leu Asn Leu Tyr
            275                 280                 285
Phe Arg Gln His Pro Gly His Leu Leu Cys Glu Arg Ile Leu Glu Asp
            290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
            355                 360                 365
Leu Glu Ser Pro Glu Ser Gly Asn His Ser Thr Ser Val Gln Ser Trp
            370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
            435                 440                 445
Thr Ile Thr Leu Trp Asp Leu Glu Thr Gln Gly Met Gln Cys Ser Ser
            450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
            515                 520                 525
```

```
Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Xaa
                725                 730

<210> SEQ ID NO 157
<211> LENGTH: 953
<212> TYPE: PRT
<213> ORGANISM: Homo sapiens
<220> FEATURE:
<221> NAME/KEY: misc_feature
<222> LOCATION: (953)..(953)
<223> OTHER INFORMATION: Xaa can be any naturally occurring amino acid

<400> SEQUENCE: 157

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140
```

```
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
            165                 170                 175

Ile Phe Pro Glu Arg Asp Ala Ala Ile Arg Val Leu Asn Cys Phe Thr
        180                 185                 190

Leu Pro Leu Pro Ala Gln Ala Val Asp Met Ile Ile Asp Thr Gln Leu
    195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
        500                 505                 510

Thr Val Asp Thr Leu Cys His Leu Asn Gly Trp Gly Arg Cys Ser Ile
    515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
```

```
                565                 570                 575
Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
        610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
                740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
        770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
                820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
        850                 855                 860

Ile Leu Leu Pro Arg Ile Ser Pro Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
                900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
        930                 935                 940

Arg Asn Gly Gly Phe Phe Gly Ile Xaa
945                 950

<210> SEQ ID NO 158
<211> LENGTH: 953
<212> TYPE: PRT
<213> ORGANISM: Homo sapiens
```

-continued

```
<220> FEATURE:
<221> NAME/KEY: misc_feature
<222> LOCATION: (953)..(953)
<223> OTHER INFORMATION: Xaa can be any naturally occurring amino acid

<400> SEQUENCE: 158
```

| Met | Ala | Ala | Glu | Glu | Gly | Val | Ala | Ser | Ala | Ser | Ala | Gly | Gly | Ser |
|---|---|---|---|---|---|---|---|---|---|---|---|---|---|---|
| 1 | | | | 5 | | | | | 10 | | | | | 15 |

| Trp | Gly | Thr | Ala | Ala | Met | Gly | Arg | Val | Leu | Pro | Met | Leu | Leu | Val | Pro |
|---|---|---|---|---|---|---|---|---|---|---|---|---|---|---|---|
| | | | 20 | | | | | 25 | | | | | 30 | | |

| Val | Pro | Ala | Glu | Ala | Met | Gly | Gln | Leu | Gly | Ser | Arg | Ala | Gln | Leu | Arg |
|---|---|---|---|---|---|---|---|---|---|---|---|---|---|---|---|
| | | | 35 | | | | | 40 | | | | | 45 | | |

| Thr | Gln | Pro | Glu | Ala | Leu | Gly | Ser | Leu | Thr | Ala | Ala | Gly | Ser | Leu | Gln |
|---|---|---|---|---|---|---|---|---|---|---|---|---|---|---|---|
| | 50 | | | | | 55 | | | | | 60 | | | | |

| Val | Leu | Ser | Leu | Thr | Pro | Gly | Ser | Arg | Gly | Gly | Gly | Arg | Cys | Cys | Leu |
|---|---|---|---|---|---|---|---|---|---|---|---|---|---|---|---|
| 65 | | | | | 70 | | | | | 75 | | | | | 80 |

| Glu | Gly | Pro | Phe | Trp | His | Phe | Leu | Trp | Glu | Asp | Ser | Arg | Asn | Ser | Ser |
|---|---|---|---|---|---|---|---|---|---|---|---|---|---|---|---|
| | | | | 85 | | | | | 90 | | | | | 95 | |

| Thr | Pro | Thr | Glu | Lys | Pro | Lys | Leu | Leu | Ala | Leu | Gly | Glu | Asn | Tyr | Glu |
|---|---|---|---|---|---|---|---|---|---|---|---|---|---|---|---|
| | | | | 100 | | | | | 105 | | | | | 110 | |

| Leu | Leu | Ile | Tyr | Glu | Phe | Asn | Leu | Lys | Asp | Gly | Arg | Cys | Asp | Ala | Thr |
|---|---|---|---|---|---|---|---|---|---|---|---|---|---|---|---|
| | | | 115 | | | | | 120 | | | | | 125 | | |

| Ile | Leu | Tyr | Ser | Cys | Ser | Arg | Glu | Ala | Leu | Gln | Lys | Leu | Ile | Asp | Asp |
|---|---|---|---|---|---|---|---|---|---|---|---|---|---|---|---|
| | 130 | | | | | 135 | | | | | 140 | | | | |

| Gln | Asp | Ile | Ser | Ile | Ser | Leu | Leu | Ser | Leu | Arg | Ile | Leu | Ser | Phe | His |
|---|---|---|---|---|---|---|---|---|---|---|---|---|---|---|---|
| 145 | | | | | 150 | | | | | 155 | | | | | 160 |

| Asn | Asn | Thr | Ser | Leu | Leu | Phe | Ile | Asn | Lys | Cys | Val | Ile | Leu | His | Ile |
|---|---|---|---|---|---|---|---|---|---|---|---|---|---|---|---|
| | | | | 165 | | | | | 170 | | | | | 175 | |

| Ile | Phe | Pro | Glu | Arg | Asp | Ala | Ala | Ile | Arg | Val | Leu | Asn | Cys | Phe | Thr |
|---|---|---|---|---|---|---|---|---|---|---|---|---|---|---|---|
| | | | | 180 | | | | | 185 | | | | | 190 | |

| Leu | Pro | Leu | Pro | Ala | Gln | Ala | Val | Asp | Met | Ile | Ile | Asp | Thr | Gln | Leu |
|---|---|---|---|---|---|---|---|---|---|---|---|---|---|---|---|
| | | | 195 | | | | | 200 | | | | | 205 | | |

| Cys | Arg | Gly | Ile | Leu | Phe | Val | Leu | Ser | Ser | Leu | Gly | Trp | Ile | Tyr | Ile |
|---|---|---|---|---|---|---|---|---|---|---|---|---|---|---|---|
| | 210 | | | | | 215 | | | | | 220 | | | | |

| Phe | Asp | Val | Val | Asp | Gly | Thr | Tyr | Val | Ala | His | Val | Asp | Leu | Ala | Leu |
|---|---|---|---|---|---|---|---|---|---|---|---|---|---|---|---|
| 225 | | | | | 230 | | | | | 235 | | | | | 240 |

| His | Lys | Glu | Asp | Met | Cys | Asn | Glu | Gln | Gln | Gln | Glu | Pro | Ala | Lys | Ile |
|---|---|---|---|---|---|---|---|---|---|---|---|---|---|---|---|
| | | | | 245 | | | | | 250 | | | | | 255 | |

| Ser | Ser | Phe | Thr | Ser | Leu | Lys | Val | Ser | Gln | Asp | Leu | Asp | Val | Ala | Val |
|---|---|---|---|---|---|---|---|---|---|---|---|---|---|---|---|
| | | | | 260 | | | | | 265 | | | | | 270 | |

| Ile | Val | Ser | Ser | Ser | Asn | Ser | Ala | Val | Ala | Leu | Asn | Leu | Asn | Leu | Tyr |
|---|---|---|---|---|---|---|---|---|---|---|---|---|---|---|---|
| | | | 275 | | | | | 280 | | | | | 285 | | |

| Phe | Arg | Gln | His | Pro | Gly | His | Leu | Leu | Cys | Glu | Arg | Ile | Leu | Glu | Asp |
|---|---|---|---|---|---|---|---|---|---|---|---|---|---|---|---|
| | 290 | | | | | 295 | | | | | 300 | | | | |

| Leu | Pro | Ile | Gln | Gly | Pro | Lys | Gly | Val | Asp | Glu | Asp | Pro | Val | Asn |
|---|---|---|---|---|---|---|---|---|---|---|---|---|---|---|
| 305 | | | | | 310 | | | | | 315 | | | | | 320 |

| Ser | Ala | Tyr | Asn | Met | Lys | Leu | Ala | Lys | Phe | Ser | Phe | Gln | Ile | Asp | Arg |
|---|---|---|---|---|---|---|---|---|---|---|---|---|---|---|---|
| | | | | 325 | | | | | 330 | | | | | 335 | |

| Ser | Trp | Lys | Ala | Gln | Leu | Ser | Ser | Leu | Asn | Glu | Thr | Ile | Lys | Asn | Ser |
|---|---|---|---|---|---|---|---|---|---|---|---|---|---|---|---|
| | | | 340 | | | | | 345 | | | | | 350 | | |

| Lys | Leu | Glu | Val | Ser | Cys | Cys | Ala | Pro | Trp | Phe | Gln | Asp | Ile | Leu | His |
|---|---|---|---|---|---|---|---|---|---|---|---|---|---|---|---|
| | | | 355 | | | | | 360 | | | | | 365 | | |

| Leu | Glu | Ser | Pro | Glu | Ser | Gly | Asn | His | Ser | Thr | Ser | Val | Gln | Ser | Trp |
|---|---|---|---|---|---|---|---|---|---|---|---|---|---|---|---|
| | 370 | | | | | 375 | | | | | 380 | | | | |

```
Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
        420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
```

-continued

```
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
930                 935                 940

Arg Asn Gly Val Phe Phe Gly Ile Xaa
945                 950

<210> SEQ ID NO 159
<211> LENGTH: 1992
<212> TYPE: PRT
<213> ORGANISM: Homo sapiens
<220> FEATURE:
<221> NAME/KEY: misc_feature
<222> LOCATION: (1992)..(1992)
<223> OTHER INFORMATION: Xaa can be any naturally occurring amino acid

<400> SEQUENCE: 159

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205
```

-continued

```
Cys Arg Gly Ile Leu Phe Val Leu Ser Ser Leu Gly Trp Ile Tyr Ile
    210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Glu Pro Ala Lys Ile
                245                 250                 255
Ser Ser Phe Thr Ser Leu Lys Val Ser Gln Asp Leu Asp Val Ala Val
            260                 265                 270
Ile Val Ser Ser Ser Asn Ser Ala Val Ala Leu Asn Leu Asn Leu Tyr
        275                 280                 285
Phe Arg Gln His Pro Gly His Leu Leu Cys Glu Arg Ile Leu Glu Asp
290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
        355                 360                 365
Leu Glu Ser Pro Glu Ser Gly Asn His Ser Thr Ser Val Gln Ser Trp
370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
        435                 440                 445
Thr Ile Thr Leu Trp Asp Leu Glu Thr Gln Gly Met Gln Cys Ser Ser
450                 455                 460
Leu Gly Thr Lys Cys Ile Pro Val Asp Ser Ser Gly Asp Gln Leu
465                 470                 475                 480
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
        515                 520                 525
Pro Ile His Ala Leu Glu Ala Gly Ile Glu Asn Arg Gln Leu Asp Thr
530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
                565                 570                 575
Leu Arg Asn Val Glu Glu Leu Ile Pro Ala Leu Asp Leu Leu Cys Ser
            580                 585                 590
Ala Ile Arg Glu Ser Tyr Ser Glu Pro Gln Ser Lys His Phe Ser Glu
        595                 600                 605
Gln Leu Leu Asn Leu Thr Leu Ser Phe Leu Asn Asn Gln Ile Lys Glu
610                 615                 620
```

```
Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
            725                 730                 735

Asn Ile Lys Glu Ala Ser Glu Leu Leu Lys Asn Met Gly Phe Asp Val
            740                 745                 750

Lys Gly Gln Leu Lys Ile Cys Phe Tyr Thr Thr Asn Lys Asn Ile
755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
            805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
            885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
            965                 970                 975

Val Gln Asn Tyr Lys Thr Lys Gly Gly Trp Phe Ser Gln Phe
            980                 985                 990

Ile Leu Tyr Cys Leu Glu His Ser Leu Gln His Leu Leu Tyr Val Tyr
            995                 1000                1005

Leu Asp Cys Tyr Lys Leu Ser Pro Glu Asn Cys Pro Phe Leu Glu
        1010            1015            1020

Lys Lys Glu Leu His Glu Ala His Pro Trp Phe Glu Phe Leu Val
        1025            1030            1035

Gln Cys Arg Gln Val Ala Ser Asn Leu Thr Asp Pro Lys Leu Ile
```

-continued

```
              1040                1045                1050

Phe Gln Ala Ser Leu Ala Asn Ala Gln Ile Leu Ile Pro Thr Asn
              1055                1060                1065

Gln Ala Ser Val Ser Ser Met Leu Leu Glu Gly His Thr Leu Leu
              1070                1075                1080

Ala Leu Ala Thr Thr Met Tyr Ser Pro Gly Gly Val Ser Gln Val
              1085                1090                1095

Val Gln Asn Glu Glu Asn Glu Asn Cys Leu Lys Lys Val Asp Pro
              1100                1105                1110

Gln Leu Leu Lys Met Ala Leu Thr Pro Tyr Pro Lys Leu Lys Thr
              1115                1120                1125

Ala Leu Phe Pro Gln Cys Thr Pro Pro Ser Val Leu Pro Ser Asp
              1130                1135                1140

Ile Thr Ile Tyr His Leu Ile Gln Ser Leu Ser Pro Phe Asp Pro
              1145                1150                1155

Ser Arg Leu Phe Gly Trp Gln Ser Ala Asn Thr Leu Ala Ile Gly
              1160                1165                1170

Asp Ala Trp Ser His Leu Pro His Phe Ser Ser Pro Asp Leu Val
              1175                1180                1185

Asn Lys Tyr Ala Ile Val Glu Arg Leu Asn Phe Ala Tyr Tyr Leu
              1190                1195                1200

His Asn Gly Arg Pro Ser Phe Ala Phe Gly Thr Phe Leu Val Gln
              1205                1210                1215

Glu Leu Ile Lys Ser Lys Thr Pro Lys Gln Leu Ile Gln Gln Val
              1220                1225                1230

Gly Asn Glu Ala Tyr Val Ile Gly Leu Ser Ser Phe His Ile Pro
              1235                1240                1245

Ser Ile Gly Ala Ala Cys Val Cys Phe Leu Glu Leu Leu Gly Leu
              1250                1255                1260

Asp Ser Leu Lys Leu Arg Val Asp Met Lys Val Ala Asn Ile Ile
              1265                1270                1275

Leu Ser Tyr Lys Cys Arg Asn Glu Asp Ala Gln Tyr Ser Phe Ile
              1280                1285                1290

Arg Glu Ser Val Ala Glu Lys Leu Ser Lys Leu Ala Asp Gly Glu
              1295                1300                1305

Lys Thr Thr Thr Glu Glu Leu Leu Val Leu Leu Glu Glu Gly Thr
              1310                1315                1320

Trp Asn Ser Ile Gln Gln Gln Glu Ile Lys Arg Leu Ser Ser Glu
              1325                1330                1335

Ser Ser Ser Gln Trp Ala Leu Val Val Gln Phe Cys Arg Leu His
              1340                1345                1350

Asn Met Lys Leu Ser Ile Ser Tyr Leu Arg Glu Cys Ala Lys Ala
              1355                1360                1365

Asn Asp Trp Leu Gln Phe Ile Ile His Ser Gln Leu His Asn Tyr
              1370                1375                1380

His Pro Ala Glu Val Lys Ser Leu Ile Gln Tyr Phe Ser Pro Val
              1385                1390                1395

Ile Gln Asp His Leu Arg Leu Ala Phe Glu Asn Leu Pro Ser Val
              1400                1405                1410

Pro Thr Ser Lys Met Asp Ser Asp Gln Val Cys Asn Lys Cys Pro
              1415                1420                1425

Gln Glu Leu Gln Gly Ser Lys Gln Glu Met Thr Asp Leu Phe Glu
              1430                1435                1440
```

```
Ile Leu Leu Gln Cys Ser Glu Glu Pro Asp Ser Trp His Trp Leu
    1445            1450                1455

Leu Val Glu Ala Val Lys Gln Gln Ala Pro Ile Leu Ser Val Leu
    1460            1465                1470

Ala Ser Cys Leu Gln Gly Ala Ser Ala Ile Ser Cys Leu Cys Val
    1475            1480                1485

Trp Ile Ile Thr Ser Val Glu Asp Asn Val Ala Thr Glu Ala Met
    1490            1495                1500

Gly His Ile Gln Asp Ser Thr Glu Asp His Thr Trp Asn Leu Glu
    1505            1510                1515

Asp Leu Ser Val Ile Trp Arg Thr Leu Thr Arg Gln Lys Ser
    1520            1525                1530

Lys Thr Leu Ile Arg Gly Phe Gln Leu Phe Phe Lys Asp Ser Pro
    1535            1540                1545

Leu Leu Leu Val Met Glu Met Tyr Glu Leu Cys Met Phe Phe Arg
    1550            1555                1560

Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
    1670            1675                1680

Gly Gln Phe Ala Leu Ala Arg Arg Val Ala Glu Leu Ala Glu Leu
    1685            1690                1695

Pro Val Asp Asn Leu Val Ile Lys Glu Ile Thr Gln Glu Met Gln
    1700            1705                1710

Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Glu Leu Glu Lys Gln Ile Trp Leu
    1790            1795                1800

Cys Arg Ile Thr Gln His Thr Leu Gly Arg Asn Gln Glu Glu Thr
    1805            1810                1815

Glu Pro Arg Phe Ser Arg Gln Ile Ser Thr Ser Gly Glu Leu Ser
    1820            1825                1830
```

```
Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Xaa
    1985                1990

<210> SEQ ID NO 160
<211> LENGTH: 2034
<212> TYPE: PRT
<213> ORGANISM: Homo sapiens
<220> FEATURE:
<221> NAME/KEY: misc_feature
<222> LOCATION: (2034)..(2034)
<223> OTHER INFORMATION: Xaa can be any naturally occurring amino acid

<400> SEQUENCE: 160

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
```

```
                180                 185                 190
Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
        210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
        290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605
```

```
Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
                740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser  Leu Gln His Leu Leu  Tyr Val Tyr
            995                 1000                1005

Leu Asp Cys  Tyr Lys Leu Ser  Pro Glu Asn Cys  Phe Leu Glu
    1010                1015                1020
```

```
Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
```

```
                1415                1420                1425

Gln  Glu  Leu  Gln  Gly  Ser  Lys  Gln  Glu  Met  Thr  Asp  Leu  Phe  Glu
          1430                1435                1440

Ile  Leu  Leu  Gln  Cys  Ser  Glu  Glu  Pro  Asp  Ser  Trp  His  Trp  Leu
          1445                1450                1455

Leu  Val  Glu  Ala  Val  Lys  Gln  Gln  Ala  Pro  Ile  Leu  Ser  Val  Leu
          1460                1465                1470

Ala  Ser  Cys  Leu  Gln  Gly  Ala  Ser  Ala  Ile  Ser  Cys  Leu  Cys  Val
          1475                1480                1485

Trp  Ile  Ile  Thr  Ser  Val  Glu  Asp  Asn  Val  Ala  Thr  Glu  Ala  Met
          1490                1495                1500

Gly  His  Ile  Gln  Asp  Ser  Thr  Glu  Asp  His  Thr  Trp  Asn  Leu  Glu
          1505                1510                1515

Asp  Leu  Ser  Val  Ile  Trp  Arg  Thr  Leu  Leu  Thr  Arg  Gln  Lys  Ser
          1520                1525                1530

Lys  Thr  Leu  Ile  Arg  Gly  Phe  Gln  Leu  Phe  Phe  Lys  Asp  Ser  Pro
          1535                1540                1545

Leu  Leu  Leu  Val  Met  Glu  Met  Tyr  Glu  Leu  Cys  Met  Phe  Phe  Arg
          1550                1555                1560

Asn  Tyr  Lys  Glu  Ala  Glu  Ala  Lys  Leu  Leu  Glu  Phe  Gln  Lys  Ser
          1565                1570                1575

Leu  Glu  Thr  Leu  Asn  Thr  Ala  Ala  Thr  Lys  Val  His  Pro  Val  Ile
          1580                1585                1590

Pro  Ala  Met  Trp  Leu  Glu  Asp  Gln  Val  Cys  Phe  Leu  Leu  Lys  Leu
          1595                1600                1605

Met  Leu  Gln  Gln  Cys  Lys  Thr  Gln  Tyr  Glu  Leu  Gly  Lys  Leu  Leu
          1610                1615                1620

Gln  Leu  Phe  Val  Glu  Arg  Glu  His  Leu  Phe  Ser  Asp  Gly  Pro  Asp
          1625                1630                1635

Val  Lys  Lys  Leu  Cys  Ile  Leu  Cys  Gln  Ile  Leu  Lys  Asp  Thr  Ser
          1640                1645                1650

Ile  Ala  Ile  Asn  His  Thr  Ile  Ile  Thr  Ser  Tyr  Ser  Ile  Glu  Asn
          1655                1660                1665

Leu  Gln  His  Glu  Cys  Arg  Ser  Ile  Leu  Glu  Arg  Leu  Gln  Thr  Asp
          1670                1675                1680

Gly  Gln  Phe  Ala  Leu  Ala  Arg  Arg  Val  Ala  Glu  Leu  Ala  Glu  Leu
          1685                1690                1695

Pro  Val  Asp  Asn  Leu  Val  Ile  Lys  Glu  Ile  Thr  Gln  Glu  Met  Gln
          1700                1705                1710

Thr  Leu  Lys  His  Ile  Glu  Gln  Trp  Ser  Leu  Lys  Gln  Ala  Arg  Ile
          1715                1720                1725

Asp  Phe  Trp  Lys  Lys  Cys  His  Glu  Asn  Phe  Lys  Lys  Asn  Ser  Ile
          1730                1735                1740

Ser  Ser  Lys  Ala  Ala  Ser  Ser  Phe  Phe  Ser  Thr  Gln  Ala  His  Val
          1745                1750                1755

Ala  Cys  Glu  His  Pro  Thr  Gly  Trp  Ser  Ser  Met  Glu  Glu  Arg  His
          1760                1765                1770

Leu  Leu  Leu  Thr  Leu  Ala  Gly  His  Trp  Leu  Ala  Gln  Glu  Asp  Val
          1775                1780                1785

Val  Pro  Leu  Asp  Lys  Leu  Glu  Glu  Leu  Glu  Lys  Gln  Ile  Trp  Leu
          1790                1795                1800

Cys  Arg  Ile  Thr  Gln  His  Thr  Leu  Gly  Arg  Asn  Gln  Glu  Glu  Thr
          1805                1810                1815
```

```
Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Leu Tyr
    1985                1990                1995

Asp Leu Ala Lys Glu Leu Gly Cys Ser Tyr Thr Asp Val Ala Ala
    2000                2005                2010

Gln Asp Gly Glu Ala Met Leu Arg Lys Ile Leu Ala Ser Gln Gln
    2015                2020                2025

Pro Asp Arg Cys Lys Xaa
    2030
```

<210> SEQ ID NO 161
<211> LENGTH: 2172
<212> TYPE: PRT
<213> ORGANISM: Homo sapiens
<220> FEATURE:
<221> NAME/KEY: misc_feature
<222> LOCATION: (2172)..(2172)
<223> OTHER INFORMATION: Xaa can be any naturally occurring amino acid

<400> SEQUENCE: 161

```
Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110
```

```
Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
```

```
                530             535             540
Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
                595                 600                 605

Gln Leu Leu Asn Leu Thr Leu Ser Phe Leu Asn Asn Gln Ile Lys Glu
                610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
                675                 680                 685

Glu Glu Val Ile Ala Ser Ala Ile Leu Asn Asn Lys Ile Pro Glu Ala
                690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
                740                 745                 750

Lys Gly Gln Leu Leu Lys Ile Cys Phe Tyr Thr Thr Asn Lys Asn Ile
                755                 760                 765

Arg Asp Phe Leu Val Glu Ile Leu Lys Glu Lys Asn Tyr Phe Ser Glu
                770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
                820                 825                 830

Phe Leu Lys Tyr Asp Cys Lys Asp Glu Phe Asn Lys Gln Asp His Arg
                835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
                900                 905                 910

Gln Gln Asn Lys Trp Pro Leu Leu Thr Val Asp Val Ile Asn Gln Asn
                915                 920                 925

Thr Ser Cys Asn Asn Tyr Met Arg Asn Glu Ile Leu Asp Lys Leu Ala
                930                 935                 940

Arg Asn Gly Val Phe Leu Ala Ser Glu Leu Glu Asp Phe Glu Cys Phe
945                 950                 955                 960
```

```
Leu Leu Arg Leu Ser Arg Ile Gly Gly Val Ile Gln Asp Thr Leu Pro
            965                 970                 975
Val Gln Asn Tyr Lys Thr Lys Glu Gly Trp Asp Phe His Ser Gln Phe
            980                 985                 990
Ile Leu Tyr Cys Leu Glu His Ser Leu Gln His Leu Leu Tyr Val Tyr
            995                 1000                1005
Leu Asp Cys Tyr Lys Leu Ser Pro Glu Asn Cys Pro Phe Leu Glu
        1010                1015                1020
Lys Lys Glu Leu His Glu Ala His Pro Trp Phe Glu Phe Leu Val
        1025                1030                1035
Gln Cys Arg Gln Val Ala Ser Asn Leu Thr Asp Pro Lys Leu Ile
        1040                1045                1050
Phe Gln Ala Ser Leu Ala Asn Ala Gln Ile Leu Ile Pro Thr Asn
        1055                1060                1065
Gln Ala Ser Val Ser Ser Met Leu Leu Glu Gly His Thr Leu Leu
        1070                1075                1080
Ala Leu Ala Thr Thr Met Tyr Ser Pro Gly Gly Val Ser Gln Val
        1085                1090                1095
Val Gln Asn Glu Glu Asn Glu Asn Cys Leu Lys Lys Val Asp Pro
        1100                1105                1110
Gln Leu Leu Lys Met Ala Leu Thr Pro Tyr Pro Lys Leu Lys Thr
        1115                1120                1125
Ala Leu Phe Pro Gln Cys Thr Pro Pro Ser Val Leu Pro Ser Asp
        1130                1135                1140
Ile Thr Ile Tyr His Leu Ile Gln Ser Leu Ser Pro Phe Asp Pro
        1145                1150                1155
Ser Arg Leu Phe Gly Trp Gln Ser Ala Asn Thr Leu Ala Ile Gly
        1160                1165                1170
Asp Ala Trp Ser His Leu Pro His Phe Ser Ser Pro Asp Leu Val
        1175                1180                1185
Asn Lys Tyr Ala Ile Val Glu Arg Leu Asn Phe Ala Tyr Tyr Leu
        1190                1195                1200
His Asn Gly Arg Pro Ser Phe Ala Phe Gly Thr Phe Leu Val Gln
        1205                1210                1215
Glu Leu Ile Lys Ser Lys Thr Pro Lys Gln Leu Ile Gln Gln Val
        1220                1225                1230
Gly Asn Glu Ala Tyr Val Ile Gly Leu Ser Ser Phe His Ile Pro
        1235                1240                1245
Ser Ile Gly Ala Ala Cys Val Cys Phe Leu Glu Leu Leu Gly Leu
        1250                1255                1260
Asp Ser Leu Lys Leu Arg Val Asp Met Lys Val Ala Asn Ile Ile
        1265                1270                1275
Leu Ser Tyr Lys Cys Arg Asn Glu Asp Ala Gln Tyr Ser Phe Ile
        1280                1285                1290
Arg Glu Ser Val Ala Glu Lys Leu Ser Lys Leu Ala Asp Gly Glu
        1295                1300                1305
Lys Thr Thr Thr Glu Glu Leu Leu Val Leu Leu Glu Glu Gly Thr
        1310                1315                1320
Trp Asn Ser Ile Gln Gln Gln Glu Ile Lys Arg Leu Ser Ser Glu
        1325                1330                1335
Ser Ser Ser Gln Trp Ala Leu Val Val Gln Phe Cys Arg Leu His
        1340                1345                1350
```

```
Asn Met Lys Leu Ser Ile Ser Tyr Leu Arg Glu Cys Ala Lys Ala
    1355            1360                1365

Asn Asp Trp Leu Gln Phe Ile Ile His Ser Gln Leu His Asn Tyr
    1370            1375                1380

His Pro Ala Glu Val Lys Ser Leu Ile Gln Tyr Phe Ser Pro Val
    1385            1390                1395

Ile Gln Asp His Leu Arg Leu Ala Phe Glu Asn Leu Pro Ser Val
    1400            1405                1410

Pro Thr Ser Lys Met Asp Ser Asp Gln Val Cys Asn Lys Cys Pro
    1415            1420                1425

Gln Glu Leu Gln Gly Ser Lys Gln Glu Met Thr Asp Leu Phe Glu
    1430            1435                1440

Ile Leu Leu Gln Cys Ser Glu Glu Pro Asp Ser Trp His Trp Leu
    1445            1450                1455

Leu Val Glu Ala Val Lys Gln Gln Ala Pro Ile Leu Ser Val Leu
    1460            1465                1470

Ala Ser Cys Leu Gln Gly Ala Ser Ala Ile Ser Cys Leu Cys Val
    1475            1480                1485

Trp Ile Ile Thr Ser Val Glu Asp Asn Val Ala Thr Glu Ala Met
    1490            1495                1500

Gly His Ile Gln Asp Ser Thr Glu Asp His Thr Trp Asn Leu Glu
    1505            1510                1515

Asp Leu Ser Val Ile Trp Arg Thr Leu Leu Thr Arg Gln Lys Ser
    1520            1525                1530

Lys Thr Leu Ile Arg Gly Phe Gln Leu Phe Phe Lys Asp Ser Pro
    1535            1540                1545

Leu Leu Leu Val Met Glu Met Tyr Glu Leu Cys Met Phe Phe Arg
    1550            1555                1560

Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
    1670            1675                1680

Gly Gln Phe Ala Leu Ala Arg Arg Val Ala Glu Leu Ala Glu Leu
    1685            1690                1695

Pro Val Asp Asn Leu Val Ile Lys Glu Ile Thr Gln Glu Met Gln
    1700            1705                1710

Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
```

```
                1745                1750                1755

Ala Cys Glu His Pro Thr Gly Trp Ser Ser Met Glu Glu Arg His
        1760                1765                1770

Leu Leu Leu Thr Leu Ala Gly His Trp Leu Ala Gln Glu Asp Val
        1775                1780                1785

Val Pro Leu Asp Lys Leu Glu Glu Leu Glu Lys Gln Ile Trp Leu
        1790                1795                1800

Cys Arg Ile Thr Gln His Thr Leu Gly Arg Asn Gln Glu Glu Thr
        1805                1810                1815

Glu Pro Arg Phe Ser Arg Gln Ile Ser Thr Ser Gly Glu Leu Ser
        1820                1825                1830

Phe Asp Ser Leu Ala Ser Glu Phe Ser Phe Ser Lys Leu Ala Ala
        1835                1840                1845

Leu Asn Thr Ser Lys Tyr Leu Glu Leu Asn Ser Leu Pro Ser Lys
        1850                1855                1860

Glu Thr Cys Glu Asn Arg Leu Asp Trp Lys Gln Glu Ser Leu
        1865                1870                1875

Asn Phe Leu Ile Gly Arg Leu Leu Asp Asp Gly Cys Val His Glu
        1880                1885                1890

Ala Ser Arg Val Cys Arg Tyr Phe His Phe Tyr Asn Pro Asp Val
        1895                1900                1905

Ala Leu Val Leu His Cys Arg Ala Leu Ala Ser Gly Glu Ala Ser
        1910                1915                1920

Met Glu Asp Leu His Pro Glu Ile His Ala Leu Leu Gln Ser Ala
        1925                1930                1935

Glu Leu Leu Glu Glu Glu Ala Pro Asp Ile Pro Leu Arg Arg Val
        1940                1945                1950

His Ser Thr Ser Ser Leu Asp Ser Gln Lys Phe Val Thr Val Pro
        1955                1960                1965

Ser Ser Asn Glu Val Val Thr Asn Leu Glu Val Leu Thr Ser Lys
        1970                1975                1980

Cys Leu His Gly Lys Asn Tyr Cys Arg Gln Val Leu Cys Leu Tyr
        1985                1990                1995

Asp Leu Ala Lys Glu Leu Gly Cys Ser Tyr Thr Asp Val Ala Ala
        2000                2005                2010

Gln Asp Gly Glu Ala Met Leu Arg Lys Ile Leu Ala Ser Gln Gln
        2015                2020                2025

Pro Asp Arg Cys Lys Arg Ala Gln Ala Phe Ile Ser Thr Gln Gly
        2030                2035                2040

Leu Lys Pro Asp Thr Val Ala Glu Leu Val Ala Glu Glu Val Thr
        2045                2050                2055

Arg Glu Leu Leu Thr Ser Ser Gln Gly Thr Gly His Lys Gln Met
        2060                2065                2070

Phe Asn Pro Thr Glu Glu Ser Gln Thr Phe Leu Gln Leu Thr Thr
        2075                2080                2085

Leu Cys Gln Asp Arg Thr Leu Val Gly Met Lys Leu Leu Asp Lys
        2090                2095                2100

Ile Ser Ser Val Pro His Gly Glu Leu Ser Cys Thr Thr Glu Leu
        2105                2110                2115

Leu Ile Leu Ala His His Cys Phe Thr Leu Thr Cys His Met Glu
        2120                2125                2130

Gly Ile Ile Arg Val Leu Gln Ala Ala His Met Leu Thr Asp Asn
        2135                2140                2145
```

```
His Leu Pro Pro Val Arg Ser Met Gly Trp Trp Tyr Gly Ser Ser
    2150                2155                2160

Leu Ala Leu Glu Gly Thr Thr Arg Xaa
    2165                2170

<210> SEQ ID NO 162
<211> LENGTH: 2260
<212> TYPE: PRT
<213> ORGANISM: Homo sapiens
<220> FEATURE:
<221> NAME/KEY: misc_feature
<222> LOCATION: (2260)..(2260)
<223> OTHER INFORMATION: Xaa can be any naturally occurring amino acid

<400> SEQUENCE: 162

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320
```

```
Ser Ala Tyr Asn Met Lys Leu Ala Lys Phe Ser Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
                420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
                515                 520                 525

Pro Ile His Ala Leu Glu Ala Gly Ile Glu Asn Arg Gln Leu Asp Thr
                530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
                595                 600                 605

Gln Leu Leu Asn Leu Thr Leu Ser Phe Leu Asn Asn Gln Ile Lys Glu
                610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
                675                 680                 685

Glu Glu Val Ile Ala Ser Ala Ile Leu Asn Asn Lys Ile Pro Glu Ala
                690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
```

-continued

```
                 740                 745                 750
Lys Gly Gln Leu Leu Lys Ile Cys Phe Tyr Thr Thr Asn Lys Asn Ile
             755                 760                 765

Arg Asp Phe Leu Val Glu Ile Leu Lys Glu Lys Asn Tyr Phe Ser Glu
         770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                 805                 810                 815

Trp Ile Lys Glu Gln Asp Phe Phe Lys His Lys Ser Val Leu Asp Ser
             820                 825                 830

Phe Leu Lys Tyr Asp Cys Lys Asp Glu Phe Asn Lys Gln Asp His Arg
         835                 840                 845

Ile Val Leu Asn Trp Ala Leu Trp Trp Asp Gln Leu Thr Gln Glu Ser
     850                 855                 860

Ile Leu Leu Pro Arg Ile Ser Pro Glu Tyr Lys Ser Tyr Ser Pro
865                 870                 875                 880

Glu Ala Leu Trp Arg Tyr Leu Thr Ala Arg His Asp Trp Leu Asn Ile
                 885                 890                 895

Ile Leu Trp Ile Gly Glu Phe Gln Thr Gln His Ser Tyr Ala Ser Leu
             900                 905                 910

Gln Gln Asn Lys Trp Pro Leu Leu Thr Val Asp Val Ile Asn Gln Asn
         915                 920                 925

Thr Ser Cys Asn Asn Tyr Met Arg Asn Glu Ile Leu Asp Lys Leu Ala
     930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                 965                 970                 975

Val Gln Asn Tyr Lys Thr Lys Leu Gly Trp Asp Phe His Ser Gln Phe
             980                 985                 990

Ile Leu Tyr Cys Leu Glu His Ser  Leu Gln His Leu Leu  Tyr Val Tyr
         995                  1000                1005

Leu Asp Cys Tyr Lys Leu Ser  Pro Glu Asn Cys Pro  Phe Leu Glu
    1010                 1015                1020

Lys Lys Glu Leu His Glu Ala  His Pro Trp Phe Glu  Phe Leu Val
    1025                 1030                1035

Gln Cys Arg Gln Val Ala Ser  Asn Leu Thr Asp Pro  Lys Leu Ile
    1040                 1045                1050

Phe Gln Ala Ser Leu Ala Asn  Ala Gln Ile Leu Ile  Pro Thr Asn
    1055                 1060                1065

Gln Ala Ser Val Ser Ser Met  Leu Leu Glu Gly His  Thr Leu Leu
    1070                 1075                1080

Ala Leu Ala Thr Thr Met Tyr  Ser Pro Gly Gly Val  Ser Gln Val
    1085                 1090                1095

Val Gln Asn Glu Glu Asn Glu  Asn Cys Leu Lys Lys  Val Asp Pro
    1100                 1105                1110

Gln Leu Leu Lys Met Ala Leu  Thr Pro Tyr Pro Lys  Leu Lys Thr
    1115                 1120                1125

Ala Leu Phe Pro Gln Cys Thr  Pro Pro Ser Val Leu  Pro Ser Asp
    1130                 1135                1140

Ile Thr Ile Tyr His Leu Ile  Gln Ser Leu Ser Pro  Phe Asp Pro
    1145                 1150                1155
```

```
Ser Arg Leu Phe Gly Trp Gln Ser Ala Asn Thr Leu Ala Ile Gly
    1160                1165                1170

Asp Ala Trp Ser His Leu Pro His Phe Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545
```

```
Leu Leu Leu Val Met Glu Met Tyr Glu Leu Cys Met Phe Phe Arg
    1550            1555            1560

Asn Tyr Lys Glu Ala Glu Ala Lys Leu Leu Glu Phe Gln Lys Ser
    1565            1570            1575

Leu Glu Thr Leu Asn Thr Ala Ala Thr Lys Val His Pro Val Ile
    1580            1585            1590

Pro Ala Met Trp Leu Glu Asp Gln Val Cys Phe Leu Leu Lys Leu
    1595            1600            1605

Met Leu Gln Gln Cys Lys Thr Gln Tyr Glu Leu Gly Lys Leu Leu
    1610            1615            1620

Gln Leu Phe Val Glu Arg Glu His Leu Phe Ser Asp Gly Pro Asp
    1625            1630            1635

Val Lys Lys Leu Cys Ile Leu Cys Gln Ile Leu Lys Asp Thr Ser
    1640            1645            1650

Ile Ala Ile Asn His Thr Ile Ile Thr Ser Tyr Ser Ile Glu Asn
    1655            1660            1665

Leu Gln His Glu Cys Arg Ser Ile Leu Glu Arg Leu Gln Thr Asp
    1670            1675            1680

Gly Gln Phe Ala Leu Ala Arg Arg Val Ala Glu Leu Ala Glu Leu
    1685            1690            1695

Pro Val Asp Asn Leu Val Ile Lys Glu Ile Thr Gln Glu Met Gln
    1700            1705            1710

Thr Leu Lys His Ile Glu Gln Trp Ser Leu Lys Gln Ala Arg Ile
    1715            1720            1725

Asp Phe Trp Lys Lys Cys His Glu Asn Phe Lys Lys Asn Ser Ile
    1730            1735            1740

Ser Ser Lys Ala Ala Ser Ser Phe Phe Ser Thr Gln Ala His Val
    1745            1750            1755

Ala Cys Glu His Pro Thr Gly Trp Ser Ser Met Glu Glu Arg His
    1760            1765            1770

Leu Leu Leu Thr Leu Ala Gly His Trp Leu Ala Gln Glu Asp Val
    1775            1780            1785

Val Pro Leu Asp Lys Leu Glu Glu Leu Glu Lys Gln Ile Trp Leu
    1790            1795            1800

Cys Arg Ile Thr Gln His Thr Leu Gly Arg Asn Gln Glu Glu Thr
    1805            1810            1815

Glu Pro Arg Phe Ser Arg Gln Ile Ser Thr Ser Gly Glu Leu Ser
    1820            1825            1830

Phe Asp Ser Leu Ala Ser Glu Phe Ser Phe Ser Lys Leu Ala Ala
    1835            1840            1845

Leu Asn Thr Ser Lys Tyr Leu Glu Leu Asn Ser Leu Pro Ser Lys
    1850            1855            1860

Glu Thr Cys Glu Asn Arg Leu Asp Trp Lys Glu Gln Glu Ser Leu
    1865            1870            1875

Asn Phe Leu Ile Gly Arg Leu Leu Asp Asp Gly Cys Val His Glu
    1880            1885            1890

Ala Ser Arg Val Cys Arg Tyr Phe His Phe Tyr Asn Pro Asp Val
    1895            1900            1905

Ala Leu Val Leu His Cys Arg Ala Leu Ala Ser Gly Glu Ala Ser
    1910            1915            1920

Met Glu Asp Leu His Pro Glu Ile His Ala Leu Leu Gln Ser Ala
    1925            1930            1935

Glu Leu Leu Glu Glu Glu Ala Pro Asp Ile Pro Leu Arg Arg Val
```

1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Leu Tyr
    1985                1990                1995

Asp Leu Ala Lys Glu Leu Gly Cys Ser Tyr Thr Asp Val Ala Ala
    2000                2005                2010

Gln Asp Gly Glu Ala Met Leu Arg Lys Ile Leu Ala Ser Gln Gln
    2015                2020                2025

Pro Asp Arg Cys Lys Arg Ala Gln Ala Phe Ile Ser Thr Gln Gly
    2030                2035                2040

Leu Lys Pro Asp Thr Val Ala Glu Leu Val Ala Glu Val Thr
    2045                2050                2055

Arg Glu Leu Leu Thr Ser Ser Gln Gly Thr Gly His Lys Gln Met
    2060                2065                2070

Phe Asn Pro Thr Glu Glu Ser Gln Thr Phe Leu Gln Leu Thr Thr
    2075                2080                2085

Leu Cys Gln Asp Arg Thr Leu Val Gly Met Lys Leu Leu Asp Lys
    2090                2095                2100

Ile Ser Ser Val Pro His Gly Glu Leu Ser Cys Thr Thr Glu Leu
    2105                2110                2115

Leu Ile Leu Ala His His Cys Phe Thr Leu Thr Cys His Met Glu
    2120                2125                2130

Gly Ile Ile Arg Val Leu Gln Ala Ala His Met Leu Thr Asp Asn
    2135                2140                2145

His Leu Ala Pro Ser Glu Glu Tyr Gly Leu Val Val Arg Leu Leu
    2150                2155                2160

Thr Gly Ile Gly Arg Tyr Asn Glu Met Thr Tyr Ile Phe Asp Leu
    2165                2170                2175

Leu His Lys Lys His Tyr Phe Glu Val Leu Met Arg Lys Lys Leu
    2180                2185                2190

Asp Pro Ser Gly Thr Leu Lys Thr Ala Leu Leu Asp Tyr Ile Lys
    2195                2200                2205

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ser Leu Ser Pro Gly Arg Thr Ala
    2240                2245                2250

Ser Arg Met Gly Thr Ser Xaa
    2255                2260

<210> SEQ ID NO 163
<211> LENGTH: 2338
<212> TYPE: PRT
<213> ORGANISM: Homo sapiens
<220> FEATURE:
<221> NAME/KEY: misc_feature
<222> LOCATION: (2338)..(2338)
<223> OTHER INFORMATION: Xaa can be any naturally occurring amino acid

<400> SEQUENCE: 163

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

```
Thr Gly Phe Thr Ala Leu Phe Thr Trp Glu Val Glu Arg Met Gly Tyr
            435                 440                 445
Thr Ile Thr Leu Trp Asp Leu Glu Thr Gln Gly Met Gln Cys Ser Ser
        450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
                    485                 490                 495
Thr Gln Glu Glu Phe Leu Asn Arg Leu Met Ile His Gly Ser Ala Ser
                500                 505                 510
Thr Val Asp Thr Leu Cys His Leu Asn Gly Trp Gly Arg Cys Ser Ile
        515                 520                 525
Pro Ile His Ala Leu Glu Ala Gly Ile Glu Asn Arg Gln Leu Asp Thr
        530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
                    565                 570                 575
Leu Arg Asn Val Glu Glu Leu Ile Pro Ala Leu Asp Leu Leu Cys Ser
                580                 585                 590
Ala Ile Arg Glu Ser Tyr Ser Glu Pro Gln Ser Lys His Phe Ser Glu
        595                 600                 605
Gln Leu Leu Asn Leu Thr Leu Ser Phe Leu Asn Asn Gln Ile Lys Glu
        610                 615                 620
Leu Phe Ile His Thr Glu Glu Leu Asp Glu His Leu Gln Lys Gly Val
625                 630                 635                 640
Asn Ile Leu Thr Ser Tyr Ile Asn Glu Leu Arg Thr Phe Met Ile Lys
                    645                 650                 655
Phe Pro Trp Lys Leu Thr Asp Ala Ile Asp Glu Tyr Asp Val His Glu
                660                 665                 670
Asn Val Pro Lys Val Lys Glu Ser Asn Ile Trp Lys Lys Leu Ser Phe
        675                 680                 685
Glu Glu Val Ile Ala Ser Ala Ile Leu Asn Asn Lys Ile Pro Glu Ala
        690                 695                 700
Gln Thr Phe Phe Arg Ile Asp Ser His Ser Ala Gln Lys Leu Glu Glu
705                 710                 715                 720
Leu Ile Gly Ile Gly Leu Asn Leu Val Phe Asp Asn Leu Lys Lys Asn
                    725                 730                 735
Asn Ile Lys Glu Ala Ser Glu Leu Leu Lys Asn Met Gly Phe Asp Val
                740                 745                 750
Lys Gly Gln Leu Leu Lys Ile Cys Phe Tyr Thr Thr Asn Lys Asn Ile
        755                 760                 765
Arg Asp Phe Leu Val Glu Ile Leu Lys Glu Lys Asn Tyr Phe Ser Glu
        770                 775                 780
Lys Glu Lys Arg Thr Ile Asp Phe Val His Gln Val Glu Lys Leu Tyr
785                 790                 795                 800
Leu Gly His Phe Gln Glu Asn Met Gln Ile Gln Ser Phe Pro Arg Tyr
                    805                 810                 815
Trp Ile Lys Glu Gln Asp Phe Lys His Lys Ser Val Leu Asp Ser
                820                 825                 830
Phe Leu Lys Tyr Asp Cys Lys Asp Glu Phe Asn Lys Gln Asp His Arg
        835                 840                 845
Ile Val Leu Asn Trp Ala Leu Trp Trp Asp Gln Leu Thr Gln Glu Ser
```

```
                850               855                860
Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
            930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
                980                 985                 990

Ile Leu Tyr Cys Leu Glu His Ser  Leu Gln His Leu Leu  Tyr Val Tyr
            995                 1000                1005

Leu Asp  Cys Tyr Lys Leu Ser  Pro Glu Asn Cys Pro  Phe Leu Glu
     1010                1015                1020

Lys Lys  Glu Leu His Glu Ala  His Pro Trp Phe Glu  Phe Leu Val
     1025                1030                1035

Gln Cys  Arg Gln Val Ala Ser  Asn Leu Thr Asp Pro  Lys Leu Ile
     1040                1045                1050

Phe Gln  Ala Ser Leu Ala Asn  Ala Gln Ile Leu Ile  Pro Thr Asn
     1055                1060                1065

Gln Ala  Ser Val Ser Ser Met  Leu Leu Glu Gly His  Thr Leu Leu
     1070                1075                1080

Ala Leu  Ala Thr Thr Met Tyr  Ser Pro Gly Gly Val  Ser Gln Val
     1085                1090                1095

Val Gln  Asn Glu Glu Asn Glu  Asn Cys Leu Lys Lys  Val Asp Pro
     1100                1105                1110

Gln Leu  Leu Lys Met Ala Leu  Thr Pro Tyr Pro Lys  Leu Lys Thr
     1115                1120                1125

Ala Leu  Phe Pro Gln Cys Thr  Pro Pro Ser Val Leu  Pro Ser Asp
     1130                1135                1140

Ile Thr  Ile Tyr His Leu Ile  Gln Ser Leu Ser Pro  Phe Asp Pro
     1145                1150                1155

Ser Arg  Leu Phe Gly Trp Gln  Ser Ala Asn Thr Leu  Ala Ile Gly
     1160                1165                1170

Asp Ala  Trp Ser His Leu Pro  His Phe Ser Pro Asp  Leu Val
     1175                1180                1185

Asn Lys  Tyr Ala Ile Val Glu  Arg Leu Asn Phe Ala  Tyr Tyr Leu
     1190                1195                1200

His Asn  Gly Arg Pro Ser Phe  Ala Phe Gly Thr Phe  Leu Val Gln
     1205                1210                1215

Glu Leu  Ile Lys Ser Lys Thr  Pro Lys Gln Leu Ile  Gln Gln Val
     1220                1225                1230

Gly Asn  Glu Ala Tyr Val Ile  Gly Leu Ser Ser Phe  His Ile Pro
     1235                1240                1245

Ser Ile  Gly Ala Ala Cys Val  Cys Phe Leu Glu Leu  Leu Gly Leu
     1250                1255                1260
```

-continued

Asp Ser Leu Lys Leu Arg Val Asp Met Lys Val Ala Asn Ile Ile
1265                1270                1275

Leu Ser Tyr Lys Cys Arg Asn Glu Asp Ala Gln Tyr Ser Phe Ile
1280                1285                1290

Arg Glu Ser Val Ala Glu Lys Leu Ser Lys Leu Ala Asp Gly Glu
1295                1300                1305

Lys Thr Thr Thr Glu Glu Leu Leu Val Leu Leu Glu Glu Gly Thr
1310                1315                1320

Trp Asn Ser Ile Gln Gln Glu Ile Lys Arg Leu Ser Ser Glu
1325                1330                1335

Ser Ser Ser Gln Trp Ala Leu Val Val Gln Phe Cys Arg Leu His
1340                1345                1350

Asn Met Lys Leu Ser Ile Ser Tyr Leu Arg Glu Cys Ala Lys Ala
1355                1360                1365

Asn Asp Trp Leu Gln Phe Ile Ile His Ser Gln Leu His Asn Tyr
1370                1375                1380

His Pro Ala Glu Val Lys Ser Leu Ile Gln Tyr Phe Ser Pro Val
1385                1390                1395

Ile Gln Asp His Leu Arg Leu Ala Phe Glu Asn Leu Pro Ser Val
1400                1405                1410

Pro Thr Ser Lys Met Asp Ser Asp Gln Val Cys Asn Lys Cys Pro
1415                1420                1425

Gln Glu Leu Gln Gly Ser Lys Gln Glu Met Thr Asp Leu Phe Glu
1430                1435                1440

Ile Leu Leu Gln Cys Ser Glu Glu Pro Asp Ser Trp His Trp Leu
1445                1450                1455

Leu Val Glu Ala Val Lys Gln Gln Ala Pro Ile Leu Ser Val Leu
1460                1465                1470

Ala Ser Cys Leu Gln Gly Ala Ser Ala Ile Ser Cys Leu Cys Val
1475                1480                1485

Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515

Asp Leu Ser Val Ile Trp Arg Thr Leu Leu Thr Arg Gln Lys Ser
1520                1525                1530

Lys Thr Leu Ile Arg Gly Phe Gln Leu Phe Phe Lys Asp Ser Pro
1535                1540                1545

Leu Leu Leu Val Met Glu Met Tyr Glu Leu Cys Met Phe Phe Arg
1550                1555                1560

Asn Tyr Lys Glu Ala Glu Ala Lys Leu Leu Glu Phe Gln Lys Ser
1565                1570                1575

Leu Glu Thr Leu Asn Thr Ala Ala Thr Lys Val His Pro Val Ile
1580                1585                1590

Pro Ala Met Trp Leu Glu Asp Gln Val Cys Phe Leu Leu Lys Leu
1595                1600                1605

Met Leu Gln Gln Cys Lys Thr Gln Tyr Glu Leu Gly Lys Leu Leu
1610                1615                1620

Gln Leu Phe Val Glu Arg Glu His Leu Phe Ser Asp Gly Pro Asp
1625                1630                1635

Val Lys Lys Leu Cys Ile Leu Cys Gln Ile Leu Lys Asp Thr Ser
1640                1645                1650

```
Ile Ala Ile Asn His Thr Ile Ile Thr Ser Tyr Ser Ile Glu Asn
1655                1660                1665

Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

Asp Phe Trp Lys Lys Cys His Glu Asn Phe Lys Lys Asn Ser Ile
1730                1735                1740

Ser Ser Lys Ala Ala Ser Ser Phe Phe Ser Thr Gln Ala His Val
1745                1750                1755

Ala Cys Glu His Pro Thr Gly Trp Ser Ser Met Glu Glu Arg His
1760                1765                1770

Leu Leu Leu Thr Leu Ala Gly His Trp Leu Ala Gln Glu Asp Val
1775                1780                1785

Val Pro Leu Asp Lys Leu Glu Glu Leu Glu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Glu Leu Ser
1820                1825                1830

Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Glu Gln Glu Ser Leu
1865                1870                1875

Asn Phe Leu Ile Gly Arg Leu Leu Asp Asp Gly Cys Val His Glu
1880                1885                1890

Ala Ser Arg Val Cys Arg Tyr Phe His Phe Tyr Asn Pro Asp Val
1895                1900                1905

Ala Leu Val Leu His Cys Arg Ala Leu Ala Ser Gly Glu Ala Ser
1910                1915                1920

Met Glu Asp Leu His Pro Glu Ile His Ala Leu Leu Gln Ser Ala
1925                1930                1935

Glu Leu Leu Glu Glu Glu Ala Pro Asp Ile Pro Leu Arg Arg Val
1940                1945                1950

His Ser Thr Ser Ser Leu Asp Ser Gln Lys Phe Val Thr Val Pro
1955                1960                1965

Ser Ser Asn Glu Val Val Thr Asn Leu Glu Val Leu Thr Ser Lys
1970                1975                1980

Cys Leu His Gly Lys Asn Tyr Cys Arg Gln Val Leu Cys Leu Tyr
1985                1990                1995

Asp Leu Ala Lys Glu Leu Gly Cys Ser Tyr Thr Asp Val Ala Ala
2000                2005                2010

Gln Asp Gly Glu Ala Met Leu Arg Lys Ile Leu Ala Ser Gln Gln
2015                2020                2025

Pro Asp Arg Cys Lys Arg Ala Gln Ala Phe Ile Ser Thr Gln Gly
2030                2035                2040

Leu Lys Pro Asp Thr Val Ala Glu Leu Val Ala Glu Glu Val Thr
```

```
            2045               2050                2055
Arg Glu Leu Leu Thr Ser Ser Gln Gly Thr Gly His Lys Gln Met
        2060               2065                2070

Phe Asn Pro Thr Glu Glu Ser Gln Thr Phe Leu Gln Leu Thr Thr
        2075               2080                2085

Leu Cys Gln Asp Arg Thr Leu Val Gly Met Lys Leu Leu Asp Lys
        2090               2095                2100

Ile Ser Ser Val Pro His Gly Glu Leu Ser Cys Thr Thr Glu Leu
        2105               2110                2115

Leu Ile Leu Ala His His Cys Phe Thr Leu Thr Cys His Met Glu
        2120               2125                2130

Gly Ile Ile Arg Val Leu Gln Ala Ala His Met Leu Thr Asp Asn
        2135               2140                2145

His Leu Ala Pro Ser Glu Glu Tyr Gly Leu Val Val Arg Leu Leu
        2150               2155                2160

Thr Gly Ile Gly Arg Tyr Asn Glu Met Thr Tyr Ile Phe Asp Leu
        2165               2170                2175

Leu His Lys Lys His Tyr Phe Glu Val Leu Met Arg Lys Lys Leu
        2180               2185                2190

Asp Pro Ser Gly Thr Leu Lys Thr Ala Leu Leu Asp Tyr Ile Lys
        2195               2200                2205

Arg Cys Arg Pro Gly Asp Ser Glu Lys His Asn Met Ile Ala Leu
        2210               2215                2220

Cys Phe Ser Met Cys Arg Glu Ile Gly Glu Asn His Glu Ala Ala
        2225               2230                2235

Ala Arg Ile Gln Leu Lys Leu Ile Glu Ser Gln Pro Trp Glu Asp
        2240               2245                2250

Ser Leu Lys Asp Gly His Gln Leu Lys Gln Leu Leu Lys Ala
        2255               2260                2265

Leu Thr Leu Met Leu Asp Ala Ala Glu Leu Cys Gln Gly Leu Leu
        2270               2275                2280

Cys Ala Thr Gly Pro Ala Leu Ser Ala Ala His Gln Val Asp Asn
        2285               2290                2295

Ser Ala Asp Ser Leu Ser Glu His Trp Pro Glu His Asn Ala His
        2300               2305                2310

Gln Leu Gly Pro Pro Gln Ala Asp Gly Leu Tyr Ser Gly Pro Thr
        2315               2320                2325

Ser Val Leu Pro Gly Phe Tyr Cys Gly Xaa
        2330               2335

<210> SEQ ID NO 164
<211> LENGTH: 2349
<212> TYPE: PRT
<213> ORGANISM: Homo sapiens
<220> FEATURE:
<221> NAME/KEY: misc_feature
<222> LOCATION: (2349)..(2349)
<223> OTHER INFORMATION: Xaa can be any naturally occurring amino acid

<400> SEQUENCE: 164

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
        35                  40                  45
```

```
Thr Gln Pro Glu Ala Leu Gly Ser Leu Thr Ala Ala Gly Ser Leu Gln
 50                  55                  60

Val Leu Ser Leu Thr Pro Gly Ser Arg Gly Gly Arg Cys Cys Leu
 65                  70                  75                  80

Glu Gly Pro Phe Trp His Phe Leu Trp Glu Asp Ser Arg Asn Ser Ser
                     85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
                115                 120                 125

Ile Leu Tyr Ser Cys Ser Arg Glu Ala Leu Gln Lys Leu Ile Asp Asp
                130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
                290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
                370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
                435                 440                 445

Thr Ile Thr Leu Trp Asp Leu Glu Thr Gln Gly Met Gln Cys Ser Ser
                450                 455                 460
```

-continued

```
Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
        500                 505                 510

Thr Val Asp Thr Leu Cys His Leu Asn Gly Trp Gly Arg Cys Ser Ile
    515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
        610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
            805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
        850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
```

-continued

```
                885                 890                 895
Ile Leu Trp Ile Gly Glu Phe Gln Thr Gln His Ser Tyr Ala Ser Leu
                900                 905                 910
Gln Gln Asn Lys Trp Pro Leu Leu Thr Val Asp Val Ile Asn Gln Asn
                915                 920                 925
Thr Ser Cys Asn Asn Tyr Met Arg Asn Glu Ile Leu Asp Lys Leu Ala
                930                 935                 940
Arg Asn Gly Val Phe Leu Ala Ser Glu Leu Glu Asp Phe Glu Cys Phe
945                 950                 955                 960
Leu Leu Arg Leu Ser Arg Ile Gly Gly Val Ile Gln Asp Thr Leu Pro
                965                 970                 975
Val Gln Asn Tyr Lys Thr Lys Glu Gly Trp Asp Phe His Ser Gln Phe
                980                 985                 990
Ile Leu Tyr Cys Leu Glu His Ser  Leu Gln His Leu Leu  Tyr Val Tyr
                995                 1000                1005
Leu Asp  Cys Tyr Lys Leu Ser  Pro Glu Asn Cys Pro  Phe Leu Glu
         1010                1015                1020
Lys Lys  Glu Leu His Glu Ala  His Pro Trp Phe Glu  Phe Leu Val
         1025                1030                1035
Gln Cys  Arg Gln Val Ala Ser  Asn Leu Thr Asp Pro  Lys Leu Ile
         1040                1045                1050
Phe Gln  Ala Ser Leu Ala Asn  Ala Gln Ile Leu Ile  Pro Thr Asn
         1055                1060                1065
Gln Ala  Ser Val Ser Ser Met  Leu Leu Glu Gly His  Thr Leu Leu
         1070                1075                1080
Ala Leu  Ala Thr Thr Met Tyr  Ser Pro Gly Gly Val  Ser Gln Val
         1085                1090                1095
Val Gln  Asn Glu Glu Asn Glu  Asn Cys Leu Lys Lys  Val Asp Pro
         1100                1105                1110
Gln Leu  Leu Lys Met Ala Leu  Thr Pro Tyr Pro Lys  Leu Lys Thr
         1115                1120                1125
Ala Leu  Phe Pro Gln Cys Thr  Pro Pro Ser Val Leu  Pro Ser Asp
         1130                1135                1140
Ile Thr  Ile Tyr His Leu Ile  Gln Ser Leu Ser Pro  Phe Asp Pro
         1145                1150                1155
Ser Arg  Leu Phe Gly Trp Gln  Ser Ala Asn Thr Leu  Ala Ile Gly
         1160                1165                1170
Asp Ala  Trp Ser His Leu Pro  His Phe Ser Ser Pro  Asp Leu Val
         1175                1180                1185
Asn Lys  Tyr Ala Ile Val Glu  Arg Leu Asn Phe Ala  Tyr Tyr Leu
         1190                1195                1200
His Asn  Gly Arg Pro Ser Phe  Ala Phe Gly Thr Phe  Leu Val Gln
         1205                1210                1215
Glu Leu  Ile Lys Ser Lys Thr  Pro Lys Gln Leu Ile  Gln Gln Val
         1220                1225                1230
Gly Asn  Glu Ala Tyr Val Ile  Gly Leu Ser Ser Phe  His Ile Pro
         1235                1240                1245
Ser Ile  Gly Ala Ala Cys Val  Cys Phe Leu Glu Leu  Leu Gly Leu
         1250                1255                1260
Asp Ser  Leu Lys Leu Arg Val  Asp Met Lys Val Ala  Asn Ile Ile
         1265                1270                1275
Leu Ser  Tyr Lys Cys Arg Asn  Glu Asp Ala Gln Tyr  Ser Phe Ile
         1280                1285                1290
```

```
Arg Glu Ser Val Ala Glu Lys Leu Ser Lys Leu Ala Asp Gly Glu
1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680
```

-continued

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

Asp Phe Trp Lys Lys Cys His Glu Asn Phe Lys Lys Asn Ser Ile
1730                1735                1740

Ser Ser Lys Ala Ala Ser Ser Phe Phe Ser Thr Gln Ala His Val
1745                1750                1755

Ala Cys Glu His Pro Thr Gly Trp Ser Ser Met Glu Glu Arg His
1760                1765                1770

Leu Leu Leu Thr Leu Ala Gly His Trp Leu Ala Gln Glu Asp Val
1775                1780                1785

Val Pro Leu Asp Lys Leu Glu Glu Leu Glu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Glu Leu Ser
1820                1825                1830

Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Glu Gln Glu Ser Leu
1865                1870                1875

Asn Phe Leu Ile Gly Arg Leu Leu Asp Asp Gly Cys Val His Glu
1880                1885                1890

Ala Ser Arg Val Cys Arg Tyr Phe His Phe Tyr Asn Pro Asp Val
1895                1900                1905

Ala Leu Val Leu His Cys Arg Ala Leu Ala Ser Gly Glu Ala Ser
1910                1915                1920

Met Glu Asp Leu His Pro Glu Ile His Ala Leu Leu Gln Ser Ala
1925                1930                1935

Glu Leu Leu Glu Glu Glu Ala Pro Asp Ile Pro Leu Arg Arg Val
1940                1945                1950

His Ser Thr Ser Ser Leu Asp Ser Gln Lys Phe Val Thr Val Pro
1955                1960                1965

Ser Ser Asn Glu Val Val Thr Asn Leu Glu Val Leu Thr Ser Lys
1970                1975                1980

Cys Leu His Gly Lys Asn Tyr Cys Arg Gln Val Leu Cys Leu Tyr
1985                1990                1995

Asp Leu Ala Lys Glu Leu Gly Cys Ser Tyr Thr Asp Val Ala Ala
2000                2005                2010

Gln Asp Gly Glu Ala Met Leu Arg Lys Ile Leu Ala Ser Gln Gln
2015                2020                2025

Pro Asp Arg Cys Lys Arg Ala Gln Ala Phe Ile Ser Thr Gln Gly
2030                2035                2040

Leu Lys Pro Asp Thr Val Ala Glu Leu Val Ala Glu Glu Val Thr
2045                2050                2055

Arg Glu Leu Leu Thr Ser Ser Gln Gly Thr Gly His Lys Gln Met
2060                2065                2070

Phe Asn Pro Thr Glu Glu Ser Gln Thr Phe Leu Gln Leu Thr Thr

```
                    2075                2080                2085
Leu Cys Gln Asp Arg Thr Leu Val Gly Met Lys Leu Leu Asp Lys
        2090                2095                2100
Ile Ser Ser Val Pro His Gly Glu Leu Ser Cys Thr Thr Glu Leu
        2105                2110                2115
Leu Ile Leu Ala His His Cys Phe Thr Leu Thr Cys His Met Glu
        2120                2125                2130
Gly Ile Ile Arg Val Leu Gln Ala Ala His Met Leu Thr Asp Asn
        2135                2140                2145
His Leu Ala Pro Ser Glu Glu Tyr Gly Leu Val Val Arg Leu Leu
        2150                2155                2160
Thr Gly Ile Gly Arg Tyr Asn Glu Met Thr Tyr Ile Phe Asp Leu
        2165                2170                2175
Leu His Lys Lys His Tyr Phe Glu Val Leu Met Arg Lys Lys Leu
        2180                2185                2190
Asp Pro Ser Gly Thr Leu Lys Thr Ala Leu Leu Asp Tyr Ile Lys
        2195                2200                2205
Arg Cys Arg Pro Gly Asp Ser Glu Lys His Asn Met Ile Ala Leu
        2210                2215                2220
Cys Phe Ser Met Cys Arg Glu Ile Gly Glu Asn His Glu Ala Ala
        2225                2230                2235
Ala Arg Ile Gln Leu Lys Leu Ile Glu Ser Gln Pro Trp Glu Asp
        2240                2245                2250
Ser Leu Lys Asp Gly His Gln Leu Lys Gln Leu Leu Lys Ala
        2255                2260                2265
Leu Thr Leu Met Leu Asp Ala Ala Glu Ser Tyr Ala Lys Asp Ser
        2270                2275                2280
Cys Val Arg Gln Ala Gln His Cys Gln Arg Leu Thr Lys Leu Ile
        2285                2290                2295
Thr Leu Gln Ile His Phe Leu Asn Thr Gly Gln Asn Thr Met Leu
        2300                2305                2310
Ile Asn Leu Gly Arg His Lys Leu Met Asp Cys Ile Leu Ala Leu
        2315                2320                2325
Pro Arg Phe Tyr Gln Ala Ser Ile Val Ala Glu Ala Tyr Asp Phe
        2330                2335                2340
Cys Ser Arg Leu Gly Xaa
        2345

<210> SEQ ID NO 165
<211> LENGTH: 2443
<212> TYPE: PRT
<213> ORGANISM: homo sapiens

<400> SEQUENCE: 165

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Gly Arg Cys Cys Leu
65                  70                  75                  80
```

-continued

```
Glu Gly Pro Phe Trp His Phe Leu Trp Glu Asp Ser Arg Asn Ser Ser
                 85                  90                  95
Thr Pro Thr Glu Lys Pro Lys Leu Leu Ala Leu Gly Glu Asn Tyr Glu
            100                 105                 110
Leu Leu Ile Tyr Glu Phe Asn Leu Lys Asp Gly Arg Cys Asp Ala Thr
            115                 120                 125
Ile Leu Tyr Ser Cys Ser Arg Glu Ala Leu Gln Lys Leu Ile Asp Asp
            130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
            165                 170                 175
Ile Phe Pro Glu Arg Asp Ala Ala Ile Arg Val Leu Asn Cys Phe Thr
            180                 185                 190
Leu Pro Leu Pro Ala Gln Ala Val Asp Met Ile Ile Asp Thr Gln Leu
            195                 200                 205
Cys Arg Gly Ile Leu Phe Val Leu Ser Ser Leu Gly Trp Ile Tyr Ile
            210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Glu Pro Ala Lys Ile
            245                 250                 255
Ser Ser Phe Thr Ser Leu Lys Val Ser Gln Asp Leu Asp Val Ala Val
            260                 265                 270
Ile Val Ser Ser Ser Asn Ser Ala Val Ala Leu Asn Leu Asn Leu Tyr
            275                 280                 285
Phe Arg Gln His Pro Gly His Leu Leu Cys Glu Arg Ile Leu Glu Asp
            290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
            325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
            355                 360                 365
Leu Glu Ser Pro Glu Ser Gly Asn His Ser Thr Ser Val Gln Ser Trp
            370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
            405                 410                 415
His Ile Ser Glu Gln Glu Pro Ile Glu Leu Lys Cys Val Ser Val
            420                 425                 430
Thr Gly Phe Thr Ala Leu Phe Thr Trp Glu Val Glu Arg Met Gly Tyr
            435                 440                 445
Thr Ile Thr Leu Trp Asp Leu Glu Thr Gln Gly Met Gln Cys Ser Ser
            450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
            485                 490                 495
Thr Gln Glu Glu Phe Leu Asn Arg Leu Met Ile His Gly Ser Ala Ser
```

```
                500             505             510
Thr Val Asp Thr Leu Cys His Leu Asn Gly Trp Gly Arg Cys Ser Ile
            515                 520             525

Pro Ile His Ala Leu Glu Ala Gly Ile Glu Asn Arg Gln Leu Asp Thr
            530                 535             540

Val Asn Phe Phe Leu Lys Ser Lys Glu Asn Leu Phe Asn Pro Ser Ser
545             550             555                 560

Lys Ser Ser Val Ser Asp Gln Phe Asp His Leu Ser Ser His Leu Tyr
                565             570             575

Leu Arg Asn Val Glu Glu Leu Ile Pro Ala Leu Asp Leu Leu Cys Ser
            580                 585             590

Ala Ile Arg Glu Ser Tyr Ser Glu Pro Gln Ser Lys His Phe Ser Glu
            595                 600             605

Gln Leu Leu Asn Leu Thr Leu Ser Phe Leu Asn Asn Gln Ile Lys Glu
            610                 615             620

Leu Phe Ile His Thr Glu Glu Leu Asp Glu His Leu Gln Lys Gly Val
625             630             635                 640

Asn Ile Leu Thr Ser Tyr Ile Asn Glu Leu Arg Thr Phe Met Ile Lys
                645             650             655

Phe Pro Trp Lys Leu Thr Asp Ala Ile Asp Glu Tyr Asp Val His Glu
            660                 665             670

Asn Val Pro Lys Val Lys Glu Ser Asn Ile Trp Lys Lys Leu Ser Phe
            675                 680             685

Glu Glu Val Ile Ala Ser Ala Ile Leu Asn Asn Lys Ile Pro Glu Ala
            690                 695             700

Gln Thr Phe Phe Arg Ile Asp Ser His Ser Ala Gln Lys Leu Glu Glu
705             710             715                 720

Leu Ile Gly Ile Gly Leu Asn Leu Val Phe Asp Asn Leu Lys Lys Asn
            725                 730             735

Asn Ile Lys Glu Ala Ser Glu Leu Leu Lys Asn Met Gly Phe Asp Val
            740                 745             750

Lys Gly Gln Leu Leu Lys Ile Cys Phe Tyr Thr Thr Asn Lys Asn Ile
            755                 760             765

Arg Asp Phe Leu Val Glu Ile Leu Lys Glu Lys Asn Tyr Phe Ser Glu
770             775             780

Lys Glu Lys Arg Thr Ile Asp Phe Val His Gln Val Glu Lys Leu Tyr
785             790             795                 800

Leu Gly His Phe Gln Glu Asn Met Gln Ile Gln Ser Phe Pro Arg Tyr
            805                 810             815

Trp Ile Lys Glu Gln Asp Phe Phe Lys His Lys Ser Val Leu Asp Ser
            820                 825             830

Phe Leu Lys Tyr Asp Cys Lys Asp Glu Phe Asn Lys Gln Asp His Arg
            835                 840             845

Ile Val Leu Asn Trp Ala Leu Trp Trp Asp Gln Leu Thr Gln Glu Ser
            850                 855             860

Ile Leu Leu Pro Arg Ile Ser Pro Glu Glu Tyr Lys Ser Tyr Ser Pro
865             870             875                 880

Glu Ala Leu Trp Arg Tyr Leu Thr Ala Arg His Asp Trp Leu Asn Ile
            885                 890             895

Ile Leu Trp Ile Gly Glu Phe Gln Thr Gln His Ser Tyr Ala Ser Leu
            900                 905             910

Gln Gln Asn Lys Trp Pro Leu Leu Thr Val Asp Val Ile Asn Gln Asn
            915                 920             925
```

```
Thr Ser Cys Asn Asn Tyr Met Arg Asn Glu Ile Leu Asp Lys Leu Ala
    930                 935                 940

Gly Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
        995                1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320
```

```
Trp Asn Ser Ile Gln Gln Gln Glu Ile Lys Arg Leu Ser Ser Glu
1325                1330                1335

Ser Ser Ser Gln Trp Ala Leu Val Val Gln Phe Cys Arg Leu His
1340                1345                1350

Asn Met Lys Leu Ser Ile Ser Tyr Leu Arg Glu Cys Ala Lys Ala
1355                1360                1365

Asn Asp Trp Leu Gln Phe Ile Ile His Ser Gln Leu His Asn Tyr
1370                1375                1380

His Pro Ala Glu Val Lys Ser Leu Ile Gln Tyr Phe Ser Pro Val
1385                1390                1395

Ile Gln Asp His Leu Arg Leu Ala Phe Glu Asn Leu Pro Ser Val
1400                1405                1410

Pro Thr Ser Lys Met Asp Ser Asp Gln Val Cys Asn Lys Cys Pro
1415                1420                1425

Gln Glu Leu Gln Gly Ser Lys Gln Glu Met Thr Asp Leu Phe Glu
1430                1435                1440

Ile Leu Leu Gln Cys Ser Glu Glu Pro Asp Ser Trp His Trp Leu
1445                1450                1455

Leu Val Glu Ala Val Lys Gln Gln Ala Pro Ile Leu Ser Val Leu
1460                1465                1470

Ala Ser Cys Leu Gln Gly Ala Ser Ala Ile Ser Cys Leu Cys Val
1475                1480                1485

Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515

Asp Leu Ser Val Ile Trp Arg Thr Leu Leu Thr Arg Gln Lys Ser
1520                1525                1530

Lys Thr Leu Ile Arg Gly Phe Gln Leu Phe Phe Lys Asp Ser Pro
1535                1540                1545

Leu Leu Leu Val Met Glu Met Tyr Glu Leu Cys Met Phe Phe Arg
1550                1555                1560

Asn Tyr Lys Glu Ala Glu Ala Lys Leu Leu Glu Phe Gln Lys Ser
1565                1570                1575

Leu Glu Thr Leu Asn Thr Ala Ala Thr Lys Val His Pro Val Ile
1580                1585                1590

Pro Ala Met Trp Leu Glu Asp Gln Val Cys Phe Leu Leu Lys Leu
1595                1600                1605

Met Leu Gln Gln Cys Lys Thr Gln Tyr Glu Leu Gly Lys Leu Leu
1610                1615                1620

Gln Leu Phe Val Glu Arg Glu His Leu Phe Ser Asp Gly Pro Asp
1625                1630                1635

Val Lys Lys Leu Cys Ile Leu Cys Gln Ile Leu Lys Asp Thr Ser
1640                1645                1650

Ile Ala Ile Asn His Thr Ile Ile Thr Ser Tyr Ser Ile Glu Asn
1655                1660                1665

Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
```

-continued

```
            1715                1720                1725
Asp Phe Trp Lys Lys Cys His Glu Asn Phe Lys Lys Asn Ser Ile
        1730                1735                1740
Ser Ser Lys Ala Ala Ser Ser Phe Phe Ser Thr Gln Ala His Val
        1745                1750                1755
Ala Cys Glu His Pro Thr Gly Trp Ser Ser Met Glu Arg His
        1760                1765                1770
Leu Leu Leu Thr Leu Ala Gly His Trp Leu Ala Gln Glu Asp Val
        1775                1780                1785
Val Pro Leu Asp Lys Leu Glu Glu Leu Glu Lys Gln Ile Trp Leu
        1790                1795                1800
Cys Arg Ile Thr Gln His Thr Leu Gly Arg Asn Gln Glu Glu Thr
        1805                1810                1815
Glu Pro Arg Phe Ser Arg Gln Ile Ser Thr Ser Gly Glu Leu Ser
        1820                1825                1830
Phe Asp Ser Leu Ala Ser Glu Phe Ser Phe Ser Lys Leu Ala Ala
        1835                1840                1845
Leu Asn Thr Ser Lys Tyr Leu Glu Leu Asn Ser Leu Pro Ser Lys
        1850                1855                1860
Glu Thr Cys Glu Asn Arg Leu Asp Trp Lys Glu Gln Glu Ser Leu
        1865                1870                1875
Asn Phe Leu Ile Gly Arg Leu Leu Asp Asp Gly Cys Val His Glu
        1880                1885                1890
Ala Ser Arg Val Cys Arg Tyr Phe His Phe Tyr Asn Pro Asp Val
        1895                1900                1905
Ala Leu Val Leu His Cys Arg Ala Leu Ala Ser Gly Glu Ala Ser
        1910                1915                1920
Met Glu Asp Leu His Pro Glu Ile His Ala Leu Leu Gln Ser Ala
        1925                1930                1935
Glu Leu Leu Glu Glu Glu Ala Pro Asp Ile Pro Leu Arg Arg Val
        1940                1945                1950
His Ser Thr Ser Ser Leu Asp Ser Gln Lys Phe Val Thr Val Pro
        1955                1960                1965
Ser Ser Asn Glu Val Val Thr Asn Leu Glu Val Leu Thr Ser Lys
        1970                1975                1980
Cys Leu His Gly Lys Asn Tyr Cys Arg Gln Val Leu Cys Leu Tyr
        1985                1990                1995
Asp Leu Ala Lys Glu Leu Gly Cys Ser Tyr Thr Asp Val Ala Ala
        2000                2005                2010
Gln Asp Gly Glu Ala Met Leu Arg Lys Ile Leu Ala Ser Gln Gln
        2015                2020                2025
Pro Asp Arg Cys Lys Arg Ala Gln Ala Phe Ile Ser Thr Gln Gly
        2030                2035                2040
Leu Lys Pro Asp Thr Val Ala Glu Leu Val Ala Glu Glu Val Thr
        2045                2050                2055
Arg Glu Leu Leu Thr Ser Ser Gln Gly Thr Gly His Lys Gln Met
        2060                2065                2070
Phe Asn Pro Thr Glu Glu Ser Gln Thr Phe Leu Gln Leu Thr Thr
        2075                2080                2085
Leu Cys Gln Asp Arg Thr Leu Val Gly Met Lys Leu Leu Asp Lys
        2090                2095                2100
Ile Ser Ser Val Pro His Gly Glu Leu Ser Cys Thr Thr Glu Leu
        2105                2110                2115
```

Leu Ile Leu Ala His His Cys Phe Thr Leu Thr Cys His Met Glu
2120                2125                2130

Gly Ile Ile Arg Val Leu Gln Ala Ala His Met Leu Thr Asp Asn
    2135                2140                2145

His Leu Ala Pro Ser Glu Glu Tyr Gly Leu Val Val Arg Leu Leu
2150                2155                2160

Thr Gly Ile Gly Arg Tyr Asn Glu Met Thr Tyr Ile Phe Asp Leu
2165                2170                2175

Leu His Lys Lys His Tyr Phe Glu Val Leu Met Arg Lys Lys Leu
2180                2185                2190

Asp Pro Ser Gly Thr Leu Lys Thr Ala Leu Leu Asp Tyr Ile Lys
2195                2200                2205

Arg Cys Arg Pro Gly Asp Ser Glu Lys His Asn Met Ile Ala Leu
2210                2215                2220

Cys Phe Ser Met Cys Arg Glu Ile Gly Glu Asn His Glu Ala Ala
2225                2230                2235

Ala Arg Ile Gln Leu Lys Leu Ile Glu Ser Gln Pro Trp Glu Asp
2240                2245                2250

Ser Leu Lys Asp Gly His Gln Leu Lys Gln Leu Leu Lys Ala
2255                2260                2265

Leu Thr Leu Met Leu Asp Ala Ala Glu Ser Tyr Ala Lys Asp Ser
2270                2275                2280

Cys Val Arg Gln Ala Gln His Cys Gln Arg Leu Thr Lys Leu Ile
2285                2290                2295

Thr Leu Gln Ile His Phe Leu Asn Thr Gly Gln Asn Thr Met Leu
2300                2305                2310

Ile Asn Leu Gly Arg His Lys Leu Met Asp Cys Ile Leu Ala Leu
2315                2320                2325

Pro Arg Phe Tyr Gln Ala Ser Ile Val Ala Glu Ala Tyr Asp Phe
2330                2335                2340

Val Pro Asp Trp Ala Glu Ile Leu Tyr Gln Gln Val Ile Leu Lys
2345                2350                2355

Gly Asp Phe Asn Tyr Leu Glu Glu Phe Lys Gln Arg Leu Leu
2360                2365                2370

Lys Ser Ser Ile Phe Glu Glu Ile Ser Lys Lys Tyr Lys Gln His
2375                2380                2385

Gln Pro Thr Asp Met Val Met Glu Asn Leu Lys Lys Leu Leu Thr
2390                2395                2400

Tyr Cys Glu Asp Val Tyr Leu Tyr Tyr Lys Leu Ala Tyr Glu His
2405                2410                2415

Lys Phe Tyr Glu Ile Val Asn Val Leu Leu Lys Asp Pro Gln Thr
2420                2425                2430

Gly Cys Cys Leu Lys Asp Met Leu Ala Gly
2435                2440

<210> SEQ ID NO 166
<211> LENGTH: 245
<212> TYPE: PRT
<213> ORGANISM: homo sapiens

<400> SEQUENCE: 166

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro

```
                20              25              30
Val Pro Ala Glu Ala Met Gly Gln Leu Gly Ser Arg Ala Gln Leu Arg
            35                  40                  45
Thr Gln Pro Glu Ala Leu Gly Ser Leu Thr Ala Ala Gly Ser Leu Gln
        50                  55                  60
Val Leu Ser Leu Thr Pro Gly Ser Arg Gly Gly Arg Cys Cys Leu
65                  70                  75                  80
Glu Gly Pro Phe Trp His Phe Leu Trp Glu Asp Ser Arg Asn Ser Ser
                85                  90                  95
Thr Pro Thr Glu Lys Pro Lys Leu Leu Ala Leu Gly Glu Asn Tyr Glu
            100                 105                 110
Leu Leu Ile Tyr Glu Phe Asn Leu Lys Asp Gly Arg Cys Asp Ala Thr
        115                 120                 125
Ile Leu Tyr Ser Cys Ser Arg Glu Ala Leu Gln Lys Leu Ile Asp Asp
    130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
            180                 185                 190
Leu Pro Leu Pro Ala Gln Ala Val Asp Met Ile Ile Asp Thr Gln Leu
        195                 200                 205
Cys Arg Gly Ile Leu Phe Val Leu Ser Ser Leu Gly Trp Ile Tyr Ile
    210                 215                 220
Phe Asp Val Val Asp Gly Thr Tyr Val Ala Arg Gly Phe Ser Thr Ser
225                 230                 235                 240
Gln Arg Arg His Val
            245

<210> SEQ ID NO 167
<211> LENGTH: 427
<212> TYPE: PRT
<213> ORGANISM: Homo sapiens

<400> SEQUENCE: 167

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30
Val Pro Ala Glu Ala Met Gly Gln Leu Gly Ser Arg Ala Gln Leu Arg
        35                  40                  45
Thr Gln Pro Glu Ala Leu Gly Ser Leu Thr Ala Ala Gly Ser Leu Gln
    50                  55                  60
Val Leu Ser Leu Thr Pro Gly Ser Arg Gly Gly Arg Cys Cys Leu
65                  70                  75                  80
Glu Gly Pro Phe Trp His Phe Leu Trp Glu Asp Ser Arg Asn Ser Ser
                85                  90                  95
Thr Pro Thr Glu Lys Pro Lys Leu Leu Ala Leu Gly Glu Asn Tyr Glu
            100                 105                 110
Leu Leu Ile Tyr Glu Phe Asn Leu Lys Asp Gly Arg Cys Asp Ala Thr
        115                 120                 125
Ile Leu Tyr Ser Cys Ser Arg Glu Ala Leu Gln Lys Leu Ile Asp Asp
    130                 135                 140
```

```
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
            165                 170                 175

Ile Phe Pro Glu Arg Asp Ala Ala Ile Arg Val Leu Asn Cys Phe Thr
        180                 185                 190

Leu Pro Leu Pro Ala Gln Ala Val Asp Met Ile Ile Asp Thr Gln Leu
    195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu
                420                 425

<210> SEQ ID NO 168
<211> LENGTH: 555
<212> TYPE: PRT
<213> ORGANISM: Homo sapiens

<400> SEQUENCE: 168

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95
```

```
Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Leu
465                 470                 475                 480

Cys Phe Val Leu Thr Glu Asn Gly Leu Ser Asp Phe Val Trp Phe Asp
                485                 490                 495

Ser Arg Arg Val Phe Lys Gln Thr His Asp Pro Trp Lys Cys Gln His
            500                 505                 510
```

-continued

```
Cys Gly His Ser Leu Ser Ser Gln Trp Leu Gly Lys Val Leu Asn Ser
            515                 520                 525

His Thr Cys Thr Arg Gly Arg Asp Arg Lys Ser Ser Ala Gly His Ser
            530                 535                 540

Lys Phe Leu Phe Glu Glu Gln Gly Lys Ser Phe
545                 550                 555

<210> SEQ ID NO 169
<211> LENGTH: 576
<212> TYPE: PRT
<213> ORGANISM: Homo sapiens

<400> SEQUENCE: 169

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335
```

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Leu Ile His Pro Gln
545                 550                 555                 560

Asn Leu Leu Tyr Leu Ile Ser Leu Ile Thr Cys His Pro Ile Tyr Ile
                565                 570                 575

<210> SEQ ID NO 170
<211> LENGTH: 559
<212> TYPE: PRT
<213> ORGANISM: Homo sapiens

<400> SEQUENCE: 170

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp

```
            130                 135                 140
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
            210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
            290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
                435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
                515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser
545                 550                 555
```

<210> SEQ ID NO 171
<211> LENGTH: 576
<212> TYPE: PRT
<213> ORGANISM: Homo sapiens

<400> SEQUENCE: 171

Met Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp

```
                370                 375                 380
Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
                450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
                515                 520                 525

Pro Ile His Ala Leu Glu Ala Gly Ile Glu Asn Arg Gln Leu Asp Thr
                530                 535                 540

Val Asn Phe Phe Leu Lys Ser Lys Glu Asn Leu Phe Asn Pro Ser Ser
545                 550                 555                 560

Lys Ser Ser Val Leu Ile Ser Leu Ile Thr Cys His Pro Ile Tyr Ile
                565                 570                 575

<210> SEQ ID NO 172
<211> LENGTH: 2443
<212> TYPE: PRT
<213> ORGANISM: Homo sapiens

<400> SEQUENCE: 172

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175
```

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu

```
                    595                 600                 605
        Gln Leu Leu Asn Leu Thr Leu Ser Phe Leu Asn Asn Gln Ile Lys Glu
            610                 615                 620
        Leu Phe Ile His Thr Glu Glu Leu Asp Glu His Leu Gln Lys Gly Val
        625                 630                 635                 640
        Asn Ile Leu Thr Ser Tyr Ile Asn Glu Leu Arg Thr Phe Met Ile Lys
                        645                 650                 655
        Phe Pro Trp Lys Leu Thr Asp Ala Ile Asp Glu Tyr Asp Val His Glu
                    660                 665                 670
        Asn Val Pro Lys Val Lys Glu Ser Asn Ile Trp Lys Lys Leu Ser Phe
                    675                 680                 685
        Glu Glu Val Ile Ala Ser Ala Ile Leu Asn Asn Lys Ile Pro Glu Ala
                    690                 695                 700
        Gln Thr Phe Phe Arg Ile Asp Ser His Ser Ala Gln Lys Leu Glu Glu
        705                 710                 715                 720
        Leu Ile Gly Ile Gly Leu Asn Leu Val Phe Asp Asn Leu Lys Lys Asn
                        725                 730                 735
        Asn Ile Lys Glu Ala Ser Glu Leu Leu Lys Asn Met Gly Phe Asp Val
                        740                 745                 750
        Lys Gly Gln Leu Leu Lys Ile Cys Phe Tyr Thr Thr Asn Lys Asn Ile
                    755                 760                 765
        Arg Asp Phe Leu Val Glu Ile Leu Lys Glu Lys Asn Tyr Phe Ser Glu
        770                 775                 780
        Lys Glu Lys Arg Thr Ile Asp Phe Val His Gln Val Glu Lys Leu Tyr
        785                 790                 795                 800
        Leu Gly His Phe Gln Glu Asn Met Gln Ile Gln Ser Phe Pro Met Tyr
                        805                 810                 815
        Trp Ile Lys Glu Gln Asp Phe Phe Lys His Lys Ser Val Leu Asp Ser
                    820                 825                 830
        Phe Leu Lys Tyr Asp Cys Lys Asp Glu Phe Asn Lys Gln Asp His Arg
                    835                 840                 845
        Ile Val Leu Asn Trp Ala Leu Trp Trp Asp Gln Leu Thr Gln Glu Ser
        850                 855                 860
        Ile Leu Leu Pro Arg Ile Ser Pro Glu Glu Tyr Lys Ser Tyr Ser Pro
        865                 870                 875                 880
        Glu Ala Leu Trp Arg Tyr Leu Thr Ala Arg His Asp Trp Leu Asn Ile
                        885                 890                 895
        Ile Leu Trp Ile Gly Glu Phe Gln Thr Gln His Ser Tyr Ala Ser Leu
                    900                 905                 910
        Gln Gln Asn Lys Trp Pro Leu Leu Thr Val Asp Val Ile Asn Gln Asn
                    915                 920                 925
        Thr Ser Cys Asn Asn Tyr Met Arg Asn Glu Ile Leu Asp Lys Leu Ala
                    930                 935                 940
        Arg Asn Gly Val Phe Leu Ala Ser Glu Leu Glu Asp Phe Glu Cys Phe
        945                 950                 955                 960
        Leu Leu Arg Leu Ser Arg Ile Gly Gly Val Ile Gln Asp Thr Leu Pro
                        965                 970                 975
        Val Gln Asn Tyr Lys Thr Lys Gly Trp Asp Phe Ser Gln Phe
                    980                 985                 990
        Ile Leu Tyr Cys Leu Glu His Ser  Leu Gln His Leu Leu  Tyr Val Tyr
                    995                 1000                1005
        Leu Asp  Cys Tyr Lys Leu Ser  Pro Glu Asn Cys Pro  Phe Leu Glu
            1010                1015                1020
```

```
Lys Lys Glu Leu His Glu Ala His Pro Trp Phe Glu Phe Leu Val
    1025            1030                1035
Gln Cys Arg Gln Val Ala Ser Asn Leu Thr Asp Pro Lys Leu Ile
    1040            1045                1050
Phe Gln Ala Ser Leu Ala Asn Ala Gln Ile Leu Ile Pro Thr Asn
    1055            1060                1065
Gln Ala Ser Val Ser Ser Met Leu Leu Glu Gly His Thr Leu Leu
    1070            1075                1080
Ala Leu Ala Thr Thr Met Tyr Ser Pro Gly Gly Val Ser Gln Val
    1085            1090                1095
Val Gln Asn Glu Glu Asn Glu Asn Cys Leu Lys Lys Val Asp Pro
    1100            1105                1110
Gln Leu Leu Lys Met Ala Leu Thr Pro Tyr Pro Lys Leu Lys Thr
    1115            1120                1125
Ala Leu Phe Pro Gln Cys Thr Pro Pro Ser Val Leu Pro Ser Asp
    1130            1135                1140
Ile Thr Ile Tyr His Leu Ile Gln Ser Leu Ser Pro Phe Asp Pro
    1145            1150                1155
Ser Arg Leu Phe Gly Trp Gln Ser Ala Asn Thr Leu Ala Ile Gly
    1160            1165                1170
Asp Ala Trp Ser His Leu Pro His Phe Ser Ser Pro Asp Leu Val
    1175            1180                1185
Asn Lys Tyr Ala Ile Val Glu Arg Leu Asn Phe Ala Tyr Tyr Leu
    1190            1195                1200
His Asn Gly Arg Pro Ser Phe Ala Phe Gly Thr Phe Leu Val Gln
    1205            1210                1215
Glu Leu Ile Lys Ser Lys Thr Pro Lys Gln Leu Ile Gln Gln Val
    1220            1225                1230
Gly Asn Glu Ala Tyr Val Ile Gly Leu Ser Ser Phe His Ile Pro
    1235            1240                1245
Ser Ile Gly Ala Ala Cys Val Cys Phe Leu Glu Leu Leu Gly Leu
    1250            1255                1260
Asp Ser Leu Lys Leu Arg Val Asp Met Lys Val Ala Asn Ile Ile
    1265            1270                1275
Leu Ser Tyr Lys Cys Arg Asn Glu Asp Ala Gln Tyr Ser Phe Ile
    1280            1285                1290
Arg Glu Ser Val Ala Glu Lys Leu Ser Lys Leu Ala Asp Gly Glu
    1295            1300                1305
Lys Thr Thr Thr Glu Glu Leu Leu Val Leu Leu Glu Glu Gly Thr
    1310            1315                1320
Trp Asn Ser Ile Gln Gln Gln Glu Ile Lys Arg Leu Ser Ser Glu
    1325            1330                1335
Ser Ser Ser Gln Trp Ala Leu Val Val Gln Phe Cys Arg Leu His
    1340            1345                1350
Asn Met Lys Leu Ser Ile Ser Tyr Leu Arg Glu Cys Ala Lys Ala
    1355            1360                1365
Asn Asp Trp Leu Gln Phe Ile Ile His Ser Gln Leu His Asn Tyr
    1370            1375                1380
His Pro Ala Glu Val Lys Ser Leu Ile Gln Tyr Phe Ser Pro Val
    1385            1390                1395
Ile Gln Asp His Leu Arg Leu Ala Phe Glu Asn Leu Pro Ser Val
    1400            1405                1410
```

```
Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
```

```
            1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Leu Tyr
    1985                1990                1995

Asp Leu Ala Lys Glu Leu Gly Cys Ser Tyr Thr Asp Val Ala Ala
    2000                2005                2010

Gln Asp Gly Glu Ala Met Leu Arg Lys Ile Leu Ala Ser Gln Gln
    2015                2020                2025

Pro Asp Arg Cys Lys Arg Ala Gln Ala Phe Ile Ser Thr Gln Gly
    2030                2035                2040

Leu Lys Pro Asp Thr Val Ala Glu Leu Val Ala Glu Glu Val Thr
    2045                2050                2055

Arg Glu Leu Leu Thr Ser Ser Gln Gly Thr Gly His Lys Gln Met
    2060                2065                2070

Phe Asn Pro Thr Glu Glu Ser Gln Thr Phe Leu Gln Leu Thr Thr
    2075                2080                2085

Leu Cys Gln Asp Arg Thr Leu Val Gly Met Lys Leu Leu Asp Lys
    2090                2095                2100

Ile Ser Ser Val Pro His Gly Glu Leu Ser Cys Thr Thr Glu Leu
    2105                2110                2115

Leu Ile Leu Ala His His Cys Phe Thr Leu Thr Cys His Met Glu
    2120                2125                2130

Gly Ile Ile Arg Val Leu Gln Ala Ala His Met Leu Thr Asp Asn
    2135                2140                2145

His Leu Ala Pro Ser Glu Glu Tyr Gly Leu Val Val Arg Leu Leu
    2150                2155                2160

Thr Gly Ile Gly Arg Tyr Asn Glu Met Thr Tyr Ile Phe Asp Leu
    2165                2170                2175

Leu His Lys Lys His Tyr Phe Glu Val Leu Met Arg Lys Lys Leu
    2180                2185                2190

Asp Pro Ser Gly Thr Leu Lys Thr Ala Leu Leu Asp Tyr Ile Lys
    2195                2200                2205
```

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ile Glu Ser Gln Pro Trp Glu Asp
    2240                2245                2250

Ser Leu Lys Asp Gly His Gln Leu Lys Gln Leu Leu Lys Ala
    2255                2260                2265

Leu Thr Leu Met Leu Asp Ala Ala Glu Ser Tyr Ala Lys Asp Ser
    2270                2275                2280

Cys Val Arg Gln Ala Gln His Cys Gln Arg Leu Thr Lys Leu Ile
    2285                2290                2295

Thr Leu Gln Ile His Phe Leu Asn Thr Gly Gln Asn Thr Met Leu
    2300                2305                2310

Ile Asn Leu Gly Arg His Lys Leu Met Asp Cys Ile Leu Ala Leu
    2315                2320                2325

Pro Arg Phe Tyr Gln Ala Ser Ile Val Ala Glu Ala Tyr Asp Phe
    2330                2335                2340

Val Pro Asp Trp Ala Glu Ile Leu Tyr Gln Gln Val Ile Leu Lys
    2345                2350                2355

Gly Asp Phe Asn Tyr Leu Glu Glu Phe Lys Gln Gln Arg Leu Leu
    2360                2365                2370

Lys Ser Ser Ile Phe Glu Glu Ile Ser Lys Lys Tyr Lys Gln His
    2375                2380                2385

Gln Pro Thr Asp Met Val Met Glu Asn Leu Lys Lys Leu Leu Thr
    2390                2395                2400

Tyr Cys Glu Asp Val Tyr Leu Tyr Tyr Lys Leu Ala Tyr Glu His
    2405                2410                2415

Lys Phe Tyr Glu Ile Val Asn Val Leu Leu Lys Asp Pro Gln Thr
    2420                2425                2430

Gly Cys Cys Leu Lys Asp Met Leu Ala Gly
    2435                2440

<210> SEQ ID NO 173
<211> LENGTH: 898
<212> TYPE: PRT
<213> ORGANISM: Homo sapiens

<400> SEQUENCE: 173

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr

```
            115                 120                 125
Ile Leu Tyr Ser Cys Ser Arg Glu Ala Leu Gln Lys Leu Ile Asp Asp
            130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
            180                 185                 190
Leu Pro Leu Pro Ala Gln Ala Val Asp Met Ile Ile Asp Thr Gln Leu
            195                 200                 205
Cys Arg Gly Ile Leu Phe Val Leu Ser Ser Leu Gly Trp Ile Tyr Ile
            210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Glu Pro Ala Lys Ile
                245                 250                 255
Ser Ser Phe Thr Ser Leu Lys Val Ser Gln Asp Leu Asp Val Ala Val
                260                 265                 270
Ile Val Ser Ser Ser Asn Ser Ala Val Ala Leu Asn Leu Asn Leu Tyr
            275                 280                 285
Phe Arg Gln His Pro Gly His Leu Leu Cys Glu Arg Ile Leu Glu Asp
            290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
            355                 360                 365
Leu Glu Ser Pro Glu Ser Gly Asn His Ser Thr Ser Val Gln Ser Trp
            370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
            435                 440                 445
Thr Ile Thr Leu Trp Asp Leu Glu Thr Gln Gly Met Gln Cys Ser Ser
            450                 455                 460
Leu Gly Thr Lys Cys Ile Pro Val Asp Ser Ser Gly Asp Gln Leu
465                 470                 475                 480
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
            515                 520                 525
Pro Ile His Ala Leu Glu Ala Gly Ile Glu Asn Arg Gln Leu Asp Thr
            530                 535                 540
```

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
        580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
        770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
        850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu

<210> SEQ ID NO 174
<211> LENGTH: 919
<212> TYPE: PRT
<213> ORGANISM: Homo sapiens

<400> SEQUENCE: 174

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

-continued

```
Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
```

```
                850             855             860
Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Ser Ile Val Met Leu His Phe
            900                 905                 910

Ser Arg Thr Asn Gly Pro Phe
            915

<210> SEQ ID NO 175
<211> LENGTH: 1028
<212> TYPE: PRT
<213> ORGANISM: Homo sapiens

<400> SEQUENCE: 175

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300
```

```
Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
                435                 440                 445

Thr Ile Thr Leu Trp Asp Leu Glu Thr Gln Gly Met Gln Cys Ser Ser
                450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
                515                 520                 525

Pro Ile His Ala Leu Glu Ala Gly Ile Glu Asn Arg Gln Leu Asp Thr
                530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
                595                 600                 605

Gln Leu Leu Asn Leu Thr Leu Ser Phe Leu Asn Asn Gln Ile Lys Glu
                610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
                675                 680                 685

Glu Glu Val Ile Ala Ser Ala Ile Leu Asn Asn Lys Ile Pro Glu Ala
                690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
```

```
                725                 730                 735
Asn Ile Lys Glu Ala Ser Glu Leu Leu Lys Asn Met Gly Phe Asp Val
            740                 745                 750
Lys Gly Gln Leu Leu Lys Ile Cys Phe Tyr Thr Thr Asn Lys Asn Ile
        755                 760                 765
Arg Asp Phe Leu Val Glu Ile Leu Lys Glu Lys Asn Tyr Phe Ser Glu
    770                 775                 780
Lys Glu Lys Arg Thr Ile Asp Phe Val His Gln Val Glu Lys Leu Tyr
785                 790                 795                 800
Leu Gly His Phe Gln Glu Asn Met Gln Ile Gln Ser Phe Pro Arg Tyr
            805                 810                 815
Trp Ile Lys Glu Gln Asp Phe Phe Lys His Lys Ser Val Leu Asp Ser
        820                 825                 830
Phe Leu Lys Tyr Asp Cys Lys Asp Glu Phe Asn Lys Gln Asp His Arg
    835                 840                 845
Ile Val Leu Asn Trp Ala Leu Trp Trp Asp Gln Leu Thr Gln Glu Ser
850                 855                 860
Ile Leu Leu Pro Arg Ile Ser Pro Glu Glu Tyr Lys Ser Tyr Ser Pro
865                 870                 875                 880
Glu Ala Leu Trp Arg Tyr Leu Thr Ala Arg His Asp Trp Leu Asn Ile
            885                 890                 895
Ile Leu Trp Ile Gly Glu Phe Gln Thr Gln His Ser Tyr Ala Ser Leu
        900                 905                 910
Gln Gln Asn Lys Trp Pro Leu Leu Thr Val Asp Val Ile Asn Gln Asn
    915                 920                 925
Thr Ser Cys Asn Asn Tyr Met Arg Asn Glu Ile Leu Asp Lys Leu Ala
930                 935                 940
Arg Asn Gly Val Phe Leu Ala Ser Glu Leu Glu Asp Phe Glu Cys Phe
945                 950                 955                 960
Leu Leu Arg Leu Ser Arg Ile Gly Gly Val Ile Gln Asp Thr Leu Pro
            965                 970                 975
Val Gln Asn Tyr Lys Thr Lys Glu Gly Trp Asp Phe His Ser Gln Phe
        980                 985                 990
Ile Leu Tyr Cys Leu Glu His Ser Leu Gln His Leu Leu Tyr Val Tyr
    995                 1000                1005
Leu Asp Cys Tyr Lys Leu Ser Pro Glu Asn Cys Pro Phe Leu Glu
    1010                1015                1020
Lys Lys Arg Val Thr
    1025

<210> SEQ ID NO 176
<211> LENGTH: 1263
<212> TYPE: PRT
<213> ORGANISM: Homo sapiens

<400> SEQUENCE: 176

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60
```

-continued

```
Val Leu Ser Leu Thr Pro Gly Ser Arg Gly Gly Arg Cys Cys Leu
 65                  70                  75                  80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
            130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
            165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
            245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
```

```
            485             490             495
Thr Gln Glu Glu Phe Leu Asn Arg Leu Met Ile His Gly Ser Ala Ser
            500             505             510

Thr Val Asp Thr Leu Cys His Leu Asn Gly Trp Gly Arg Cys Ser Ile
            515             520             525

Pro Ile His Ala Leu Glu Ala Gly Ile Glu Asn Arg Gln Leu Asp Thr
            530             535             540

Val Asn Phe Phe Leu Lys Ser Lys Glu Asn Leu Phe Asn Pro Ser Ser
545             550             555             560

Lys Ser Ser Val Ser Asp Gln Phe Asp His Leu Ser Ser His Leu Tyr
            565             570             575

Leu Arg Asn Val Glu Glu Leu Ile Pro Ala Leu Asp Leu Leu Cys Ser
            580             585             590

Ala Ile Arg Glu Ser Tyr Ser Glu Pro Gln Ser Lys His Phe Ser Glu
            595             600             605

Gln Leu Leu Asn Leu Thr Leu Ser Phe Leu Asn Asn Gln Ile Lys Glu
            610             615             620

Leu Phe Ile His Thr Glu Glu Leu Asp Glu His Leu Gln Lys Gly Val
625             630             635             640

Asn Ile Leu Thr Ser Tyr Ile Asn Glu Leu Arg Thr Phe Met Ile Lys
            645             650             655

Phe Pro Trp Lys Leu Thr Asp Ala Ile Asp Glu Tyr Asp Val His Glu
            660             665             670

Asn Val Pro Lys Val Lys Glu Ser Asn Ile Trp Lys Lys Leu Ser Phe
            675             680             685

Glu Glu Val Ile Ala Ser Ala Ile Leu Asn Asn Lys Ile Pro Glu Ala
690             695             700

Gln Thr Phe Phe Arg Ile Asp Ser His Ser Ala Gln Lys Leu Glu Glu
705             710             715             720

Leu Ile Gly Ile Gly Leu Asn Leu Val Phe Asp Asn Leu Lys Lys Asn
            725             730             735

Asn Ile Lys Glu Ala Ser Glu Leu Leu Lys Asn Met Gly Phe Asp Val
            740             745             750

Lys Gly Gln Leu Leu Lys Ile Cys Phe Tyr Thr Thr Asn Lys Asn Ile
755             760             765

Arg Asp Phe Leu Val Glu Ile Leu Lys Glu Lys Asn Tyr Phe Ser Glu
770             775             780

Lys Glu Lys Arg Thr Ile Asp Phe Val His Gln Val Glu Lys Leu Tyr
785             790             795             800

Leu Gly His Phe Gln Glu Asn Met Gln Ile Gln Ser Phe Pro Arg Tyr
            805             810             815

Trp Ile Lys Glu Gln Asp Phe Lys His Lys Ser Val Leu Asp Ser
            820             825             830

Phe Leu Lys Tyr Asp Cys Lys Asp Glu Phe Asn Lys Gln Asp His Arg
            835             840             845

Ile Val Leu Asn Trp Ala Leu Trp Trp Asp Gln Leu Thr Gln Glu Ser
            850             855             860

Ile Leu Leu Pro Arg Ile Ser Pro Glu Tyr Lys Ser Tyr Ser Pro
865             870             875             880

Glu Ala Leu Trp Arg Tyr Leu Thr Ala Arg His Asp Trp Leu Asn Ile
            885             890             895

Ile Leu Trp Ile Gly Glu Phe Gln Thr Gln His Ser Tyr Ala Ser Leu
            900             905             910
```

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
        995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Thr
    1235                1240                1245

Phe Asn Arg Ser Cys Met Cys Leu Phe Leu Arg Ile Ala Trp Pro
    1250                1255                1260

<210> SEQ ID NO 177
<211> LENGTH: 1441
<212> TYPE: PRT
<213> ORGANISM: Homo sapiens

<400> SEQUENCE: 177

Met Ala Ala Glu Glu Gly Val Ala Ser Ala Ala Ser Ala Gly Gly Ser

-continued

```
1               5                   10                  15
Trp Gly Thr Ala Ala Met Gly Arg Val Leu Pro Met Leu Leu Val Pro
                20                  25                  30
Val Pro Ala Glu Ala Met Gly Gln Leu Gly Ser Arg Ala Gln Leu Arg
                35                  40                  45
Thr Gln Pro Glu Ala Leu Gly Ser Leu Thr Ala Ala Gly Ser Leu Gln
                50                  55                  60
Val Leu Ser Leu Thr Pro Gly Ser Arg Gly Gly Gly Arg Cys Cys Leu
65              70                  75                  80
Glu Gly Pro Phe Trp His Phe Leu Trp Glu Asp Ser Arg Asn Ser Ser
                85                  90                  95
Thr Pro Thr Glu Lys Pro Lys Leu Leu Ala Leu Gly Glu Asn Tyr Glu
                100                 105                 110
Leu Leu Ile Tyr Glu Phe Asn Leu Lys Asp Gly Arg Cys Asp Ala Thr
                115                 120                 125
Ile Leu Tyr Ser Cys Ser Arg Glu Ala Leu Gln Lys Leu Ile Asp Asp
                130                 135                 140
Gln Asp Ile Ser Ile Ser Leu Leu Ser Leu Arg Ile Leu Ser Phe His
145             150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
                180                 185                 190
Leu Pro Leu Pro Ala Gln Ala Val Asp Met Ile Ile Asp Thr Gln Leu
                195                 200                 205
Cys Arg Gly Ile Leu Phe Val Leu Ser Ser Leu Gly Trp Ile Tyr Ile
                210                 215                 220
Phe Asp Val Val Asp Gly Thr Tyr Val Ala His Val Asp Leu Ala Leu
225             230                 235                 240
His Lys Glu Asp Met Cys Asn Glu Gln Gln Gln Glu Pro Ala Lys Ile
                245                 250                 255
Ser Ser Phe Thr Ser Leu Lys Val Ser Gln Asp Leu Asp Val Ala Val
                260                 265                 270
Ile Val Ser Ser Ser Asn Ser Ala Val Ala Leu Asn Leu Asn Leu Tyr
                275                 280                 285
Phe Arg Gln His Pro Gly His Leu Leu Cys Glu Arg Ile Leu Glu Asp
                290                 295                 300
Leu Pro Ile Gln Gly Pro Lys Gly Val Asp Glu Asp Pro Val Asn
305             310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
                340                 345                 350
Lys Leu Glu Val Ser Cys Cys Ala Pro Trp Phe Gln Asp Ile Leu His
                355                 360                 365
Leu Glu Ser Pro Glu Ser Gly Asn His Ser Thr Ser Val Gln Ser Trp
                370                 375                 380
Ala Phe Ile Pro Gln Asp Ile Met His Gly Gln Tyr Asn Val Leu Gln
385             390                 395                 400
Lys Asp His Ala Lys Thr Ser Asp Pro Gly Arg Ser Trp Lys Ile Met
                405                 410                 415
His Ile Ser Glu Gln Glu Glu Pro Ile Glu Leu Lys Cys Val Ser Val
                420                 425                 430
```

```
Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845
```

```
Ile Val Leu Asn Trp Ala Leu Trp Trp Asp Gln Leu Thr Gln Glu Ser
        850                 855                 860
Ile Leu Leu Pro Arg Ile Ser Pro Glu Glu Tyr Lys Ser Tyr Ser Pro
865                 870                 875                 880
Glu Ala Leu Trp Arg Tyr Leu Thr Ala Arg His Asp Trp Leu Asn Ile
            885                 890                 895
Ile Leu Trp Ile Gly Glu Phe Gln Thr Gln His Ser Tyr Ala Ser Leu
        900                 905                 910
Gln Gln Asn Lys Trp Pro Leu Thr Val Asp Val Ile Asn Gln Asn
        915                 920                 925
Thr Ser Cys Asn Asn Tyr Met Arg Asn Glu Ile Leu Asp Lys Leu Ala
930                 935                 940
Arg Asn Gly Val Phe Leu Ala Ser Glu Leu Glu Asp Phe Glu Cys Phe
945                 950                 955                 960
Leu Leu Arg Leu Ser Arg Ile Gly Gly Val Ile Gln Asp Thr Leu Pro
            965                 970                 975
Val Gln Asn Tyr Lys Thr Lys Gly Gly Trp Asp Phe His Ser Gln Phe
        980                 985                 990
Ile Leu Tyr Cys Leu Glu His Ser Leu Gln His Leu Leu Tyr Val Tyr
        995                 1000                1005
Leu Asp Cys Tyr Lys Leu Ser Pro Glu Asn Cys Pro Phe Leu Glu
    1010                1015                1020
Lys Lys Glu Leu His Glu Ala His Pro Trp Phe Glu Phe Leu Val
    1025                1030                1035
Gln Cys Arg Gln Val Ala Ser Asn Leu Thr Asp Pro Lys Leu Ile
    1040                1045                1050
Phe Gln Ala Ser Leu Ala Asn Ala Gln Ile Leu Ile Pro Thr Asn
    1055                1060                1065
Gln Ala Ser Val Ser Ser Met Leu Leu Glu Gly His Thr Leu Leu
    1070                1075                1080
Ala Leu Ala Thr Thr Met Tyr Ser Pro Gly Gly Val Ser Gln Val
    1085                1090                1095
Val Gln Asn Glu Glu Asn Glu Asn Cys Leu Lys Lys Val Asp Pro
    1100                1105                1110
Gln Leu Leu Lys Met Ala Leu Thr Pro Tyr Pro Lys Leu Lys Thr
    1115                1120                1125
Ala Leu Phe Pro Gln Cys Thr Pro Pro Ser Val Leu Pro Ser Asp
    1130                1135                1140
Ile Thr Ile Tyr His Leu Ile Gln Ser Leu Ser Pro Phe Asp Pro
    1145                1150                1155
Ser Arg Leu Phe Gly Trp Gln Ser Ala Asn Thr Leu Ala Ile Gly
    1160                1165                1170
Asp Ala Trp Ser His Leu Pro His Phe Ser Ser Pro Asp Leu Val
    1175                1180                1185
Asn Lys Tyr Ala Ile Val Glu Arg Leu Asn Phe Ala Tyr Tyr Leu
    1190                1195                1200
His Asn Gly Arg Pro Ser Phe Ala Phe Gly Thr Phe Leu Val Gln
    1205                1210                1215
Glu Leu Ile Lys Ser Lys Thr Pro Lys Gln Leu Ile Gln Gln Val
    1220                1225                1230
Gly Asn Glu Ala Tyr Val Ile Gly Leu Ser Ser Phe His Ile Pro
    1235                1240                1245
Ser Ile Gly Ala Ala Cys Val Cys Phe Leu Glu Leu Leu Gly Leu
```

-continued

```
            1250                1255                1260

Asp Ser Leu Lys Leu Arg Val Asp Met Lys Val Ala Asn Ile Ile
        1265                1270                1275

Leu Ser Tyr Lys Cys Arg Asn Glu Asp Ala Gln Tyr Ser Phe Ile
        1280                1285                1290

Arg Glu Ser Val Ala Glu Lys Leu Ser Lys Leu Ala Asp Gly Glu
        1295                1300                1305

Lys Thr Thr Thr Glu Glu Leu Leu Val Leu Leu Glu Glu Gly Thr
        1310                1315                1320

Trp Asn Ser Ile Gln Gln Glu Ile Lys Arg Leu Ser Ser Glu
        1325                1330                1335

Ser Ser Ser Gln Trp Ala Leu Val Val Gln Phe Cys Arg Leu His
        1340                1345                1350

Asn Met Lys Leu Ser Ile Ser Tyr Leu Arg Glu Cys Ala Lys Ala
        1355                1360                1365

Asn Asp Trp Leu Gln Phe Ile Ile His Ser Gln Leu His Asn Tyr
        1370                1375                1380

His Pro Ala Glu Val Lys Ser Leu Ile Gln Tyr Phe Ser Pro Val
        1385                1390                1395

Ile Gln Asp His Leu Arg Leu Ala Phe Glu Asn Leu Pro Ser Val
        1400                1405                1410

Pro Thr Ser Lys Met Asp Ser Asp Gln Val Cys Asn Lys Cys Pro
        1415                1420                1425

Gln Glu Leu Gln Gly Ser Lys Arg Asp Asp Arg Phe Ile
        1430                1435                1440

<210> SEQ ID NO 178
<211> LENGTH: 1823
<212> TYPE: PRT
<213> ORGANISM: Homo sapiens

<400> SEQUENCE: 178

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175
```

```
Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
        210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
```

```
            595                 600                 605
Gln Leu Leu Asn Leu Thr Leu Ser Phe Leu Asn Asn Gln Ile Lys Glu
    610                 615                 620
Leu Phe Ile His Thr Glu Glu Leu Asp Glu His Leu Gln Lys Gly Val
625                 630                 635                 640
Asn Ile Leu Thr Ser Tyr Ile Asn Glu Leu Arg Thr Phe Met Ile Lys
                645                 650                 655
Phe Pro Trp Lys Leu Thr Asp Ala Ile Asp Glu Tyr Asp Val His Glu
                660                 665                 670
Asn Val Pro Lys Val Lys Glu Ser Asn Ile Trp Lys Lys Leu Ser Phe
            675                 680                 685
Glu Glu Val Ile Ala Ser Ala Ile Leu Asn Asn Lys Ile Pro Glu Ala
            690                 695                 700
Gln Thr Phe Phe Arg Ile Asp Ser His Ser Ala Gln Lys Leu Glu Glu
705                 710                 715                 720
Leu Ile Gly Ile Gly Leu Asn Leu Val Phe Asp Asn Leu Lys Lys Asn
                725                 730                 735
Asn Ile Lys Glu Ala Ser Glu Leu Leu Lys Asn Met Gly Phe Asp Val
                740                 745                 750
Lys Gly Gln Leu Leu Lys Ile Cys Phe Tyr Thr Thr Asn Lys Asn Ile
            755                 760                 765
Arg Asp Phe Leu Val Glu Ile Leu Lys Glu Lys Asn Tyr Phe Ser Glu
770                 775                 780
Lys Glu Lys Arg Thr Ile Asp Phe Val His Gln Val Glu Lys Leu Tyr
785                 790                 795                 800
Leu Gly His Phe Gln Glu Asn Met Gln Ile Gln Ser Phe Pro Arg Tyr
                805                 810                 815
Trp Ile Lys Glu Gln Asp Phe Phe Lys His Lys Ser Val Leu Asp Ser
            820                 825                 830
Phe Leu Lys Tyr Asp Cys Lys Asp Glu Phe Asn Lys Gln Asp His Arg
            835                 840                 845
Ile Val Leu Asn Trp Ala Leu Trp Trp Asp Gln Leu Thr Gln Glu Ser
850                 855                 860
Ile Leu Leu Pro Arg Ile Ser Pro Glu Glu Tyr Lys Ser Tyr Ser Pro
865                 870                 875                 880
Glu Ala Leu Trp Arg Tyr Leu Thr Ala Arg His Asp Trp Leu Asn Ile
                885                 890                 895
Ile Leu Trp Ile Gly Glu Phe Gln Thr Gln His Ser Tyr Ala Ser Leu
                900                 905                 910
Gln Gln Asn Lys Trp Pro Leu Leu Thr Val Asp Val Ile Asn Gln Asn
            915                 920                 925
Thr Ser Cys Asn Asn Tyr Met Arg Asn Glu Ile Leu Asp Lys Leu Ala
930                 935                 940
Arg Asn Gly Val Phe Leu Ala Ser Glu Leu Glu Asp Phe Glu Cys Phe
945                 950                 955                 960
Leu Leu Arg Leu Ser Arg Ile Gly Gly Val Ile Gln Asp Thr Leu Pro
                965                 970                 975
Val Gln Asn Tyr Lys Thr Lys Gly Trp Asp Phe Ser Gln Phe
            980                 985                 990
Ile Leu Tyr Cys Leu Glu His Ser  Leu Gln His Leu Leu  Tyr Val Tyr
            995                 1000                1005
Leu Asp  Cys Tyr Lys Leu Ser  Pro Glu Asn Cys Pro  Phe Leu Glu
    1010                1015                1020
```

```
Lys Lys Glu Leu His Glu Ala His Pro Trp Phe Glu Phe Leu Val
    1025            1030                1035

Gln Cys Arg Gln Val Ala Ser Asn Leu Thr Asp Pro Lys Leu Ile
    1040            1045                1050

Phe Gln Ala Ser Leu Ala Asn Ala Gln Ile Leu Ile Pro Thr Asn
    1055            1060                1065

Gln Ala Ser Val Ser Ser Met Leu Leu Glu Gly His Thr Leu Leu
    1070            1075                1080

Ala Leu Ala Thr Thr Met Tyr Ser Pro Gly Gly Val Ser Gln Val
    1085            1090                1095

Val Gln Asn Glu Glu Asn Glu Asn Cys Leu Lys Lys Val Asp Pro
    1100            1105                1110

Gln Leu Leu Lys Met Ala Leu Thr Pro Tyr Pro Lys Leu Lys Thr
    1115            1120                1125

Ala Leu Phe Pro Gln Cys Thr Pro Pro Ser Val Leu Pro Ser Asp
    1130            1135                1140

Ile Thr Ile Tyr His Leu Ile Gln Ser Leu Ser Pro Phe Asp Pro
    1145            1150                1155

Ser Arg Leu Phe Gly Trp Gln Ser Ala Asn Thr Leu Ala Ile Gly
    1160            1165                1170

Asp Ala Trp Ser His Leu Pro His Phe Ser Ser Pro Asp Leu Val
    1175            1180                1185

Asn Lys Tyr Ala Ile Val Glu Arg Leu Asn Phe Ala Tyr Tyr Leu
    1190            1195                1200

His Asn Gly Arg Pro Ser Phe Ala Phe Gly Thr Phe Leu Val Gln
    1205            1210                1215

Glu Leu Ile Lys Ser Lys Thr Pro Lys Gln Leu Ile Gln Gln Val
    1220            1225                1230

Gly Asn Glu Ala Tyr Val Ile Gly Leu Ser Ser Phe His Ile Pro
    1235            1240                1245

Ser Ile Gly Ala Ala Cys Val Cys Phe Leu Glu Leu Leu Gly Leu
    1250            1255                1260

Asp Ser Leu Lys Leu Arg Val Asp Met Lys Val Ala Asn Ile Ile
    1265            1270                1275

Leu Ser Tyr Lys Cys Arg Asn Glu Asp Ala Gln Tyr Ser Phe Ile
    1280            1285                1290

Arg Glu Ser Val Ala Glu Lys Leu Ser Lys Leu Ala Asp Gly Glu
    1295            1300                1305

Lys Thr Thr Thr Glu Glu Leu Leu Val Leu Leu Glu Glu Gly Thr
    1310            1315                1320

Trp Asn Ser Ile Gln Gln Gln Glu Ile Lys Arg Leu Ser Ser Glu
    1325            1330                1335

Ser Ser Ser Gln Trp Ala Leu Val Val Gln Phe Cys Arg Leu His
    1340            1345                1350

Asn Met Lys Leu Ser Ile Ser Tyr Leu Arg Glu Cys Ala Lys Ala
    1355            1360                1365

Asn Asp Trp Leu Gln Phe Ile Ile His Ser Gln Leu His Asn Tyr
    1370            1375                1380

His Pro Ala Glu Val Lys Ser Leu Ile Gln Tyr Phe Ser Pro Val
    1385            1390                1395

Ile Gln Asp His Leu Arg Leu Ala Phe Glu Asn Leu Pro Ser Val
    1400            1405                1410
```

```
Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
```

Glu Pro Arg Phe Ser
         1820

<210> SEQ ID NO 179
<211> LENGTH: 1856
<212> TYPE: PRT
<213> ORGANISM: Homo sapiens

<400> SEQUENCE: 179

Met Ala Ala Glu Glu Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

-continued

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
    435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
    515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
    595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
    675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
    755                 760                 765

Arg Asp Phe Leu Val Glu Ile Leu Lys Glu Lys Asn Tyr Phe Ser Glu

```
                770             775             780
Lys Glu Lys Arg Thr Ile Asp Phe Val His Gln Val Glu Lys Leu Tyr
785             790             795             800

Leu Gly His Phe Gln Glu Asn Met Gln Ile Gln Ser Phe Pro Arg Tyr
                805             810             815

Trp Ile Lys Glu Gln Asp Phe Phe Lys His Lys Ser Val Leu Asp Ser
                820             825             830

Phe Leu Lys Tyr Asp Cys Lys Asp Glu Phe Asn Lys Gln Asp His Arg
                835             840             845

Ile Val Leu Asn Trp Ala Leu Trp Trp Asp Gln Leu Thr Gln Glu Ser
850             855             860

Ile Leu Leu Pro Arg Ile Ser Pro Glu Glu Tyr Lys Ser Tyr Ser Pro
865             870             875             880

Glu Ala Leu Trp Arg Tyr Leu Thr Ala Arg His Asp Trp Leu Asn Ile
                885             890             895

Ile Leu Trp Ile Gly Glu Phe Gln Thr Gln His Ser Tyr Ala Ser Leu
                900             905             910

Gln Gln Asn Lys Trp Pro Leu Leu Thr Val Asp Val Ile Asn Gln Asn
                915             920             925

Thr Ser Cys Asn Asn Tyr Met Arg Asn Glu Ile Leu Asp Lys Leu Ala
930             935             940

Arg Asn Gly Val Phe Leu Ala Ser Glu Leu Glu Asp Phe Glu Cys Phe
945             950             955             960

Leu Leu Arg Leu Ser Arg Ile Gly Gly Val Ile Gln Asp Thr Leu Pro
                965             970             975

Val Gln Asn Tyr Lys Thr Lys Glu Gly Trp Asp Phe His Ser Gln Phe
                980             985             990

Ile Leu Tyr Cys Leu Glu His Ser  Leu Gln His Leu Leu  Tyr Val Tyr
                995             1000            1005

Leu Asp Cys Tyr Lys Leu Ser  Pro Glu Asn Cys Pro  Phe Leu Glu
1010            1015            1020

Lys Lys Glu Leu His Glu Ala  His Pro Trp Phe Glu  Phe Leu Val
1025            1030            1035

Gln Cys Arg Gln Val Ala Ser  Asn Leu Thr Asp Pro  Lys Leu Ile
1040            1045            1050

Phe Gln Ala Ser Leu Ala Asn  Ala Gln Ile Leu Ile  Pro Thr Asn
1055            1060            1065

Gln Ala Ser Val Ser Ser Met  Leu Leu Glu Gly His  Thr Leu Leu
1070            1075            1080

Ala Leu Ala Thr Thr Met Tyr  Ser Pro Gly Gly Val  Ser Gln Val
1085            1090            1095

Val Gln Asn Glu Glu Asn Glu  Asn Cys Leu Lys Lys  Val Asp Pro
1100            1105            1110

Gln Leu Leu Lys Met Ala Leu  Thr Pro Tyr Pro Lys  Leu Lys Thr
1115            1120            1125

Ala Leu Phe Pro Gln Cys Thr  Pro Pro Ser Val Leu  Pro Ser Asp
1130            1135            1140

Ile Thr Ile Tyr His Leu Ile  Gln Ser Leu Ser Pro  Phe Asp Pro
1145            1150            1155

Ser Arg Leu Phe Gly Trp Gln  Ser Ala Asn Thr Leu  Ala Ile Gly
1160            1165            1170

Asp Ala Trp Ser His Leu Pro  His Phe Ser Ser Pro  Asp Leu Val
1175            1180            1185
```

```
Asn Lys Tyr Ala Ile Val Glu Arg Leu Asn Phe Ala Tyr Tyr Leu
1190            1195            1200

His Asn Gly Arg Pro Ser Phe Ala Phe Gly Thr Phe Leu Val Gln
1205            1210            1215

Glu Leu Ile Lys Ser Lys Thr Pro Lys Gln Leu Ile Gln Gln Val
1220            1225            1230

Gly Asn Glu Ala Tyr Val Ile Gly Leu Ser Ser Phe His Ile Pro
1235            1240            1245

Ser Ile Gly Ala Ala Cys Val Cys Phe Leu Glu Leu Leu Gly Leu
1250            1255            1260

Asp Ser Leu Lys Leu Arg Val Asp Met Lys Val Ala Asn Ile Ile
1265            1270            1275

Leu Ser Tyr Lys Cys Arg Asn Glu Asp Ala Gln Tyr Ser Phe Ile
1280            1285            1290

Arg Glu Ser Val Ala Glu Lys Leu Ser Lys Leu Ala Asp Gly Glu
1295            1300            1305

Lys Thr Thr Thr Glu Glu Leu Leu Val Leu Leu Glu Glu Gly Thr
1310            1315            1320

Trp Asn Ser Ile Gln Gln Gln Glu Ile Lys Arg Leu Ser Ser Glu
1325            1330            1335

Ser Ser Ser Gln Trp Ala Leu Val Val Gln Phe Cys Arg Leu His
1340            1345            1350

Asn Met Lys Leu Ser Ile Ser Tyr Leu Arg Glu Cys Ala Lys Ala
1355            1360            1365

Asn Asp Trp Leu Gln Phe Ile Ile His Ser Gln Leu His Asn Tyr
1370            1375            1380

His Pro Ala Glu Val Lys Ser Leu Ile Gln Tyr Phe Ser Pro Val
1385            1390            1395

Ile Gln Asp His Leu Arg Leu Ala Phe Glu Asn Leu Pro Ser Val
1400            1405            1410

Pro Thr Ser Lys Met Asp Ser Asp Gln Val Cys Asn Lys Cys Pro
1415            1420            1425

Gln Glu Leu Gln Gly Ser Lys Gln Glu Met Thr Asp Leu Phe Glu
1430            1435            1440

Ile Leu Leu Gln Cys Ser Glu Glu Pro Asp Ser Trp His Trp Leu
1445            1450            1455

Leu Val Glu Ala Val Lys Gln Gln Ala Pro Ile Leu Ser Val Leu
1460            1465            1470

Ala Ser Cys Leu Gln Gly Ala Ser Ala Ile Ser Cys Leu Cys Val
1475            1480            1485

Trp Ile Ile Thr Ser Val Glu Asp Asn Val Ala Thr Glu Ala Met
1490            1495            1500

Gly His Ile Gln Asp Ser Thr Glu Asp His Thr Trp Asn Leu Glu
1505            1510            1515

Asp Leu Ser Val Ile Trp Arg Thr Leu Leu Thr Arg Gln Lys Ser
1520            1525            1530

Lys Thr Leu Ile Arg Gly Phe Gln Leu Phe Phe Lys Asp Ser Pro
1535            1540            1545

Leu Leu Leu Val Met Glu Met Tyr Glu Leu Cys Met Phe Phe Arg
1550            1555            1560

Asn Tyr Lys Glu Ala Glu Ala Lys Leu Leu Glu Phe Gln Lys Ser
1565            1570            1575
```

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
    1670            1675                1680

Gly Gln Phe Ala Leu Ala Arg Arg Val Ala Glu Leu Ala Glu Leu
    1685            1690                1695

Pro Val Asp Asn Leu Val Ile Lys Glu Ile Thr Gln Glu Met Gln
    1700            1705                1710

Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Glu Leu Glu Lys Gln Ile Trp Leu
    1790            1795                1800

Cys Arg Ile Thr Gln His Thr Leu Gly Arg Asn Gln Glu Glu Thr
    1805            1810                1815

Glu Pro Arg Phe Ser Arg Gln Ile Ser Thr Ser Gly Glu Leu Ser
    1820            1825                1830

Phe Asp Ser Leu Ala Ser Glu Phe Ser Phe Ser Val Gly Cys Ser
    1835            1840                1845

Glu His Ile Lys Ile Leu Arg Thr
    1850            1855

<210> SEQ ID NO 180
<211> LENGTH: 1949
<212> TYPE: PRT
<213> ORGANISM: Homo sapiens

<400> SEQUENCE: 180

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Gly Arg Cys Cys Leu
65                  70                  75                  80

```
Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495
```

```
Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
```

```
            915                 920                 925
Thr Ser Cys Asn Asn Tyr Met Arg Asn Glu Ile Leu Asp Lys Leu Ala
    930                 935                 940
Arg Asn Gly Val Phe Leu Ala Ser Glu Leu Glu Asp Phe Glu Cys Phe
945                 950                 955                 960
Leu Leu Arg Leu Ser Arg Ile Gly Gly Val Ile Gln Asp Thr Leu Pro
                965                 970                 975
Val Gln Asn Tyr Lys Thr Lys Glu Gly Trp Asp Phe His Ser Gln Phe
                980                 985                 990
Ile Leu Tyr Cys Leu Glu His Ser Leu Gln His Leu Leu Tyr Val Tyr
                995                 1000                1005
Leu Asp Cys Tyr Lys Leu Ser Pro Glu Asn Cys Pro Phe Leu Glu
    1010                1015                1020
Lys Lys Glu Leu His Glu Ala His Pro Trp Phe Glu Phe Leu Val
    1025                1030                1035
Gln Cys Arg Gln Val Ala Ser Asn Leu Thr Asp Pro Lys Leu Ile
    1040                1045                1050
Phe Gln Ala Ser Leu Ala Asn Ala Gln Ile Leu Ile Pro Thr Asn
    1055                1060                1065
Gln Ala Ser Val Ser Ser Met Leu Leu Glu Gly His Thr Leu Leu
    1070                1075                1080
Ala Leu Ala Thr Thr Met Tyr Ser Pro Gly Gly Val Ser Gln Val
    1085                1090                1095
Val Gln Asn Glu Glu Asn Glu Asn Cys Leu Lys Lys Val Asp Pro
    1100                1105                1110
Gln Leu Leu Lys Met Ala Leu Thr Pro Tyr Pro Lys Leu Lys Thr
    1115                1120                1125
Ala Leu Phe Pro Gln Cys Thr Pro Pro Ser Val Leu Pro Ser Asp
    1130                1135                1140
Ile Thr Ile Tyr His Leu Ile Gln Ser Leu Ser Pro Phe Asp Pro
    1145                1150                1155
Ser Arg Leu Phe Gly Trp Gln Ser Ala Asn Thr Leu Ala Ile Gly
    1160                1165                1170
Asp Ala Trp Ser His Leu Pro His Phe Ser Ser Pro Asp Leu Val
    1175                1180                1185
Asn Lys Tyr Ala Ile Val Glu Arg Leu Asn Phe Ala Tyr Tyr Leu
    1190                1195                1200
His Asn Gly Arg Pro Ser Phe Ala Phe Gly Thr Phe Leu Val Gln
    1205                1210                1215
Glu Leu Ile Lys Ser Lys Thr Pro Lys Gln Leu Ile Gln Gln Val
    1220                1225                1230
Gly Asn Glu Ala Tyr Val Ile Gly Leu Ser Ser Phe His Ile Pro
    1235                1240                1245
Ser Ile Gly Ala Ala Cys Val Cys Phe Leu Glu Leu Leu Gly Leu
    1250                1255                1260
Asp Ser Leu Lys Leu Arg Val Asp Met Lys Val Ala Asn Ile Ile
    1265                1270                1275
Leu Ser Tyr Lys Cys Arg Asn Glu Asp Ala Gln Tyr Ser Phe Ile
    1280                1285                1290
Arg Glu Ser Val Ala Glu Lys Leu Ser Lys Leu Ala Asp Gly Glu
    1295                1300                1305
Lys Thr Thr Thr Glu Glu Leu Leu Val Leu Leu Glu Glu Gly Thr
    1310                1315                1320
```

-continued

```
Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710
```

-continued

```
Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Arg
    1910                1915                1920

Trp Arg Ile Cys Thr Gln Arg Ser Met Leu Ser Tyr Lys Val Leu
    1925                1930                1935

Ser Cys Leu Arg Lys Lys His Pro Thr Phe Pro
    1940                1945

<210> SEQ ID NO 181
<211> LENGTH: 1956
<212> TYPE: PRT
<213> ORGANISM: Homo sapiens

<400> SEQUENCE: 181

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125
```

```
Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540
```

```
Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
        580                 585                 590

Ala Ile Arg Glu Ser Tyr Ser Glu Pro Gln Ser Lys His Phe Ser Glu
    595                 600                 605

Gln Leu Leu Asn Leu Thr Leu Ser Phe Leu Asn Asn Gln Ile Lys Glu
610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
```

```
                965                 970                 975
Val Gln Asn Tyr Lys Thr Lys Glu Gly Trp Asp Phe His Ser Gln Phe
                    980                 985                 990

Ile Leu Tyr Cys Leu Glu His Ser  Leu Gln His Leu  Tyr Val Tyr
            995                 1000                1005

Leu Asp  Cys Tyr Lys Leu Ser  Pro Glu Asn Cys  Pro Phe Leu Glu
    1010                 1015                1020

Lys Lys  Glu Leu His Glu Ala  His Pro Trp Phe  Glu Phe Leu Val
    1025                 1030                1035

Gln Cys  Arg Gln Val Ala Ser  Asn Leu Thr Asp  Pro Lys Leu Ile
    1040                 1045                1050

Phe Gln  Ala Ser Leu Ala Asn  Ala Gln Ile Leu  Ile Pro Thr Asn
    1055                 1060                1065

Gln Ala  Ser Val Ser Ser Met  Leu Leu Glu Gly  His Thr Leu Leu
    1070                 1075                1080

Ala Leu  Ala Thr Thr Met Tyr  Ser Pro Gly Gly  Val Ser Gln Val
    1085                 1090                1095

Val Gln  Asn Glu Glu Asn Glu  Asn Cys Leu Lys  Lys Val Asp Pro
    1100                 1105                1110

Gln Leu  Leu Lys Met Ala Leu  Thr Pro Tyr Pro  Lys Leu Lys Thr
    1115                 1120                1125

Ala Leu  Phe Pro Gln Cys Thr  Pro Pro Ser Val  Leu Pro Ser Asp
    1130                 1135                1140

Ile Thr  Ile Tyr His Leu Ile  Gln Ser Leu Ser  Pro Phe Asp Pro
    1145                 1150                1155

Ser Arg  Leu Phe Gly Trp Gln  Ser Ala Asn Thr  Leu Ala Ile Gly
    1160                 1165                1170

Asp Ala  Trp Ser His Leu Pro  His Phe Ser Pro  Asp Leu Val
    1175                 1180                1185

Asn Lys  Tyr Ala Ile Val Glu  Arg Leu Asn Phe  Ala Tyr Tyr Leu
    1190                 1195                1200

His Asn  Gly Arg Pro Ser Phe  Ala Phe Gly Thr  Phe Leu Val Gln
    1205                 1210                1215

Glu Leu  Ile Lys Ser Lys Thr  Pro Lys Gln Leu  Ile Gln Gln Val
    1220                 1225                1230

Gly Asn  Glu Ala Tyr Val Ile  Gly Leu Ser Ser  Phe His Ile Pro
    1235                 1240                1245

Ser Ile  Gly Ala Ala Cys Val  Cys Phe Leu Glu  Leu Leu Gly Leu
    1250                 1255                1260

Asp Ser  Leu Lys Leu Arg Val  Asp Met Lys Val  Ala Asn Ile Ile
    1265                 1270                1275

Leu Ser  Tyr Lys Cys Arg Asn  Glu Asp Ala Gln  Tyr Ser Phe Ile
    1280                 1285                1290

Arg Glu  Ser Val Ala Glu Lys  Leu Ser Lys Leu  Ala Asp Gly Glu
    1295                 1300                1305

Lys Thr  Thr Thr Glu Glu Leu  Leu Val Leu Leu  Glu Glu Gly Thr
    1310                 1315                1320

Trp Asn  Ser Ile Gln Gln Gln  Glu Ile Lys Arg  Leu Ser Ser Glu
    1325                 1330                1335

Ser Ser  Ser Gln Trp Ala Leu  Val Val Gln Phe  Cys Arg Leu His
    1340                 1345                1350

Asn Met  Lys Leu Ser Ile Ser  Tyr Leu Arg Glu  Cys Ala Lys Ala
    1355                 1360                1365
```

-continued

```
Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755
```

```
Ala Cys Glu His Pro Thr Gly Trp Ser Ser Met Glu Arg His
    1760                1765            1770

Leu Leu Leu Thr Leu Ala Gly His Trp Leu Ala Gln Glu Asp Val
    1775                1780            1785

Val Pro Leu Asp Lys Leu Glu Glu Leu Glu Lys Gln Ile Trp Leu
    1790                1795            1800

Cys Arg Ile Thr Gln His Thr Leu Gly Arg Asn Gln Glu Glu Thr
    1805                1810            1815

Glu Pro Arg Phe Ser Arg Gln Ile Ser Thr Ser Gly Glu Leu Ser
    1820                1825            1830

Phe Asp Ser Leu Ala Ser Glu Phe Ser Phe Ser Lys Leu Ala Ala
    1835                1840            1845

Leu Asn Thr Ser Lys Tyr Leu Glu Leu Asn Ser Leu Pro Ser Lys
    1850                1855            1860

Glu Thr Cys Glu Asn Arg Leu Asp Trp Lys Glu Gln Glu Ser Leu
    1865                1870            1875

Asn Phe Leu Ile Gly Arg Leu Leu Asp Asp Gly Cys Val His Glu
    1880                1885            1890

Ala Ser Arg Val Cys Arg Tyr Phe His Phe Tyr Asn Pro Asp Val
    1895                1900            1905

Ala Leu Val Leu His Cys Arg Ala Leu Ala Ser Gly Glu Ala Ser
    1910                1915            1920

Met Glu Asp Leu His Pro Glu Ile His Ala Leu Leu Gln Ser Ala
    1925                1930            1935

Glu Leu Leu Glu Glu Glu Ala Pro Asp Ile Pro Leu Arg Arg Val
    1940                1945            1950

His Ser Thr
    1955

<210> SEQ ID NO 182
<211> LENGTH: 1999
<212> TYPE: PRT
<213> ORGANISM: Homo sapiens

<400> SEQUENCE: 182

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160
```

-continued

```
Asn Asn Thr Ser Leu Leu Phe Ile Asn Lys Cys Val Ile Leu His Ile
            165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
            210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
            290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575
```

Leu Arg Asn Val Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser  Leu Gln His Leu Leu  Tyr Val Tyr

```
                995               1000              1005
Leu Asp Cys Tyr Lys Leu Ser Pro Glu Asn Cys Pro Phe Leu Glu
    1010            1015            1020

Lys Lys Glu Leu His Glu Ala His Pro Trp Phe Glu Phe Leu Val
    1025            1030            1035

Gln Cys Arg Gln Val Ala Ser Asn Leu Thr Asp Pro Lys Leu Ile
    1040            1045            1050

Phe Gln Ala Ser Leu Ala Asn Ala Gln Ile Leu Ile Pro Thr Asn
    1055            1060            1065

Gln Ala Ser Val Ser Ser Met Leu Leu Glu Gly His Thr Leu Leu
    1070            1075            1080

Ala Leu Ala Thr Thr Met Tyr Ser Pro Gly Gly Val Ser Gln Val
    1085            1090            1095

Val Gln Asn Glu Glu Asn Glu Asn Cys Leu Lys Lys Val Asp Pro
    1100            1105            1110

Gln Leu Leu Lys Met Ala Leu Thr Pro Tyr Pro Lys Leu Lys Thr
    1115            1120            1125

Ala Leu Phe Pro Gln Cys Thr Pro Pro Ser Val Leu Pro Ser Asp
    1130            1135            1140

Ile Thr Ile Tyr His Leu Ile Gln Ser Leu Ser Pro Phe Asp Pro
    1145            1150            1155

Ser Arg Leu Phe Gly Trp Gln Ser Ala Asn Thr Leu Ala Ile Gly
    1160            1165            1170

Asp Ala Trp Ser His Leu Pro His Phe Ser Ser Pro Asp Leu Val
    1175            1180            1185

Asn Lys Tyr Ala Ile Val Glu Arg Leu Asn Phe Ala Tyr Tyr Leu
    1190            1195            1200

His Asn Gly Arg Pro Ser Phe Ala Phe Gly Thr Phe Leu Val Gln
    1205            1210            1215

Glu Leu Ile Lys Ser Lys Thr Pro Lys Gln Leu Ile Gln Gln Val
    1220            1225            1230

Gly Asn Glu Ala Tyr Val Ile Gly Leu Ser Ser Phe His Ile Pro
    1235            1240            1245

Ser Ile Gly Ala Ala Cys Val Cys Phe Leu Glu Leu Leu Gly Leu
    1250            1255            1260

Asp Ser Leu Lys Leu Arg Val Asp Met Lys Val Ala Asn Ile Ile
    1265            1270            1275

Leu Ser Tyr Lys Cys Arg Asn Glu Asp Ala Gln Tyr Ser Phe Ile
    1280            1285            1290

Arg Glu Ser Val Ala Glu Lys Leu Ser Lys Leu Ala Asp Gly Glu
    1295            1300            1305

Lys Thr Thr Thr Glu Glu Leu Leu Val Leu Leu Glu Glu Gly Thr
    1310            1315            1320

Trp Asn Ser Ile Gln Gln Gln Glu Ile Lys Arg Leu Ser Ser Glu
    1325            1330            1335

Ser Ser Ser Gln Trp Ala Leu Val Val Gln Phe Cys Arg Leu His
    1340            1345            1350

Asn Met Lys Leu Ser Ile Ser Tyr Leu Arg Glu Cys Ala Lys Ala
    1355            1360            1365

Asn Asp Trp Leu Gln Phe Ile Ile His Ser Gln Leu His Asn Tyr
    1370            1375            1380

His Pro Ala Glu Val Lys Ser Leu Ile Gln Tyr Phe Ser Pro Val
    1385            1390            1395
```

```
Ile Gln Asp His Leu Arg Leu Ala Phe Glu Asn Leu Pro Ser Val
    1400            1405                1410

Pro Thr Ser Lys Met Asp Ser Asp Gln Val Cys Asn Lys Cys Pro
    1415            1420                1425

Gln Glu Leu Gln Gly Ser Lys Gln Glu Met Thr Asp Leu Phe Glu
    1430            1435                1440

Ile Leu Leu Gln Cys Ser Glu Glu Pro Asp Ser Trp His Trp Leu
    1445            1450                1455

Leu Val Glu Ala Val Lys Gln Gln Ala Pro Ile Leu Ser Val Leu
    1460            1465                1470

Ala Ser Cys Leu Gln Gly Ala Ser Ala Ile Ser Cys Leu Cys Val
    1475            1480                1485

Trp Ile Ile Thr Ser Val Glu Asp Asn Val Ala Thr Glu Ala Met
    1490            1495                1500

Gly His Ile Gln Asp Ser Thr Glu Asp His Thr Trp Asn Leu Glu
    1505            1510                1515

Asp Leu Ser Val Ile Trp Arg Thr Leu Leu Thr Arg Gln Lys Ser
    1520            1525                1530

Lys Thr Leu Ile Arg Gly Phe Gln Leu Phe Phe Lys Asp Ser Pro
    1535            1540                1545

Leu Leu Leu Val Met Glu Met Tyr Glu Leu Cys Met Phe Phe Arg
    1550            1555                1560

Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
    1670            1675                1680

Gly Gln Phe Ala Leu Ala Arg Arg Val Ala Glu Leu Ala Glu Leu
    1685            1690                1695

Pro Val Asp Asn Leu Val Ile Lys Glu Ile Thr Gln Glu Met Gln
    1700            1705                1710

Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785
```

-continued

```
Val Pro Leu Asp Lys Leu Glu Glu Leu Glu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Glu Leu Ser
1820                1825                1830

Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Gln Glu Ser Leu
1865                1870                1875

Asn Phe Leu Ile Gly Arg Leu Leu Asp Asp Gly Cys Val His Glu
1880                1885                1890

Ala Ser Arg Val Cys Arg Tyr Phe His Phe Tyr Asn Pro Asp Val
1895                1900                1905

Ala Leu Val Leu His Cys Arg Ala Leu Ala Ser Gly Glu Ala Ser
1910                1915                1920

Met Glu Asp Leu His Pro Glu Ile His Ala Leu Leu Gln Ser Ala
1925                1930                1935

Glu Leu Leu Glu Glu Glu Ala Pro Asp Ile Pro Leu Arg Arg Val
1940                1945                1950

His Ser Thr Ser Ser Leu Asp Ser Gln Lys Phe Val Thr Val Pro
1955                1960                1965

Ser Ser Asn Glu Val Val Thr Asn Leu Glu Val Leu Thr Ser Lys
1970                1975                1980

Cys Leu His Gly Lys Asn Tyr Cys Arg Gln Val Leu Ser Leu Ser
1985                1990                1995

Val
```

<210> SEQ ID NO 183
<211> LENGTH: 1998
<212> TYPE: PRT
<213> ORGANISM: Homo sapiens

<400> SEQUENCE: 183

```
Met Ala Glu Glu Gly Val Ala Ser Ala Ala Ser Ala Gly Gly Ser
1                 5                  10                 15

Trp Gly Thr Ala Ala Met Gly Arg Val Leu Pro Met Leu Leu Val Pro
          20                  25                  30

Val Pro Ala Glu Ala Met Gly Gln Leu Gly Ser Arg Ala Gln Leu Arg
              35                  40                  45

Thr Gln Pro Glu Ala Leu Gly Ser Leu Thr Ala Gly Ser Leu Gln
50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                    85                  90                  95

Thr Pro Thr Glu Lys Pro Lys Leu Leu Ala Leu Gly Glu Asn Tyr Glu
              100                 105                 110

Leu Leu Ile Tyr Glu Phe Asn Leu Lys Asp Gly Arg Cys Asp Ala Thr
          115                 120                 125

Ile Leu Tyr Ser Cys Ser Arg Glu Ala Leu Gln Lys Leu Ile Asp Asp
      130                 135                 140
```

```
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
            165                 170                 175

Ile Phe Pro Glu Arg Asp Ala Ala Ile Arg Val Leu Asn Cys Phe Thr
        180                 185                 190

Leu Pro Leu Pro Ala Gln Ala Val Asp Met Ile Ile Asp Thr Gln Leu
    195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
            245                 250                 255

Ser Ser Phe Thr Ser Leu Lys Val Ser Gln Asp Leu Asp Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
```

```
                565                 570                 575
Leu Arg Asn Val Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
            850                 855                 860

Ile Leu Leu Pro Arg Ile Ser Pro Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
            930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990
```

```
Ile Leu Tyr Cys Leu Glu His Ser  Leu Gln His Leu Leu  Tyr Val Tyr
        995                 1000                 1005

Leu Asp Cys Tyr Lys Leu Ser  Pro Glu Asn Cys Pro  Phe Leu Glu
    1010                1015                1020

Lys Lys Glu Leu His Glu Ala  His Pro Trp Phe Glu  Phe Leu Val
    1025                1030                1035

Gln Cys Arg Gln Val Ala Ser  Asn Leu Thr Asp Pro  Lys Leu Ile
    1040                1045                1050

Phe Gln Ala Ser Leu Ala Asn  Ala Gln Ile Leu Ile  Pro Thr Asn
    1055                1060                1065

Gln Ala Ser Val Ser Ser Met  Leu Leu Glu Gly His  Thr Leu Leu
    1070                1075                1080

Ala Leu Ala Thr Thr Met Tyr  Ser Pro Gly Gly Val  Ser Gln Val
    1085                1090                1095

Val Gln Asn Glu Glu Asn Glu  Asn Cys Leu Lys Lys  Val Asp Pro
    1100                1105                1110

Gln Leu Leu Lys Met Ala Leu  Thr Pro Tyr Pro Lys  Leu Lys Thr
    1115                1120                1125

Ala Leu Phe Pro Gln Cys Thr  Pro Pro Ser Val Leu  Pro Ser Asp
    1130                1135                1140

Ile Thr Ile Tyr His Leu Ile  Gln Ser Leu Ser Pro  Phe Asp Pro
    1145                1150                1155

Ser Arg Leu Phe Gly Trp Gln  Ser Ala Asn Thr Leu  Ala Ile Gly
    1160                1165                1170

Asp Ala Trp Ser His Leu Pro  His Phe Ser Ser Pro  Asp Leu Val
    1175                1180                1185

Asn Lys Tyr Ala Ile Val Glu  Arg Leu Asn Phe Ala  Tyr Tyr Leu
    1190                1195                1200

His Asn Gly Arg Pro Ser Phe  Ala Phe Gly Thr Phe  Leu Val Gln
    1205                1210                1215

Glu Leu Ile Lys Ser Lys Thr  Pro Lys Gln Leu Ile  Gln Gln Val
    1220                1225                1230

Gly Asn Glu Ala Tyr Val Ile  Gly Leu Ser Ser Phe  His Ile Pro
    1235                1240                1245

Ser Ile Gly Ala Ala Cys Val  Cys Phe Leu Glu Leu  Leu Gly Leu
    1250                1255                1260

Asp Ser Leu Lys Leu Arg Val  Asp Met Lys Val Ala  Asn Ile Ile
    1265                1270                1275

Leu Ser Tyr Lys Cys Arg Asn  Glu Asp Ala Gln Tyr  Ser Phe Ile
    1280                1285                1290

Arg Glu Ser Val Ala Glu Lys  Leu Ser Lys Leu Ala  Asp Gly Glu
    1295                1300                1305

Lys Thr Thr Thr Glu Glu Leu  Leu Val Leu Leu Glu  Glu Gly Thr
    1310                1315                1320

Trp Asn Ser Ile Gln Gln Gln  Glu Ile Lys Arg Leu  Ser Ser Glu
    1325                1330                1335

Ser Ser Ser Gln Trp Ala Leu  Val Val Gln Phe Cys  Arg Leu His
    1340                1345                1350

Asn Met Lys Leu Ser Ile Ser  Tyr Leu Arg Glu Cys  Ala Lys Ala
    1355                1360                1365

Asn Asp Trp Leu Gln Phe Ile  Ile His Ser Gln Leu  His Asn Tyr
    1370                1375                1380
```

```
His Pro Ala Glu Val Lys Ser  Leu Ile Gln Tyr Phe  Ser Pro Val
1385                1390                1395

Ile Gln Asp His Leu Arg Leu  Ala Phe Glu Asn Leu  Pro Ser Val
1400                1405                1410

Pro Thr Ser Lys Met Asp Ser  Asp Gln Val Cys Asn  Lys Cys Pro
1415                1420                1425

Gln Glu Leu Gln Gly Ser Lys  Gln Glu Met Thr Asp  Leu Phe Glu
1430                1435                1440

Ile Leu Leu Gln Cys Ser Glu  Glu Pro Asp Ser Trp  His Trp Leu
1445                1450                1455

Leu Val Glu Ala Val Lys Gln  Gln Ala Pro Ile Leu  Ser Val Leu
1460                1465                1470

Ala Ser Cys Leu Gln Gly Ala  Ser Ala Ile Ser Cys  Leu Cys Val
1475                1480                1485

Trp Ile Ile Thr Ser Val Glu  Asp Asn Val Ala Thr  Glu Ala Met
1490                1495                1500

Gly His Ile Gln Asp Ser Thr  Glu Asp His Thr Trp  Asn Leu Glu
1505                1510                1515

Asp Leu Ser Val Ile Trp Arg  Thr Leu Leu Thr Arg  Gln Lys Ser
1520                1525                1530

Lys Thr Leu Ile Arg Gly Phe  Gln Leu Phe Phe Lys  Asp Ser Pro
1535                1540                1545

Leu Leu Leu Val Met Glu Met  Tyr Glu Leu Cys Met  Phe Phe Arg
1550                1555                1560

Asn Tyr Lys Glu Ala Glu Ala  Lys Leu Leu Glu Phe  Gln Lys Ser
1565                1570                1575

Leu Glu Thr Leu Asn Thr Ala  Ala Thr Lys Val His  Pro Val Ile
1580                1585                1590

Pro Ala Met Trp Leu Glu Asp  Gln Val Cys Phe Leu  Leu Lys Leu
1595                1600                1605

Met Leu Gln Gln Cys Lys Thr  Gln Tyr Glu Leu Gly  Lys Leu Leu
1610                1615                1620

Gln Leu Phe Val Glu Arg Glu  His Leu Phe Ser Asp  Gly Pro Asp
1625                1630                1635

Val Lys Lys Leu Cys Ile Leu  Cys Gln Ile Leu Lys  Asp Thr Ser
1640                1645                1650

Ile Ala Ile Asn His Thr Ile  Ile Thr Ser Tyr Ser  Ile Glu Asn
1655                1660                1665

Leu Gln His Glu Cys Arg Ser  Ile Leu Glu Arg Leu  Gln Thr Asp
1670                1675                1680

Gly Gln Phe Ala Leu Ala Arg  Arg Val Ala Glu Leu  Ala Glu Leu
1685                1690                1695

Pro Val Asp Asn Leu Val Ile  Lys Glu Ile Thr Gln  Glu Met Gln
1700                1705                1710

Thr Leu Lys His Ile Glu Gln  Trp Ser Leu Lys Gln  Ala Arg Ile
1715                1720                1725

Asp Phe Trp Lys Lys Cys His  Glu Asn Phe Lys Lys  Asn Ser Ile
1730                1735                1740

Ser Ser Lys Ala Ala Ser Ser  Phe Phe Ser Thr Gln  Ala His Val
1745                1750                1755

Ala Cys Glu His Pro Thr Gly  Trp Ser Ser Met Glu  Glu Arg His
1760                1765                1770

Leu Leu Leu Thr Leu Ala Gly  His Trp Leu Ala Gln  Glu Asp Val
```

```
                     1775                1780                1785

Val  Pro  Leu  Asp  Lys  Leu  Glu  Glu  Leu  Glu  Lys  Gln  Ile  Trp  Leu
               1790                1795                1800

Cys  Arg  Ile  Thr  Gln  His  Thr  Leu  Gly  Arg  Asn  Gln  Glu  Glu  Thr
1805                1810                1815

Glu  Pro  Arg  Phe  Ser  Arg  Gln  Ile  Ser  Thr  Ser  Gly  Glu  Leu  Ser
1820                1825                1830

Phe  Asp  Ser  Leu  Ala  Ser  Glu  Phe  Ser  Phe  Ser  Lys  Leu  Ala  Ala
1835                1840                1845

Leu  Asn  Thr  Ser  Lys  Tyr  Leu  Glu  Leu  Asn  Ser  Leu  Pro  Ser  Lys
1850                1855                1860

Glu  Thr  Cys  Glu  Asn  Arg  Leu  Asp  Trp  Lys  Glu  Gln  Glu  Ser  Leu
1865                1870                1875

Asn  Phe  Leu  Ile  Gly  Arg  Leu  Leu  Asp  Asp  Gly  Cys  Val  His  Glu
1880                1885                1890

Ala  Ser  Arg  Val  Cys  Arg  Tyr  Phe  His  Phe  Tyr  Asn  Pro  Asp  Val
1895                1900                1905

Ala  Leu  Val  Leu  His  Cys  Arg  Ala  Leu  Ala  Ser  Gly  Glu  Ala  Ser
1910                1915                1920

Met  Glu  Asp  Leu  His  Pro  Glu  Ile  His  Ala  Leu  Leu  Gln  Ser  Ala
1925                1930                1935

Glu  Leu  Leu  Glu  Glu  Ala  Pro  Asp  Ile  Pro  Leu  Arg  Arg  Val
1940                1945                1950

His  Ser  Thr  Ser  Ser  Leu  Asp  Ser  Gln  Lys  Phe  Val  Thr  Val  Pro
1955                1960                1965

Ser  Ser  Asn  Glu  Val  Val  Thr  Asn  Leu  Glu  Val  Leu  Thr  Ser  Lys
1970                1975                1980

Cys  Leu  His  Gly  Lys  Asn  Tyr  Cys  Arg  Gln  Val  Leu  Leu  Ser  Val
1985                1990                1995

<210> SEQ ID NO 184
<211> LENGTH: 2055
<212> TYPE: PRT
<213> ORGANISM: Homo sapiens

<400> SEQUENCE: 184

Met  Ala  Ala  Glu  Glu  Gly  Val  Ala  Ser  Ala  Ser  Ala  Gly  Gly  Ser
1                   5                   10                  15

Trp  Gly  Thr  Ala  Ala  Met  Gly  Arg  Val  Leu  Pro  Met  Leu  Leu  Val  Pro
                20                  25                  30

Val  Pro  Ala  Glu  Ala  Met  Gly  Gln  Leu  Gly  Ser  Arg  Ala  Gln  Leu  Arg
            35                  40                  45

Thr  Gln  Pro  Glu  Ala  Leu  Gly  Ser  Leu  Thr  Ala  Gly  Ser  Leu  Gln
        50                  55                  60

Val  Leu  Ser  Leu  Thr  Pro  Gly  Ser  Arg  Gly  Gly  Arg  Cys  Cys  Leu
65                  70                  75                  80

Glu  Gly  Pro  Phe  Trp  His  Phe  Leu  Trp  Glu  Asp  Ser  Arg  Asn  Ser  Ser
                85                  90                  95

Thr  Pro  Thr  Glu  Lys  Pro  Lys  Leu  Leu  Ala  Leu  Gly  Glu  Asn  Tyr  Glu
            100                 105                 110

Leu  Leu  Ile  Tyr  Glu  Phe  Asn  Leu  Lys  Asp  Gly  Arg  Cys  Asp  Ala  Thr
        115                 120                 125

Ile  Leu  Tyr  Ser  Cys  Ser  Arg  Glu  Ala  Leu  Gln  Lys  Leu  Ile  Asp  Asp
        130                 135                 140
```

```
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
            165                 170                 175

Ile Phe Pro Glu Arg Asp Ala Ala Ile Arg Val Leu Asn Cys Phe Thr
        180                 185                 190

Leu Pro Leu Pro Ala Gln Ala Val Asp Met Ile Ile Asp Thr Gln Leu
    195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
            245                 250                 255

Ser Ser Phe Thr Ser Leu Lys Val Ser Gln Asp Leu Asp Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
```

```
                565                 570                 575
Leu Arg Asn Val Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
                755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
            850                 855                 860

Ile Leu Leu Pro Arg Ile Ser Pro Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
                900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
            930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990
```

```
Ile Leu Tyr Cys Leu Glu His Ser  Leu Gln His Leu Leu  Tyr Val Tyr
        995                 1000                1005

Leu Asp Cys Tyr Lys Leu Ser  Pro Glu Asn Cys Pro  Phe Leu Glu
    1010                1015                1020

Lys Lys Glu Leu His Glu Ala  His Pro Trp Phe Glu  Phe Leu Val
    1025                1030                1035

Gln Cys Arg Gln Val Ala Ser  Asn Leu Thr Asp Pro  Lys Leu Ile
    1040                1045                1050

Phe Gln Ala Ser Leu Ala Asn  Ala Gln Ile Leu Ile  Pro Thr Asn
    1055                1060                1065

Gln Ala Ser Val Ser Ser Met  Leu Leu Glu Gly His  Thr Leu Leu
    1070                1075                1080

Ala Leu Ala Thr Thr Met Tyr  Ser Pro Gly Gly Val  Ser Gln Val
    1085                1090                1095

Val Gln Asn Glu Glu Asn Glu  Asn Cys Leu Lys Lys  Val Asp Pro
    1100                1105                1110

Gln Leu Leu Lys Met Ala Leu  Thr Pro Tyr Pro Lys  Leu Lys Thr
    1115                1120                1125

Ala Leu Phe Pro Gln Cys Thr  Pro Pro Ser Val Leu  Pro Ser Asp
    1130                1135                1140

Ile Thr Ile Tyr His Leu Ile  Gln Ser Leu Ser Pro  Phe Asp Pro
    1145                1150                1155

Ser Arg Leu Phe Gly Trp Gln  Ser Ala Asn Thr Leu  Ala Ile Gly
    1160                1165                1170

Asp Ala Trp Ser His Leu Pro  His Phe Ser Ser Pro  Asp Leu Val
    1175                1180                1185

Asn Lys Tyr Ala Ile Val Glu  Arg Leu Asn Phe Ala  Tyr Tyr Leu
    1190                1195                1200

His Asn Gly Arg Pro Ser Phe  Ala Phe Gly Thr Phe  Leu Val Gln
    1205                1210                1215

Glu Leu Ile Lys Ser Lys Thr  Pro Lys Gln Leu Ile  Gln Gln Val
    1220                1225                1230

Gly Asn Glu Ala Tyr Val Ile  Gly Leu Ser Ser Phe  His Ile Pro
    1235                1240                1245

Ser Ile Gly Ala Ala Cys Val  Cys Phe Leu Glu Leu  Leu Gly Leu
    1250                1255                1260

Asp Ser Leu Lys Leu Arg Val  Asp Met Lys Val Ala  Asn Ile Ile
    1265                1270                1275

Leu Ser Tyr Lys Cys Arg Asn  Glu Asp Ala Gln Tyr  Ser Phe Ile
    1280                1285                1290

Arg Glu Ser Val Ala Glu Lys  Leu Ser Lys Leu Ala  Asp Gly Glu
    1295                1300                1305

Lys Thr Thr Thr Glu Glu Leu  Leu Val Leu Leu Glu  Glu Gly Thr
    1310                1315                1320

Trp Asn Ser Ile Gln Gln Gln  Glu Ile Lys Arg Leu  Ser Ser Glu
    1325                1330                1335

Ser Ser Ser Gln Trp Ala Leu  Val Val Gln Phe Cys  Arg Leu His
    1340                1345                1350

Asn Met Lys Leu Ser Ile Ser  Tyr Leu Arg Glu Cys  Ala Lys Ala
    1355                1360                1365

Asn Asp Trp Leu Gln Phe Ile  Ile His Ser Gln Leu  His Asn Tyr
    1370                1375                1380
```

His Pro Ala Glu Val Lys Ser Leu Ile Gln Tyr Phe Ser Pro Val
1385                     1390                1395

Ile Gln Asp His Leu Arg Leu Ala Phe Glu Asn Leu Pro Ser Val
1400                     1405                1410

Pro Thr Ser Lys Met Asp Ser Asp Gln Val Cys Asn Lys Cys Pro
1415                     1420                1425

Gln Glu Leu Gln Gly Ser Lys Gln Glu Met Thr Asp Leu Phe Glu
1430                     1435                1440

Ile Leu Leu Gln Cys Ser Glu Glu Pro Asp Ser Trp His Trp Leu
1445                     1450                1455

Leu Val Glu Ala Val Lys Gln Gln Ala Pro Ile Leu Ser Val Leu
1460                     1465                1470

Ala Ser Cys Leu Gln Gly Ala Ser Ala Ile Ser Cys Leu Cys Val
1475                     1480                1485

Trp Ile Ile Thr Ser Val Glu Asp Asn Val Ala Thr Glu Ala Met
1490                     1495                1500

Gly His Ile Gln Asp Ser Thr Glu Asp His Thr Trp Asn Leu Glu
1505                     1510                1515

Asp Leu Ser Val Ile Trp Arg Thr Leu Leu Thr Arg Gln Lys Ser
1520                     1525                1530

Lys Thr Leu Ile Arg Gly Phe Gln Leu Phe Phe Lys Asp Ser Pro
1535                     1540                1545

Leu Leu Leu Val Met Glu Met Tyr Glu Leu Cys Met Phe Phe Arg
1550                     1555                1560

Asn Tyr Lys Glu Ala Glu Ala Lys Leu Leu Glu Phe Gln Lys Ser
1565                     1570                1575

Leu Glu Thr Leu Asn Thr Ala Ala Thr Lys Val His Pro Val Ile
1580                     1585                1590

Pro Ala Met Trp Leu Glu Asp Gln Val Cys Phe Leu Leu Lys Leu
1595                     1600                1605

Met Leu Gln Gln Cys Lys Thr Gln Tyr Glu Leu Gly Lys Leu Leu
1610                     1615                1620

Gln Leu Phe Val Glu Arg Glu His Leu Phe Ser Asp Gly Pro Asp
1625                     1630                1635

Val Lys Lys Leu Cys Ile Leu Cys Gln Ile Leu Lys Asp Thr Ser
1640                     1645                1650

Ile Ala Ile Asn His Thr Ile Ile Thr Ser Tyr Ser Ile Glu Asn
1655                     1660                1665

Leu Gln His Glu Cys Arg Ser Ile Leu Glu Arg Leu Gln Thr Asp
1670                     1675                1680

Gly Gln Phe Ala Leu Ala Arg Arg Val Ala Glu Leu Ala Glu Leu
1685                     1690                1695

Pro Val Asp Asn Leu Val Ile Lys Glu Ile Thr Gln Glu Met Gln
1700                     1705                1710

Thr Leu Lys His Ile Glu Gln Trp Ser Leu Lys Gln Ala Arg Ile
1715                     1720                1725

Asp Phe Trp Lys Lys Cys His Glu Asn Phe Lys Lys Asn Ser Ile
1730                     1735                1740

Ser Ser Lys Ala Ala Ser Ser Phe Phe Ser Thr Gln Ala His Val
1745                     1750                1755

Ala Cys Glu His Pro Thr Gly Trp Ser Ser Met Glu Glu Arg His
1760                     1765                1770

Leu Leu Leu Thr Leu Ala Gly His Trp Leu Ala Gln Glu Asp Val

```
                1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Met Ile
    1985                1990                1995

Leu Pro Arg Ser Trp Ala Val Pro Thr Gln Met Leu Leu Leu Arg
    2000                2005                2010

Met Val Lys Pro Cys Ser Gly Lys Ser Trp Pro Leu Ser Ser Leu
    2015                2020                2025

Thr Asp Ala Asn Glu Pro Arg Pro Ser Ser Ala His Arg Ala Leu
    2030                2035                2040

Ser Gln Ile Leu Trp Leu Asn Ser Trp Gln Lys Arg
    2045                2050                2055

<210> SEQ ID NO 185
<211> LENGTH: 2030
<212> TYPE: PRT
<213> ORGANISM: Homo sapiens

<400> SEQUENCE: 185

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80
```

-continued

```
Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
```

```
              500                 505                 510
Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925
```

```
Thr Ser Cys Asn Asn Tyr Met Arg Asn Glu Ile Leu Asp Lys Leu Ala
    930                 935             940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
        995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320
```

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile

```
                    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Leu Tyr
    1985                1990                1995

Asp Leu Ala Lys Glu Leu Gly Cys Ser Tyr Thr Asp Val Ala Ala
    2000                2005                2010

Gln Asp Gly Glu Ala Met Leu Arg Lys Ile Leu Ala Ser Gln Gln
    2015                2020                2025

Pro Asp
    2030

<210> SEQ ID NO 186
<211> LENGTH: 2259
<212> TYPE: PRT
<213> ORGANISM: Homo sapiens

<400> SEQUENCE: 186

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30
```

```
Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
    355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
                420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
```

```
            450                 455                 460
Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
                675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
                820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
            850                 855                 860

Ile Leu Leu Pro Arg Ile Ser Pro Glu Glu Tyr Lys Ser Tyr Ser Pro
865                 870                 875                 880
```

```
Glu Ala Leu Trp Arg Tyr Leu Thr Ala Arg His Asp Trp Leu Asn Ile
            885                 890                 895
Ile Leu Trp Ile Gly Glu Phe Gln Thr Gln His Ser Tyr Ala Ser Leu
            900                 905                 910
Gln Gln Asn Lys Trp Pro Leu Leu Thr Val Asp Val Ile Asn Gln Asn
            915                 920                 925
Thr Ser Cys Asn Asn Tyr Met Arg Asn Glu Ile Leu Asp Lys Leu Ala
        930                 935                 940
Arg Asn Gly Val Phe Leu Ala Ser Glu Leu Glu Asp Phe Glu Cys Phe
945                 950                 955                 960
Leu Leu Arg Leu Ser Arg Ile Gly Gly Val Ile Gln Asp Thr Leu Pro
                965                 970                 975
Val Gln Asn Tyr Lys Thr Lys Glu Gly Trp Asp Phe His Ser Gln Phe
            980                 985                 990
Ile Leu Tyr Cys Leu Glu His Ser Leu Gln His Leu Leu Tyr Val Tyr
            995                 1000                1005
Leu Asp Cys Tyr Lys Leu Ser Pro Glu Asn Cys Pro Phe Leu Glu
        1010                1015                1020
Lys Lys Glu Leu His Glu Ala His Pro Trp Phe Glu Phe Leu Val
        1025                1030                1035
Gln Cys Arg Gln Val Ala Ser Asn Leu Thr Asp Pro Lys Leu Ile
        1040                1045                1050
Phe Gln Ala Ser Leu Ala Asn Ala Gln Ile Leu Ile Pro Thr Asn
        1055                1060                1065
Gln Ala Ser Val Ser Ser Met Leu Leu Glu Gly His Thr Leu Leu
        1070                1075                1080
Ala Leu Ala Thr Thr Met Tyr Ser Pro Gly Gly Val Ser Gln Val
        1085                1090                1095
Val Gln Asn Glu Glu Asn Glu Asn Cys Leu Lys Lys Val Asp Pro
        1100                1105                1110
Gln Leu Leu Lys Met Ala Leu Thr Pro Tyr Pro Lys Leu Lys Thr
        1115                1120                1125
Ala Leu Phe Pro Gln Cys Thr Pro Pro Ser Val Leu Pro Ser Asp
        1130                1135                1140
Ile Thr Ile Tyr His Leu Ile Gln Ser Leu Ser Pro Phe Asp Pro
        1145                1150                1155
Ser Arg Leu Phe Gly Trp Gln Ser Ala Asn Thr Leu Ala Ile Gly
        1160                1165                1170
Asp Ala Trp Ser His Leu Pro His Phe Ser Ser Pro Asp Leu Val
        1175                1180                1185
Asn Lys Tyr Ala Ile Val Glu Arg Leu Asn Phe Ala Tyr Tyr Leu
        1190                1195                1200
His Asn Gly Arg Pro Ser Phe Ala Phe Gly Thr Phe Leu Val Gln
        1205                1210                1215
Glu Leu Ile Lys Ser Lys Thr Pro Lys Gln Leu Ile Gln Gln Val
        1220                1225                1230
Gly Asn Glu Ala Tyr Val Ile Gly Leu Ser Ser Phe His Ile Pro
        1235                1240                1245
Ser Ile Gly Ala Ala Cys Val Cys Phe Leu Glu Leu Leu Gly Leu
        1250                1255                1260
Asp Ser Leu Lys Leu Arg Val Asp Met Lys Val Ala Asn Ile Ile
        1265                1270                1275
```

```
Leu Ser Tyr Lys Cys Arg Asn Glu Asp Ala Gln Tyr Ser Phe Ile
    1280            1285                1290

Arg Glu Ser Val Ala Glu Lys Leu Ser Lys Leu Ala Asp Gly Glu
1295                1300                1305

Lys Thr Thr Thr Glu Glu Leu Leu Val Leu Leu Glu Glu Gly Thr
    1310            1315                1320

Trp Asn Ser Ile Gln Gln Gln Glu Ile Lys Arg Leu Ser Ser Glu
    1325            1330                1335

Ser Ser Ser Gln Trp Ala Leu Val Val Gln Phe Cys Arg Leu His
    1340            1345                1350

Asn Met Lys Leu Ser Ile Ser Tyr Leu Arg Glu Cys Ala Lys Ala
    1355            1360                1365

Asn Asp Trp Leu Gln Phe Ile Ile His Ser Gln Leu His Asn Tyr
    1370            1375                1380

His Pro Ala Glu Val Lys Ser Leu Ile Gln Tyr Phe Ser Pro Val
    1385            1390                1395

Ile Gln Asp His Leu Arg Leu Ala Phe Glu Asn Leu Pro Ser Val
    1400            1405                1410

Pro Thr Ser Lys Met Asp Ser Asp Gln Val Cys Asn Lys Cys Pro
    1415            1420                1425

Gln Glu Leu Gln Gly Ser Lys Gln Glu Met Thr Asp Leu Phe Glu
    1430            1435                1440

Ile Leu Leu Gln Cys Ser Glu Glu Pro Asp Ser Trp His Trp Leu
    1445            1450                1455

Leu Val Glu Ala Val Lys Gln Gln Ala Pro Ile Leu Ser Val Leu
    1460            1465                1470

Ala Ser Cys Leu Gln Gly Ala Ser Ala Ile Ser Cys Leu Cys Val
    1475            1480                1485

Trp Ile Ile Thr Ser Val Glu Asp Asn Val Ala Thr Glu Ala Met
    1490            1495                1500

Gly His Ile Gln Asp Ser Thr Glu Asp His Thr Trp Asn Leu Glu
    1505            1510                1515

Asp Leu Ser Val Ile Trp Arg Thr Leu Leu Thr Arg Gln Lys Ser
    1520            1525                1530

Lys Thr Leu Ile Arg Gly Phe Gln Leu Phe Phe Lys Asp Ser Pro
    1535            1540                1545

Leu Leu Leu Val Met Glu Met Tyr Glu Leu Cys Met Phe Phe Arg
    1550            1555                1560

Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
```

-continued

```
            1670                1675                1680
Gly Gln Phe Ala Leu Ala Arg Arg Val Ala Glu Leu Ala Glu Leu
        1685                1690                1695
Pro Val Asp Asn Leu Val Ile Lys Glu Ile Thr Gln Glu Met Gln
        1700                1705                1710
Thr Leu Lys His Ile Glu Gln Trp Ser Leu Lys Gln Ala Arg Ile
        1715                1720                1725
Asp Phe Trp Lys Lys Cys His Glu Asn Phe Lys Lys Asn Ser Ile
        1730                1735                1740
Ser Ser Lys Ala Ala Ser Ser Phe Phe Ser Thr Gln Ala His Val
        1745                1750                1755
Ala Cys Glu His Pro Thr Gly Trp Ser Ser Met Glu Glu Arg His
        1760                1765                1770
Leu Leu Leu Thr Leu Ala Gly His Trp Leu Ala Gln Glu Asp Val
        1775                1780                1785
Val Pro Leu Asp Lys Leu Glu Glu Leu Glu Lys Gln Ile Trp Leu
        1790                1795                1800
Cys Arg Ile Thr Gln His Thr Leu Gly Arg Asn Gln Glu Glu Thr
        1805                1810                1815
Glu Pro Arg Phe Ser Arg Gln Ile Ser Thr Ser Gly Glu Leu Ser
        1820                1825                1830
Phe Asp Ser Leu Ala Ser Glu Phe Ser Phe Ser Lys Leu Ala Ala
        1835                1840                1845
Leu Asn Thr Ser Lys Tyr Leu Glu Leu Asn Ser Leu Pro Ser Lys
        1850                1855                1860
Glu Thr Cys Glu Asn Arg Leu Asp Trp Lys Glu Gln Glu Ser Leu
        1865                1870                1875
Asn Phe Leu Ile Gly Arg Leu Leu Asp Asp Gly Cys Val His Glu
        1880                1885                1890
Ala Ser Arg Val Cys Arg Tyr Phe His Phe Tyr Asn Pro Asp Val
        1895                1900                1905
Ala Leu Val Leu His Cys Arg Ala Leu Ala Ser Gly Glu Ala Ser
        1910                1915                1920
Met Glu Asp Leu His Pro Glu Ile His Ala Leu Leu Gln Ser Ala
        1925                1930                1935
Glu Leu Leu Glu Glu Glu Ala Pro Asp Ile Pro Leu Arg Arg Val
        1940                1945                1950
His Ser Thr Ser Ser Leu Asp Ser Gln Lys Phe Val Thr Val Pro
        1955                1960                1965
Ser Ser Asn Glu Val Val Thr Asn Leu Glu Val Leu Thr Ser Lys
        1970                1975                1980
Cys Leu His Gly Lys Asn Tyr Cys Arg Gln Val Leu Cys Leu Tyr
        1985                1990                1995
Asp Leu Ala Lys Glu Leu Gly Cys Ser Tyr Thr Asp Val Ala Ala
        2000                2005                2010
Gln Asp Gly Glu Ala Met Leu Arg Lys Ile Leu Ala Ser Gln Gln
        2015                2020                2025
Pro Asp Arg Cys Lys Arg Ala Gln Ala Phe Ile Ser Thr Gln Gly
        2030                2035                2040
Leu Lys Pro Asp Thr Val Ala Glu Leu Val Ala Glu Glu Val Thr
        2045                2050                2055
Arg Glu Leu Leu Thr Ser Ser Gln Gly Thr Gly His Lys Gln Met
        2060                2065                2070
```

```
Phe Asn Pro Thr Glu Glu Ser Gln Thr Phe Leu Gln Leu Thr Thr
    2075                2080                2085

Leu Cys Gln Asp Arg Thr Leu Val Gly Met Lys Leu Leu Asp Lys
    2090                2095                2100

Ile Ser Ser Val Pro His Gly Glu Leu Ser Cys Thr Thr Glu Leu
    2105                2110                2115

Leu Ile Leu Ala His His Cys Phe Thr Leu Thr Cys His Met Glu
    2120                2125                2130

Gly Ile Ile Arg Val Leu Gln Ala Ala His Met Leu Thr Asp Asn
    2135                2140                2145

His Leu Ala Pro Ser Glu Glu Tyr Gly Leu Val Val Arg Leu Leu
    2150                2155                2160

Thr Gly Ile Gly Arg Tyr Asn Glu Met Thr Tyr Ile Phe Asp Leu
    2165                2170                2175

Leu His Lys Lys His Tyr Phe Glu Val Leu Met Arg Lys Lys Leu
    2180                2185                2190

Asp Pro Ser Gly Thr Leu Lys Thr Ala Leu Leu Asp Tyr Ile Lys
    2195                2200                2205

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ile Leu Ser Pro Gly Arg Thr Ala
    2240                2245                2250

Ser Arg Met Gly Thr Ser
    2255

<210> SEQ ID NO 187
<211> LENGTH: 2285
<212> TYPE: PRT
<213> ORGANISM: Homo sapiens

<400> SEQUENCE: 187

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
```

-continued

```
            165                 170                 175
Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
            210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
                290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
                435                 440                 445

Thr Ile Thr Leu Trp Asp Leu Glu Thr Gln Gly Met Gln Cys Ser Ser
                450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
                515                 520                 525

Pro Ile His Ala Leu Glu Ala Gly Ile Glu Asn Arg Gln Leu Asp Thr
                530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590
```

Ala Ile Arg Glu Ser Tyr Ser Glu Pro Gln Ser Lys His Phe Ser Glu
          595                 600                 605

Gln Leu Leu Asn Leu Thr Leu Ser Phe Leu Asn Asn Gln Ile Lys Glu
          610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
          645                 650                 655

Phe Pro Trp Lys Leu Thr Asp Ala Ile Asp Glu Tyr Asp Val His Glu
          660                 665                 670

Asn Val Pro Lys Val Lys Glu Ser Asn Ile Trp Lys Lys Leu Ser Phe
          675                 680                 685

Glu Glu Val Ile Ala Ser Ala Ile Leu Asn Asn Lys Ile Pro Glu Ala
          690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
          725                 730                 735

Asn Ile Lys Glu Ala Ser Glu Leu Leu Lys Asn Met Gly Phe Asp Val
          740                 745                 750

Lys Gly Gln Leu Leu Lys Ile Cys Phe Tyr Thr Thr Asn Lys Asn Ile
          755                 760                 765

Arg Asp Phe Leu Val Glu Ile Leu Lys Glu Lys Asn Tyr Phe Ser Glu
          770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
          805                 810                 815

Trp Ile Lys Glu Gln Asp Phe Phe Lys His Lys Ser Val Leu Asp Ser
          820                 825                 830

Phe Leu Lys Tyr Asp Cys Lys Asp Glu Phe Asn Lys Gln Asp His Arg
          835                 840                 845

Ile Val Leu Asn Trp Ala Leu Trp Trp Asp Gln Leu Thr Gln Glu Ser
          850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
          885                 890                 895

Ile Leu Trp Ile Gly Glu Phe Gln Thr Gln His Ser Tyr Ala Ser Leu
          900                 905                 910

Gln Gln Asn Lys Trp Pro Leu Leu Thr Val Asp Val Ile Asn Gln Asn
          915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
          965                 970                 975

Val Gln Asn Tyr Lys Thr Lys Glu Gly Trp Asp Phe His Ser Gln Phe
          980                 985                 990

Ile Leu Tyr Cys Leu Glu His Ser  Leu Gln His Leu Leu  Tyr Val Tyr
          995                 1000                1005

| | | | | | | | | | | | |
|---|---|---|---|---|---|---|---|---|---|---|---|
|Leu|Asp|Cys|Tyr|Lys|Leu|Ser|Pro|Glu|Asn|Cys|Pro|Phe|Leu|Glu|
| |1010| | | |1015| | | |1020| | | | | |

Leu Asp Cys Tyr Lys Leu Ser Pro Glu Asn Cys Pro Phe Leu Glu
    1010            1015            1020

Lys Lys Glu Leu His Glu Ala His Pro Trp Phe Glu Phe Leu Val
    1025            1030            1035

Gln Cys Arg Gln Val Ala Ser Asn Leu Thr Asp Pro Lys Leu Ile
    1040            1045            1050

Phe Gln Ala Ser Leu Ala Asn Ala Gln Ile Leu Ile Pro Thr Asn
    1055            1060            1065

Gln Ala Ser Val Ser Ser Met Leu Leu Glu Gly His Thr Leu Leu
    1070            1075            1080

Ala Leu Ala Thr Thr Met Tyr Ser Pro Gly Gly Val Ser Gln Val
    1085            1090            1095

Val Gln Asn Glu Glu Asn Glu Asn Cys Leu Lys Lys Val Asp Pro
    1100            1105            1110

Gln Leu Leu Lys Met Ala Leu Thr Pro Tyr Pro Lys Leu Lys Thr
    1115            1120            1125

Ala Leu Phe Pro Gln Cys Thr Pro Pro Ser Val Leu Pro Ser Asp
    1130            1135            1140

Ile Thr Ile Tyr His Leu Ile Gln Ser Leu Ser Pro Phe Asp Pro
    1145            1150            1155

Ser Arg Leu Phe Gly Trp Gln Ser Ala Asn Thr Leu Ala Ile Gly
    1160            1165            1170

Asp Ala Trp Ser His Leu Pro His Phe Ser Ser Pro Asp Leu Val
    1175            1180            1185

Asn Lys Tyr Ala Ile Val Glu Arg Leu Asn Phe Ala Tyr Tyr Leu
    1190            1195            1200

His Asn Gly Arg Pro Ser Phe Ala Phe Gly Thr Phe Leu Val Gln
    1205            1210            1215

Glu Leu Ile Lys Ser Lys Thr Pro Lys Gln Leu Ile Gln Gln Val
    1220            1225            1230

Gly Asn Glu Ala Tyr Val Ile Gly Leu Ser Ser Phe His Ile Pro
    1235            1240            1245

Ser Ile Gly Ala Ala Cys Val Cys Phe Leu Glu Leu Leu Gly Leu
    1250            1255            1260

Asp Ser Leu Lys Leu Arg Val Asp Met Lys Val Ala Asn Ile Ile
    1265            1270            1275

Leu Ser Tyr Lys Cys Arg Asn Glu Asp Ala Gln Tyr Ser Phe Ile
    1280            1285            1290

Arg Glu Ser Val Ala Glu Lys Leu Ser Lys Leu Ala Asp Gly Glu
    1295            1300            1305

Lys Thr Thr Thr Glu Glu Leu Leu Val Leu Leu Glu Glu Gly Thr
    1310            1315            1320

Trp Asn Ser Ile Gln Gln Gln Glu Ile Lys Arg Leu Ser Ser Glu
    1325            1330            1335

Ser Ser Ser Gln Trp Ala Leu Val Val Gln Phe Cys Arg Leu His
    1340            1345            1350

Asn Met Lys Leu Ser Ile Ser Tyr Leu Arg Glu Cys Ala Lys Ala
    1355            1360            1365

Asn Asp Trp Leu Gln Phe Ile Ile His Ser Gln Leu His Asn Tyr
    1370            1375            1380

His Pro Ala Glu Val Lys Ser Leu Ile Gln Tyr Phe Ser Pro Val
    1385            1390            1395

Ile Gln Asp His Leu Arg Leu Ala Phe Glu Asn Leu Pro Ser Val

-continued

```
                1400                1405                1410
Pro Thr Ser Lys Met Asp Ser Asp Gln Val Cys Asn Lys Cys Pro
            1415                1420                1425
Gln Glu Leu Gln Gly Ser Lys Gln Glu Met Thr Asp Leu Phe Glu
            1430                1435                1440
Ile Leu Leu Gln Cys Ser Glu Glu Pro Asp Ser Trp His Trp Leu
            1445                1450                1455
Leu Val Glu Ala Val Lys Gln Gln Ala Pro Ile Leu Ser Val Leu
            1460                1465                1470
Ala Ser Cys Leu Gln Gly Ala Ser Ala Ile Ser Cys Leu Cys Val
            1475                1480                1485
Trp Ile Ile Thr Ser Val Glu Asp Asn Val Ala Thr Glu Ala Met
            1490                1495                1500
Gly His Ile Gln Asp Ser Thr Glu Asp His Thr Trp Asn Leu Glu
            1505                1510                1515
Asp Leu Ser Val Ile Trp Arg Thr Leu Leu Thr Arg Gln Lys Ser
            1520                1525                1530
Lys Thr Leu Ile Arg Gly Phe Gln Leu Phe Phe Lys Asp Ser Pro
            1535                1540                1545
Leu Leu Leu Val Met Glu Met Tyr Glu Leu Cys Met Phe Phe Arg
            1550                1555                1560
Asn Tyr Lys Glu Ala Glu Ala Lys Leu Leu Glu Phe Gln Lys Ser
            1565                1570                1575
Leu Glu Thr Leu Asn Thr Ala Ala Thr Lys Val His Pro Val Ile
            1580                1585                1590
Pro Ala Met Trp Leu Glu Asp Gln Val Cys Phe Leu Leu Lys Leu
            1595                1600                1605
Met Leu Gln Gln Cys Lys Thr Gln Tyr Glu Leu Gly Lys Leu Leu
            1610                1615                1620
Gln Leu Phe Val Glu Arg Glu His Leu Phe Ser Asp Gly Pro Asp
            1625                1630                1635
Val Lys Lys Leu Cys Ile Leu Cys Gln Ile Leu Lys Asp Thr Ser
            1640                1645                1650
Ile Ala Ile Asn His Thr Ile Ile Thr Ser Tyr Ser Ile Glu Asn
            1655                1660                1665
Leu Gln His Glu Cys Arg Ser Ile Leu Glu Arg Leu Gln Thr Asp
            1670                1675                1680
Gly Gln Phe Ala Leu Ala Arg Arg Val Ala Glu Leu Ala Glu Leu
            1685                1690                1695
Pro Val Asp Asn Leu Val Ile Lys Glu Ile Thr Gln Glu Met Gln
            1700                1705                1710
Thr Leu Lys His Ile Glu Gln Trp Ser Leu Lys Gln Ala Arg Ile
            1715                1720                1725
Asp Phe Trp Lys Lys Cys His Glu Asn Phe Lys Lys Asn Ser Ile
            1730                1735                1740
Ser Ser Lys Ala Ala Ser Ser Phe Phe Ser Thr Gln Ala His Val
            1745                1750                1755
Ala Cys Glu His Pro Thr Gly Trp Ser Ser Met Glu Glu Arg His
            1760                1765                1770
Leu Leu Leu Thr Leu Ala Gly His Trp Leu Ala Gln Glu Asp Val
            1775                1780                1785
Val Pro Leu Asp Lys Leu Glu Leu Glu Lys Gln Ile Trp Leu
            1790                1795                1800
```

```
Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Glu Leu Ser
1820                1825                1830

Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Glu Gln Glu Ser Leu
1865                1870                1875

Asn Phe Leu Ile Gly Arg Leu Leu Asp Asp Gly Cys Val His Glu
1880                1885                1890

Ala Ser Arg Val Cys Arg Tyr Phe His Phe Tyr Asn Pro Asp Val
1895                1900                1905

Ala Leu Val Leu His Cys Arg Ala Leu Ala Ser Gly Glu Ala Ser
1910                1915                1920

Met Glu Asp Leu His Pro Glu Ile His Ala Leu Leu Gln Ser Ala
1925                1930                1935

Glu Leu Leu Glu Glu Ala Pro Asp Ile Pro Leu Arg Arg Val
1940                1945                1950

His Ser Thr Ser Ser Leu Asp Ser Gln Lys Phe Val Thr Val Pro
1955                1960                1965

Ser Ser Asn Glu Val Val Thr Asn Leu Glu Val Leu Thr Ser Lys
1970                1975                1980

Cys Leu His Gly Lys Asn Tyr Cys Arg Gln Val Leu Cys Leu Tyr
1985                1990                1995

Asp Leu Ala Lys Glu Leu Gly Cys Ser Tyr Thr Asp Val Ala Ala
2000                2005                2010

Gln Asp Gly Glu Ala Met Leu Arg Lys Ile Leu Ala Ser Gln Gln
2015                2020                2025

Pro Asp Arg Cys Lys Arg Ala Gln Ala Phe Ile Ser Thr Gln Gly
2030                2035                2040

Leu Lys Pro Asp Thr Val Ala Glu Leu Val Ala Glu Glu Val Thr
2045                2050                2055

Arg Glu Leu Leu Thr Ser Ser Gln Gly Thr Gly His Lys Gln Met
2060                2065                2070

Phe Asn Pro Thr Glu Glu Ser Gln Thr Phe Leu Gln Leu Thr Thr
2075                2080                2085

Leu Cys Gln Asp Arg Thr Leu Val Gly Met Lys Leu Leu Asp Lys
2090                2095                2100

Ile Ser Ser Val Pro His Gly Glu Leu Ser Cys Thr Thr Glu Leu
2105                2110                2115

Leu Ile Leu Ala His His Cys Phe Thr Leu Thr Cys His Met Glu
2120                2125                2130

Gly Ile Ile Arg Val Leu Gln Ala Ala His Met Leu Thr Asp Asn
2135                2140                2145

His Leu Ala Pro Ser Glu Glu Tyr Gly Leu Val Val Arg Leu Leu
2150                2155                2160

Thr Gly Ile Gly Arg Tyr Asn Glu Met Thr Tyr Ile Phe Asp Leu
2165                2170                2175

Leu His Lys Lys His Tyr Phe Glu Val Leu Met Arg Lys Lys Leu
2180                2185                2190
```

Asp Pro Ser Gly Thr Leu Lys Thr Ala Leu Leu Asp Tyr Ile Lys
    2195                2200                2205

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ile Glu Ser Gln Pro Trp Glu Asp
    2240                2245                2250

Ser Leu Lys Asp Gly His Gln Leu Lys Gln Leu Leu Lys Ala
    2255                2260                2265

Leu Thr Leu Met Leu Asp Ala Ala Glu Ser Tyr Ala Lys Asp Ser
    2270                2275                2280

Cys Val
    2285

<210> SEQ ID NO 188
<211> LENGTH: 949
<212> TYPE: PRT
<213> ORGANISM: Homo sapiens

<400> SEQUENCE: 188

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

-continued

```
Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685
```

-continued

```
Glu Glu Val Ile Ala Ser Ala Ile Leu Asn Asn Lys Ile Pro Glu Ala
    690             695             700
Gln Thr Phe Phe Arg Ile Asp Ser His Ser Ala Gln Lys Leu Glu Glu
705             710             715                 720
Leu Ile Gly Ile Gly Leu Asn Leu Val Phe Asp Asn Leu Lys Lys Asn
                725             730             735
Asn Ile Lys Glu Ala Ser Glu Leu Leu Lys Asn Met Gly Phe Asp Val
            740             745             750
Lys Gly Gln Leu Leu Lys Ile Cys Phe Tyr Thr Thr Asn Lys Asn Ile
            755             760             765
Arg Asp Phe Leu Val Glu Ile Leu Lys Glu Lys Asn Tyr Phe Ser Glu
770             775             780
Lys Glu Lys Arg Thr Ile Asp Phe Val His Gln Val Glu Lys Leu Tyr
785             790             795             800
Leu Gly His Phe Gln Glu Asn Met Gln Ile Gln Ser Phe Pro Arg Tyr
                805             810             815
Trp Ile Lys Glu Gln Asp Phe Phe Lys His Lys Ser Val Leu Asp Ser
            820             825             830
Phe Leu Lys Tyr Asp Cys Lys Asp Glu Phe Asn Lys Gln Asp His Arg
            835             840             845
Ile Val Leu Asn Trp Ala Leu Trp Trp Asp Gln Leu Thr Gln Glu Ser
    850             855             860
Ile Leu Leu Pro Arg Ile Ser Pro Glu Glu Tyr Lys Ser Tyr Ser Pro
865             870             875             880
Glu Ala Leu Trp Arg Tyr Leu Thr Ala Arg His Asp Trp Leu Asn Ile
            885             890             895
Ile Leu Trp Ile Gly Glu Phe Gln Thr Gln His Ser Tyr Ala Ser Leu
            900             905             910
Gln Gln Asn Lys Trp Pro Leu Leu Thr Val Asp Val Ile Asn Gln Asn
        915             920             925
Thr Ser Cys Asn Asn Tyr Met Arg Asn Glu Ile Leu Asp Lys Leu Ala
    930             935             940
Gly Tyr Tyr Asn Cys
945
```

DIAGNOSIS OF HEREDITARY SPASTIC PARAPLEGIAS (HSP) BY DETECTION OF A MUTATION IN THE KIAA1840 GENE OR PROTEIN

CROSS-REFERENCE TO RELATED APPLICATIONS

This application is a divisional application of U.S. application Ser. No. 14/206,840, filed Mar. 12, 2014, which was a divisional application of U.S. application Ser. No. 13/567,790, filed Aug. 6, 2012, now U.S. Pat. No. 8,728,727, issued May 20, 2014, which was a continuation application of U.S. application Ser. No. 12/440,644, filed Jan. 4, 2010, which was a 371 application of PCT/IB2007/003535, filed Sep. 11, 2007, all of said applications incorporated herein by reference.

The invention relates to the identification of mutations in the KIAA1840 gene or protein, associated with a hereditary spastic paraplegias (HSP), and to diagnostic applications that benefit from this identification.

Hereditary spastic paraplegias (HSP) are genetically heterogeneous Mendelian disorders characterized by weakness, spasticity and loss of vibratory sense in the lower limbs (Harding et al. 1983 and Tallaksen et al. 2001). They reveal themselves clinically through difficulties in walking possibly evolving into total paralysis of both legs. The physiopathology of this set of diseases is, to date, relatively undocumented; however, anatomopathological data make it possible to conclude that the attack is limited to the pyramidal tracts responsible for voluntary motricity in the spinal cord (Reid, 1997). The incidence of HSPs, which remains difficult to estimate because of rare epidemiological studies and the considerable clinical variability, varies from 0.9:100000 in Denmark, 3 to 9.6:100000 in certain regions of Spain (Polo et al., 1991) or 14:100000 in Norway (Skre, 1974) (approximately 3:100000 in France). Various clinical and genetic forms of HSP exist. The so-called "pure" HSPs, which correspond to isolated spasticity of the lower limbs, are clinically distinguished from the "complex" HSPs, for which the spasticity of the legs is associated with other clinical signs of neurological or non-neurological type (Bruyn et al., 1991).

Although forms of HSP have been recognized for over a century, new phenotypes are regularly described, demonstrating wide clinical heterogeneity. Genetically, autosomal dominant (AD), autosomal recessive (AR) and X-linked inheritance are observed and almost 32 genetic loci have been identified, but only 12 genes have been cloned (Flink et al. 2006). According to the putative roles of these genes, mitochondrial function, protein folding and axonal transport have been implicated in the dying back of pyramidal tract axons in these disorders.

The most common forms of AD-HSP, accounting for about 40-50% of cases, are caused by mutations in the SPG4 and SPG3A genes that encode for spastin and atlastin, respectively (Hazan et al. 1990, Zhao et al. 2001 and international patent application WO 01/18198). In contrast to AD forms, no major gene accounts for AR-HSP, which is less common and more varied in clinical presentation, implying greater genetic heterogeneity. The four AR-HSP genes cloned so far, encoding for paraplegin (SPG7, MIM#607259 (OMIM database, www.ncbi.nlm.nih.gov/entrez/query.fcgi?db=OMIM)), (Casari et al. 1998) spartin (SPG20; MIM#275900), (Patel et al. 2002) and maspardin (SPG21, MIM 248900) (Simpson et al. 2003) as well as the gene responsible for the related spastic ataxia of Charlevoix Saguenay (ARSACS, MIM#270550) (Engert et al. 2000) probably represent less than 5% of all cases (Fink et al. 2003).

A very common form of AR-HSP associates spastic paraplegia, mental or cognitive deficit and thin corpus callosum (Winner et al. 2005). The majority of the families appear to be linked to SPG11 on chromosome 15, which was the third AR-HSP locus to be identified (Martinez et al. 1999). This entity is particularly prevalent in Japan (Shibasaki et al. 2000), but is also found in North-America, the Middle-East and Europe (Martinez et al 1999 and Lossos et al. 2006 and Casali et al. 2004 and Winner et al. 2004 and Stevanin et al. 2006). The typical clinical features of SPG11 consist of early-onset spastic paraplegia (usually <20 years), urinary bladder dysfunction, deep sensory deficits in the legs and cognitive impairment that progress insidiously to severe functional disability over a period of 10-20 years. Some patients also develop arm involvement, dysarthria, contractures and muscle atrophy. Auxiliary studies frequently identify a thin corpus callosum (TCC) with white matter lesions and variable cerebral cortical atrophy on magnetic resonance imaging (MRI), variable cortical and thalamic glucose hypometabolism on positron emission tomography and predominantly axonal motor or sensorimotor peripheral neuropathy on nerve conduction studies (Winner et al. 2004).

Linkage to chromosome 15q has been reported so far in 31 families in which the patients presented with the typical SPG11 phenotype. In the initial study, a maximum multipoint combined LOD score of 3.14 was detected in seven AR-HSP families in a region between D15S1007 and D15S1012, although patients from only 2 kindreds of North-American and Italian ancestries presented with a TCC (Martinez et al. 1999). A second study reported a group of 10 out of 13 Japanese families with a homogeneous phenotype of AR-HSP-TCC with a cumulative LOD score of 9.68 in the D15S971 to D15S117 interval (Shibasaki et al. 2000). Casali et al. also reported 5 Italian kindreds that showed significant linkage (Z=3.35) to the interval flanked by markers D15S1007 and D15S978 (Casali et al. 2004). More recently, the analysis of 8 additional kindreds (Z=11.5) including 3 large consanguineous families, allowed the locus to be restricted by the inventors to the 6 cM interval between markers D15S1044 and D15S143 (Lossos et al. 2006 and Stevanin et al. 2006) a region that did not overlap with the interval defined in the originally mapped families (Martinez et al. 1999), therefore showing genetic heterogeneity among families linked to 15q and more closely resembling the locus for amyotrophic lateral sclerosis ALSS (Hentati et al, 1998). It is of note that in the work published by Martinez et al (1999), only 2 of 8 pedigrees presented with the typical SPG11 phenotype with TCC and patients from these 2 families were linked to a larger region on chromosome 15 overlapping the region described in recent reports (Lossos et al. 2006 and Stevanin et al. 2006). More recently, the SPG11 locus was further refined to the 4.6cM region (according to the Marschfield genetic map, http://research.marshfieldclinic.org/genetics/GeneticResearch/compMaps.asp) between markers D15S968-D15S132 (Olmez et al, 2006) confirming the results of the inventors (FIG. 2).

Figure 6:
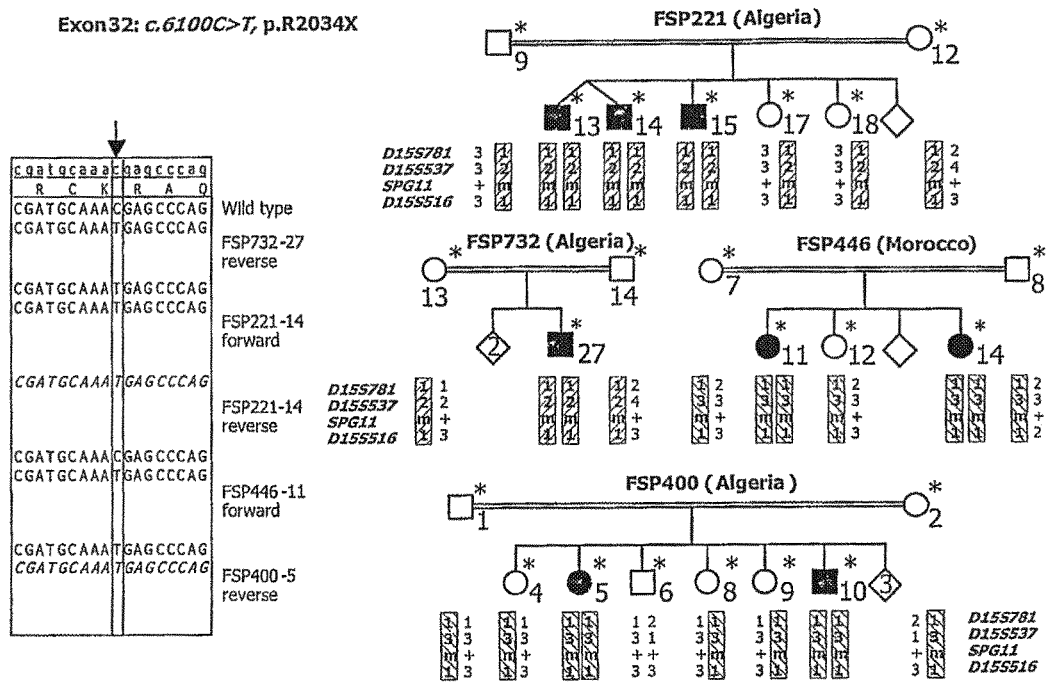
Figure 7:
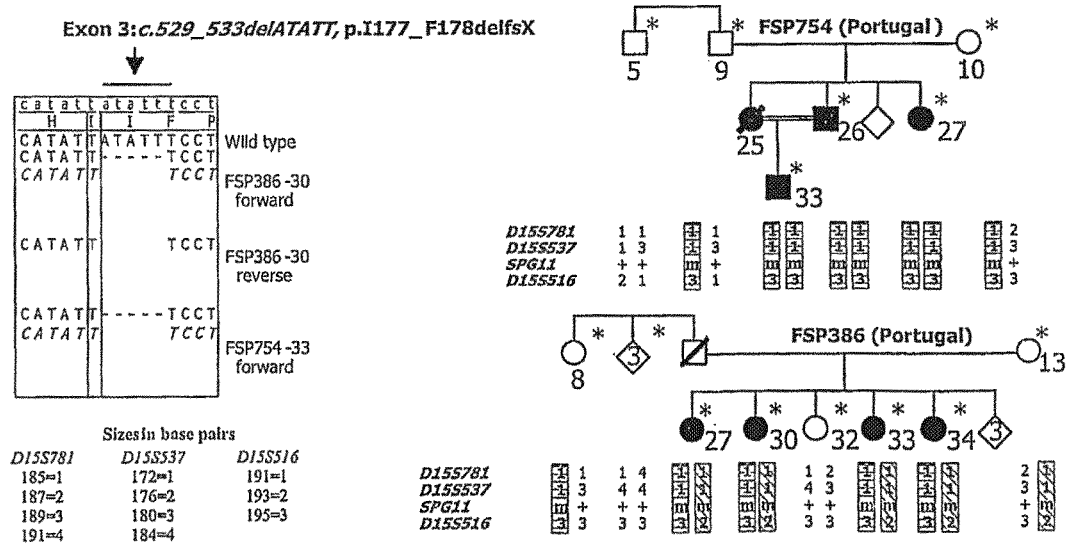
Figure 8:
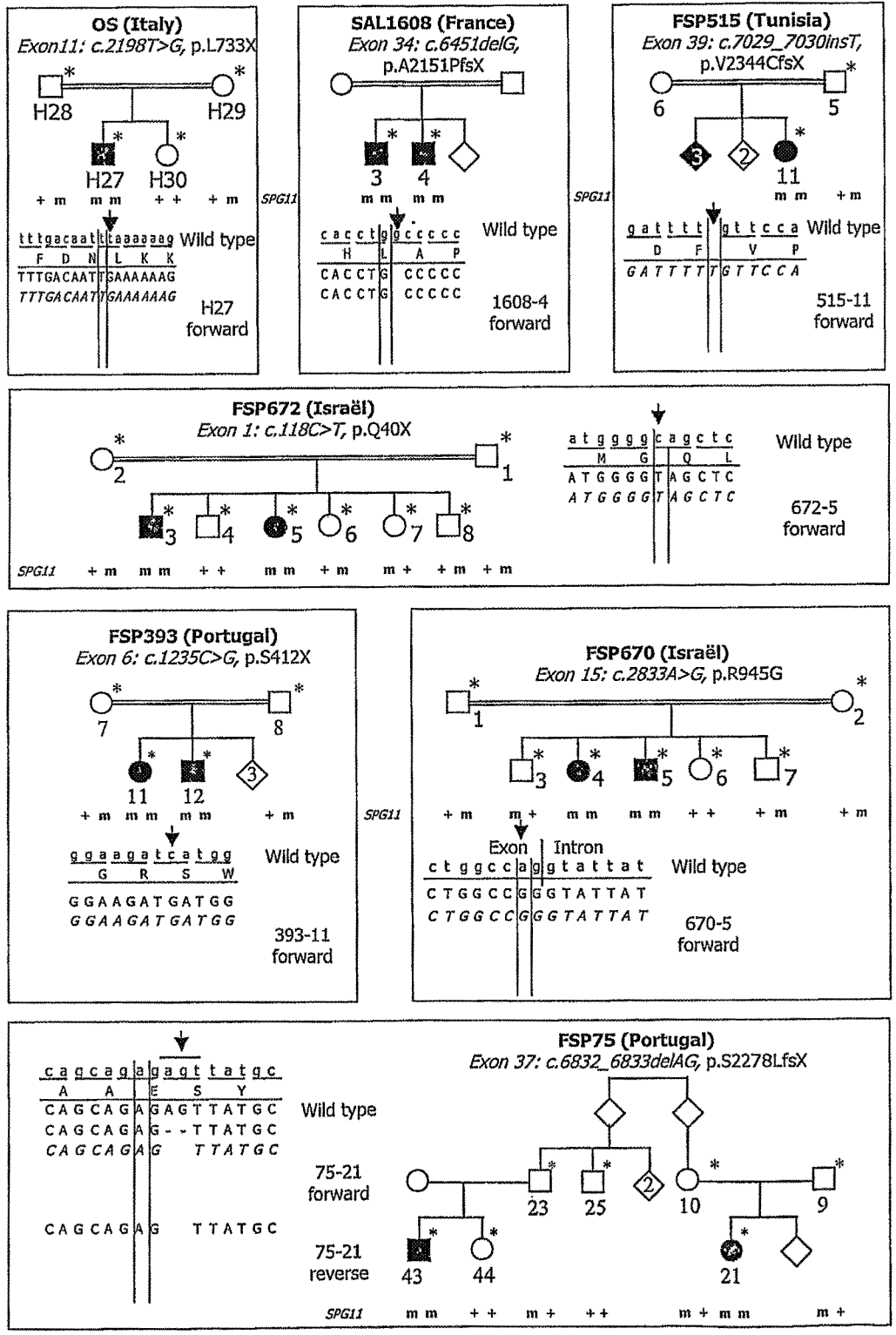
Figure 9:
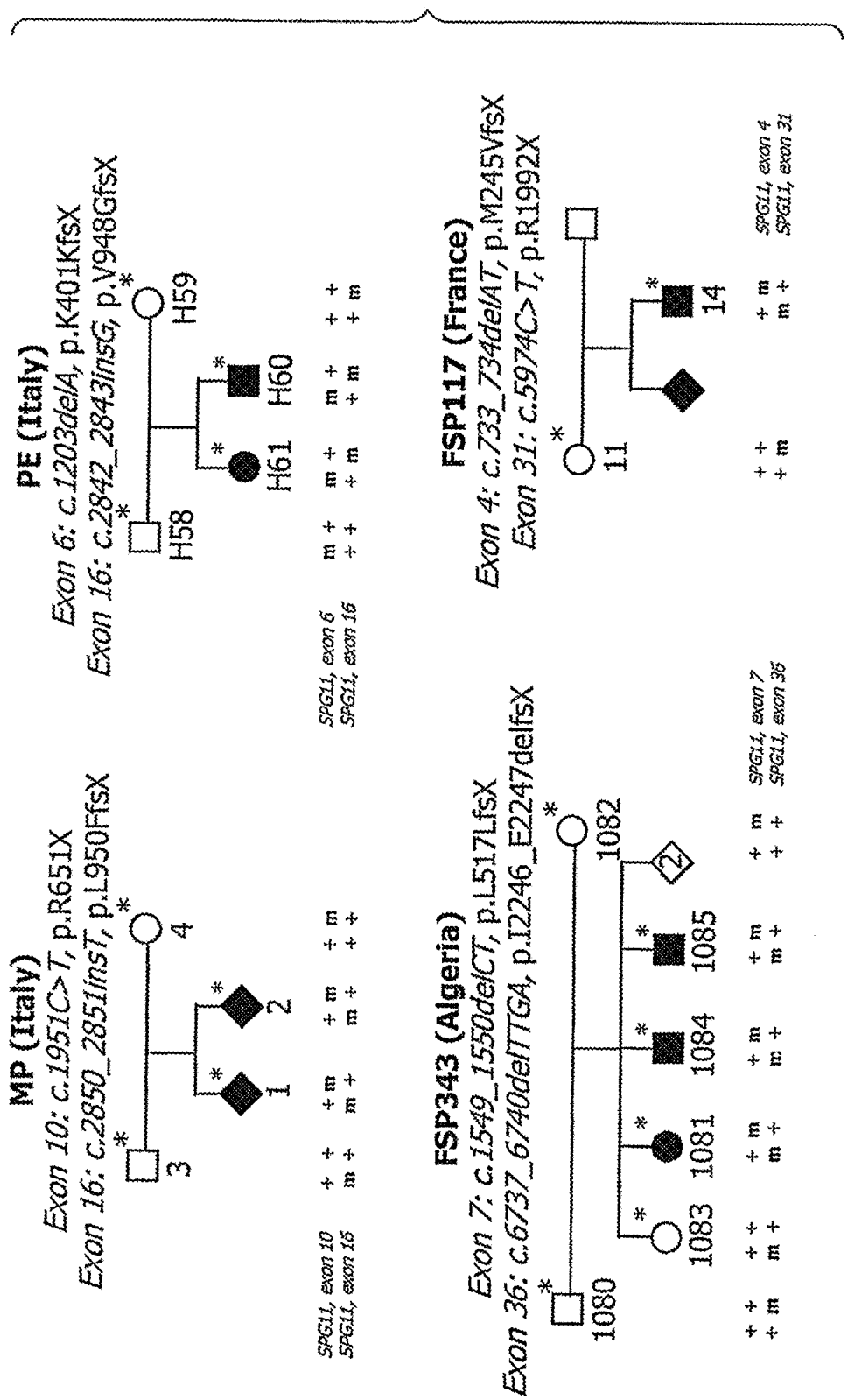

The inventors have now identified the gene responsible for the most frequent form of Autosomal Recessive Hereditary Spastic Paraplegia (AR-HSP). They have indeed demonstrated that the disease is caused by mutations in the KIAA1840 gene (also known as FLJ21439), affecting the spatacsin protein expression (Stevanin et al., 2007). This is supported by four pieces of evidence. First, the inventors have excluded 17 out of about 40 genes assigned to the SPG11 candidate interval after significant reduction of its size to the 3.2 cM interval (according to the Marschfield genetic map) between markers D15S778 and D15S659 (FIGS. 1 to 4). The analysis of 2 of these genes has been reported previously (Stevanin et al, 2006). Secondly, the inventors have identified 43 different mutations segregating in 47 families (FIGS. 5 to 9), 16 of which linked previously to the SPG11 locus with a highly significant 28.1 maximal combined lod score (FIGS. 1 and 2), 8 of them already published as linked (Casali et al, 2004; Lossos et al, 2006 and Stevanin et al, 2006). Thirdly, the inventors have identified mutations, absent in at least 140 control chromosomes, that were all, leading to abnormal splicing of the messenger RNA and/or leading to a truncated protein. Finally, the inventors have demonstrated that all mutated families, except 2 in which magnetic resonance imaging could not be performed (TUN2 and TUN14), presented with the typical AR-HSP-TCC phenotype. In addition, several of these families shared the same mutation with similar surrounding haplotypes when they came from the same geographical origins, suggesting regional founder effects (FIGS. 6 and 7). Mutations in KIAA1840 affected 47 of 91 AR-HSP-TCC families in the study carried out by the inventors making this genetic entity very frequent among AR-HSP-TCC (75% was estimated in a previous study, Stevanin et al, 2006). The invention therefore provides the identification of the major gene responsible of AR-HSP-TCC and probably of AR-HSPs in general and opens thereby new opportunities to improve diagnosis and genetic counseling of said disease. Moreover, the invention also provides a mean to improve the medical care management of patient affected with said disease. In addition, since most patients with spastic paraplegia have isolated forms, it is conceivable that this new gene could account for a small proportion of these patients as well. Indeed, in Europe, due to the small size of the families, recessively inherited diseases are often found in apparently isolated cases.

A first aspect of the invention thus relates to the identification of mutations in the KIAA1840 gene or protein, associated with a hereditary spastic paraplegias (HSP), and to diagnostic application that benefits from this identification.

A second aspect of the invention relates to an isolated nucleic acid, specifically hybridizable to a region of KIAA1840 gene sequence that contains a mutation selected from the group consisting of
 the substitutions: c.6100C>T, c.2198T>G, c.118C>T, c.1235C>G, c.2833A>G, c.1951C>T, c.869+1G>A, c. 1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T and c.5974C>T,
 the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA and c.733_734delAT, and
 the insertions: c.7029_7030insT, c.2850_2851insT, c.3741_3742insA, c.5982_5983insCTCT, c.5986_5987insT, c.3075_3076insA and c.2842_2843insG.

Such an isolated nucleic acid can be used as a primer or probe.

More preferentially the invention relates to an isolated nucleic acid, which comprises a KIAA1840 gene sequence that contains one or several mutation(s) selected from the group consisting of
 the substitutions: c.6100C>T, c.2198T>G, c.118C>T, c.1235C>G, c.2833A>G, c.1951C>T, c.869+1G>A, c. 1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T c.5974C>T,
 the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA c.733_734delAT, and
 the insertions: c.7029_7030insT, c.2850_2851insT, c.3741_3742insA, c.5982_5983insCTCT, c.5986_5987insT, c.3075_3076insA c.2842_2843insG
or a sequence complementary thereto.

Another aspect of the invention relates to an isolated polypeptide which comprises the amino acid sequence of KIAA1840 containing one or several mutation(s) selected from the group consisting of p.Q40X, p.I177_F178delfsX178, p.H235RfsX246, p.M245VfsX246, p.K401KfsX415, p.S412X, p.K428X, p.L491DfsX556, p.L517LfsX556, p.F556LfsX577, p.S560X, p.V564VfsX577, p.R651X, p.L733X, p.R815M, p.W899X, p.Q906SfsX920, p.R945G, p.R945GfsX950, p.L950FfsX953, p.V948GfsX953, p.E1026RfsX1029, p.P1248TfsX1264, p.Q1436RfsX1442, p.R1824X, p.S1844SfsX1857, p.S1923RfsX1950, p.S1957X, p.R1992X, p.L1995LfsX2000, p.C1996LfsX1999, p.L1997_1998delfsX2056, p.R2031X, p.R2034X, p.A2151PfsX2172, p.I2246_E2247delfsX2260, p.E2247_S2248delfsX2260, p.S2278LfsX2338, p.R2286X and p.V2344CfsX2349.

Another aspect of the invention relates to an isolated monoclonal or polyclonal antibody that specifically recognizes a KIAA1840 protein containing a mutation selected from the group consisting of p.Q40X, p.I177_F178delfsX178, p.H235RfsX246, p.M245VfsX246, p.K401KfsX415, p.S412X, p.K428X, p.L491DfsX556, p.L517LfsX556, p.F556LfsX577, p.S560X, p.V564VfsX577, p.R651X, p.L733X, p.R815M, p.W899X, p.Q906SfsX920, p.R945G, p.R945GfsX950, p.L950FfsX953, p.V948GfsX953, p.E1026RfsX1029, p.P1248TfsX1264, p.Q1436RfsX1442, p.R1824X, p.S1844SfsX1857, p.S1923RfsX1950, p.S1957X, p.R1992X, p.L1995LfsX2000, p.C1996LfsX1999, p.L1997_1998delfsX2056, p.R2031X, p.R2034X, p.A2151PfsX2172, p.I2246_E2247delfsX2260, p.E2247_S2248delfsX2260, p.S2278LfsX2338, p.R2286X and p.V2344CfsX2349.

Another aspect of the present invention relates to the use of a monoclonal or polyclonal antibody recognizing the wild type protein to identify truncated forms of the protein.

Definitions

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

As used herein, the term "oligonucleotide" refers to a nucleic acid, generally of at least 10, preferably at least 15, and more preferably at least 20 nucleotides, preferably no more than 100 nucleotides, still preferably no more than 70 nucleotides, and which is hybridizable to a KIAA1840 genomic DNA, cDNA, or mRNA. Oligonucleotides can be labelled according to any technique known in the art, such as with radiolabels, fluorescent labels, enzymatic labels, sequence tags, etc. A labelled oligonucleotide may be used as a probe to detect the presence of a mutated KIAA1840 nucleic acid. Alternatively, oligonucleotides (one or both of which may be labelled) can be used for amplifying a KIAA1840 nucleic acid, for instance by PCR (Saiki et al., 1988), to detect the presence of a mutation. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A nucleic acid molecule is "hybridizable" or "hybridizes" to another nucleic acid molecule, such as a cDNA, genomic DNA, or RNA, when a single stranded form of the nucleic acid molecule can anneal to the other nucleic acid molecule under the appropriate conditions of temperature and solution ionic strength (Sambrook et al., 1989).

The conditions of temperature and ionic strength determine the "stringency" of the hybridization. For preliminary screening for homologous nucleic acids, low stringency hybridization conditions, corresponding to a Tm (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher Tm, e.g., 40% formamide, with 5× or 6×SCC. High stringency hybridization conditions correspond to the highest Tm, e.g., 50% formamide, 5× or 6×SCC. SCC is a 0.15 M NaCl, 0.015 M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., 1989, 9.50-9.51). For hybridization with shorter nucleic acids, i.e., oligonucleotides, the position of mismatches becomes more important, and the length of the oligonucleotide determines its specificity (see Sambrook et al., 1989 II.7-11.8). A minimum length for a hybridizable nucleic acid is at least about 10 nucleotides, preferably at least about 15 nucleotides, and more preferably the length is at least about 20 nucleotides.

In a specific embodiment, the term "standard hybridization conditions" refers to a Tm of 55° C., and utilizes conditions as set forth above. In a preferred embodiment, the Tm is 60° C. In a more preferred embodiment, the Tm is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, an "amplification primer" is an oligonucleotide for amplification of a target sequence by extension of the oligonucleotide after hybridization to the target sequence or by ligation of multiple oligonucleotides which are adjacent when hybridized to the target sequence. At least a portion of the amplification primer hybridizes to the target. This portion is referred to as the target binding sequence and it determines the target-specificity of the primer. In addition to the target binding sequence, certain amplification methods require specialized non-target binding sequences in the amplification primer. These specialized sequences are necessary for the amplification reaction to proceed and typically serve to append the specialized sequence to the target. For example, the amplification primers used in Strand Displacement Amplification (SDA) include a restriction endonuclease recognition site 5' to the target binding sequence (U.S. Pat. Nos. 5,455,166 and 5,270,184). Nucleic Acid Based Amplification (NASBA), self-sustaining sequence replication (3SR) and transcription based amplification primers require an RNA polymerase promoter linked to the target binding sequence of the primer. Linking such specialized sequences to a target binding sequence for use in a selected amplification reaction is routine in the art. In contrast, amplification methods such as PCR which do not require specialized sequences at the ends of the target, generally employ amplification primers consisting of only target binding sequence.

As used herein, the terms "primer" and "probe" refer to the function of the oligonucleotide. A primer is typically extended by polymerase or ligation following hybridization to the target but a probe typically is not. A hybridized oligonucleotide may function as a probe if it is used to capture or detect a target sequence, and the same oligonucleotide may function as a primer when it is employed as a target binding sequence in an amplification primer. It will therefore be appreciated that any of the target binding sequences disclosed herein for amplification, detection or quantisation of KIAA1840 may be used either as hybridization probes or as target binding sequences in primers for detection or amplification, optionally linked to a specialized sequence required by the selected amplification reaction or to facilitate detection.

As used herein, the terms "KIAA1840 gene" (or its synonyms: FLJ21439, ENSG00000104133 or SPG11) denotes a KIAA1840 gene of any species, especially human, but also other mammals or vertebrates to which the methods of the invention can apply. The human KIAA1840 gene encodes a large protein of 2443 amino-acids (aa) of unknown function that the inventors have named Spatacsin (SEQ ID NO: 2). *Homo sapiens* KIAA1840 gene is localized on chromosome 15 and its Coding Sequence (CDS) is deposited in Genebank under accession number NM_025137, or AB058743 (5'-3' forward strand shown SEQ ID NO: 1). Human KIAA1840 gene shares 85% identity with the homologous protein in dog, and 76% and 73% identity with the mouse and rat homologues and 59% with the chicken homologue. Homology is less than 25% with orthologous proteins, of smaller sizes, in tetraodon and *drosophila*. KIAA1840 homologous proteins at NCBI database are: dog XP_544657, *gallus* XP_413940.1, mouse BAE27954, rat XP 242139.3, and at Ensembl database; *drosophila* CG13531, tetraodon GSTENG00003909001. The human KIAA1840 gene contains 40 exons spanning 101 Kbases of genomic DNA on chromosome 15q21.1. The intron-exon structure of the complementary strand of the KIAA1840 gene is further indicated in Table 1 below and in FIG. 5.

TABLE 1

Exon-intron boundaries of the human KIAA1840 gene (according to the Ensembl database)

| No | Exon/intron | Position in SEQ ID NO: 1 | Length (bp) | Sequence |
|---|---|---|---|---|
|  | 5' upstream sequence |  |  | . . cgacgcagtcaggttccggcgagttacccggggccaa |
| 1 | ENSE00001183257 | 0 | 258 | GATGGGCTGCAGAGGAAGGGGTCGCCGAGTGCTTCCGCCGGCGGTAGCTGGGCACCGCGGCCATGGGG CGGGTTCTACCGATGCTCTTGGTGCCCGCCCCGAGGCGATGGGCAGCTCGGCTCCCGGGCCAGC TGCGCACACAGCCGGGGCGGGAGCTCTGGGACCCTCGCGCGTGCGGGCAGCCTCCAAGTGCTTCTTTGACGCCT GGCAGCCGGGGCGGGGGTCGCTGCTCGTCCTGAGGGGCCCCTTCTGGCA |
|  | Intron 1-2 |  | 2,774 | gtaagtgctgagggagagttgggcc . . aataatctaaactttttttcttag |
| 2 | ENSE00001183253 | 258 | 185 | CTTTCTATGGGAGGATTCTGTAACAGCAGCACACCAACTGAAAAGCCAAACTGCTCGCTCTTGGTGAAAAT TATGAACTGCTTATCTATGAATTCATTTAATTTGAAGATGAAGATGTGATGCAACCATTTGTATAGCTGTAGTAGG GAGGCATTGCAAAAGCTCATTGACGATCAAGATATCA |
|  | Intron 2-3 |  | 1,128 | gtaagtatctacaggtgtctttca . . . gaaataatcctttgtttttgtag |
| 3 | ENSE00001183250 | 443 | 225 | GTATTCCTTATTGTCTTTGAGAATCTGTCATTTCACAATAACACATCATTTACTGTTCATCAACAAATGTCAT CCTACATATTATATTTCCTGAAAGAGATGCTGCAATTAGAGTACTCAACTGTTCACACTTCCCTTGCCTGCAC AGGCAGTGGACATGATTATTGACACGCAGCTCTGCAGAGGAATTCTTTTTGTTTTGAGTAGTTTAGGCTGGAT CT |
|  | Intron 3-4 |  | 1,782 | gtatccttggtgtagaagtgttga . . . attttcttttaactctaactaaaag |
| 4 | ENSE00001183246 | 668 | 202 | ACATTTTGATGTTGTGGATACATATGCTCATGTGGATTTAGCACTTCACAAAGAAGACATGTGTAAT GAGCAGCAACAGAGACCCAAGATTTCTTCATTTACTTCACTGAAAGTTTCTCAAGACCTCGATGTTGCAG TGATTGTCAGCTCCTCCAACTCCGCAGTTGCTCTTAACTAAATTGTATTTCAG |
|  | Intron 4-5 |  | 4,828 | gtatgtagatgactgcagtttcaa . . . tgtctcattatttttaaatgtag |
| 5 | ENSE00001183241 | 870 | 138 | GCAACACCCAGGACACCTACTGTGTGAAAGAATACTAGAAGATCTCCTATTCAAGGACCTAAGGGCTAGAT GAAGATGATCCTGTTAACTCGCCTACACAACATGGCCAAGTTTCCTTCCAAATTGATAG |
|  | Intron 5-6 |  | 189 | gtacagaaacttcctttttcatgtag . . . aagtatatttaccttgtttccag |
| 6 | ENSE00001183238 | 1008 | 449 | GTCTTGGAAAGCCCAGCTACTCATCATCATTGAATGAAACAATAAAGAAACTCCAAACTGGAGGTTTCCTGTTGTGCTC CATGGTTCCAGGATATTTGCATTGGAGTCACCTGGAGTCGTAACACAGTACAAGTGTGCAGAGCTGGGC CTTCATTCCACAGGACATAATGCATGGCAATATAATGTTCTACAGAAAGATCATGCCAAGACCAGTGATCCA GGAAGATCATGGAAAATAATGCACATCAGTGAACAAGAGGAACCCATAGAGCTTAAATGTGTCTGTGACAG GATTCAC TGCACTGTTTACTTGGGAAGTGAAAGATGGCTATACCATTACCCCTCGGATTGGAGACCAGGCAT GCAGTGTTTTCCCTTGGCACACAAGTGTATTCCTGAGACAGTAGTGGAGACCAGCAGCTGTGCTTTGTTTG ACAG |
|  | Intron 6-7 |  | 2,479 | gtgagactgtcttgtgtattagattga . . . aagctaacttttatttttcctatag |
| 7 | ENSE00001183236 | 1457 | 146 | AGAATGGACTCTCTGTGATTTTGTTTGGTTTGACTCAAGAAGAGTTTTAAACAGACTCATGATCCATGGAAGT GCCAGCACTGTGACACTCTTTGTCATCTCAATGGCTGGGAAGGTGCTCAATTCCATACATGCACTAGAG |
|  | Intron 7-8 |  | 15,228 | gtaacagaatttaaatgcccaagaac . . . atttttattttcctcctcatttcag |
| 8 | ENSE00001105929 | 1603 | 133 | GCCGGATAGAAAATCGTCAGCTGGACACAGTAAATTTCTTTTGAAGAGCAAGGAAATCTTTTTAATCCATC CTCAAATTCTTCTGTATCTGATCAGTTTGATCACTGTGATCCCATTTATATTTAAGAA |
|  | Intron 8-9 |  | 4,116 | gtaagtgaataagattctcat . . . gtaattctttggttctttctcag |

TABLE 1 -continued

Exon-intron boundaries of the human KIAA1840 gene (according to the Ensembl database)

| No | Exon/intron | Position in SEQ ID NO: 1 | Length (bp) | Sequence |
|---|---|---|---|---|
| 9 | ENSE00001105933 | 1736 | 156 | ATGTGGAAGAGCTGATCACCAGCATTGATTTACTTTGCTCGGCAATTAGAGAAGTTATTCTGAACCCAAAG<br>CAAACACTTTCAGAACACTTCTTAATCTTACACTGTCTTTCCTTAACAACAAATAAAGGAGCTTTCATTCA<br>CACTGAAG |
|  | Intron 9-10 |  | 388 | gtaagaatagcagctaggaaggggg . . . attggcacattggtatttccatag |
| 10 | ENSE00001105923 | 1892 | 176 | AACTAGATGAAACATCTGAAAAAGGAGTGAACATTTTGACTTGCTACATTAATGAACTTCGAACCTTCATGATA<br>AAGTTTCCTTGGAAGCTAACAGATGCTATAGATGATGTACATGAAAATGTCCCCAAAGTAAAGGAGAG<br>CAATATATGGAAGAAACTCAGCTTTGAG |
|  | Intron 10-11 |  | 2,161 | gtaagtacgaataatcatcacttct . . . aaggcaaacgttttctttcctag |
| 11 | ENSE00001105941 | 2068 | 177 | GAAGTTATTGCCAGCGCCATTTTAAACAACAAAATACCAGAGGCACAGACTTTTCTTCAGGATTGATAGTCATTC<br>TGCTCAAAAACTTGAGGAGCTTATTGCCATAGGCCTAAATTTGGTCTTTGACAATTTAAAAAGAACAATATAAA<br>GGAAGCCTCTGAACTTTTGAAGAATATG |
|  | Intron 11-12 |  | 3,531 | gtgagtggtgtaatccataaagtct . . . ttttggtttctatgttattttag |
| 12 | ENSE00001183220 | 2245 | 72 | GGGTTTGATGTAAAAGGCCAATTGCTCAAGATCTGCTTCTATACAACTAATAAAAATATACGTGACTTTTG |
|  | Intron 12-13 |  | 380 | gtaaggtagagtgagactacatagt . . . ctgcttaattacttttattcaag |
| 13 | ENSE00001183213 | 2317 | 128 | GTTGAAATTTAAAGAAACAAGATTATTTTCTGAAAAAGAGAAAAGAACTATAGACTTCGTCGTGCATCAAGTGAAG<br>AAGCTTTATTTGGACATTTCCAAGAAAATATGCAAATCCAGTCATTTCCAG |
|  | Intron 13-14 |  | 285 | gtagtctcattagtcctcctttgat . . . aaaaattatatactgtttttag |
| 14 | ENSE00001183208 | 2445 | 176 | GTACTGGATAAAGGAACAAGATTTTTCAAGCACAAGTCTGTTTTGGACTCATTCCTGAAATATGATTGATTGTAAAG<br>ATGAATTTAACAACAGGACCATAGAATTGTGTTAAATTGGGCTCTCGTGGGATCAACTAACAACAAGAATCC<br>ATCCTTCTCCCCAGGATAAGTCCAGAAG |
|  | Intron 14-15 |  | 1,355 | gcaagtgtgagagctgaaatat . . . ttaaaatgtgttttttcatgtag |
| 15 | ENSE00001183204 | 2621 | 214 | AATACAAATCATATTCCCCTGGAGCCCTCTGGAGATACCTCACAGCTCGCCATGATTGGTTAAACATTATCTTA<br>TGGATTGGAGAATTTCAAACCCAGCAGTTATGCTTCACTTCAGCAGAACAAATGGCCCCTTCTGACTGTTGA<br>GTTATTAACCAGAATACTTCCTGTAACAACTACATGAGGAATGAAATTTTAGATAAGCTGGCCAG |
|  | Intron 15-16 |  | 4,623 | gtattaactgtgaactaatacc . . . tgcacctcctataactgtccatag |
| 16 | ENSE00001047610 | 2835 | 204 | GAATGGGGTTTTTTGCCATCTGAACTGGAAGACTTTGAATGCTTCCTCCTCAAGACTGAGCCGTATTGGAGGT<br>GTAATACAGGATACCCTCCCTGTTCAAAACTACAAAGAAGGTTGGGATTTCCATTCCAATTCATTCT<br>CTATTGTTGGAGCACCAGTCTGCACATCCTTGCACTCTTATGTCTACCTTGACTGTTACAA |
|  | Intron 16-17 |  | 1,826 | gtgagtactgagaatgcattgtcc . . . aggttttgtttgtttatatacag |
| 17 | ENSE00001287244 | 3039 | 107 | ACTTAGTCCTGAAAATTGTCCCTTTTGGAAAAAAAAAGAGTTACATGAAGCACACCCTTGGTTTGAATTTTTAGT<br>TCAGTGTCGACAGTTGCCAGTAACTTAACAG |
|  | Intron 17-18 |  | 2,444 | gtatgggtatactgtattaaacaca . . . aaaaacactgtctttatttccag |
| 18 | ENSE00001047605 | 3146 | 146 | ATCCCAAACTGATCTTCCAGGCTAGCCTTGCCAAATGCTCAGATTTGATTCCACCAATCAGGCCAGTGTAAG<br>CAGTATGCTATTGGAAGGACATACCCTGGCCCTTGCTACTACAATGTATTCTCCTGGGGGTGTCAGTCAG |
|  | Intron 18-19 |  | 2,234 | gtatgatggcacttatgacaaaa . . . acctgtatcgtttttacttag |
| 19 | ENSE00001047617 | 3292 | 162 | GTTGTTCAAGAATGAAGAAGAAAATGAAGAAAACTGTTTGAAGAAGATGATCCCAGCTATTGAAGATGGCATTAACTCC<br>TTACCCCAAGCTAAAACTGCTCTTCCCAGTGCACTCCTCCTAGTGTCCTGCCATCTGATATTACAATCT<br>ACCACCTTATTCAG |

TABLE 1-continued

Exon-intron boundaries of the human KIAA1840 gene (according to the Ensembl database)

| No | Exon/intron | Position in SEQ ID NO: 1 | Length (bp) | Sequence |
|---|---|---|---|---|
| | Intron 19-20 | | 2,352 | gtacagtattaggtggccaatatt . . . ctgtttaacttttcccctttttcag |
| 20 | ENSE00001047612 | 34.54 | 67 | TCATTATCACCCTTTGATCCTAGCAGATTGTTTGGCTGGCAGTCTGCTAACACACTAGCTATAGGAG |
| | Intron 20-21 | | 5,392 | gtaagtcatcatgggtacttcctga . . . taatattgtttaactttcccctag |
| 21 | ENSE00001047594 | 3521 | 166 | ATGCATGAGTCATCTCCCACATTTCTAGCCCTGACTGGTTAATAAATATGCTATAGTGAACGTCTGAAT TTTGCTTATTATTTACATAATGGGCGGCCATCATTTGCATTTGGTACTTTCTCGGTCCAGGAATTAATCAAGAGC AAGACTCCAAGCAGCT |
| | Intron 21-22 | | 1630 | gtgaptatttaaaatataatttgt . . . tgatttgattccttctttttcag |
| 22 | ENSE00001047598 | 3687 | 206 | GATCCAGCAAGTAGGCAATGAAGCCTATGTTATAGGGCTCTCCTCCTTCCACATACCTTCAATAGGAGCTGCA TGTGTTGTTTCTTAGAATTGCTTGGCCTTGACAGCCTCAGACCTCAGAGTTGATATGAAAGTGGCCAATATAT TTTGAGCTACAAGTGCAGAAATGAAGATGCTCAGTACAGCTTTATCAGAAGAGTCTGTAG |
| | Intron 22-23 | | 257 | gtacagcaccttttatctggcctgc . . . atttgtgttatatttcttacag |
| 23 | ENSE00001047622 | 3893 | 109 | CCGAAAAACTATCTAAACTAGTCGATGTGAAAAGACAACCAGAGAGAATTGCTTGTTCTTTAGAAGAAGGT ACATGGAACAGACATTCAGCAACAGGAAATAAAGAG |
| | Intron 23-24 | | 1,321 | gtttgtgagttgcagtctcagcctc . . . cccccacctctaattctgattatag |
| 24 | ENSE00001047619 | 4002 | 160 | GTTATCCAGTGAATCTAGCAGCCAATGGGCATTAGTGCTGCAGTTCTGCAGGTACACAATATGAAACTAAGC ATATCTTACCTTAGAGAATGTGCCAAAGCAAATGATTGGCTCAGTCCAGTTCATTATTCACAGCCAACTCCACAACTA CCACCCAGCAGAG |
| | Intron 24-25 | | 428 | gtaagccactaattgttagcagtca . . . tttaatcatctgatatgccttctag |
| 25 | ENSE00001047603 | 4162 | 273 | GTGAAATCCCTTATCCATTCAGCCCAGTCACTTCAAGACCACTTCAAGGCTGGCTTTTGAGAACTTGCCCTC AGTGCCCCTCCAAATGCAGCGCAAGTCTGCAATAAGTGCCCCAGGAGACTTCAAGGAAGCAAACA AGAGATGACCGATTTATTTGAAATTCTCTCCAATGCCAGAGAGCCAGACTCCTGCCACTGGCTTCTGTT GAAGCAGTGAAACAACAGGCCCCTATCCTCAGTGTTCTCGGCCTCATGTCTCCAG |
| | Intron 25-26 | | 623 | gtgaggatcatgagaagcctgaagt . . . tgttatttatttatcccgtggcag |
| 26 | ENSE00001047590 | 4435 | 201 | GGTGCCAGTGCCATTTCTGTCTCTGTGTTTGATCATCACTTCTGTGGAGGACAATGTTGCAACTGAAGCAA TGGGACACATTCAGGACTTCAAACAGAGACCATACTCCATCAGAGAGTTTCAGCTCATCTGGAGAACATT ATTAACAAGACAAAAGACAAAAGCAAAACTCTCATCAGAGGTTTCAGCTTTCTTTAAG |
| | Intron 26-27 | | 2,820 | gtagtgatagttgcttcactcttc . . . attttttcaaactctttgtcaaag |
| 27 | ENSE00001047613 | 4636 | 108 | GATTCCCCGTTACTACTGGTGATGGAGATGTATGAACTGTGTATGTTCTTCAGGAATTATAAGAAGCTGAAGC TAAACTTCTGGAGTTTCAGAAGAGCCTTGAAACG |
| | Intron 27-28 | | 2,916 | gtaagttggaattatggtgtcttt . . . ctaagctctctctttctttcatag |
| 28 | ENSE00001047595 | 4744 | 163 | CTTAACACAGCAGCCACAAAGGTCCACCCTGTCATCCTCCGCCATGCTGGAGATCAGGTGTGTTTCCTTT TGAAGCTTATGCTACACAGCAGTTGAAGACCCAGTATGAGCTCGGGAAGCTTTTACAGCTCTTTGTTGAAAGAGA GCATCTCTTCTCTGATG |
| | Intron 28-29 | | 3,401 | gtaagacaatccttacagtaagtt . . . ttatatcctttctctttggcacag |
| 29 | ENSE00001047608 | 4907 | 215 | GTCCAGATGTGAAAAGCTTTGCATCCTTTGCCAGATTTTGAAGGATACATCCATTAGCCCATTAATCATACATT AATACCAGCTACAGCCATTGAGAATCTTCAGCATGAAGATCTATTTTGGAAAAGACTGCAGACAGATGGACA ATTCGCTTTGGCCAGGAGGGTAGCAGAATTAGCTGAGTTACCTGAGTTACCTGTTATTAAGAG |
| | Intron 29-30 | | 1,077 | gtatcatcggtctttttttttt . . . aaatcgctttgtaaatttcacag |

TABLE 1 -continued

Exon-intron boundaries of the human KIAA1840 gene (according to the Ensembl database)

| No | Exon/intron | Position in SEQ ID NO: 1 | Length (bp) | Sequence |
|---|---|---|---|---|
| 30 | ENSE00001047607 | 5122 | 745 | ATAACACAGGAAATGCAGACCCTAAAACACATTGAACAGTGGTCACTAAAACAAGCAAGAATTGACTTCTGGA<br>AAAAATGCCATGAGTGAGAATTTAAGAAAAAATTCAATTTCAAGCAAAGCAAGAGCTTCTTCCTTTTCTCAACCCAGGCCC<br>ATGTGGCATGTGAGCACCCAACTGGATGGAGCAGCAGTGGAGGAGCGCCATCTGCTGCTCACCTTGGCAGTG<br>CACTGGCTTGCCCAGGAGGACTGGTCGTGCCCTTGGATAAGCTGGAGAAGCAGATCTGCTGTG<br>CCCATCACACCCAGGAACAGATGGAAGAAACAGGAGGACCCAGATTTTCTGCACAGATCTCAACT<br>AGTGGTGAACTTTCCTTTGATAGTTTAGCCAGTGAGTTTTCCTTCCAAGTTGGCTGCTCTGAACACATCAAA<br>ATACTTAGAACTTAACAGCCTTCCATCCAAAGAGACATGCGAGAATAGATTGGATTGGAAGAGCAGGAGTCA<br>CTAAACTTTTTGATTGGGCGCCTCTACTGGATGATGGCTGTGTGCATGAAGCAAGTAGAGTATGCCGGTATTTC<br>ATTTTTATATATCCAGATGTGCCTTGGTATTGCCTCCAGAGACCTGCCTCAGGGAAGCTAGTATGGAGGA<br>TCTGCACCCAGAGATCCATGCTCTCCTACAAAGTGCTCAGCTGCTTGAGGAAGAGCACCCGACATTCCCCTA<br>AGGAGAGTCCACAGCA |
| | Intron 30-31 | | 8,772 | gtaagtgaaggagatcagatgccc . . . ccctcagacttgtatttgcttcag |
| 31 | ENSE00001047614 | 5867 | 140 | CTTCAAGTCTGGATAGTCAGAAGTTGTGACAGTGCCCTCCAGTAATGAAGTGGTAACTAACCTGGAAGTGCT<br>GACAAGCAAATGCCTCATGGGAAGAACTACTGTCGACAGTGTCCTCTGTCTGTATGATCTTGCCAAG |
| | Intron 31-32 | | 1,156 | gtatgtgccaaggggtgggctcct . . . ttgactggcttgtcttcctctcag |
| 32 | ENSE00001123435 | 6007 | 199 | GAGTTGGGCTGTGTTCCTACACAGATGTTGCTGCTCAGGATGGTGAAGCCATGCTCCGGAAAATCTTGGCCTCT<br>CAGCAGCCTGACCGATGCAAACGAGCCCAGGCCTTCATCAGCACACAGGGCCTTAAGCACAGATACTGTGGCT<br>GAACTCGTGGCAGGAAGAGGTGACACGGAGCTGCTTACTTCATCACAGGAACAG |
| | Intron 32-33 | | 726 | gtgcccctaccccccgggattccca . . . cctgtcttcacacctctgtacag |
| 33 | ENSE00001123426 | 6206 | 138 | GACATAAGCAGATGTTCAACCAACAGAGGAAAGCCAGACATTTCTTCAGCTGACCACTCTGTCAAGACCG<br>CACATTGGTAGGCACGATGAAGTTGTTGGATAAGATTTCCTCCGTTCCCCATGG GAACTGTCTTGCA |
| | Intron 33-34 | | 2024 | gtaagtattgaccttttttcttaca . . . atcttaccagtgccacctaccag |
| 34 | ENSE00001123415 | 6344 | 134 | CCACAGAGTCCTCTGATCCTGGCCATCATTGCTTCACCCTGACGTGCCACATGGAGGGCATCATCCGAGTCC<br>TACAGGCCGCCACATGCTCACAGATAACCACCTGGCCCCAGTGAGGATATGGGCTGGTG |
| | Intron 34-35 | | 1,019 | gtaagtagcccccctcaacccagtc . . . tgcgagctgcctccacttcacag |
| 35 | ENSE00001123405 | 6478 | 108 | GTTACGGCTTCCTCCTCACTGGCATTGGAAGGTACAACGAGATGACATACATATTTGATTTGCTCATAAAAAGCACT<br>ACTTTGAAGTGCTAATGAGGAAGAAGTTGGATCCG |
| | Intron 35-36 | | 1,805 | gtaagtgcaaagtaatgagctccag . . . gcttttttccctttattctgggcag |
| 36 | ENSE00001123397 | 6586 | 169 | AGTGGTACCCTGAAAACAGCCCTGCTGGACTACATCAAACGCTGCCTCTGGAGACAGTGAAAAGCACACAAT<br>ATGATTGCCCTGTGCTTCAGCATGTGCCGGAGATTGGCGAGAACCACGAGGCAGCTGCCCGCCATCCAACTG<br>AAATTGATTGAGTCTCAGCCCTGGG |
| | Intron 36-37 | | 1,118 | gtgagtgaggtcacagccacactac . . . caaatcttctattcccctacag |
| 37 | ENSE00000684756 | 6755 | 89 | AGGAGAGCCTCAAGGATGGGCACCAGTGAAACAACTGCTGCTGAAGGCCCTGACTCTGATGTTGATGCAG<br>CAGAGAGTTATGCCAAG |
| | Intron 37-38 | | 207 | gtaaccaaaggctttttcagact . . . gtgcctctccacccttgtcctcag |
| 38 | ENSE00000684735 | 6844 | 156 | GACTCCTGTGTCGACAGGCCCAGCACTGTCAGCACTGTCAGCCGGCTCACCAAGTTGATAACTCTGCAGATTCACTTTCTGA<br>ACACTGGCCAGAACACACATTGCTCATCAACTTGGGCCGCCACAGCTGATGGACTGTATTCTGCCCTACCTC<br>GGTTCTACCAG |
| | Intron 38-39 | | 1,155 | gtgagcaagaaagcaaactgtagcc . . . gtccttcttcacctcccttttaag |

TABLE 1-continued

Exon-intron boundaries of the human KIAA1840 gene (according to the Ensembl database)

| No | Exon/intron | Position in SEQ ID NO: 1 | Length (bp) | Sequence |
|---|---|---|---|---|
| 39 | ENSE00000684706 | 7000 | 152 | GCTTCTATTGTGGCTGAGGCCTACGATTTTGTTCCAGATTGGGCTGAAATTTTATACCAGCAAGTGATTCTTAA<br>AGGAGACTTTAATTACTTGGAAGAATTTAAGCAGCAAAGGTTATTAAAGTCCAGTATATTTGAAGAGATTTCCAA<br>AAA |
|  | Intron 39-40 |  | 1,245 | gtaagtattaaaagttgactgtaaa . . . ctgtacattatgtttcttatctag |
| 40 | ENSE00000884381 | 7152 | 600 | ATATAAACAACATCAGCCTACTGACATGGTCATGGAAAACCTGAAGAAATTACTCACATATTGTGAAGATGTTT<br>ACCTGTATTACAAGTTGCATACGAACACAAGTTTTATGAAATTGTAAATGTGCTTCTGAAGGACCCTCAGACA<br>GGTTGCTGTCTAAAGGACATGCTAGCCAGGTTAGATGATTTCATAGGGTCTGTTTTATGTACTGTAGCAGAT<br>TCTTGACAGAATGTGATGAAGAAGAAGACATGGAGAGATCTTTACTAAAGTGAACAATCCGGTACTGTACCA<br>TATCAGTCCCTTTGTGAGTACTAGGTAGCAAGTAAGAAGAACTTTTCAGGAGGAAATTCCTATTTAAAATAGATTGA<br>TTTTAGATGATTGTTCATCCACACCATTTTATTAGTACTAGTATTAAGATCAAAAGCTTCCTCTTCCTCAGGA<br>CAGCTTCTACTATTAGATGATCCAATAATGATTAAAGAATAACCGTACCTGCAGATTCCGAGTTTCCAGTAATTTA<br>ATTAATATTTACACAGTTAAGGAACAGGTGATACAATTTCATTGTTAGAAAACTGATCTTTCTGTAATAAATAGA<br>TTTC |
|  | 3' downstream sequence |  |  | aattcagtgtatgtcattattactgctaaggaaatcttagccccttgtctg . . . |

As used herein, the term "Spatacsin" denotes the SPAsticity with Thin or Corpus callosum Syndrom protein, which is encoded by the KIAA1840 gene. The sequence of the human form is shown in SEQ ID NO:2.

The terms "mutant" and "mutation" mean any detectable change in genetic material, e.g. DNA, RNA, cDNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. Generally a mutation is identified in a subject by comparing the sequence of a nucleic acid or polypeptide expressed by said subject with the corresponding nucleic acid or polypeptide expressed in a control population. A mutation in the genetic material may also be "silent", i.e. the mutation does not result in an alteration of the amino acid sequence of the expression product.

In the context of the instant application, mutations identified in KIAA1840 gene are designated pursuant to the nomenclature of Den Dunnen et al. 2001 (http://www.genomic.unimelb.edu.au/mdi/mutnomen/). As defined by Dunnen and Antonarakis at the nucleic acid level, substitutions are designated by "c.position(nt)>(nt)", e.g. "c.118C>G denotes that at nucleotide 118 of the reference sequence C is changed to a G. The mutation at the protein level is denoted p.Q40X: which means that a glutamine (Q) at position 40 encoded by CAG is replaced by a STOP (TAG) codon (Q40X). Deletions are designated by "del" after the deleted interval (followed by the deleted nucleotides). For instance 529_533delATATT denotes a ATATT deletion from nucleotides 529 to 533. The consequence of this deletion, p.I177_F178delfsX, is a deletion of aminoacids at positions 177 and 178 and a frameshift (fs) in the coding sequence leading to the appearance of a premature STOP codon (X). An alternative nomenclature is to indicate the position of the stop codon in the resulting protein after the X; p.I177_178delfsX178 indicates that the stop codon resulting from the mutation is at codon 178. Insertions are designated by "ins," followed by the inserted nucleotides. For example, c.7029_7030 insT denotes that a T was inserted after nucleotide 7029. This leads to the replacement of valine (V) by cysteine (C) at position 2344 and to a frameshift of the coding sequence and a premature STOP codon at amino-acid 2349 (fsX): p.V2344CfsX or p.V2344CfsX2349. When a mutation is predicted to alter the splicing of the mRNA because the variant modifies a nucleotide of the consensus sequence for splicing (acceptor or donor site), the "r.?" denotes that the consequences of the mutation could not be checked at the RNA level, but is likely (as verified at http://rulai.cshl.edu/new_alt_exon_db2/HTML/score.html).

The term "hereditary spastic paraplegias (HSP)" denotes genetically heterogeneous Mendelian disorders characterized by weakness, spasticity and loss of vibratory sense in the lower limbs. The term "Autosomal Recessive Hereditary Spastic Paraplegia" or "AR-HSP" denotes spastic paraplegia that is transmitted as an autosomal recessive trait. Patients with HSP or AR-HSP can have a pure phenotype, or, more often, a complex phenotype that associates various neurological signs (cerebellar ataxia, mental retardation, peripheral neuropathy, etc). The term "AR-HSP-TCC" denotes an AR-HSP with Thin Corpus Callosum usually associated with, mental or cognitive deficit and peripheral neuropathy. Families without proved TCC can also be mutated in this gene either because of slow progression of the disease in the patient or because magnetic resonance imaging (MRI) couldn't be performed due to patient refusal or impossibility (patients leaving far from cities in North-Africa—this is the case for families FSP400, FSP393 and FSP343).

As used herein, the term "subject" denotes a mammal, such as a rodent, a feline, a canine, and a primate. Preferably a subject according to the invention is a human.

Mutations in the KIAA1840 Gene and Spatacsin Protein

The inventors identified various mutations in the KIAA1840 gene.

Fortythree different mutations on human KIAA1840 gene were indeed identified in 47 families, including the 16 linked ones, all at the homozygous state, except in 16 kindreds. They were either nonsense mutations (n=13), deletions (n=17), insertions (n=7), or splice site mutations (n=6) in the coding sequence, and resulted theoretically in an abnormally spliced mRNA or a truncated protein in all cases.

In one family, linked with a maximal 3.1 multipoint lod score to SPG11, a missense R945G mutation segregated at the homozygous state in both patients and was not detected in 150 control chromosomes. The mutation is probably not only affecting the nature of the amino-acid. Position of this variant was in the 5'-splice site consensus sequence (2 bases before the end of exon 15). The score of the 5'-splicing sequence changed from 4.9 for the wild type to 2.7 for the variant (Alternative Splicing Database: :http://rulai.cshl.edu/new_alt_exon_db2/HTML/score.html) suggesting that this variant could act at both the RNA level (splicing effect) and at the protein level (missense change). Indeed, this was confirmed by direct sequencing (using primers GCTCTGTGGTGGGATCAACT and TGCTTACACTGGCCTGATTG) on mRNA isolated from lymphoblasts of an affected family member (FSP670-5) in which an alternative splice site is generated downstream in intron 15 leading to a 65 bp insertion and a premature stop codon (c.2833A>G, r.2834+1_2834+65 ins, p.R945GfsX950). It cannot be excluded, however, that splicing occurs at its normal place in a small amount of messenger RNA and that a full length protein is generated with the G variant at position 945. Similarly, the mutation c.2444G>T, p.R815M likely affects not only the amino-acid but also splicing of exon 13 since the splice score down from 3.7 to 0.2 for the mutation. In addition, the c.869+1G>A, c.2316+1G>A, c.2444+1G>C and c.6477+4A>G, are all clearly affecting the acceptor splicing consensus sequence (see splice scores in table 2) and likely alter the splicing of exons 4, 12, 13 and 34, respectively. The mutations identified by the inventors are presented on the following Table 2.

TABLE 2

Mutations identified in the KIAA1840 CDS (SEQ ID NO: 1) and protein (SEQ ID NO: 2)

| Exons | Nucleotide variants | mRNA or Protein variants | SEQ ID NO: | Family code (Origins) at the homozygous state | Family code (Origins) at the heterozygous state |
|---|---|---|---|---|---|
| 1 | c.118C > T, | p.Q40X | 149 | FSP672 (Israel) | |
| 3 | c.529_533delATATT | p.I177_F178 > S177fsX178 | 150 | FSP386 (Portugal) FSP754 (Portugal) FSP831 (Portugal) | ITA17 (Brazil) |
| 4 | c.704_705delAT | p.H235RfsX246 | 166 | SPD199 (Turkey) | |
| 4 | c.733_734delAT, | p.M245VfsX246 | 151 | TUN2 (Tunisia) TUN3 (Tunisia) TUN4 (Tunisia) TUN22 (Tunisia) | FSP117 (France) |
| Intron 4 | c.869 + 1G > A | r.? Splice score down from 9.8 to −0.9 | | FSP847 (Argentina) | |
| 6 | c.1203delA, | p.K401KfsX415 | 152 | | PE (Italy) |
| 6 | c.1235C > G, | p.S412X | 153 | FSP393 (Portugal) | |
| 6 | c.1282A > T | p.K428X | 167 | | FSP830 (Portugal) |
| 7 | c.1471_1472delCT | p.L491DfsX556 | 168 | | FSP522 (France) |
| 7 | c.1549_1550delCT, | p.L517LfsX556 | 154 | | FSP343 (Algeria) (non typical) |
| 8 | c.1668delT | p.F556LfsX577 | 169 | | SAL646 (France) |
| 8 | c.1679C > G | p.S560X | 170 | | ITA16SB (Italy) |
| 8 | c.1692delA | p.V564VfsX577 | 171 | | DKD (Italy) |
| 10 | c.1951C > T, | p.R651X | 155 | | MP (Italy) FSP683 (Romania) ITA28VAC (Italy) |
| 11 | c.2198T > G, | p.L733X | 156 | OS (Italy) | |
| Intron 12 | c.2316 + 1G > A | r.? Splice score down from 6.2 to −4.5 | | FSP892 (Norway) | |
| 13 | c.2444G > T | p.R815M and/or r.? Splice score down from 3.7 to 0.2 | 172 | | ITA28VAC (Italy) |
| Intron 13 | c.2444 + 1G > C | r.? Splice score down from 3.7 to −7 | | | ITA16 (Brazil) |
| 15 | c.2697G > A | p.W899X | 173 | ITA10 (Italy) | |
| 15 | c.2716delC | p.Q906SfsX920 | 174 | ITA9 (Italy) | |
| 15 | c.2833A > G, | r.2834 + 1_2834 + 65ins, p.R945G or p.R945GfsX950 Splice score down from 4.9 to 2.7 | 165 188 | FSP670 (Israel) | ITA14 (Italy) |
| 16 | c.2842_2843insG, | p.V948GfsX953 | 157 | | PE (Italy) |
| 16 | c.2850_2851insT, | p.L950FfsX953 | 158 | | MP (Italy) |
| 17 | c.3075_3076insA | p.E1026RfsX1029 | 175 | | ITA8 (Germany) |
| 22 | c.3741_3742insA | p.P1248TfsX1264 | 176 | | ITA17 (Brazil) |
| 25 | c.4307_4308delAA | p.Q1436RfsX1442 | 177 | | FSP398 (Israel) ITA16 (Brazil) |
| 30 | c.5470C > T | p.R1824X | 178 | | ITA8 (Germany) |
| 30 | c.5532_5533delCA | p.S1844SfsX1857 | 179 | | FSP522 (France) |
| 30 | c.5769delT | p.S1923RfsX1950 | 180 | FSP838 (Saudi-Arabia) | |
| 31 | c.5870C > G | p.S1957X | 181 | | ITA16SB (Italy) |
| 31 | c.5974C > T, | p.R1992X | 159 | | FSP117 (France) |
| 31 | c.5982_5983insCTCT | p.L1995LfsX2000 | 182 | | DKD (Italy) |
| 31 | c.5986_5987insT | p.C1996LfsX1999 | 183 | | FSP398 (Israel) |
| 31 | c.5989_5992delCTGT | p.L1997_Y1998 > M1997fsX2056 | 184 | | FSP683 (Romania) |

TABLE 2-continued

Mutations identified in the KIAA1840 CDS (SEQ ID NO: 1) and protein (SEQ ID NO: 2)

| Exons | Nucleotide variants | mRNA or Protein variants | SEQ ID NO: | Family code (Origins) at the homozygous state | Family code (Origins) at the heterozygous state |
|---|---|---|---|---|---|
| 32 | c.6091C > T | p.R2031X | 185 | ITA1 (Turkey) | |
| 32 | c.6100C > T, | p.R2034X | 160 | FSP446 (Morocco), FSP221 (Algeria), FSP732 (Algeria), FSP400 (Algeria) FSP792 (Algeria) FSP845 (Morocco) TUN9 (Tunisia) TUN12 (Tunisia) TUN14 (Tunisia) | |
| 34 Intron 34 | c.6451delG, c.6477 + 4 A > G | p. A2151 P fsX2172 r.? Splice score down from 9.6 to 6.6 | 161 | SAL1608 (France) | FSP830 (Portugal) |
| 36 | c.6737_6740delTTGA, | p.I2246_E2247 > S2246fsX2260 | 162 | FSP920 (Japan) | FSP343 (Algeria) |
| 36 | c.6739_6742delGAGT | p.E2247_S2248 > L2247fsX2260 | 186 | | SAL646 (France) |
| 37 | c.6832_6833delAG, | p.S2278LfsX2338 | 163 | FSP75 (Portugal) | |
| 38 | c.6856C > T | p.R2286X | 187 | | ITA14 (Italy) |
| 39 | c.7029_7030insT, | p.V2344CfsX2349 | 164 | FSP515 (Tunisia) | |

Each mutation are herein numbered according to human KIAA1840 CDS and amino acid sequence as shown in SEQ ID NO: 1 and SEQ ID NO:2.

Accordingly, the invention relates to an isolated nucleic acid specifically hybridizable to a region of KIAA1840 gene coding sequence (SEQ ID NO:1) that contains a mutation selected from the group consisting of the substitutions c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T and c.5974C>T, the deletions: c.529_533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA and c.733_734delAT, and the insertions: c.7029_7030insT, c.2850_2851insT, c.3741_3742insA, c.5982_5983insCTCT, c.5986_5987insT, c.3075_3076insA and c.2842_2843insG.

In one embodiment of this aspect of the invention, the isolated nucleic acid according to the invention consists of at least 10 nucleotides, preferably 20 nucleotides, more preferably 40 nucleotides.

In a preferred embodiment, such an isolated nucleic acid is specifically hybridizable to a region consisting of 10 nucleotides upstream and 10 nucleotides downstream of a mutation selected from the group consisting of the substitutions: c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T c.5974C>T, the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA c.733_734delAT, and the insertions: c.7029_7030insT, c.2850_2851insT, c.3741_3742insA, c.5982_5983insCTCT, c.5986_5987insT, c.3075_3076insA c.2842_2843insG, of the KIAA1840 gene sequence.

Preferably, "specifically hybridizable" means "hybridizable under conditions at 68° C. in 0.2×SSC, at 42° C. in 50% formamide, 4×SSC, or under conditions that afford levels of hybridization equivalent to those observed under either of these two conditions".

In an alternative manner, a sequence "specifically hybridizable" to a target sequence means a sequence showing a percentage of sequence identity with the sequence complementary of said target sequence of at least about 70%, preferably at least about 80%, more preferably at least about 90%, most preferably at least about 95%.

Said nucleic acid according to the invention may be an oligonucleotide.

Preferably, said nucleic acid or oligonucleotide is complementary to a region of the KIAA1840 gene that contains at least one of the identified mutations.

In one embodiment of this aspect of the invention, the isolated nucleic acid according to the invention consists of at least 10 nucleotides, preferably 20 nucleotides, more preferably 40 nucleotides.

Such a nucleic acid according to the invention may advantageously be used as a primer or probe.

A further object of the present invention relates to an isolated nucleic acid, which comprises or consists in a KIAA1840 gene coding sequence (SEQ ID NO:1) that contains one or several mutation(s) selected from the group consisting of the substitutions: c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T c.5974C>T, the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA c.733_734delAT, and the insertions: c.7029_7030insT, c.2850_2851insT, c.3741_3742insA, c.5982_5983insCTCT, c.5986_5987insT, c.3075_3076insA c.2842_2843insG or a sequence complementary thereto.

In one embodiment of this aspect of the invention, the isolated nucleic acid according to the invention consists of at least 10 nucleotides, preferably 20 nucleotides, more preferably 40 nucleotides.

In another embodiment, the invention relates to an isolated polypeptide which comprises the polypeptide sequence of KIAA1840 containing one or several mutation(s) selected from the group consisting of p.Q40X, p.I177_F178delfsX178, p.H235RfsX246, p.M245VfsX246, p.K401KfsX415, p.S412X, p.K428X, p.L491DfsX556, p.L517LfsX556, p.F556LfsX577, p.S560X, p.V564VfsX577, p.R651X, p.L733X, p.R815M, p.W899X, p.Q906SfsX920, p.R945G, p.R945GfsX950, p.L950FfsX953, p.V948GfsX953, p.E1026RfsX1029, p.P1248TfsX1264, p.Q1436RfsX1442, p.R1824X, p.S1844SfsX1857, p.S1923RfsX1950, p.S1957X, p.R1992X, p.L1995LfsX2000, p.C1996LfsX1999, p.L1997_1998delfsX2056, p.R2031X, p.R2034X, p.A2151PfsX2172, p.I2246_E2247delfsX2260, p.E2247_S2248delfsX2260, p.S2278LfsX2338, p.R2286X and p.V2344CfsX2349.

Diagnostic Method

The inventors have further shown that KIAA1840 mutants are associated with a hereditary spastic paraplegias (HSP) which is characterized by weakness, spasticity and often loss of vibration sense in the lower limbs. More particular, the inventors have shown that KIAA1840 mutations as above described correlate in all patients with mild mental impairment, a thin corpus callosum (TCC) (AR-HSP-TCC) and frequent polyneuropathy (72% of the patients) in a series of 45 families with the full clinical criteria of SPG11. In the 2 other kindreds, cerebral imaging was not available to verify the presence of a thin corpus callosum (TUN2 and TUN14).

Therefore the invention provides an ex vivo method of diagnosing or predicting a hereditary spastic paraplegia (HSP) in a subject, which method comprises detecting a mutation in the KIAA1840 gene or protein (spatacsin), as compared to a control population, wherein the presence of a mutation is indicative of an hereditary spastic paraplegia (HSP).

Nucleic Acids Assays:

According to a first embodiment the mutations may be detected by analysing a KIAA1840 nucleic acid molecule. In the context of the invention, KIAA1840 nucleic acid molecules include mRNA, genomic DNA and cDNA derived from mRNA. DNA or RNA can be single stranded or double stranded. These may be utilized for detection by amplification and/or hybridization with a probe, for instance.

Thus the invention provides an ex vivo method of diagnosing or predicting a hereditary spastic paraplegia (HSP), in a subject, which method may comprise the step consisting of detecting a KIAA1840 mutation in a nucleic acid sample obtained from the subject, wherein the presence of a mutation is indicative of a hereditary spastic paraplegia (HSP).

The nucleic acid sample may be obtained from any cell source or tissue biopsy. Non-limiting examples of cell sources available include without limitation blood cells, buccal cells, epithelial cells, fibroblasts, or any cells present in a tissue obtained by biopsy or post-mortem. Cells may also be obtained from body fluids, such as blood, plasma, serum, lymph, etc. DNA may be extracted using any methods known in the art, such as described in Sambrook et al., 1989. RNA may also be isolated, for instance from tissue biopsy, using standard methods well known to the one skilled in the art such as guanidium thiocyanate-phenol-chloroform extraction (Chomocyznski et al., 1987).

A KIAA1840 mutation according to the invention may be found and located in many exons, including exon 1 and exon 39 (Table 2).

KIAA1840 mutations may be detected in a RNA or DNA sample, preferably after amplification. For instance, the isolated RNA may be subjected to coupled reverse transcription and amplification, such as reverse transcription and amplification by polymerase chain reaction (RT-PCR), using specific oligonucleotide primers that are specific for a mutated site or that enable amplification of a region containing the mutated site. According to a first alternative, conditions for primer annealing may be chosen to ensure specific reverse transcription (where appropriate) and amplification; so that the appearance of an amplification product be a diagnostic of the presence of a particular KIAA1840 mutation. Otherwise, RNA may be reverse-transcribed and amplified, or DNA may be amplified, after which a mutated site may be detected in the amplified sequence by hybridization with a suitable probe or by direct sequencing, or any other appropriate method known in the art. For instance, a cDNA obtained from RNA may be cloned and sequenced to identify a mutation in KIAA1840 sequence.

Actually numerous strategies for genotype analysis are available (Antonarakis et al., 1989; Cooper et al., 1991; Grompe, 1993). Briefly, the nucleic acid molecule may be tested for the presence or absence of a restriction site. When a base substitution mutation creates or abolishes the recognition site of a restriction enzyme, this allows a simple direct enzymatic test for the mutation. Further strategies include, but are not limited to, direct sequencing, restriction fragment length polymorphism (RFLP) analysis; hybridization with allele-specific oligonucleotides (ASO) that are short synthetic probes which hybridize only to a perfectly matched sequence under suitably stringent hybridization conditions; allele-specific PCR; PCR using mutagenic primers; ligase-PCR, HOT cleavage; denaturing gradient gel electrophoresis (DGGE), temperature denaturing gradient gel electrophoresis (TGGE), single-stranded conformational polymorphism (SSCP) and denaturing high performance liquid chromatography (DHPLC) (Kuklin et al., 1997). Direct sequencing may be accomplished by any method, including without limitation chemical sequencing, using the Maxam-Gilbert method; by enzymatic sequencing, using the Sanger method; mass spectrometry sequencing; sequencing using a chip-based technology (see e.g. Little et al., 1996); and real-time quantitative PCR. Preferably, DNA from a subject is first subjected to amplification by polymerase chain reaction (PCR) using specific amplification primers. However several other methods are available, allowing DNA to be studied independently of PCR, such as the rolling circle amplification (RCA), the Invader™assay, or oligonucleotide ligation assay (OLA). OLA may be used for revealing base substitution mutations. According to this method, two oligonucleotides are constructed that hybridize to adjacent sequences in the target nucleic acid, with the join sited at the position of the mutation. DNA ligase will covalently join the two oligonucleotides only if they are perfectly hybridized (Nickerson et al., 1990).

The inventors designed a series of primers, manually or using Oligo6 (MBI, Cascade, Colo.), in order to amplify all coding exons of 18 genes from the candidate interval (primers and conditions available on request), including the mutated KIAA1840 gene (see Table 4). PCR-amplified fragments of genomic DNA were then purified using exonuclease 1 (New England Biolabs, 2 U/5 µl PCR product) and shrimp alkaline phosphatase (Roche, 1 U/5 µl of PCR product) and sequenced using the fluorescent dideoxy-terminator method (BigDye v3, Applied Biosystem) on an automated ABI-3730 sequencer according to the manufacturer's recommendations. With the use of the software package SeqScape (Applied Biosystems), sequences were aligned and compared to consensus sequences.

Protein Assays

According to a second embodiment said mutation may be detected in KIAA1840 protein or a truncated form of the KIAA1840 protein may be detected, as compared to a control population.

Figure 5:
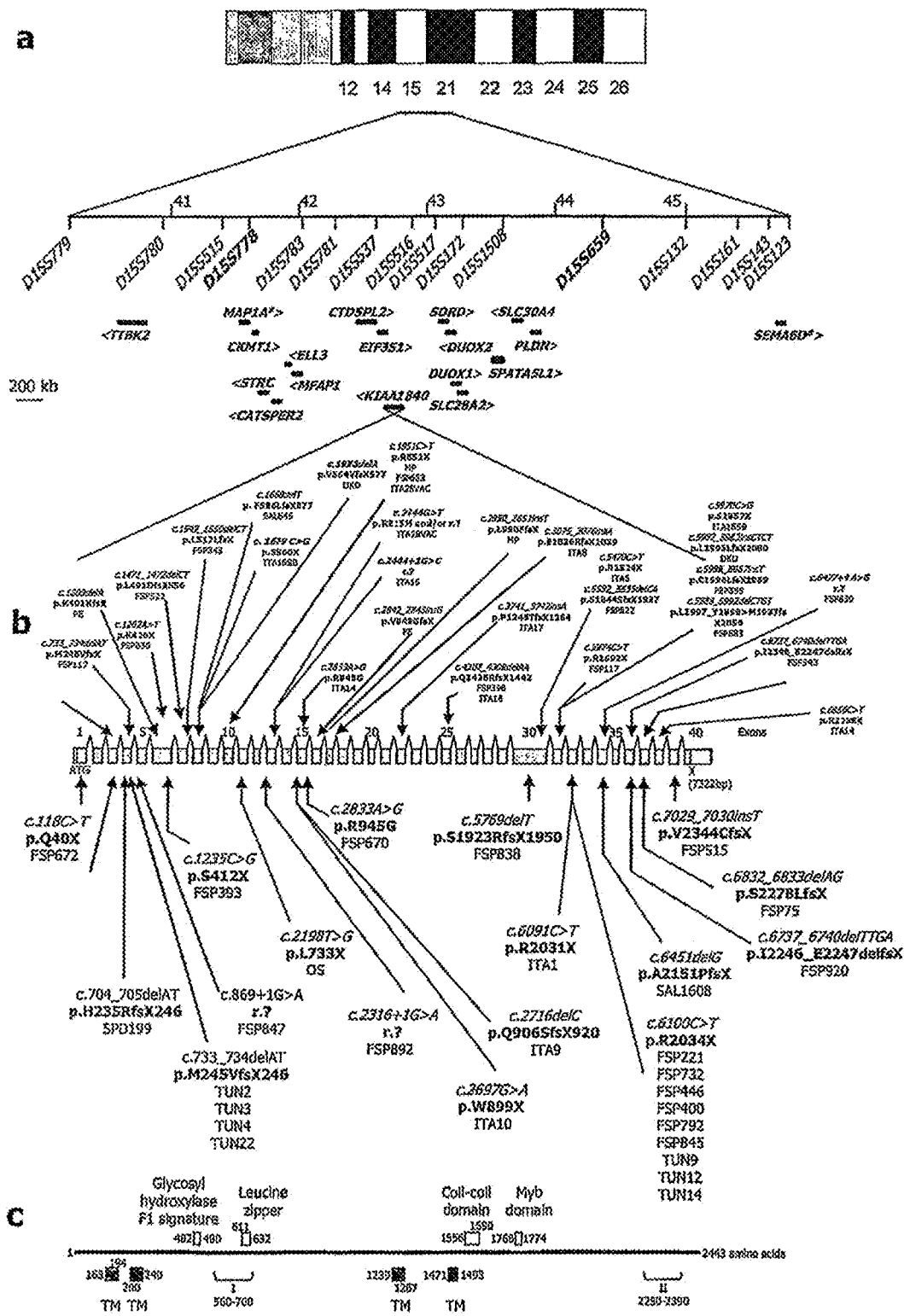

All of the identified mutations of the KIAA840 gene create some deletions of the C-terminal part of the spatacsin protein, in some cases because of aberrant splicing (FIG. 5). These deletions result in truncated proteins of sequences SEQ ID NO: 149 to SEQ ID NO:164 and SEQ ID NO:166 to SEQ ID NO:188, respectively. Those due to aberrant splicing, either very likely, could not be precised because the modification of the splicing could not be evidenced in mRNA directly, except in family FSP670 (r.2834+1_2834+65ins, p.R945GfsX950). It can not be excluded, however, that a shorten protein fragment may be synthesized due to the activation of new ATGs after the stop codon.

Said mutation may be detected according to any appropriate method known in the art. In particular a sample, such as a tissue biopsy, obtained from a subject may be contacted with antibodies specific of the truncated form of KIAA1840 protein, i.e. antibodies that are capable of distinguishing between a mutated form of KIAA1840 and the wild-type protein (or any other protein), to determine the presence or absence of a KIAA1840 specified by the antibody. An antibody recognizing the wild type protein could also be used to check the presence of the protein or its abnormal location or size and could then be used as a diagnostic tool as well.

Antibodies that specifically recognize a mutated KIAA1840 protein also make part of the invention. The antibodies are specific of mutated KIAA1840 protein, that is to say they do not cross-react with the wild-type KIAA1840 protein.

A monoclonal or polyclonal antibody recognizing the wild-type KIAA1840 protein may be used to detect the presence of the wild-type protein or one of its truncated forms. For instance, an antibody recognizing the N-terminal part of the wild-type KIAA1840 protein may also recognize one or several truncated forms and can be used to reveal by immunoblotting, the different forms, wild-type and truncated, according to their molecular weights. An antibody recognizing the wild-type KIAA1840 protein, but not recognizing the truncated forms, can be used for immunoblotting or in immunoassay as ELISA; in that case, an absence of signal reveals the presence of a truncated form in the sample or the absence of synthesis of a stable protein as compared with a positive control comprising the wild-type KIAA1840 protein.

The antibodies of the present invention may be monoclonal or polyclonal antibodies, single chain or double chain, chimeric antibodies, humanized antibodies, or portions of an immunoglobulin molecule, including those portions known in the art as antigen binding fragments Fab, Fab', F(ab')$_2$ and F(v). They can also be immunoconjugated, e.g. with a toxin, or labelled antibodies.

Whereas polyclonal antibodies may be used, monoclonal antibodies are preferred for since they are more reproducible in the long run.

Procedures for raising "polyclonal antibodies" are also well known. Polyclonal antibodies can be obtained from serum of an animal immunized against the spatacsin complex, which may be produced by genetic engineering for example according to standard methods well-known by one skilled in the art. Typically, such antibodies can be raised by administering mutated KIAA1840 protein or peptides of this protein subcutaneously to New Zealand white rabbits which have first been bled to obtain pre-immune serum. The antigens can be injected at a total volume of 100 µl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed by Harlow et al. (1988) which is hereby incorporated in the references.

A "monoclonal antibody" in its various grammatical forms refers to a population of antibody molecules that contains only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Laboratory methods for preparing monoclonal antibodies are well known in the art (see, for example, Harlow et al., 1988). Monoclonal antibodies (mAbs) may be prepared by immunizing purified mutated KIAA1840 protein into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al.

Antibody generation techniques not involving immunisation are also contemplated such as for example using phage display technology to examine naive libraries (from non-immunised animals); see Barbas et al. (1992), and Waterhouse et al. (1993).

Antibodies raised against mutated KIAA1840 protein may be cross reactive with wild-type KIAA1840 protein. Accordingly a selection of antibodies specific for mutated KIAA1840 protein is required. This may be achieved by depleting the pool of antibodies from those that are reactive with the wild-type KIAA1840 protein, for instance by submitting the raised antibodies to an affinity chromatography against wild-type KIAA1840 protein.

Alternatively, binding agents other than antibodies may be used for the purpose of the invention. These may be for instance aptamers, which are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Kits

According to another aspect of the invention, the KIAA1840 mutation is detected by contacting the DNA of the subject with a nucleic acid probe, which is optionally labeled.

Primers may also be useful to amplify, analyse (dHPLC, Southern . . . ) or sequence the portion of the KIAA1840 gene containing the mutated positions of interest.

Such probes or primers are nucleic acids that are capable of specifically hybridizing with a portion of the KIAA1840 gene sequence containing the mutated positions of interest. That means that they are sequences that hybridize with the portion mutated KIAA1840 nucleic acid sequence to which they refer under conditions of high stringency.

The present invention further provides kits suitable for determining at least one of the mutations of the KIAA1840 gene.

The kits may include the following components:
(i) a probe, usually made of DNA, and that may be pre-labelled. Alternatively, the probe may be unlabelled and the ingredients for labelling may be included in the kit in separate containers; and
(ii) hybridization reagents: the kit may also contain other suitably packaged reagents and materials needed for the particular hybridization protocol, including solid-phase matrices, if applicable, and standards.

In another embodiment, the kits may include:
(i) sequence determination or amplification primers: sequencing primers may be pre-labelled or may contain an affinity purification or attachment moiety; and
(2) sequence determination or amplification reagents: the kit may also contain other suitably packaged reagents and materials needed for the particular sequencing amplification protocol. In one preferred embodiment, the kit comprises a panel of sequencing or amplification primers, whose sequences correspond to sequences adjacent to at least one of the polymorphic positions, as well as a means for detecting the presence of each polymorphic sequence.
In a particular embodiment, it is provided a kit which comprises a pair of oligonucleotide primers specific for amplifying all or part of the KIAA1840 gene comprising at least one of the mutated positions that are identified above (see Table 2).

More preferably, the kits of the invention comprise a pair of primers selected from the pairs shown in Table 3 either for detection by direct sequencing or by screening by dHPLC when they could be set-up (second set of primer pairs).

TABLE 3

Primers used for PCR or for dHPLC (in parentheses)

| Exons | Mutations | For/Rev primers | SEQ ID NO: |
|---|---|---|---|
| 1 | c.118C > T, p.Q40X | ccacaggaaacgaatggaat /ggttctgtgaggaaaccacg | 3/4 |
| 3 | c.529_533delATATT, p.I177_F178delfsX | cagggacattgtaggccatc/tcccagctcccaaaactaaa (ccagttgtaaaattgtgacc)/(tcaatcaacacttctaccac) | 5/7 (6)/(8) |
| 4 | c.733_734delAT, p.M245VfsX c.704_705delAT, p.H235RfsX246 c.869 + 1G > A, r.? | caggttctttcttgtggcatca/cgaggatattttaacctcttatca (gttaggcatacttacaaaactggc)/(cgaggatattttaacctcttatca) | 9/10 (11)/(12) |
| 6 | c.1203delA, p.K401KfsX; c.1235C > G, p.S412X c.1282A > T, p.K428X | gaacatctttgccctggttt/caggcactgaggcagaagta (ctgtgacaggtgttaagtta)/(atctaatacaagacagtctc) | 13/15 (16) |
| 7 | c.1549_1550deICT, p.L517LfsX | aaaaatcaattcctaaatcataatcc/tcttttaaagccaaaaagggtaaa (tagtactgaagtattgagta) / (ttaagtaatgttcttgggca) | 17/19 (20) |

TABLE 3-continued

Primers used for PCR or for dHPLC (in parentheses)

| Exons | Mutations | For/Rev primers | SEQ ID NO: |
|---|---|---|---|
| 8 | c.1668delT, p.F556Lfs5X577<br>c.1679C > G, p.S560X<br>c.1692delA, p.V564VfsX577 | cttgccccagattgcataat / tccaaaaagtacgtaaaatccca | 57/58 |
| 10 | c.1951C > T, p.R651X | cccaggactaatcatgaagga /atccccaaaccgataaaacc | 21/22 |
| 11 | c.2198T > G, p.L733X | cggtgtgtcttccactagctc /acccagccattctcagtgtt<br>(gttacataaatgtataatccctg )/(cattttaagactttatggattac) | 23/25<br>(24)/(26) |
| 12 | c.2316 + 1G > A, r.? | tttgaaagagcagaaagctatgg / tgaaggggttgtcacacttt | 61/62 |
| 13 | c.2444G > T, p.R815M and/or r.?<br>c.2444+301G > C, r.? | ttgtggcaaaagaaaatttgtg / gagaatgcaggctcagttcc | 63/64 |
| 15 | c.2833A > G,<br>r.2834 + 1_2834 + 65ins,<br>p.R945GfsX950 or p.R945G<br>c.2697G > A, p.W899X<br>c.2716delC, pQ906SfsX920 | cacagcgagatcctgtctca /cctcactgtaagatgatgccc | 27/28 |
| 16 | c.2842_2843insG, p.V948GfsX;<br>c.2850_2851insT, p.L950FfsX | cctttaaatactacagtggtgcaga /ccaactgttgagatggagaaaa<br>(tgtgggcatgatttggtcta)/(acctgctcaaggacaaatgc) | 29/31<br>(30)/(32) |
| 17 | c.3075_3076insA, p.E1026RfsX1029 | ttgtttccagatcatgaagaatatg / tcagatagctgaccacagcc | 67/68 |
| 22 | c.3741_3742insA, p.P1248TfsX1264 | agtcagcttaagggaagcgg / gaagataaccatttctcccca | 77/78 |
| 25 | c.4307_4308delAA, p.Q1436RfsX1442 | aaaaggcaccatacagctttg / ggaaacacatgctggaacct | 83/84 |
| 30 | c.5470C > T, p.R1824X<br>c.5532_5533delCA, p.S1844SfsX1857<br>c.5769delT, p.S1923RfsX1950 | tgaggtgggaggatctcttg / gatgtgttcagagcagccaa and<br>taagctggaggagctggaga / ttgttgtccccttaacttgg | 93/94<br>95/96 |
| 31 | c.5974C > T, p.R1992X<br>c.5870C > G, p.S1957X<br>c.5982_5983insCTCT, p.L1995LfsX2000<br>c.5986_5987insT, p.C1996LfsX1999<br>c.5989_5992delCTGT, p.L1997_Y1998 > M1997fsX2056 | tttgaagtatcccagggtgg /ccaccattcccccaaagataa | 33/34 |
| 32 | c.6100C > T, R2034X<br>c.6091C > T, p.R2031X | ttacctggatttggctttgg /tgcaatccagaaacttgagaga<br>(cctggcttctaaaagtggcc)/(aagcacaacatccaaatcctt) | 35/37<br>(36)(38) |
| 34 | c.6451delG, p.A2151PfsX<br>c.6477 + 4 A > G, r.? | atgttggcaggaactccatc /ctcctttggagcaacctctg | 39/40 |
| 36 | c.6737_6740delTTGA, p.I2246_E2247delfsX<br>c.6739_6742delGAGT, p.E2247_S2248 > L2247fsX2260 | ttccaacaggaaagcacaca /cagctacttgggaggctgag<br>(caacaggaaagcacacatgc)/(gtgtggctgtgacctcactc) | 41/43<br>(42)/(44) |
| 37 | c.6832_6833delAG, p.S2278LfxX | gcattagaaggggcactgaa /ctcacaacggtattcaccccc<br>(aacatggctgggatgtttct)/(ttcctggttggcctatgatg) | 45/47<br>(46)/(48) |
| 38 | c.6856C > T, p.R2286X | ttttgtccttgggctctttc / cctggttctgtcactagccc | 101/102 |
| 39 | c.7029_7030insT, p.V2344CfsX | aagggtttaagataatttgggga /ggattcttgatactgctttgcc<br>(aatgccaaacacacacctga)/(ctcaaagcagaggcaaggag) | 49/51<br>(50)/(52) |

Therapeutic Methods

The inventors have demonstrated that the all, except one, mutations identified in the KIAA1840 gene cause truncation of the protein, suggesting that pathogenicity results from loss of function.

These results identify mutated KIAA1840 gene as target for the preventive or curative treatment of a hereditary spastic paraplegia.

Thus the invention further relates to a method of treatment of an HSP which comprises the step of administering a subject in need thereof with a KIAA1840 nucleic acid, i.e. a nucleic acid sequence that encodes a wild-type KIAA1840 protein, so that spatacsin is expressed in vivo by the cells of the subject that have been transfected with said nucleic acid. Accordingly, said method leads to an overexpression of wild-type spatacsin which compensates expression of defective mutated KIAA1840 protein.

The invention also relates to the use of a KIAA1840 nucleic acid for the manufacture of a medicament intended for the treatment of an HSP.

In the context of the invention, the term "treating" or "treatment", as used herein, means reversing, alleviating, inhibiting the progress of, or preventing the disorder or condition to which such term applies, or one or more symptoms of such disorder or condition.

Preferably said KIAA1840 nucleic acid is administered in a therapeutically effective amount. A "therapeutically effective amount" is intended for a minimal amount of active agent (e.g., KIAA1840 nucleic acid) which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

The administered polynucleotide comprises the nucleotide sequence SEQ ID NO:1, or any homologous or similar sequence as defined below:

a) a sequence showing at least 70%, preferably at least 75% or 80% or 85% or 90% or 95% or 99%, sequence similarity with SEQ ID NO:1;

b) a sequence hybridizing with SEQ ID NO:1, or its complementary sequence, under stringent conditions;

c) a sequence encoding a protein of sequence SEQ ID NO:2, or any sequence substantially similar with SEQ ID NO:2.

The term "sequence similarity" in all its grammatical forms refers to the degree of identity or correspondence between nucleic acid or amino acid sequences of proteins that may or may not share a common evolutionary origin. Preferably the degree of sequence identity is calculated compared with the totality of a reference sequence.

In a specific embodiment, two DNA sequences are "substantially homologous" or "substantially similar" when at least 70%, preferably at least 75% or 80% or 85% or 90% or 95% or 99%, of the nucleotides match over the defined length of the DNA sequences, as determined by sequence comparison algorithms, such as BLAST, FASTA, DNA Strider, etc. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially similar" when greater than 80%, preferably than 85% or 90% or 95% or 99%, of the amino acids are similar (functionally identical). "Functionally identical" polypeptides are those in which a given amino acid residue has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Preferably, the similar sequences are identified by alignment using, for example, the GCG (Genetics Computer Group, Program Manual for the GCG Package, Version 7, Madison, Wis.) pileup program, or any of the programs described above (BLAST, FASTA, etc.).

Preferably the KIAA1840 nucleic acid sequence according to the invention is associated with elements that enable for regulation of its expression, such as a promoter sequence.

Such a nucleic acid may be in the form of a DNA vector. The terms "vector" means the vehicle by which a DNA or RNA sequence (e.g. a foreign gene) can be introduced into a host cell, so as to transform the host and promote expression (e.g. transcription and translation) of the introduced sequence. A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA.

The KIAA1840 nucleic acid may be introduced into a target cell by means of any procedure known for the delivery of nucleic acids to the nucleus of cells, ex vivo, on cells in culture or removed from an animal or a patient, or in vivo.

Ex vivo introduction may be performed by any standard method well known by one skilled in the art, e.g. transfection, electroporation, lipofection, microinjection, transduction, cell fusion, DEAE dextran, calcium phosphate precipitation, or use of a gene gun.

The above methods do not limit the scope of the invention and it is to be understood that the one skilled in the art may readily make use of any other known appropriate methods for delivering a nucleic acid to a cell in vivo or in vitro.

The invention also relates to the use of wild-type KIAA1840 protein (spatacsin) for the manufacture of a medicament intended for the treatment of an HSP.

Thus the invention further relates to a method of treatment of an HSP which comprises the step of administering a subject in need thereof with a therapeutically effective amount of wild-type KIAA1840 protein.

The KIAA1840 protein may be introduced to a target cell by means of any procedure known for the delivery of proteins to cells, ex vivo, on cells in culture or removed from an animal or a patient, or in vivo.

Protein delivery is the process by which a protein crosses the cell plasma membrane. Traditionally, methods to introduce antibodies, peptides or other membrane-impermeable molecules into cells include micro-injection and electroporation.

A number of protein-transduction domains (PTDs) have also been developed that mediate protein delivery into cells. These PTDs or signal peptide sequences are naturally occurring polypeptides of 15 to 30 amino acids, which normally mediate protein secretion in the cells. They are composed of a positively charged amino terminus, a central hydrophobic core and a carboxyl-terminal cleavage site recognized by a signal peptidase. Examples of such membrane-transducing peptides include Trojan peptides, human immunodeficiency virus (HIV)-1 transcriptional activator (TAT) protein or its functional domain peptides, and other peptides containing protein-transduction domains (PTDs) derived from translocation proteins such as Drosophilia homeotic transcription factor Antennapedia (Antp) and herpes simplex virus DNA-binding protein, VP22, and the like. Some commercially available peptides, for example, penetratin 1, Pep-1 (Chariot reagent, Active Motif Inc., CA) and HIV GP41 fragment (519-541), can be used for protein delivery.

Recently, the use of lipid liposomes or the like that can complex with a protein of interest and promote the delivery of the protein into the cell has also been demonstrated. Products available commercially can be used, such as Bio-PORTER (Gene Therapy Systems), or ProVectin (Imgenex, San Diego, Calif.).

The above methods do not limit the scope of the invention and it is to be understood that the one skilled in the art may readily make use of any other known appropriate methods for delivering a protein to a cell in vivo or in vitro.

The invention will be further illustrated by the following figures and examples.

FIGURES

FIGS. 1 and 2: Multipoint linkage analysis performed in 16 families for 34 microsatellite markers from chromosome 15q. cM=centimorgan.

(FIG. 1) Multipoint LOD score values for each family. * Relative position on the genetic map of chromosome 15 (according to http://research.marshfieldclinic.org/genetics).

(FIG. 2) Cumulative multipoint LOD scores in the 16 linked-families plotted according to the genetic map of chromosome 15.

Figure 3:
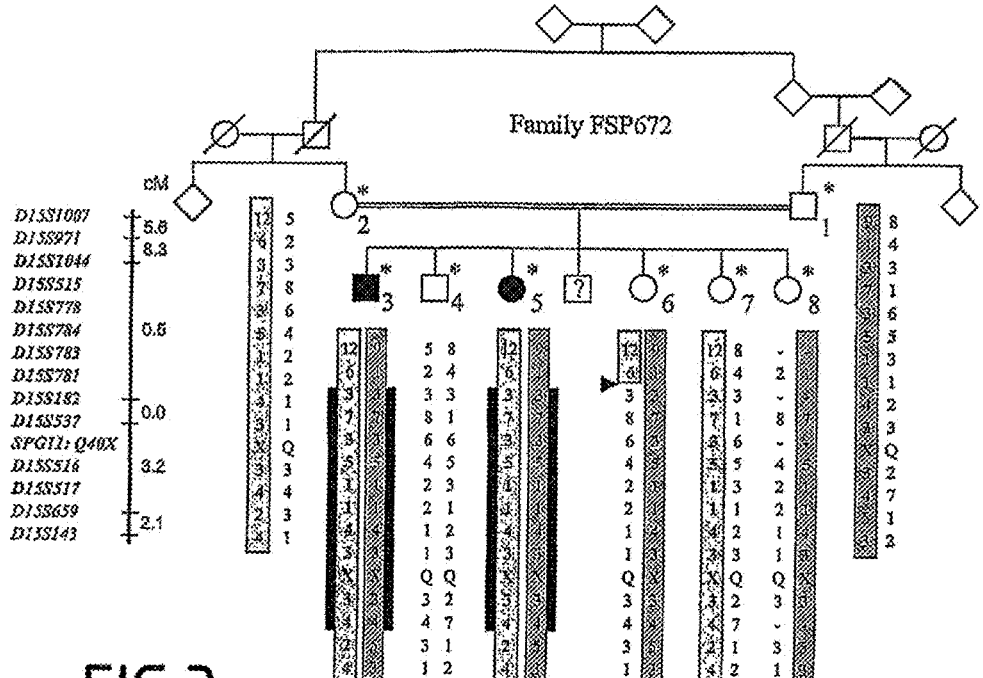
Figure 4:
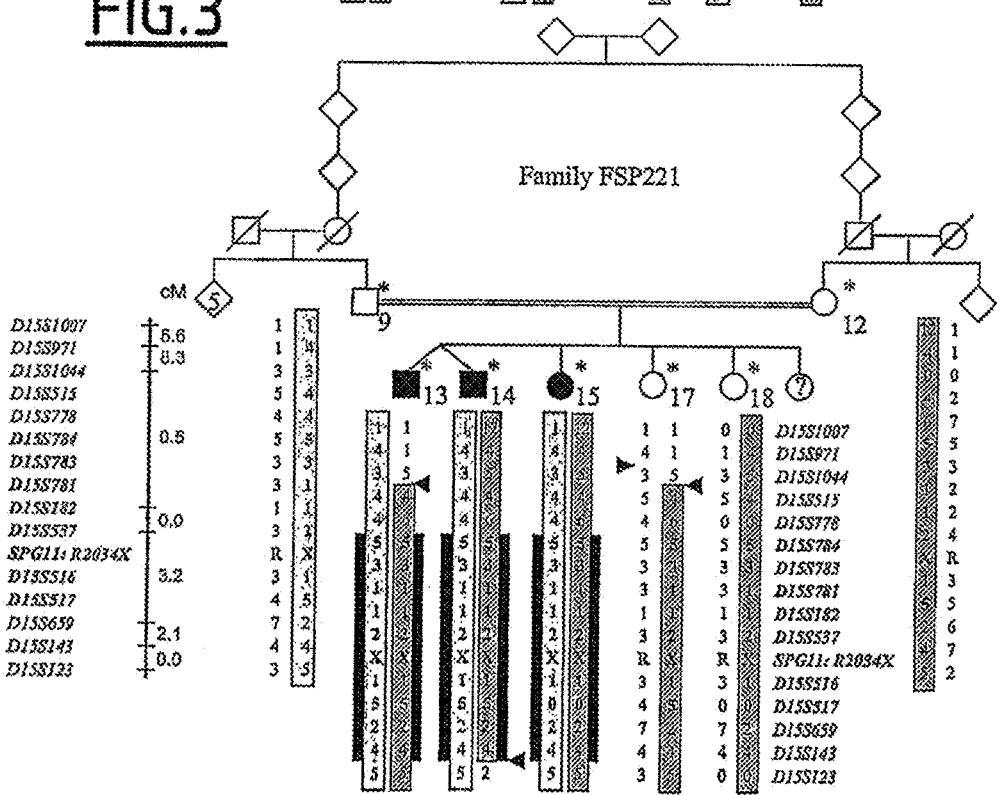

FIGS. 3 and 4: Pedigrees of 2 SPG11 families that reduced the candidate interval. Black circles (women) and squares (men) indicate affected members compared to previous publications. The numbers are an internal reference for each sampled individual. Asterisks indicate sampled subjects. Haplotype reconstruction for selected microsatellite markers positioned according to the human genome draft sequence (www.ncbi.nlm.nih.gov, www.ensembl.org) is shown. The homozygous haplotype, in which the mutated gene has been located, is flanked by black boxes. Arrowheads indicate the position of probable recombination events. cM=centimorgan (according to http://research-.marshfieldclinic.org/genetics).

FIG. 5: Critical region of SPG11. (a) Physical map of human chromosome 15q15-21 with selected genetic markers and candidate genes that were sequenced. Distances in megabases are indicated relative to chromosome 15 according to the Ensembl database. Markers defining the reduced candidate interval are in bold. # indicates that these genes (SEMA6D and MAP1A) were analyzed in a previous study (Stevanin et al, 2006). > and < indicate the orientation of the open reading frame (ORF) of each gene. (b) Exon-intron structure of the 101 Kb of the KIAA1840 gene, also known as FLJ21439, with positions of mutations identified in 17 SPG11 families. (c) Putative functional domains (boxes) and their positions on the protein sequence. TM=transmembrane domains. Regions I and II correspond to structurally similar domains based on their hydrophobicity status analysed with DomHCA software.

FIGS. 6 to 17: Pedigrees and segregation of the 17 mutations detected in KIAA1840. Square symbols are men, the circles are women. The filled symbols are affected individuals, grey or ? symbols indicate patients with an unknown status. The numbers are an internal reference for each sampled individual. Stars indicate sampled subjects. M or m=mutation; +=wild type. Electrophoregrams are shown for the homozygous mutations only. (6,7) Families with common origins sharing the same mutations. Haplotypes for three close microsatellites segregating with the mutations are highlighted. The correspondence between the numbering of alleles and their size in base pairs is indicated. (8, 10 to 14) Other homozygous mutations. (15) New homozygous mutations. (9, 16, 17) Compound heterozygous mutations.

Figure 18:
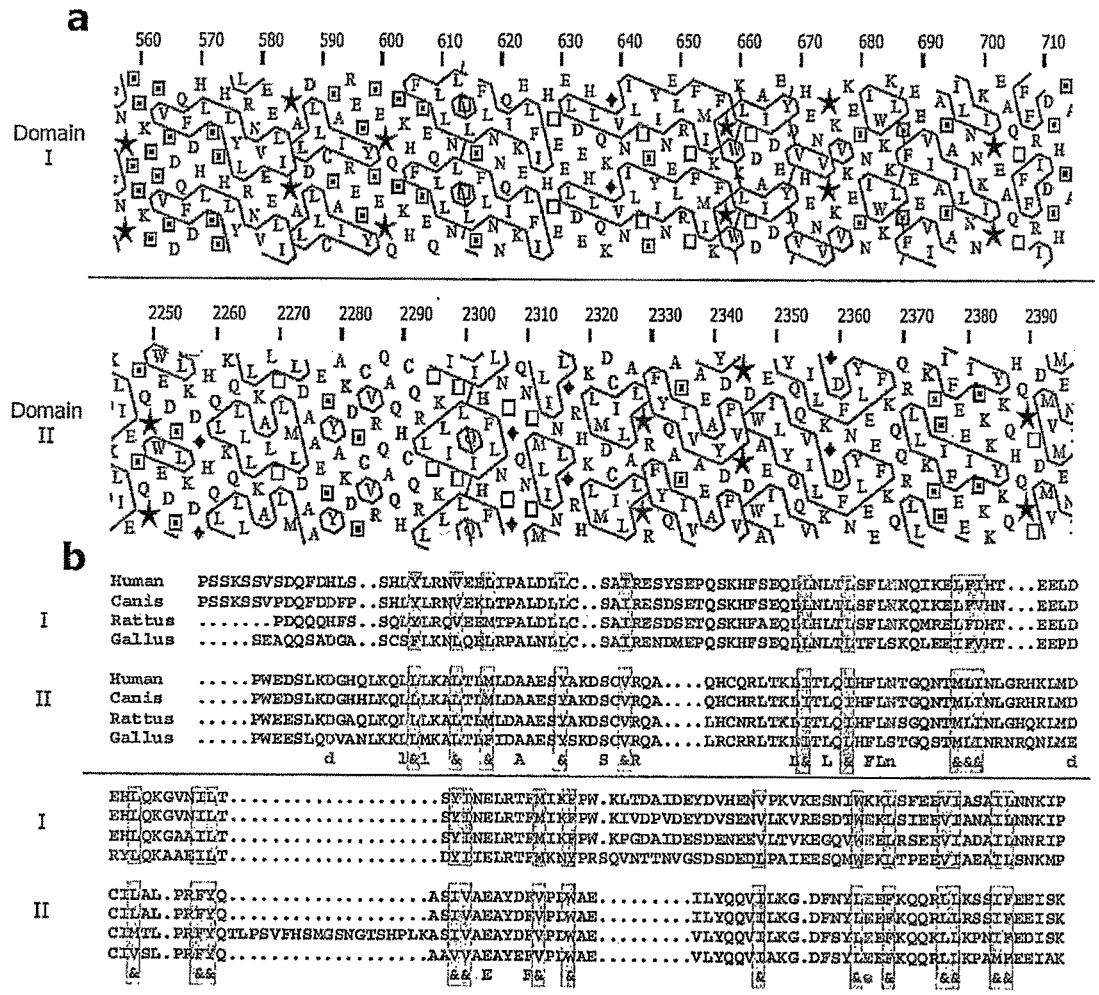

FIG. 18: Internal structural duplication in spatacsin (a) Hydrophobic cluster analysis (HCA) plots of the internal duplication of two regions in the human sequence. The HCA method is based on the use of a bidimensional plot (HCA plot) from the drawing of the 1D sequence on an alpha helix (3.6 residue/turn, connectivity distance of 4 residues separating two different clusters) which has been shown to offer the best correspondence between clusters and regular secondary structures. Examination of the HCA plot of a protein sequence enables globular regions to be easily distinguished from non globular ones and, in globular regions, secondary structures to be identified. This 2D signature, which is much more highly conserved than the 1D sequence and can be enriched from the comparison of families of highly divergent sequences, enables relevant similarities to be successfully detected at low levels of sequence identity. The form of the clusters is generally indicative of the type of secondary structures (vertical clusters are often associated with beta strands whereas horizontal ones often correspond to alpha helices). Dom-HCA software: http://www.lmcp.jussieu.fr/%7Emornon/hca.html. Special symbols are used for some amino acids: star for proline, square and dotted square for threonine and serine, diamond for glycine.

(b) Multiple alignment of the structural repeat domains (I and II, FIG. 3) corresponding to the HCA plots (DomHCA software). Under the multiple alignment, highly conserved residues are indicated by a capital letter when strictly conserved or in lower case if there is some homology. The character "&" means that this position is always occupied by a hydrophobic residue (amino acids FILMVW and Y).

Figure 19:
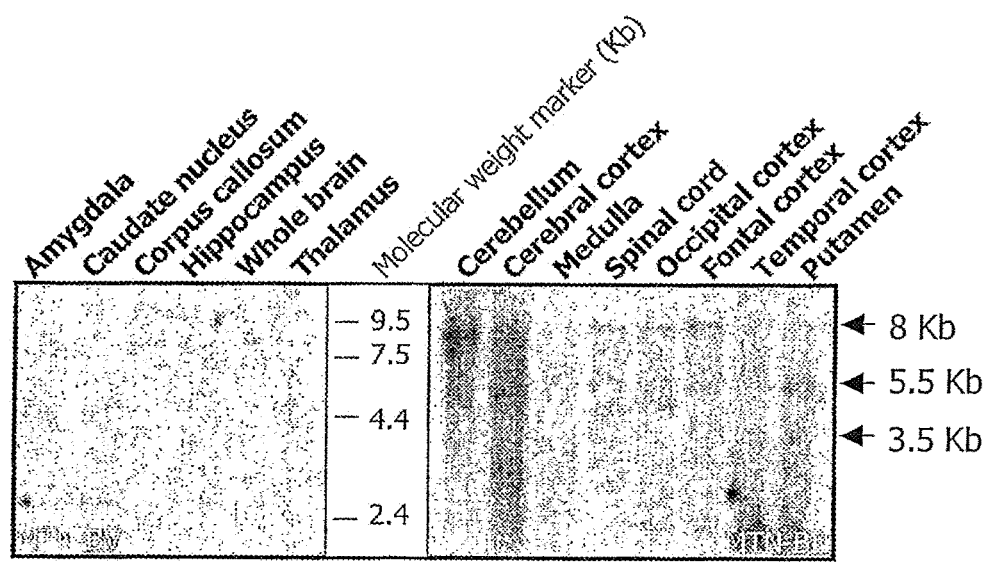

FIG. 19: Expression profile of KIAA1840 examined by northern blot in human adult brain. The transcripts were present in all brain tissues. Note the 8-Kb transcript more intensely expressed in the cerebellum while the 5.5-Kb transcript is mainly found in the cerebral cortex.

Table 1: Exon-intron boundaries in the KIAA1840 gene

Table 2: Mutations found in the KIAA1840 gene in families with AR-HSP-TCC.

Table 3: Primers used for detecting the mutations either by direct sequencing or by dHPLC Table 4: Primers used for the amplification of all exons of the KIAA1840 gene and PCR amplification conditions Table 5: PCR conditions and dHPLC conditions to analyze exons of KIAA1840.

Table 6: dHPLC primers to analyze exons of KIAA1840

EXAMPLE

Method:

Subjects: 211 individuals, including 83 affected members and 44 non mutated members, from 91 families.

All patients were examined by a neurologist. They were selected among 216 families with hereditary spastic paraparesis compatible with recessive transmission collected in our neurogenetic reference center in collaboration with the SPATAX network. They presented a typical "SPG11" phenotype defined as the presence of progressive spastic paraparesis associated with thin corpus callosum on cerebral MRI and mental retardation and neuropathy.

Blood samples was obtained after written consent from all affected patients and their relatives with approval of the local Ethic committee of Paris-Necker (approval n°03.12.07 of the comité Consultatif pour la Protection des Personnes et la Recherche Biomédicale, to A.D). Genomic DNA was extracted from leukocytes using standard procedures.

Linkage Analysis: The genome scan in family FSP221 was performed using 400 microsatellites, regularly spaced on all chromosomes (ABI-Prism mapping set v2, Applied Biosystems, Foster City, Calif.) and 50 additional polymorphic markers were used to analyze the results. Genotypes were determined by PCR with a fluorescently-labeled primer, electrophoretic migration in an ABI-3730 sequencer (Applied Biosystems) and analysis with Genescan 3.5 (Applied Biosystems). Allegro 1.2c was used to calculate two-point and multipoint lod scores between the disease phenotype and each of the markers or the map of the markers assuming a complete penetrance, equal allele frequencies for the markers and a mutated allele frequency of 0.0005 (Gudbjartsson et al. 2000). Marker order and genetic distances were obtained from the Ensembl (http://www.ensembl.org) and Marshfield databases (http://research.marshfield-clinic.org/genetics), respectively.

Mutation Detection: A series of primers was designed manually or using Oligo6 (MBI, Cascade, Colo.) in order to amplify all coding exons of 18 genes from the candidate interval (primers and conditions available on request). PCR-amplified fragments of genomic DNA were then purified using exonuclease 1 (New England Biolabs, 2 U/5 µl PCR product) and shrimp alkaline phosphatase (Roche, 1 U/5 µl of PCR product) and sequenced using the fluorescent dideoxy-terminator method (BigDye v3, Applied Biosystem) on an automated ABI-3730 sequencer according to the manufacturer's recommendations. With the use of the software package SeqScape (Applied Biosystems), sequences were aligned and compared to consensus sequences.

Primers used for the amplification of the KIAA1840 gene are listed in the following Table 4.

The conditions of the PCR programme are as follows:
95° C., 12 min
then 40 cycles of:
95° C., 30 s
Annealing Temperature (see Table 4), 30 s,
72° C., 30 s
then
72° C., 10 min, and
15° C., 15 min.

PCR were performed in 25 µl final volume using 10 pmol of each primer, at final concentrations of 1.5 mM MgCl2 and 0.24 mM dNTP.

Taq pol, which is commercially available from Quiagen was used except for exons 6, 12 and 40B where Taq GOLD (Applied Biosystems) was used.

TABLE 4

| Exon | Annealing temperature | SEQ ID NO: | Forward primer | Reverse primer |
|---|---|---|---|---|
| ex1 | 60° C. | 3/4 | ccacaggaaacgaatggaat | ggttctgtgaggaaaccacg |
| ex2 | 60° C. | 53/54 | ctgagccccacattttgtt | caagtgctcaatagcccat |
| ex3 | 60° C. | 5/7 | cagggacattgtaggccatc | tcccagctcccaaaactaaa |
| ex4 | 60° C. | 9/10 | caggttctttattgtggcatca | cgaggatattttaacctcttatca |
| ex5 | 62° C. | 55/56 | gctaactgcccttaatagagtaaaa | aaagggtacagcgtcagcat |
| ex6 | TD62-58 | 13/15 | gaacatctttgccctggttt | caggcactgaggcagaagta |
| ex7 | 60° C. | 17/19 | aaaaatcaattcctaaatcataatcc | tcttttaaagccaaaagggtaaa |
| ex8 | 60° C. | 57/58 | cttgccccagattgcataat | tccaaaaagtacgtaaaatccca |
| ex9 | 60° C. | 59/60 | cagcaaaagggtaatagcagtg | cccaaatgtagtaaatggcg |
| ex10 | 60° C. | 21/22 | cccaggactaatcatgaagga | atcccaaaccgataaaacc |
| ex11 | 60° C. | 23/25 | cggtgtgtcttccactagctc | acccagccattctcagtgtt |
| ex12 | TD62-58 | 61/62 | tttgaaagagcagaaagctatgg | tgaaggggttgtcacactttt |
| ex13 | 60° C. | 63/64 | ttgtggcaaaagaaaatttgtg | gagaatgcaggctcagttcc |
| ex14 | 60° C. | 65/66 | atgtggaactgagcctgcat | cgacttgcattttaaagaacctg |
| ex15 | 60° C. | 27/28 | cacagcgagatcctgtctca | cctcactgtaagatgatgccc |
| ex16 | 62° C. | 29/31 | cctttaaatactacagtggtgcaga | ccaactgttgagatggagaaaa |
| ex17 | 56° C. | 67/68 | ttgtttccagatcatgaagaatatg | tcagatagctgaccacagcc |
| ex18 | 60° C. | 69/70 | tccctcttaaggagaaaaacactg | accgggccgagatataaaat |
| ex19 | 60° C. | 71/72 | gctagtttgtcttagaaccagaaca | ttttggttgtctcactatcaca |
| ex20 | 60° C. | 73/74 | aaggaacatagccagttctgtttt | tgcgaactattttcctttgg |

TABLE 4-continued

| Exon | Annealing temperature | SEQ ID NO: | Forward primer | Reverse primer |
|---|---|---|---|---|
| ex21 | 60° C. | 75/76 | tgcaacttctcaggtacacatct | aggctagagtgcagtggcat |
| ex22 | 60° C. | 77/78 | agtcagcttaagggaagcgg | gaagataaccatttctcccca |
| ex23 | 60° C. | 79/80 | ttgtgagtgtttggggagaa | ggggatttagtgaaaacacca |
| ex24 | 64° C. | 81/82 | tttgttggagaatacactgtgctt | catgtctacacaacagaaagaatgc |
| ex25 | 60° C. | 83/84 | aaaaggcaccatacagctttg | ggaaacacatgctggaacct |
| ex26C | 55° C. | 85/86 | cttctgtctgcttcttggtctt | tatcatcattatctgttgttgg |
| ex27 | 60° C. | 87/88 | ttaggtgatcccactggctc | cccaggagttcaaggctgta |
| ex28 | 60° C. | 89/90 | ctgaggagggcttgtttttg | tctgtaacttgtttactcccagttg |
| ex29 | 60° C. | 91/92 | gatcacaccactgcattcca | ggcacctgtagtcccagcta |
| ex30A | 60° C. | 93/94 | tgaggtgggaggatctcttg | gatgtgttcagagcagccaa |
| ex30B | 60° C. | 95/96 | taagctggaggagctggaga | ttgttgtcccttaacttgg |
| ex31 | 60° C. | 33/34 | tttgaagtatcccagggtgg | ccaccattccccaaagataa |
| ex32 | 60° C. | 35/37 | ttacctggatttggcttttgg | tgcaatccagaaacttgagaga |
| ex33 | 60° C. | 97/98 | caataggccaagggtttcaa | tataactcctgctggagggc |
| ex34 | 62° C. | 39/40 | atgttggcaggaactccatc | ctcctttggagcaacctctg |
| ex35 | 60° C. | 99/100 | ggtagcctggaaattagccc | tgaaccagaatctgaagcca |
| ex36 | 62° C. | 41/43 | ttccaacaggaaagcacaca | cagctacttgggaggctgag |
| ex37 | 60° C. | 45/47 | gcattagaaggggcactgaa | ctcacaacggtattcacccc |
| ex38 | 60° C. | 101/102 | ttttgtccttgggctctttc | cctggttctgtcactagccc |
| ex39 | 60° C. | 49/51 | aagggtttaagataatttgggga | ggattcttgatactgcttgcc |
| ex40A | 60° C. | 103/104 | aattagccagggtggtgaca | cccacaaaggactgatatgg |
| ex40B | TD62-58 | 105/106 | aaggaccctcagacaggttg | tcctttaaggcagacaaggg |

TD = TouchDown 10 cycles decrease of annealing temperature, then 25 stable cycles. Temperatures in Celsius degrees.

For some exons, it was possible to set up dHPLC conditions to detect variants. Primers different from those used for direct sequencing were specifically designed but they can also be used for direct sequencing. The PCR conditions and dHPLC conditions are indicated on table 5.

TABLE 5 dHPLC conditions to analyze exons of KIAA1840. Temperature in Celsius degrees.

| Exon | Size | T° PCR | T° DHPLC |
|---|---|---|---|
| 2 | 323 | 62°-1'-35x | 55.3° |
| 3 | 305 | 58°-1'-35x | 55.1° |
| 4 | 320 | 62°-1'-35x | 54.8°-52.8° |
| 5 | 330 | 60°-1'-35x | 54.9° |
| 6 | 450 | 58°-1'-35x | 54°-53° |
| 7 | 275 | 58°-1'-35x | 50.6°-52.6° |
| 9 | 342 | 62°-1'-35x | 54.1 |
| 11 | 293 | 57°-1'-35x | 54.6° |
| 12 | 210 | 62°-1'-35x | 52.5° |
| 13 | 289 | 62°-1'-35x | 51.5° |
| 14 | 246 | 62°-1'-35x | 55.8° |
| 16 | 309 | 62°-1'-35x | 55.2° |
| 17 | 239 | 62°-1'-35x | 53.9° |
| 18 | 324 | 58°-1'-35x | 53°-50° |
| 20 | 311 | 62°-1'-35x | 52.3° |
| 22 | 383 | 62°-1'-35x | 55.8° |
| 23 | 356 | 62°-1'-35x | 53.1° |
| 24 | 267 | 60°-1'-35x | 57.1° |
| 25 | 361 | 60°-1'-35x | 56.6° |
| 27 | 330 | 62°-1'-35x | 53.6° |
| 28 | 329 | 62°-1'-35x | 53.5° |
| 29 | 330 | 56°-1'-35x | 54.2°-56.2° |
| 32 | 323 | 60°-1'-35x | 58.8° |
| 33 | 349 | 62°-1'-35x | 57.6° |
| 35 | 312 | 62°-1'-35x | 54° |
| 36 | 376 | 62°-1'-35x | 52° |
| 37 | 313 | 62°-1'-35x | 57.6° |
| 38 | 315 | 62°-1'-35x | 56.9° |
| 39 | 380 | 62°-1'-35x | 53.2° |
| 40 | 390 | 62°-1'-35x | 54.4° |
| 40 | 321 | 58°-1'-35x | 54.2° |

TABLE 6 dHPLC primers to analyze exons of KIAA1840

| Exon | PRIMERS F (5' - 3')/ R (5' - 3') | SEQ ID NO: |
|---|---|---|
| 2 | accaggtcaactaaactgttctct / tatgctgaaagaccacctgtaga | 107/108 |
| 3 | ccagttgtaaaattgtgacc / tcaatcaacacttctaccac | 6/8 |
| 4 | gttaggcatacttacaaaactggc / cgaggatatttttaacctcttatca | 11/12 |
| 5 | caggagcagtagtaacacaa / aaagggtacagcgtcagcat | 109/110 |
| 6 | ctgtgacaggtgttaagtta / atctaatacaagacagtctc | 14/16 |
| 7 | tagtactgaagtattgagta / ttaagtaatgttcttgggca | 18/20 |
| 9 | gcaggtaataagcctgcagaa/ccccccttcctagctgctatt | 111/112 |
| 11 | gttacataaatgtataatccctg / cattttaagactttatggattac | 24/26 |
| 12 | tgttcaaaatagttccattacaaaa / tttcttccaaggttttcttcca | 113/114 |
| 13 | tttgcaaaagtgcttgatttt / tgcaggctcagttccacata | 115/116 |
| 14 | ggaatgatgcctttttctcc / tctcacacttgccttctgga | 117/118 |
| 16 | tgtgggcatgatttggtcta / acctgctcaaggacaaatgc | 30/32 |
| 17 | aatcatcgcctgagcaaaat / ccagtgactgatccaaagca | 119/120 |
| 18 | ccctcttaaggagaaaaacac / cagccttatcctctgctctt | 121/122 |
| 20 | tggaaaggggagcagacta / tgcgaactattttttcctttgg | 123/124 |
| 22 | gaggaggccacaaatcacat / gccttagacctcgtcacacc | 125/126 |
| 23 | tgctcaggttttgactttttctc / tttcactgatggcaagatgc | 127/128 |
| 24 | accaccccacctctaattc / ctacacaacagaaagaatgc | 129/130 |
| 25 | ccagctgaaactgaaagttgg / ctgggtacttacttcaggct | 131/132 |
| 27 | cactgtgccctgccttatta / tgtgcctgagtaaccgagtg | 133/134 |
| 28 | tcccagatttggaggttttg / tgcattttaatttcctaactaccc | 135/136 |
| 29 | gctgtagtggcattttattg / cctgggtgacagagcaagac | 137/138 |
| 32 | cctggcttctaaaagtggcc / aagcacaacatccaaatcctt | 36/38 |
| 33 | agctgcagagctccataagc / taggcatccagagcaggaac | 139/140 |
| 35 | ggcatctgaaagcaaccact / ccctccatttcccaagagt | 141/142 |
| 36 | caacaggaaagcacacatgc / gtgtggctgtgacctcactc | 42/44 |
| 37 | aacatggctgggatgtttct / ttcctggttggcctatgatg | 46/48 |
| 38 | ggggtgaataccgttgtgag / acctctgggttccatgagtg | 143/144 |
| 39 | aatgccaaacacacacctga / ctcaaagcagaggcaaggag | 50/52 |
| 40 | agactgctcctctgcactcc / ccgggattgttcaactttagc | 145/146 |
| 40 | cagtatcttaacctgtacat / ccgggattgttcaactttagc | 147/148 |

Overexpression Studies: The KIAA1840 cDNA from clone pf01011 (Kazusa DNA research Institute, Japan) was excised from the pBluescript II SK(+) vector using XhoI/NotI restriction enzymes and cloned in fusion with EGFP in a SalI/Bsp120I digested pEGFP-C1 vector (Clontech). The construction was verified by direct sequencing after ligation, transformation and plasmid extraction using standard procedures.

COS-7 cells were maintained in DMEM (Invitrogen) supplemented with 10% fetal bovine serum, penicillin (100 UI/ml) and streptomycin (100 µg/ml). Cells were plated 24 h before transfection on cover slips coated with polyethylenimine and transfected with Lipofectamine-PLUS reagents according to the manufacturer's instructions (Invitrogen). For 6-well plates, 1-2 µg of plasmid DNA was used per well. Cells were analyzed by immunofluorescence 120h post-transfection. The spatacsin-EGFP fusion protein was observed directly after fixation for 15 min with 4% formaldehyde. Immunocytochemistry was performed, using classical procedures with the following antibodies: rabbit anti-Cox2 (1/200, kind gift of A. Lombes, Paris) and rabbit anti-alpha-COP (1/1000$^e$; Affinity Bioreagent). Cells were counterstained with DAPI (1 µg/ml, Sigma) and mounted with Fluoromount-G (Southern Biotech). Samples were observed with a Leica SP1 confocal microscope. Leica confocal software was used to acquire the images.

Northern-Blot Analysis (Human): Total RNA was extracted from the human post-mortem brain cortex of an healthy individual (Brain Bank of INSERM U679) using the RNAeasy Mini kit (Qiagen). The corresponding cDNAs were synthesized using random hexamers in the presence of Thermoscript reverse transcriptase as recommended by the supplier (Invitrogen). A series of 7 probes of 1.2 Kb covering the entire KIAA1840 cDNA was amplified by PCR at an annealing temperature of 60° C. (primer sequences available on request). Human multiple tissue northern blots (Clontech) were hybridized at 68° C. for 1 hour with a mix of these probes $aP^{32}$-labeled by random priming (Prime-it II Random Primer Labeling kit, Stratagene) and purified using ProbeQuant G-50 micro columns (Amersham Biosciences) in accordance to the manufacturer's recommendations to reach a specific activity of at least $1 \times 10^9$ cpm/µg. Membranes were then washed as recommended by Clontech then exposed to X-Ray film for autoradiography.

In Situ Hybridization (Rat): Young (P1, P6, P15 and P21, n=1 each) and adult (P68, 200 g, n=2) Sprague Dawley rats (Charles River) were killed by decapitation and their brains were rapidly extracted and frozen in isopentane at −50° C. Sections were prepared with a cryostat at −20° C., from medulla to striatum (+1.7 from bregma) 600 µm-spaced, thaw-mounted on glass slides and stored at −80° C. until usage. KIAA1840 mRNA expression was analyzed using 3 antisens oligonucleotides designed using Helios ETC oligo design software (Helios Biosciences, Paris, France) on the mRNA sequence (XM-242139) of Rattus norvegicus similar to hypothetical protein FLJ21439 (LOC311372). Each oligonucleotide or a mix of the 3 oligonucleotides were used for the hybridization step and gave identical results. A mix of three sens oligonucleotides was used as a negative control.

In situ hybridization was performed as described in Moutsimilli et al. (2005) Briefly, oligonucleotides were labeled with [35S]-dATP (Amersham Biosciences) using terminal transferase (Amersham Biosciences) to a specific activity of $5 \times 10^8$ dpm/µg. The day of the experiment, slides were fixed in 4% formaldehyde in PBS, washed with PBS, rinsed with water, dehydrated in 70% ethanol and air-dried. Sections were then covered with 140 µl of hybridization medium (Helios Biosciences, Paris, France) containing $3-5 \times 10^5$ dpm of the labeled oligonucleotide mix. Slides were incubated overnight at 42° C., washed and exposed to a BAS-SR Fujifilm Imaging Plate for 5-10 days. The plates were scanned with a Fujifilm BioImaging Analyzer BAS-5000 and analyzed with Multi Gauge Software (Fuji).

For double labeling experiments, brains were processed as for in situ hybridization. After the last wash step, sections were fixed in 4% paraformaldehyde in PBS and preincubated in PBS containing 6% goat serum and 0.1% triton. Sections were next incubated with mouse antibodies directed against Neu-N(Chemicon International, 1/250), in the same buffer, processed with biotinylated horse anti-mouse IgG antibodies and ABC reagents (Vector Laboratories, Burlingame, Calif.) and submitted to emulsion autoradiography. The labeling with the antisense probe in comparison with the Neu-N neuronal specific counterstaining was observed.

Bioinformatics: Functional domains were searched using bioinformatics tools available online at BABEL (http://babel.infobiogen.fr:1984/), Ressource Parisienne en Bioinformatique Structurale (http://bioserv.rpbs.jussieu.fr/RPBS) and PSORT (http://psort.nibb.ac.jp/). Psi-blast (www.ncbi.nlm.nih.gov) was used to look for homologous proteins or peptides. Alignment of homologous proteins was performed using CLUSTALW (http://www.ebi.ac.uk/clustalw/). Alteration of splicing sites was verified in the Alternative Splicing Database at http://rulai.cshl.edu/new_alt_exon_db2/HTML/score.html.

HCA is a method that allows to represent a protein sequence on a bidimensional scaffold that increases the density of the amino acids, and consequently, evidences local compacity of hydrophobic residues. They form clusters according to a connectivity that is the one of an alpha helix. It has been shown that the centers of the clusters and the centers of the secondary structures statistically match, (Woodcocks et al. 1992) and on the other hand the shape of a cluster is related to the nature of the secondary structure (Callebaut et al. 1997). HCA is a very efficient tool for recovery of highly divergent internal duplication of domains and for the detection of globular domain limits.

Results:

We selected a series of 91 families of European or North-African origins, all without mutations in the SPG7 gene and with a typical AR-HSP-TCC phenotype. Six of these families were previously reported as linked to SPG11 using a subset of polymorphic markers from the interval (Casali et al, 2004; Stevanin et al, 2006; Lossos et al, 2006). The other families were new. All available family members of 16 most informative families were genotyped using 34 microsatellite markers for linkage to three successive loci on chromosome 15 which have been associated with thin corpus callosum; SPG11, SPG21 and the locus for agenesis of corpus callosum with polyneuropathy (ACCPN). Positive multipoint LOD scores ranging from 0.60 to 3.85 and corresponding to the maximal expected values in the pedigrees were obtained in the 16 most informative families (FIGS. 1 and 2). Mutations in the ACCPN or SPG21 loci were excluded by direct sequencing in all families that showed positive linkage to these regions (data not shown). A significant combined multipoint LOD score of 28.1 was reached in the 3.3 cM interval flanked by markers D15S778 and D15S659 in the linked kindreds (FIGS. 1 and 2). Haplotype reconstructions identified two critical recombination events that allowed to restrict the candidate interval to 6.6 cM between markers D15S1044 and D15S123. The 3.2 cM of the D15S778-D15S659 interval was considered to be the region most likely containing the responsible gene on the basis of homozygosity in all consanguineous patients of two significantly linked families; family FSP221 linked to SPG11 with a maximal LOD score of 3.85 and family FSP672 linked to the same locus with a 2.6 LOD score value (FIGS. 3 and 4). In addition, a genome wide screen performed in family FSP221 at a resolution of 10 cM on all chromosomes only identified three other possible locations with multipoint lod scores of 2.2 to 2.5 that were excluded using 18 additional microsatellite markers (data not shown), therefore highly supporting linkage to SPG11.

The narrowed interval contained 40 genes in accordance with the National Center for Biotechnology Information (NCBI) and the Ensembl databases. Two were excluded in previous studies (SEMA6D and MAP1A, Stevanin et al, 2006). We evaluated 16 additional genes from the interval as candidates for SPG11, prioritizing those with a known or putative function in mitochondrial metabolism, intra-cellular trafficking or cytoskeleton integrity (FIG. 5). All coding and non-coding exons as well as their splicing sites with at least 50 bp of intronic sequences on each side were sequenced on genomic DNA of 5 index patients from 5 linked families. No mutations were found in 15 genes but sequence variations were found in the KIAA1840 gene. We then screened one affected member from the 16 linked families as well as of the uninformative kindreds and checked all other members of the families, when available, for sequence variations. 43 different mutations were identified in 47 families, including the 16 linked ones, 31 at the homozygous state, (FIGS. 5 to 9). They were either nonsense mutations (n=13), deletions (n=17), insertions (n=7) or splice site mutations (n=6) in the coding sequence, and resulted in an abnormally truncated protein or predicted to alter the splicing of the messenger RNA in all cases. In two families (FSP670 and ITA28 VAC, FIG. 8), we found a missense change (R945G or R815M) affecting a nucleotide of the 5'-splice site consensus and predicted to alter the splicing of the mRNA. This could be confirmed in family FSP670 by the analysis of mRNA from one patient (c.2833A>G, r.2834+1_2834+65 ins, p.R945GfsX950). Four mutations affected the intronic part of the consensus sequence for the acceptor splicing site (see Table 2) that also likely affect the splicing of the mRNA. The mutations segregated completely in the families with the disease and were not found on at least 140 chromosomes from unrelated control individuals of European and North-African origin suggesting that these mutations were not polymorphisms. Only 4 mutations were found in more than one pedigree (FIGS. 6 and 7). A c.6100C>T substitution that replaces an arginine by a stop codon in exon 32 (R2034X), shortening the protein from 2443 to 2034 amino acids (SEQ ID NO:160), was identified, in the homozygous state, in 4 Algerian, 3 Tunisian and 2 Moroccan consanguineous kindreds (FIG. 6). A 5 bp deletion in exon 3 (c.529_533delATATT) leading to a frameshift and a stop codon at aa 178 (SEQ ID NO:150) was found at the homozygous state in all patients of 3 Portuguese families and at the heterozygous state in one Brazilian kindred (FIG. 7). Interestingly, alleles at close flanking markers were partially similar in families with identical mutations (when it could be tested) suggesting founder effects in North-Africa and Portugal for these mutations. The c.733_734del AT mutation was also found in 4 Tunisian pedigrees, sharing partial common haplotypes (data not shown) and one French kindred. Finally, the c.1951C>T variant was found at the heterozygous state in 2 Italian and one Kindred from Romania for which we are extending the pedigrees to check for haplotype conservation.

No mutations were found in 44 families, suggesting that the responsible mutations were either in non-coding regions of KIAA1840 or in another unidentified gene.

SPG11 mutations were thus found in the majority of the families with the typical AR-HSP-TCC studied here (47/91). Most families originated from the Mediterranean basin. Complete examination of 22 affected members (Stevanin et al, 2007), 12 men and 10 women, showed a mean age of 24.8±9.5 years ranging from 12 to 49. Onset of the disease always occurred before age 24 years (mean age 11.8±5.5 years; range 2-23) and consisted in either spastic gait (57%, 12/21) or cognitive impairment (19%, 4/21), sometimes diagnosed as mental retardation. After about 10 years of evolution, the full-blown clinical picture consisted in progressive and severe spastic paraplegia with distal wasting and cognitive problems. In several cases (n=6), cognitive dysfunction clearly worsened with disease progression. Cerebral imaging showed a thin corpus callosum, but also periventricular white matter changes and cortical atrophy, in the majority of the patients. Pseudo-bulbar dysarthria was frequent (54%, n=12) and dystonic voice was noted in one patient. Interestingly, although a few patients had normal electromyographic recordings, peripheral neuropathy was frequent (72%, 13 out of 18 patients) and was mostly associated with pure motor changes. Additional signs, such as optic atrophy, retinitis pigmentosa, mild cerebellar signs, cataract, and clinodactily were occasionally observed, a finding that expands the clinical spectrum of this entity.

The human KIAA1840 gene contains 40 exons spanning 101 Kbases of genomic DNA on chromosome 15q21.1. The full length transcript encodes a predicted protein of 2443 amino acids of unknown function called spatacsin for SPAsticity with Thin or Atrophied Corpus callosum Syndrome proteIN. The sequence of spatacsin is strongly conserved through evolution with orthologues in mammalians and other vertebrates: human KIAA1840 shares 85% identity with the homologous protein in dog, 76 and 73% with the mouse and rat homologues and 59% with the chicken homologue, all of similar sizes. Less similarity was found with homologous proteins of smaller sizes from fugu (44%), tetraodon (39%), and *drosophila* (22%).

Neither the gene nor the predicted protein it encodes in many species show any significant sequence similarity to known cDNA or protein sequences. We then looked for protein motifs and domains (FIG. 3). Four putative transmembrane domains were predicted by various algorithms (aa 163-194, 200-240, 1239-1267 and 1471-1493). A glycosyl hydrolase F1 signature was also detected (aa 482-490). This motif is based on a conserved glutamic acid residue which has been shown in the beta-glucosidase of various bacteria and plants and mammalian lactase-phlorizin hydrolase, an integral membrane glycoprotein that splits lactose in the small intestine. Interestingly, this protein is assigned to the aromatic compound dioxygenase superfamily because of a 22% identity with the consensus sequence between aa 2104-2381. A leucine zipper (aa 611 to 632), involved in dimerization of many gene-regulatory proteins (C/EBP, CREB, CRE-BP1, ATFs and Jun/AP1 family of transcription factors) and a Myb domain (aa 1766 to 1774), involved in the DNA-binding of *drosophila* and vertebrate myb and related proteins, were also identified. Interestingly, there is a 47% identity, over 44 aa, with thymosyl-like peptides, small peptides which play an important role in the organization of the cytoskeleton; these peptides, bind to and sequester actin monomers, thereby inhibiting actin polymerization (Low and Golstein 1985). Furthermore, a probable coiled-coil domain of 33 residues from 1556 to 1590 was also present and such domains are reported in structural or motor proteins such as spectrin, laminin, dynein or neurofilament proteins.

We then looked at the structure of the predicted protein. The level of hydrophobicity (34.2%) over the entire sequence was typical of a globular protein. Because of it's size, a succession of globular domains is likely and we tried to identify them by the identification of inter domain regions, corresponding to a low density of hydrophobic clusters with the DomHCA software (Prat-Albeau et al, 2006). Except a small linker located between positions 1410 and 1440, no domain separation was evidenced. From the HCA plots, one of the putative transmembrane regions was confirmed at amino acids 200 to 240 on spatacsin from 5 vertebrates, but it was lacking in the homologous sequences from tetraodon and *drosophila*, as these last two sequences presented a shortened N-terminal domain. A thorough analysis of putative duplication highlighted two structurally similar regions (aa 560-700 and 2250-2390) in all vertebrate homologues of the protein with 19% sequence identity in human sequences (FIG. 10). Amino acid proportion shows a non standard distribution in some cases: high amount of leucines (13.8% vs 9.6% in standard reference databases), a low level of methionines (1.9% instead of 2.38%) and glycines (3.9% vs 6.93% in Swiss Prot). The proportion of cysteins was over 2 fold higher (2.9%) compared to the mean in databases but did not gave rise to disulfide bridges, according to the predictions of the CysState software (Mucchielli-Girgi, 2002). Cluster shapes claim for a mainly helical behavior of this protein, which is confirmed by standard prediction tools.

The spatacsin protein, fused with GFP, had a diffuse cytosolic and nuclear distribution that sometimes excluded the nucleus of COS-7 cells. In rare cases (<5%), spatacsin formed small perinuclear dots or aggresome-like structures in cells with high expression levels after 4 days post-transfection that did not colocalized with the mitochondrial marker Cox2 or the Golgi marker alpha-COP.

Figure 11:
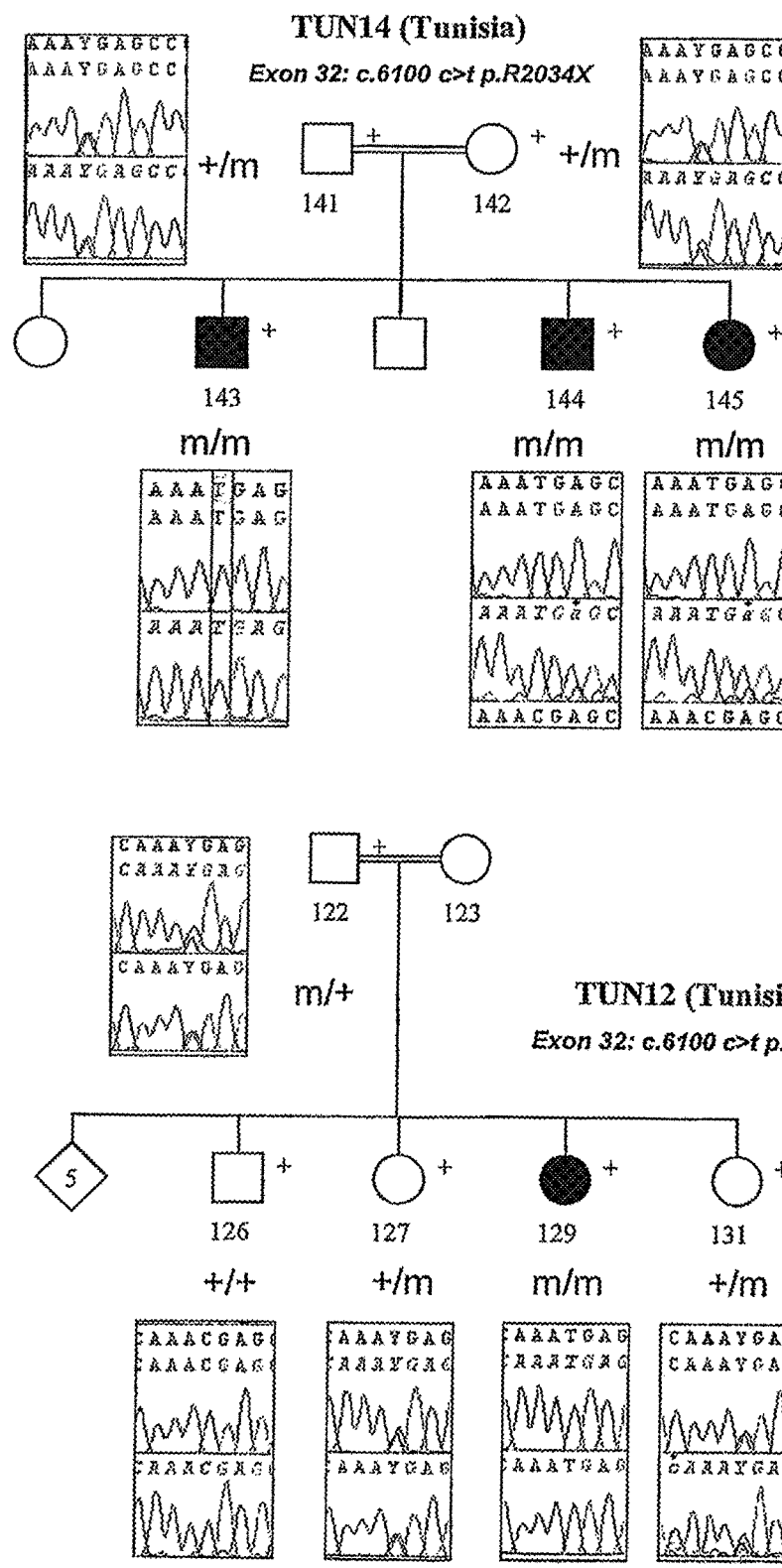
Figure 13:
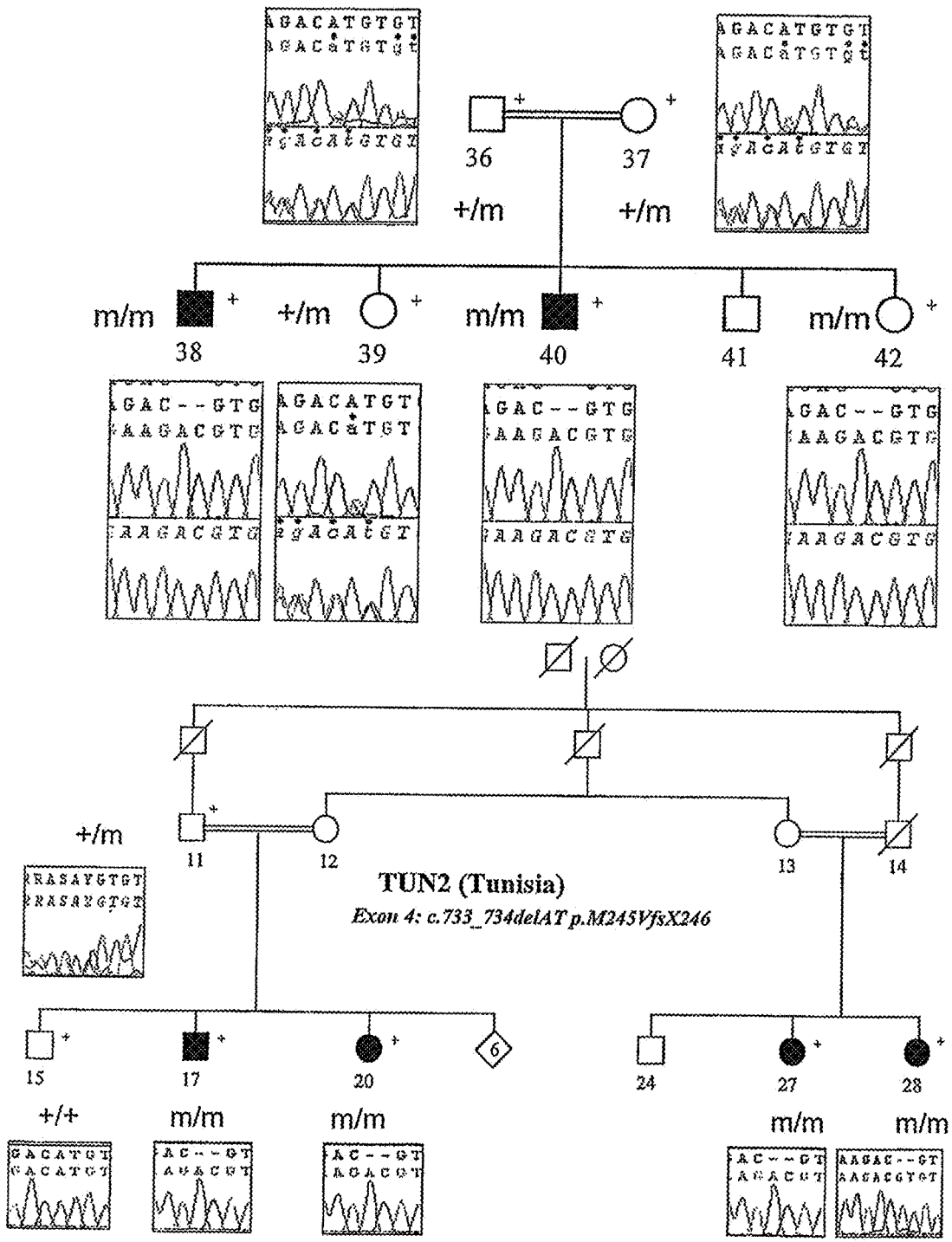

Previous expression profiling of the SPG11 gene showed that it is expressed ubiquitously at low levels in mouse tissues, including the brain (Nagase et al, 2001). Ubiquitous low level expression, even in structures apparently not related to the phenotype, has been shown for other genes responsible for neurodegenerative diseases (Paisan-Ruiz et al, 2004). We successfully amplified seven overlapping cDNA fragments from the KIAA1840 mRNA extracted from human cerebral cortex and used them to probe human adult multiple-tissue northern blots. At least three alternative transcripts were detected in all structures of adult brain. The full-length transcript (~8 Kb) was most highly expressed in the cerebellum, the 5.5-Kb transcript in the cerebral cortex (FIG. 11).

When the temporal and regional expression of the mouse KIAA1840 mRNA was investigated by in situ hybridization in rat brain, it was undetectable in newborn rats (P1). It was detected in the cerebellum, however, from P6 to P21. At adulthood (P68), expression was found throughout the brain. Expression was generally low, but stronger signals were observed in the pineal gland, the edges of the lateral ventricles, the granular layer of the cerebellum and the hippocampus. In contrast to human adult northern blots, only a weak expression was detected in the cerebral cortex. Understanding the function of spatacsin in these structures would help to explain the major features of the disease phenotype: e.g., expression in the hippocampus could be related to the cognitive impairment observed in the patients. In addition, whether the labeling of the edges of the lateral ventricles, where oligodendrocyte progenitors are located, is related to the white matter changes in patients remains to be investigated.

Our study identified the gene responsible for spastic paraplegia with thin corpus callosum linked to SPG11, KIAA1840. This is supported by four pieces of evidence; first, we have excluded 17 out of the 40 genes assigned to the SPG11 candidate interval; second, we have identified 43 different mutations segregating in 47 families, 16 of which linked previously to the SPG11 locus, and not found in at least 140 control chromosomes; third, all, these mutations were leading to a truncated protein and/or abnormally spliced mRNA, and fourth all mutated families presented with the typical AR-HSP-TCC phenotype or at least a compatible phenotype in 2 families in which cerebral imaging was not available. Mutations in KIAA1840 affected 47 of 91 AR-HSP-TCC families in this study making this genetic entity very frequent among AR-HSP-TCC (52%), 75% was estimated in a previous study (Stevanin et al, 2006), but also among recessive spastic paraplegias. At least another gene might however exist as previously shown (Lossos et al, 2006; Stevanin et al, 2006; Casali et al, 2004).

This gene has a widespread low level expression, including in the brain where it is more strongly expressed in the cerebellum, the cerebral cortex, the hippocampus, the pineal gland and the edges of the ventricles. Spastic paraplegias are supposed to results from a dying back mechanism of the exons and mitochondrial metabolism or axonal transport has been implicated in several genetic entities of HSP (Crosby et al, 2002). Indeed, three causative genes identified in AR-HSP have been implicated in defective intracellular trafficking: mutations in the mitochondrial metalloprotease protein paraplegin impair axonal transport in SPG7; spartin (SPG20) mutations affect endosomal trafficking and microtubule dynamics; maspardin (SPG21) mutations may interfere with endosomal/trans-Golgi vesicle transportation. Although, the function of spatacsin remains unknown, given it's basal expression in all tissues and it's high conservation in all species, this protein might have a crucial function which might explain the degeneration of the corticospinal tracts which might rely on the post-translational modifications or modeling/carriage of other proteins involved in axonal transport, mitochondrial metabolism as well as cerebral development. The presence of at least one transmembrane domain suggests that spatacsin may act as a receptor of a transporter.

All mutations identified so far in the KIAA1840 gene cause or are predicted to cause truncation of the protein, suggesting that pathogenicity results from loss of function. They are located in many exons, including exon 1 and exon 39 suggesting that the C-terminal domain of the protein has also an important function or effect on the structure of the protein. It is also conceivable that, given its position in the 5'splice site consensus sequence, the missense mutation R815M would also affect the transcription of the gene as demonstrated for mutation c.2833A>G, r.2834+1_2834+65 ins, p.R945GfsX950. Similarly, the mutations found in the intronic part of the acceptor splicing sites in introns 4, 12, 13 and 34 (Table 2) are likely altering the splicing of the surrounding exons and therefore the synthesis and/or stability of the mRNA or protein. No tissues from patients were available yet, however, to validate this hypothesis.

The identification of the SPG11 gene will now improve the diagnostic procedure, as well as patient management, and permit more accurate genetic counseling. This is invaluable for patients and their families.

REFERENCES

The following are all incorporated herein by reference:

Antonarakis et al. (1989), N. Engl. J. Med. 320:153-163 Diagnosis of genetic disorders at the DNA level Barbas C F, Bain J D, Hoekstra D M, Lerner R A. (1992), Semisynthetic combinatorial antibody libraries: a chemical solution to the diversity problem. PNAS USA, 89, 4457-4461

Callebaut, I. et al. Deciphering protein sequence information through hydrophobic cluster analysis (HCA): current status and perspectives. Cell Mol. Life Sci. 53, 621-645 (1997).

Casali, C. et al. Clinical and genetic studies in hereditary spastic paraplegia with thin corpus callosum. Neurology 62, 262-268 (2004).

Casari, G. et al. Spastic paraplegia and OXPHOS impairment caused by mutations in paraplegin, a nuclear-encoded mitochondrial metalloprotease. Cell 93, 973-983 (1998).

Chomocyznski et al., Anal. Biochem., 162:156, 1987

Colas et al., 1996

Cooper et al. (1991) Diagnosis of genetic disease using recombinant DNA, 3rd edition, Hum. Genet, 87:519-560

Den Dunnen J. T., Antonarakis S. E.: Hum Genet 109(1): 121-124, 2001.

Engert, J. C. et al. ARSACS, a spastic ataxia common in northeastern Quebec, is caused by mutations in a new gene encoding an 11.5-kb ORF. Nat. Genet 24, 120-125 (2000).

Fink, J. K. Advances in the hereditary spastic paraplegias. Exp. Neurol 184 Suppl 1, 5106-5110 (2003).

Fink, J. K. Hereditary spastic paraplegia. Curr. Neurol. Neurosci. Rep. 6, 65-76 (2006).

Grompe M. The rapid detection of unknown mutations in nucleic acids (1993) Nat. Genet. 5(2):111-7

Gudbjartsson, D. F., Jonasson, K., Frigge, M. L., & Kong, A. Allegro, a new computer program for multipoint linkage analysis. Nature Genet. 25, 12-13 (2000).

Harding, A. E. Classification of the hereditary ataxias and paraplegias. Lancet 1, 1151-1155 (1983).

Harlow E. et al., Antibodies: A Laboratory Manual, Cold Spring Harbor Laboratory, New York, (1988).

Hazan, J. et al. Spastin, a new AAA protein, is altered in the most frequent form of autosomal dominant spastic paraplegia. Nature Genet. 23, 296-303 (1999).

Kohler and Milstein (1975) Continuous cultures of fused cells secreting antibody of predefined specificity. Nature; 256, 495-7.

Kuklin et al. Detection of single-nucleotide polymorphisms with the WAVE DNA fragment analysis system Genet. Test (1997-98), 1(3):201-6

Lossos, A. et al. Hereditary spastic paraplegia with thin corpus callosum: reduction of the SPG11 interval and evidence for further heterogeneity. Arch Neurol 63(5):756-60 (2006).

Martinez, M. F. et al. Genetic localization of a new locus for recessive familial spastic paraparesis to 15q13-15. Neurology 53, 50-56 (1999).

Moutsimilli, L. et al. Selective cortical VGLUT1 increase as a marker for antidepressant activity. Neuropharmacology 49, 890-900 (2005).

Nickerson et al., 1990

Olmez et al. Further Clinical and Genetic Characterization of SPG11: Hereditary Spastic Paraplegia with Thin *Corpus Callosum*. Neuropediatrics. 2006; 37:59-66.

Patel, H. et al. SPG20 is mutated in Troyer syndrome, an hereditary spastic paraplegia. Nature Genet. 31, 347-348 (2002).

Saiki et al., Science 1988, 239:487

Sambrook, Fritsch & Maniatis, Molecular Cloning: A Laboratory Manual, Second Edition (1989) Cold Spring Harbor Laboratory Press, Cold Spring Harbor, N.Y.

Shibasaki, Y. et al. Linkage of autosomal recessive hereditary spastic paraplegia with mental impairment and thin corpus callosum to chromosome 15A13-15. Ann Neurol 48, 108-112 (2000).

Simpson, M. A. et al. Maspardin is mutated in mast syndrome, a complicated form of hereditary spastic paraplegia associated with dementia. Am. J. Hum. Genet. 73, 1147-1156 (2003).

Stevanin, G. et al. Spastic paraplegia with thin corpus callosum: description of 20 new families, refinement of the SPG11 locus, candidate gene analysis and evidence of genetic heterogeneity. Neurogenetics, 7, 149-156 (2006).

Stevanin, G. et al., Mutations in SPG11, encoding spatacsin, are a major cause of spastic paraplegia with thin corpus callosum Nat Genet Mar; 39(3):366-72. Epub 2007 Feb. 18. (2007)

Tallaksen, C. M., Durr, A., & Brice, A. Recent advances in hereditary spastic paraplegia. Curr. Opin. Neurol. 14, 457-463 (2001).

Waterhouse P, Griffiths A D, Johnson K S, Winter G. (1993) Combinatorial infection and in vivo recombination: a strategy for making large phage antibody repertoires. Nucleic Acids Research, 21, 2265-2266.

Winner, B. et al. Clinical progression and genetic analysis in hereditary spastic paraplegia with thin corpus callosum in spastic gait gene 11 (SPG11). Arch. Neurol. 61, 117-121 (2004).

Winner, B. et al. Thin corpus callosum and amyotrophy in spastic paraplegia-Case report and review of literature. Clin. Neurol. Neurosurg. (2005).

Woodcock, S., Mornon, J. P., & Henrissat, B. Detection of secondary structure elements in proteins by hydrophobic cluster analysis. Protein Eng 5, 629-635 (1992).

Zhao, X. et al. Mutations in a newly identified GTPase gene cause autosomal dominant hereditary spastic paraplegia. Nature Genet. 29, 326-331 (2001).

Reid, E. Pure hereditary spastic paraplegia. J. Med. Genet. 34, 499-503 (1997).

SEQUENCE LISTING

This disclosure includes a sequence list associated with this application and is accessable from the U.S. Patent Office online via its EFS-Web as follows:

Name of File: Seq_Listing.txt.
Date Created: Dec. 20, 2016.
Size of File in bytes: 519,422 bytes.

What is claimed is:

1. A nucleic acid probe comprising a fragment of KIAA1840 sequence or a complement thereof, wherein the KIAA1840 sequence has the sequence of SEQ ID NO: 1 except that the KIAA1840 sequence has a deletion of AT at positions 733-734 (KIAA1840 c.733-734delAT mutation), wherein the nucleic acid probe comprises the KIAA1840 c.733-734delAT mutation, wherein the nucleic acid probe is detectably labeled with a radiolabel, a fluorescent label, or an enzymatic label, and wherein the fragment of the KIAA1840 sequence is at least 25 nucleotides long.

2. The nucleic acid probe of claim 1, wherein the KIAA1840 sequence encodes a truncated KIAA 1840 protein that has an amino acid sequence of SEQ ID NO: 151.

3. The nucleic acid probe of claim 1, wherein the nucleic acid probe has 25 to 100 nucleotides.

4. A kit for detecting a KIAA 1840 mutation, comprising the nucleic acid probe of claim 1.

5. The kit of claim 4, further comprising one or more hybridization reagents.

* * * * *